US006949534B2

(12) United States Patent
Zheng et al.

(10) Patent No.: US 6,949,534 B2
(45) Date of Patent: Sep. 27, 2005

(54) CELL ADHESION INHIBITORS

(75) Inventors: Zhongli Zheng, Lexington, MA (US); Carol L. Ensinger, Chelmsford, MA (US); Steven P. Adams, Andover, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 171 days.

(21) Appl. No.: 10/260,340

(22) Filed: Oct. 1, 2002

(65) Prior Publication Data

US 2004/0053907 A1 Mar. 18, 2004

Related U.S. Application Data

(62) Division of application No. 09/237,273, filed on Jan. 25, 1999, now Pat. No. 6,686,350, which is a continuation of application No. PCT/US97/13013, filed on Jul. 24, 1997.
(60) Provisional application No. 60/022,890, filed on Jul. 25, 1996, and provisional application No. 60/032,786, filed on Dec. 6, 1996.

(51) Int. Cl.[7] ...................... A61K 31/33; A61K 31/135; A61K 31/195
(52) U.S. Cl. ........................ 514/183; 514/567; 514/649
(58) Field of Search ................................ 514/183, 567, 514/649

(56) References Cited

U.S. PATENT DOCUMENTS

| | | | |
|---|---|---|---|
| 4,725,583 A | 2/1988 | Luly et al. ...................... 514/18 |
| 4,826,815 A | 5/1989 | Luly et al. ...................... 514/19 |
| 4,908,360 A | 3/1990 | Martin et al. ................ 514/213 |
| 5,239,113 A | * 8/1993 | Bovy et al. .................. 562/440 |
| 5,260,277 A | 11/1993 | McKenzie ..................... 544/18 |
| 5,314,902 A | 5/1994 | Tjoeng et al. ............... 514/357 |
| 5,403,836 A | 4/1995 | Blackburn et al. .......... 514/213 |
| 5,434,188 A | 7/1995 | Boschelli et al. ............ 514/617 |
| 5,693,637 A | 12/1997 | Klinge et al. ................ 514/221 |
| 5,770,573 A | 6/1998 | Arrhenius et al. ............. 514/18 |

FOREIGN PATENT DOCUMENTS

| | | | |
|---|---|---|---|
| DE | 43 09 867 | 9/1994 | |
| EP | 0 021 234 | 1/1981 | |
| EP | 0 357 192 | 7/1990 | ......... C07C/335/06 |
| EP | 0 460 679 | 12/1991 | |
| EP | 0 519 748 | 12/1991 | |
| EP | 0 565 896 | 10/1993 | |
| EP | 0635492 | 1/1995 | |
| WO | WO 89/09786 | 10/1989 | |
| WO | WO 91/09837 | 7/1991 | |
| WO | WO 92/00995 | 1/1992 | |
| WO | WO 92/08464 | 5/1992 | |
| WO | WO 93/08174 | 4/1993 | |
| WO | WO 93/08823 | 5/1993 | |
| WO | WO 93/09795 | 5/1993 | |
| WO | WO 93/00095 | 7/1993 | |
| WO | WO 93/12809 | 7/1993 | |
| WO | WO 94/02445 | 2/1994 | |
| WO | WO 94/15958 | 5/1994 | |
| WO | WO 94/22825 | 10/1994 | |
| WO | WO 94/23714 | 10/1994 | |
| WO | WO 95/15973 | 12/1994 | |
| WO | WO 95/15963 | 6/1995 | |
| WO | WO 96/22966 | 8/1996 | |
| WO | WO 97/03094 | 1/1997 | |

OTHER PUBLICATIONS

Zablocki et al., J. Med. Chem. vol. 38(13) (1995) pp. 2378–2394.*

Thierry et al., "Synthesis and Activity of NAcSerAspLysPro Analogues on Cellular Interactions between T–Cell and Erythrocytes in Rosette Formation," Journal of Medical Chemistry, 1990, 33: 2122–2127.

Greenstein et al., "Chemistry of the Amino Acids," John Wiley & Sons, Inc., vol. 2, 1162–1186.

Kim et al., "Inhibition of [125]I–Labeled Ristocetin Binding to Micrococcus Luteus Cells by the Peptides Related to Bacterial Cell Wall Mucopeptide Precursors: Quantitative Structure–Activity Relationships," Journal Medical Chemistry, 1989, 32: 84–93.

Abraham et al., $\alpha_4$–Integrins Mediate Antigen–induced Late Bronchial Responses and Prolonged Airway hyperresponsiveness in sheep, J Clin. Invest. 1994, 93(2):776–787.

Bajusz et al., "Design and Synthesis of Peptide Inhibitors of Blood Coagulation", Folia Haematol. Leipzig, 1982, 109:16–21.

Baldwin et al., "An Efficient Substitute for the $\alpha$–Aminoadipoyl Moiety of $\Delta$–(L–$\alpha$–Aminoadipoly)–L–Cysteinyl–D–Valine in the Enzymatic Synthesis of Penicillins", Tetrahedron, 1987, 43(18): 4217–4220.

Chen et al., Chemical Abstracts, 1991, 115: 159756r.

Chisholm et al., "Monoclonal antibodies to the integrin $\alpha$–4 subunit inhibit the murine contact hypersensitivity response", European Journal of Immunology, 1993, 23:682–688.

(Continued)

*Primary Examiner*—Bennett Celsa
(74) *Attorney, Agent, or Firm*—Steptoe & Johnson LLP

(57) ABSTRACT

The present invention relates to novel compounds that are useful for inhibition and prevention of cell adhesion and cell adhesion-mediated pathologies. This invention also relates to pharmaceutical formulations comprising these compounds and methods of using them for inhibition and prevention of cell adhesion and cell adhesion-mediated pathologies. The compounds and pharmaceutical compositions of this invention can be used as therapeutic or prophylactic agents. They are particularly well-suited for treatment of many inflammatory and autoimmune diseases.

27 Claims, No Drawings

OTHER PUBLICATIONS

Elices et al., "Expression and Functional Significance of Alternatively Spliced CS1 Fibronectin in Rheumatoid Arthritis Microvasculature", The Journal of Clinical Investigation, 1994, 93:405–416.

Ferguson et al., "Two integrin–binding peptides abrogate T cell–mediated immune responses in vivo", Proceedings of the National Academy of Sciences USA, 1991, 88:8072–8076.

Ferguson et al., "Antigen–Independent Processes in Antigen–Specific Immunity", The Journal of Immunology, 1993, 150:1172–1182.

Goodman et al., "Synthesis and Conformation of Sequential Polypeptides of L–alanine and beta–Aminobutyric Acid", Macromolecules, 1976, 9:1–6.

Gruszecki et al., "Diacylamine–perfekte Acylierungsmittel fur die Peptidsynthese", Liebigs Ann. Chem., 1988, 331–336.

Hemler, "VLA Proteins in the Integrin Family: Structures. Functions. and Their Role on Leukocytes", Annual Review of Immunology, 1990, 8:365–400.

Jiang et al., "Approaches Toward the Total Synthesis of Astins A, B, And C", Tetrahedron Letters, 1994, 35:2121–2124.

Komoriya et al., "The Minimal Essential Sequence for a Major Cell Type–specific Adhesion site (CS1) within the Alternatively Spliced . . . ", Journal of Biological Chemistry, 1991, 266:15075–15079.

Lampi et al., "Comparison of Cell–Permeable Calpain Inhibitors and E64 in Reduction of Cataract in Cultured Rat Lenses", Toxicology and Applied Pharmacology, 1993, 117: 73–57.

Lobb et al., "The Pathophysiologic Role of α4 Integrins in Vivo", The Journal of Clinical Investigation, 1994, 94:1722–1728.

Molossi et al., "Blockade of Very Late Antigen–4 Integrin Binding to Fibronectin with Connecting Segment–1 Peptide Reduces Accelerated Coronary Arteriopathy . . . ", Journal of Clinical Investigation, 1995, 95:2601–2610.

Morales–Ducret et al., "$\alpha_4\beta_1$, Integrin (VLA–4) Ligands in Arthritis Vascular Cell Adhesion Molecule–1 Expression in Synovium and on . . . ", The Journal of Immunology, 1992, 149:1424–1431.

Narumiya et al., "Pre–B cells adhere to fibronectin via interactions of integrin α5/αv with RGDS as well as of integrin α4 with two distinct V region sequences at its different . . . ", Intl. Immun., 1994, 6:139–147.

Nowlin et al., "A Novel Cyclic Pentapeptide Inhibits α4β1 and α5β1 Integrin–mediated Cell Adhesion", The Journal of Biological Chemistry, 1993, 268:20352–20359.

Sawyer, "Peptidomimetic Design and Chemical Approaches to Peptide Metabolism," *Peptide–Based Drug Design*, American Chemical Society, Washington, DC 1995, Chapter 17, pp. 387–410.

Subasinghe et al., "Synthesis of Acyclic and Dehydroaspartic Acid Analogues of Ac–Asp–Glu–OH and Their Inhibition of Rat Brain N–Acetylated alpha–Linked Acidic Dipeptidase (NAALA Dipeptidase)", Journal of Medicinal Chemistry, 1990, 33:2734–44.

Wayner et al., "Activation–dependent Recognition by Hematopoietic Cells of the LDV Sequence in the V Region of Fibronectin", The Journal of Cell Biology, 1992, 116:489–497.

Yednock et al., "Prevention of experimental autoimmune encephalomyelitis by antibodies against α4β1 integrin", Nature, 1992, 356:63–66.

Goodman et al, The pharmacological basis of therapeutics. 6th ed, New York, Macmillan Publishing Inc., 1980, 1738–1740.

* cited by examiner

CELL ADHESION INHIBITORS

CROSS REFERENCE TO RELATED APPLICATIONS

This application is a divisional application of U.S. application Ser. No. 09/237,273, filed on Jan. 25, 1999, now U.S. Pat. No. 6,686,350, which is a continuation of Application No. PCT/US 97/13013, filed Jul. 24, 1997, which claims priority from U.S. provisional application Nos. 60/022,890 and 60/032,786, filed Jul. 25, 1996 and Dec. 6, 1996, respectively, each of which are incorporated by reference in their entirety.

TECHNICAL FIELD OF THE INVENTION

The present invention relates to novel compounds that are useful for inhibition, alteration, or prevention of cell adhesion and cell adhesion-mediated pathologies. This invention also relates to methods of identifying additional novel compounds having the desired activity, as well as to pharmaceutical formulations comprising these compounds, and methods of using them for inhibition and prevention of cell adhesion and cell adhesion-mediated pathologies. The compounds and pharmaceutical compositions of this invention can be used as therapeutic or prophylactic agents. They are particularly well-suited for the treatment of many inflammatory and autoimmune diseases.

BACKGROUND OF THE INVENTION

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hematopoietic cells out of blood vessels and to the site of inflammatory injury. As such, cell adhesion plays a role in numerous pathologies such as, for example, inflammation and immune reactions in mammals.

Investigations into the molecular basis for cell adhesion have revealed that various cell-surface macromolecules—collectively known as cell adhesion molecules or receptors—mediate cell-cell and cell-matrix interactions. For example, proteins of the superfamily called "integrins" are key mediators in adhesive interactions between hematopoietic cells and their micro environment (M. E. Hemler, "VLA Proteins in the Integrin Family: Structures, Functions, and Their Role on Leukocytes.", *Ann. Rev. Immunol.*, 8, p. 365 (1990)). Integrins are non-covalent heterodimeric complexes consisting of two subunits called $\alpha$ and $\beta$. There are at least 16 different "subunits ($\alpha 1$–$\alpha 9$, $\alpha$-L, $\alpha$-M, $\alpha$-D, $\alpha$-X, $\alpha$IIB, $\alpha$-V and $\alpha$-E) and at least 9 different $\beta$ ($\beta 1$–$\beta 9$) subunits which have been identified to date. Based on the type of its $\alpha$ and $\beta$ subunit components, each integrin molecule can be categorized into a subfamily.

$\alpha 4\beta 1$ integrin, also known as very late antigen of activation-4 ("VLA-4") or CD49d/CD29, is a leukocyte cell surface receptor that participates in a wide variety of both cell-cell and cell-matrix adhesive interactions (M. E. Hemler, *Ann. Rev. Immunol.*, 8, p. 365 (1990)). It serves as a receptor for the cytokine-inducible endothelial cell surface protein, vascular cell adhesion molecule-1 ("VCAM-1"), as well as to the extracellular matrix protein fibronectin ("FN") (Ruegg et al., *J. Cell Biol.*, 177, p. 179 (1991); Wayner et al., *J. Cell Biol.*, 105, p. 1873 (1987); Kramer et al., *J. Biol. Chem.*, 264, p. 4684 (1989); Gehlsen et al. *Science*, 24, p. 1228 (1988)). Anti-VLA4 monoclonal antibodies ("mAb's") have been shown to inhibit VLA4-dependent adhesive interactions both in vitro and in vivo (Ferguson et al. *Proc. Natl. Acad. Sci.*, 88, p. 8072 (1991); Ferguson et al., *J. Immunol.*, 150, p. 1172 (1993)). Results of in vivo experiments suggest that the inhibition of VLA-4-dependent cell adhesion may prevent, inhibit or alter several inflammatory and autoimmune pathologies. (R. L. Lobb et al., "The Pathophysiologic Role of $\alpha 4$ Integrins In Vivo", *J. Clin. Invest.*, 94, pp. 1722–28 (1994)).

Another integrin, $\alpha$IIb$\beta$IIIa integrin ("IIb/IIIa"), is the most abundant integrin found on the membrane surface of normal platelets. Jennings, et al., *J. Biol. Chem.*, 257, p. 10458 (1982). Platelets depend on the adhesive interactions of glycoproteins, such as "IIb8IIIa integrin, for proper function. J. Hawiger, *Atherosclerosis Reviews*, 21, pp. 165–86 (1990). Thus, inhibition of this interaction is one method of regulating platelet thrombus formation or aggregation. A variety of compounds are known to inhibit $\alpha$IIb$\beta$IIIa integrins from binding to their natural ligands and thereby can regulate human disorders associated with a hyperthrombotic state. Compounds known to inhibit IIb/IIIa are described in the following patents and patent applications: GB 2 271 567 A; GB 2 292 558 A; EP 0 645 376 A1; EP 0 668 278 A1; EP 0 608 759 A2; EP 0 635 492 A1; WO 94/22820; U.S. Pat. No. 5,340,798 and WO 94/09029; U.S. Pat. No. 5,256,812, EP 0 381 033 and U.S. Pat. No. 5,084,466; WO 94/18981; WO 94/01396 and U.S. Pat. No. 5,272,162; WO 94/21602; WO 94/22444; WO 94/29273; WO 95/18111; WO 95/18619; WO 95/25091; WO 94/18162, U.S. Pat. No. 5,220,050 and WO 93/16038; U.S. Pat. No. 4,879,313 and EP 0 352 249 B1; WO 93/16697, U.S. Pat. No. 5,227,490, EP 0 478 363 A2, U.S. Pat. No. 5,229,616 and WO 94/12181; U.S. Pat. No. 5,258,398 and WO 93/11759; WO 93/08181 and EP 0 537 980 A1; WO 93/09133; EP 0 530 505 B1; EP 0 566 919 A1; EP 0 540 334 B1; EP 0 560 730 A2; WO 93/10091, EP 0 542 363 A2 and WO 93/14077; EP 0 505 868 B1; EP 0 614 664 A1; U.S. Pat. No. 5,358,956; U.S. Pat. No. 5,334,596 and WO 94/26745; WO 94/12478; WO 94/14776; WO 93/00095; WO 93/18058, WO 93/07867, U.S. Pat. Nos. 5,239,113, 5,344, 957 and EP 0 542 708 A1; WO 94/22825; U.S. Pat. No. 5,250,679 and WO 93/08174; U.S. Pat. No. 5,084,466; EP 0 668 278 A1; U.S. Pat. No. 5,264,420; WO 94/08962; EP 0 529 858; U.S. Pat. No. 5,389,631; WO 94/08577; EP 0 632 016; EP 0 503 548; EP 0 512 831 and WO 92/19595; WO 93/22303; EP 0 525 629; EP 0 604 800; EP 0 587 134; EP 0 623 615; EP 0 655 439; U.S. Pat. No. 5,446,056 and WO 95/14682; U.S. Pat. No. 5,399,585; WO 93/12074; EP 0 512 829; EP 0 372 486 and U.S. Pat. No. 5,039,805; EP 0 632 020 and U.S. Pat. No. 5,494,922; U.S. Pat. No. 5,403,836; WO 94/22834; WO 94/21599; EP 0 478 328; WO 94/17034 WO 96/20192, WO 96/19223, WO 96/19221, WO 96/19222, EP 727425, EP 478362, EP 478363, U.S. Pat. Nos. 5,272,158, 5,227,490, 5,294,616, 5,334,596, EP 645376, EP 711770, U.S. Pat. No. 5,314,902, WO 94/00424, U.S. Pat. No. 5,523,302, EP 718287, DE 4446301, WO 96/22288, WO 96/29309, EP 719775, EP 635492, WO 96/16947, U.S. Pat. No. 5,602,155, WO 96/38426, EP 712844, U.S. Pat. No. 5,292,756, WO 96/37482, WO 96/38416, WO 96/41803, WO 97/11940

Each of these references is specifically incorporated herein in its entirety.

In order to identify the minimum active amino acid sequence necessary to bind VLA-4, Komoriya et al. synthesized a variety of overlapping peptides based on the amino acid sequence of the CS-1 region (the VLA-4 binding domain) of a particular species of fibronectin. ("The Minimal Essential Sequence for a Major Cell Type-Specific Adhesion Site (CS1) Within the Alternatively Spliced Type III Connecting Segment Domain of Fibronectin Is Leucine-Aspartic Acid-Valine", *J. Biol. Chem.,* 266 (23), pp. 15075–79 (1991)). They identified an 8-amino acid peptide, Glu-Ile-Leu-Asp-Val-Pro-Ser-Thr, as well as two smaller overlapping pentapeptides, Glu-Ile-Leu-Asp-Val and Leu-Asp-Val-Pro-Ser, that possessed inhibitory activity against FN-dependent cell adhesion. These results suggested that the tripeptide Leu-Asp-Val was the minimum sequence for cell-adhesion activity. It was later shown that Leu-Asp-Val binds only to lymphocytes that express an activated form of VLA-4, thus casting doubt on the utility of such a peptide in vivo (E. A. Wayner et al., "Activation-Dependent Recognition by Hematopoietic Cells of the LDV Sequence in the V Region of Fibronectin", *J. Cell. Biol.,* 116(2), pp. 489–497 (1992)). However, certain larger peptides containing the LDV sequence were subsequently shown to be active in vivo (T. A. Ferguson et al., "Two Integrin Binding Peptides Abrogate T-cell-Mediated Immune Responses In Vivo", *Proc. Natl. Acad. Sci. USA,* 88, pp. 8072–76 (1991); and S. M. Wahl et al., "Synthetic Fibronectin Peptides Suppress Arthritis in Rats by Interrupting Leukocyte Adhesion and Recruitment", *J. Clin. Invest.,* 94, pp. 655–62 (1994)).

A cyclic pentapeptide, Arg-Cys-Asp-TPro-Cys(wherein TPro denotes 4-thioproline), which can inhibit both VLA-4 and VLA-5 adhesion to FN has also been described. (See, e.g., D. M. Nowlin et al. "A Novel Cyclic Pentapeptide Inhibits α4β1 and α5β1 Integrin-mediated Cell Adhesion", *J. Biol. Chem.,* 268(27), pp. 20352–59 (1993); and PCT publication PCT/US91/04862). This pentapeptide was based on the tripeptide sequence Arg-Gly-Asp from FN which had been known as a common motif in the recognition site for several extracellular-matrix proteins.

Examples of other VLA-4 inhibitors have been reported, for example, in copending U.S. patent application Ser. No. 08/376,372, specifically incorporated by reference herein. U.S. Ser. No. 376,372 describes linear peptidyl compounds containing b-amino acids which have cell adhesion inhibitory activity. International patent applications WO 94/15958 and WO 92/00995, specifically incorporated by reference, describe cyclic peptide and peptidomimetic compounds with cell adhesion inhibitory activity. International patent applications WO 93/08823 and WO 92/08464 (specifically incorporated by reference herein) describe guanidinyl-, urea- and thiourea-containing cell adhesion inhibitory compounds. U.S. Pat. No. 5,260,277 describes guanidinyl cell adhesion modulation compounds, and is also specifically incorporated herein.

Despite these advances, there remains a need for small, potent inhibitors of cell adhesion, particularly for potent inhibitors of VLA-4 or IIb/IIIa cell adhesion. Ideally, such inhibitors would be small so that they may be administered orally. Such compounds would provide useful agents for treatment, alteration, prevention or suppression of various pathologies mediated by cell adhesion and VLA-4 or IIb/IIIa binding.

SUMMARY OF THE INVENTION

The present invention solves this problem by providing novel compounds that inhibit cell adhesion, and, specifically, the binding of ligands to VLA-4. These compounds are useful for inhibition, prevention and suppression of VLA-4-mediated cell adhesion, and pathologies associated with that adhesion, such as inflammation and immune reactions. The compounds of this invention may be used alone or in combination with other therapeutic or prophylactic agents to inhibit, alter, prevent or suppress cell adhesion.

The present invention thus provides novel compounds, formulations and methods which may be used in the study, diagnosis, treatment or prevention of diseases and conditions which relate to cell adhesion, including, but not limited to arthritis, asthma, allergies, adult respiratory distress syndrome, cardiovascular disease, thrombosis or harmful platelet aggregation, allograft rejection, neoplastic disease, psoriasis, multiple sclerosis, CNS inflammation, Crohn's disease, ulcerative colitis, glomerular nephritis and related inflammatory renal disease, diabetes, ocular inflammation (such as uveitis), atherosclerosis, inflammatory and autoimmune diseases. This invention also provides pharmaceutical formulations containing these VLA-4-mediated cell adhesion inhibitors and methods of using the compounds and compositions of the invention for inhibition of cell adhesion.

According to one embodiment of this invention, these novel compounds, compositions and methods are advantageously used to treat inflammatory and immune diseases. The present invention also provides methods for preparing the compounds of this invention and intermediates useful in those methods.

Accordingly, the present invention relates to cell adhesion inhibitors comprising a compound having Formula(I)

$$A\text{-}B \qquad (I)$$

where A comprises a specificity determinant which does not impart significant IIb/IIIa activity, and B comprises an integrin scaffold. More specifically, the present invention relates to a compound of Formula (I) having VLA-4 inhibitory activity and an integrin scaffold derived from a compound having IIb/IIIa activity.

In other embodiments, the claimed invention relates to preferred VLA-4 inhibitors wherein B is chosen from the integrin scaffolds of the compounds set forth in Table 2, or more preferably, from the scaffolds identified in the compounds in Table 1. Further, most preferred compounds are those in table 3, and preferred scaffolds, as well as preferred specificity determinants, are those derived from the compounds exemplified in Tables 1, 2 and 3.

Additionally, the present invention relates to methods of making cell adhesion inhibitors, generally, by removing the IIb/IIIa specificity determinant from a IIb/IIIa inhibitor, and replacing said specificity determinant with a VLA-4 specificity determinant, thereby creating a novel, heretofore undescribed, VLA-4 inhibitor.

More specifically, the methods of making the cell adhesion inhibitors of the invention comprise the steps of providing a first compound having IIb/IIIa inhibitory activity. The first compound comprises a IIB/IIIa specificity determinant, comprising a basic nitrogen functionality, which, for example, may be a phenylamidine moiety, and an integrin scaffold. One removes the phenylamidine moiety, or, if none is present, as for example, when the nitrogen functionality is a piperidine or a benzylamine, creating a "phantom" phenylamidine moiety by creating phantom bonds in the para orientation, and removing unneeded bonds, as discussed in more detail below, and removing the "phantom" moiety. The phenylamidine moiety is then replaced with a VLA-4 specificity determinant, thereby creating a second compound, having VLA-4 specificity determinant and an integrin scaffold, and having VLA-4 activity. In certain embodiments, it may be preferable to insert an additional group at the point of, or adjacent to, the connection between the integrin scaffold and the specificity determinant, to confer desirable characteristics on the compound. Such desirable characteristics are easily determined by those skilled in the art, and may, for example, encompass such characteristics as flexibility, or structural modifications designed to alter the activities of the compound. Any suitable additional groups may be used, and are known by those skilled in the art. Preferred groups may include, but are not limited to carbonyl, carboxamide, ether, nitrogen, oxygen, sulfide, sulfur amide, and methylene.

In yet other embodiments, the method described above can be used to make a pharmaceutical composition for the treatment of a condition associated with cell adhesion. The methods described above for making VLA-4 inhibitors are followed, and then suitable pharmaceutically acceptable carriers, excipients, additives, stabilizers etc. may be added. The claimed invention also encompasses "cocktail" compositions, i.e. those containing the compounds of the invention in addition to other active reagents. Such compositions are discussed in more detail below.

Certain embodiments encompass methods of treating cell adhesion associated conditions in mammals by administering a therapeutically effective amount of a composition. The claimed methods of treatment are most appropriate for humans, although other mammals are also suitable subjects. Advantageously, because of the relatively small size of the compounds of the invention, the compositions are particularly suitable for oral administration in the form of a solid, liquid or suspension.

Additional features and advantages of the invention will be set forth in the description which follows, and in part will be apparent from the description, or may be learned by practice of the invention. The objectives and other advantages of the invention will be realized and attained by the methods and compositions particularly pointed out in the written description and claims hereof.

DETAILED DESCRIPTION OF THE INVENTION

A. Definitions

The following abbreviations are used in the description:

| Designation | Reagent or Fragment |
| --- | --- |
| Ac | acetyl |
| Bn | benzyl |
| Boc | tert-butoxycarbonyl |
| Bu | butyl |
| Cbz | carbobenzyloxy |
| Cy | cyclohexyl |
| CyM | cyclohexylmethyl |
| DIPEA | diisopropylethylamine |
| EDC | 1-(3-diethylaminopropyl)-3-ethylcarbodiimide |
| HOBT | 1-hydroxybenzotriazole hydrate |
| I-amyl | isoamyl |
| I-Pn | isopentyl |
| I-Pr | isopropyl |
| Me | methyl |
| 2-MPUBA | 4-(N═-(2-methylphenyl)urea)-phenylmethylamino |
| 2-MPUPA | 4-(N═-(2-methylphenyl)urea)-phenylacetyl |
| NMP | N-methylpyrrolidinone |
| NMM | N-methylmorpholine |
| Ph | phenyl |
| PUPA | 4-(N═-phenylurea)phenylacetyl |
| Su | succinimidyl |
| TBTU | 2-(1H-benzotriazol-1-yl)-1,1,3,3-tetramethyluronium tetrafluoroborate |
| TEA | triethylamine |
| TFA | trifluoroacetic acid |
| THAM | tris (hydroxy) methylaminomethane |

Definitions

As used herein, the term "alkyl", alone or in combination, refers to a straight-chain or branched-chain alkyl radical containing from 1 to 10, preferably from 1 to 6 and more preferably from 1 to 4, carbon atoms. Examples of such radicals include, but are not limited to, methyl, ethyl, n-propyl, isopropyl, n-butyl, isobutyl, sec-butyl, tert-butyl, pentyl, iso-amyl, hexyl, decyl and the like.

The term "alkenyl", alone or in combination, refers to a straight-chain or branched-chain alkenyl radical containing from 2 to 10, preferably from 2 to 6 and more preferably from 2 to 4, carbon atoms. Examples of such radicals include, but are not limited to, ethenyl, E- and Z-propenyl, isopropenyl, E- and Z-butenyl, E- and Z-isobutenyl, E- and Z-pentenyl, decenyl and the like.

The term "alkynyl", alone or in combination, refers to a straight-chain or branched-chain alkynyl radical containing from 2 to 10, preferably from 2 to 6 and more preferably from 2 to 4, carbon atoms. Examples of such radicals include, but are not limited to, ethynyl (acetylenyl), propynyl, propargyl, butynyl, hexynyl, decynyl and the like.

The term "cycloalkyl", alone or in combination, refers to a cyclic alkyl radical containing from 3–12, preferably from 3–8 and more preferably from 3–6, carbon atoms and may be optionally aryl-fused. Examples of such radicals include, but are not limited to, cyclopropyl, cyclobutyl, cyclopentyl, cyclohexyl and the like.

The term "cycloalkenyl", alone or in combination, refers to a cyclic carbocycle containing from 4 to 8, preferably 5 or 6, carbon atoms and one or more double bonds. Examples of such cycloalkenyl radicals include, but are not limited to, cyclopentenyl, cyclohexenyl, cyclopentadienyl and the like.

The term "aryl" refers to a carbocyclic aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, pyrazolo[1,5-c]triazinyl and the like.

"Aryl", "Acycloalkyl" and "Acycloalkenyl" "Groups", as defined in this application may independently contain up to three substituents which are independently selected from the group consisting of halogen, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2- dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N-Ar' guanidino, N-N-(Ar',alkyl) guanidino, N,N-(Ar',Ar')guanidino, N,N-dialkyl guanidino, N,N,N-trialkyl guanidino, N-alkyl urea, N,N-dialkyl urea, N-Ar' urea, N,N-(Ar',alkyl) urea, N,N-(Ar')$_2$ urea, aralkyloxycarbonyl-substituted alkyl, aralkylaminocarbonyl, thioaryloxy and the like; wherein "Ar'" is analogous to aryl, but contains up to three substituents selected from the group consisting of halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "aralkyl", alone or in combination, refers to an aryl substituted alkyl radical, wherein the term "alkyl" and "aryl" are as defined above. Examples of suitable aralkyl radicals include, but are not limited to, phenylmethyl, phenethyl, phenylhexyl, diphenylmethyl, pyridylmethyl, tetrazolylmethyl, furylmethyl, imidazolyl-methyl, indolylmethyl, thienylpropyl and the like.

The term "alkoxy", alone or in combination, refers to an alkyl ether radical, wherein the term "alkyl" is as defined above. Examples of suitable alkyl ether radicals include, but are not limited to, methoxy, ethoxy, n-propoxy, iso-propoxy, n-butoxy, iso-butoxy, sec-butoxy, tert-butoxy and the like.

The term "alkenoxy", alone or in combination, refers to a radical of formula alkenyl-O—, wherein the term "alkenyl" is as defined above provided that the radical is not an enol ether. Examples of suitable alkenoxy radicals include, but are not limited to, allyloxy, E- and Z-3-methyl-2-propenoxy and the like. The term "alkynyloxy", alone or in combination, refers to a radical of formula alkynyl-O—, wherein the term "alkynyl", is as defined above, provided that the radical is not an -ynol ether. Examples of suitable alkynoxy radicals include, but are not limited to, propargyloxy, 2-butynyloxy and the like.

The term "thioalkoxy" refers to a thioether radical of formula alkyl-S—, wherein alkyl is as defined above.

The term "alkylamino", alone or in combination with other substituents, refers to a mono- or di-alkyl-substituted amino radical (i.e., a radical of formula alkyl-NH— or (alkyl)$_2$-N—), wherein the term "alkyl", is as defined above. Examples of suitable alkylamino radicals include, but are not limited to, methylamino, ethylamino, propylamino, isopropylamino, t-butylamino, N,N-diethylamino and the like.

The term "alkenylamino", alone or in combination, refers to a radical of formula alkenyl-NH— or (alkenyl)$_2$N—, wherein the term "alkenyl" is as defined above, provided that the radical is not an enamine. An example of such alkenylamino radicals is the allylamino radical.

The term "alkynylamino", alone or in combination, refers to a radical of formula alkynyl-NH— or (alkynyl)$_2$N—, wherein the term "alkynyl", is as defined above, provided that the radical is not an amine. An example of such alkynylamino radicals is the propargyl amino radical.

The term "aryloxy", alone or in combination, refers to a radical of formula aryl-O—, wherein aryl is as defined above. Examples of aryloxy radicals include, but are not limited to, phenoxy, naphthoxy, pyridyloxy and the like.

The term "arylamino", alone or in combination, refers to a radical of formula aryl-NH—, wherein aryl is as defined above. Examples of arylamino radicals include, but are not limited to, phenylamino (anilido), naphthylamino, 2-, 3- and 4-pyridylamino and the like.

The term "biaryl", alone or in combination, refers to a radical of formula aryl-aryl-, wherein the term "aryl" is as defined above.

The term "thioaryl", alone or in combination, refers to a radical of formula aryl-S—, wherein the term "aryl" is as defined above. An example of a thioaryl radical is the thiophenyl radical.

The term "aryl-fused cycloalkyl", alone or in combination, refers to a cycloalkyl radical which shares two adjacent atoms with an aryl radical, wherein the terms "cycloalkyl" and "aryl" are as defined above. An example of an aryl-fused cycloalkyl radical is the benzo-fused cyclobutyl radical.

The term "aliphatic acyl", alone or in combination, refers to radicals of formula alkyl-CO—, alkenyl-CO— and alkynyl-CO-derived from an alkane-, alkene- or alkyncarboxylic acid, wherein the terms "alkyl", "alkenyl" and "alkynyl" are as defined above. Examples of such aliphatic acyl radicals include, but are not limited to, acetyl, propionyl, butyryl, valeryl, 4-methylvaleryl, acryloyl, crotyl, propiolyl, methylpropiolyl and the like.

The terms "aromatic acyl" or "aroyl", alone or in combination, refers to a radical of formula aryl-CO—, wherein the term "aryl" is as defined above. Examples of suitable aromatic acyl radicals include, but are not limited to, benzoyl, 4-halobenzoyl, 4-carboxybenzoyl, naphthoyl, pyridylcarbonyl and the like.

The term "heterocycloyl", alone or in combination, refers to radicals of formula heterocycle-CO—, wherein the term "heterocycle" is as defined below. Examples of suitable heterocycloyl radicals include but are not limited to, tetrahydrofuranylcarbonyl, piperidinylcarbonyl, tetrahydrothiophenecarbonyl and the like.

The terms "morpholinocarbonyl" and "thiomorpholinocarbonyl", alone or in combination with other terms, refer to an N-carbonylated morpholino and an N-carbonylated thiomorpholino radical, respectively.

The term "alkylcarbonylamino", alone or in combination, refers to a radical of formula alkyl-CONH, wherein the term "alkyl" is as defined above.

The term "alkoxycarbonylamino", alone or in combination, refers to a radical of formula alkyl-OCONH—, wherein the term "alkyl" is as defined above.

The term "alkylsulfonylamino", alone or in combination, refers to a radical of formula alkyl-SO$_2$NH—, wherein the term "alkyl" is as defined above.

The term "arylsulfonylamino", alone or in combination, refers to a radical of formula aryl-SO$_2$NH—, wherein the term "aryl" is as defined above.

The term "N-alkylurea", alone or in combination, refers to a radical of formula alkyl-NH—CO—NH—, wherein the term "alkyl" is as defined above.

The term "N-arylurea", alone or in combination, refers to a radical of formula aryl-NH—CO—NH—, wherein the term "aryl" is as defined above.

The term "halogen" means fluorine, chlorine, bromine and iodine.

The terms "heterocycle" and "heterocyclic ring", alone or in combination, refer to a non-aromatic 3- to 10-membered ring containing at least one endocyclic N, O or S atom. The heterocycle may optionally be aryl-fused. The heterocycle may also be optionally substituted with one to three substituents which are independently selected from the group consisting of hydrogen, halogen, hydroxyl, amino, nitro, trifluoromethyl, trifluoromethoxy, alkyl, aralkyl, alkenyl, alkynyl, aryl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl, Ar'-substituted acyl, Ar'-substituted alkylcarbonyloxy, Ar'-substituted carbonylamino, Ar'-substituted amino, Ar'-substituted oxy, Ar'-substituted carbonyl, alkylcarbonylamino, Ar'-substituted alkylcarbonylamino, alkoxy-carbonylamino, Ar'-substituted alkoxycarbonyl-amino, Ar'-oxycarbonylamino, alkylsulfonylamino, mono- or bis-(Ar'-sulfonyl)amino, Ar'-substituted alkyl-sulfonylamino, morpholinocarbonylamino, thiomorpholinocarbonylamino, N-alkyl guanidino, N-Ar' guanidino, N-N-(Ar',alkyl) guanidino, N,N-(Ar',Ar')guanidino, N,N-dialkyl guanidino, N,N,N-trialkyl guanidino, N-alkyl urea, N,N-dialkyl urea, N-Ar' urea, N,N-(Ar',alkyl) urea, N,N-(Ar')$_2$ urea, aralkoxycarbonyl-substituted alkyl, carboxyalkyl, oxo, arylsulfonyl and aralkylaminocarbonyl.

The term "leaving group" generally refers to groups readily displaceable by a nucleophile, such as an amine, alcohol or a thiol nucleophile. Such leaving groups are well known in the art and include carboxylates, N-hydroxysuccinimide, N-hydroxybenzotriazole, halogen (halides), triflates, tosylates, mesylates, alkoxy, thioalkoxy and the like.

The term "hydrophobic group" refers to a group which is resistant to uniting with or absorbing water. Examples of such hydrophobic groups include, but are not limited to, methyl, ethyl, propy, butyl, pentyl, hexyl, phenyl, benzyl, naphthyl, N-benzylimidazolyl, methylthioethyl and the like.

The term "acidic functional group" refers to a group which has an acidic hydrogen in it. Examples of such groups include, but are not limited to, carboxylic acid, tetrazole, imidazole, hydroxyl, mercapto, hydroxylaminocarbonyl, sulfonic acid, sulfinic acid, phosphoric acid and phosphonic acid.

The terms "activated derivative of a suitably protected "-amino acid" and "activated substituted-phenylacetic acid derivative" refer to derivatives of carboxylic acids wherein the —OH group is replaced by a superior leaving group. Examples of activated acid derivatives include, but are not limited to, the corresponding acyl halides (e.g. acid fluoride, acid chloride and acid bromide), corresponding activated esters (e.g. nitrophenyl ester, the ester of 1-hydroxybenzotriazole, HOBT, or the ester of hydroxysuccinimide, HOSu), and other conventional derivatives within the skill of the art.

The term "amino acid side chain(s)" refers to the side chain attached to the α-carbon of an amino acid. Examples of amino acid side chains include, but are not limited to, methyl, isopropyl, benzyl and carboxymethyl for alanine, valine, phenylalinine and aspartic acid, respectively.

The terms "protected or protecting group" refer to a suitable chemical group which may be attached to a functional group of a molecule, then removed at a later stage to reveal the intact functional group and molecule. Examples of suitable protecting groups for various functional groups are described in T. W. Greene and P. G. M. Wuts, *Protective Groups in Organic Synthesis,* 2d. Ed., John Wiley and Sons (1991); L. Fieser and M. Fieser, *Fieser and Fieser=s Reagents for Organic Synthesis,* John Wiley and Sons (1994); L. Paquette, ed. *Encyclopedia of Reagents for Organic Synthesis,* John Wiley and Sons (1995).

The compounds of this invention may contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are envisioned as part of the invention. Although amino acids and amino acid side chains may be depicted in a particular configuration, both natural and unnatural forms are envisioned as part of the invention.

In view of the above definitions, other chemical terms used throughout this application can be easily understood by those of skill in the art. Terms may be used alone or in any combination thereof. The preferred and more preferred chain lengths of the radicals apply to all such combinations.

B. Description

The compounds of this invention result from the discoveries that existing IIb/IIIa integrin inhibitory compounds may be converted into VLA-4 inhibitory compounds, and IIb/IIIa inhibitory compounds can be made by combining a unique VLA-4 integrin scaffold with a IIb/IIIa specificity determinant. Known IIb/IIIa inhibitors can be described structurally as comprising a "specificity determinant" and an "integrin scaffold". A "specificity determinant" is that portion of a compound which confers on said compound a desired selectivity towards a binding partner. The "integrin scaffold" is the remaining portion of said compound. Thus for example, a typical IIb/IIIa specificity determinant may contain a basic nitrogen functionality, and the integrin scaffold may denote the part with an acidic functionality.

Thus, for example, the novel compounds of the invention encompass compounds of the formula (I)

$$A\text{-}B \qquad\qquad\qquad (I)$$

wherein A is a specificity determinant and B is an integrin scaffold. More specifically, for purposes of the present invention, the compound of Formula (I) has VLA-4 inhibitory activity, and, A comprises a specificity determinant which does not impart significant IIb/IIIa activity to the compound, and B is derived from a IIb/IIIa inhibitor. As used herein, the terms "significant activity" means having an $IC_{50}$ value less than about 50 μM.

VLA-4 Inhibitors Comprising a VLA-4 Specificity Determinant and a IIb/IIIa Scaffold.

In a preferred embodiment, the compound of formula (I) is a VLA-4 inhibitor wherein A is a VLA-4 specificity determinant which does not impart significant IIB/IIIa activity, and B is an integrin scaffold derived from a molecule having IIb/IIIa activity. In a more preferred embodiment, B is an integrin scaffold derived from any one of the IIb/IIIa inhibitors described in Table 2. However, it is to be understood that based upon applicants invention, and using the claimed methods, virtually any compound which has IIb/IIIa activity can be converted into a VLA-4 inhibitor by removing the IIb/IIIa specificity determinant and replacing it with a VLA-4 specificity determinant. Methods of conversion are explained in more detail below.

Surprisingly, when an integrin scaffold from a IIb/IIIa inhibitor is attached to a VLA-4 specificity determinant, a compound with VLA-4 inhibitory activity is formed. Moreover, the resulting VLA-4 inhibitors, as a class, do not demonstrate any significant IIb/IIIa inhibitory activity relative to the IIb/IIIa inhibitors from which the scaffold is derived. Thus, this invention provides VLA-4 inhibitors comprising any integrin scaffold derived from a compound having IIb/IIIa inhibitory activity, and any VLA-4 specificity determinant.

The claimed invention also encompasses methods of making these compounds having cell adhesion inhibitory activity, more preferably, VLA-4 inhibitory activity. Additionally disclosed herein are methods of making pharmaceutical compositions comprising these compounds, as well as methods of treatment using them.

Applicants provide herein methods of identifying compounds having IIb/IIIa inhibitory activity, and methods of identifying compounds having VLA-4 inhibitory activity. Furthermore, applicants describe methods of identifying the "scaffold" on any compound having IIb/IIIa activity, and methods of identifying the specificity determinant on any compound having VLA-4 inhibitory activity. Additionally disclosed are methods of combining the "scaffold" with a VLA-4 specificity determined to create a novel VLA-4 inhibitor.

Methods of Converting Compounds having IIb/IIIa Inhibitory Activity to Novel Compounds Having VLA-4 Inhibitory Activity In general, the present invention provides methods of converting compounds which have IIb/IIIa inhibitory activity into novel compounds having VLA-4 inhibitory activity and do not retain significant IIb/IIIa activity. Generally, the methods involve identifying an integrin scaffold in a IIb/IIIa inhibitor, and identifying a VLA-4 specificity determinant. The specificity determinant is that portion of the compound which imparts the binding activity on the molecule. Once these structures are identified, one can combine the IIb/IIIa integrin scaffold with the specificity determinant from a compound having VLA-4 inhibitory activity, and obtain a new VLA-4 inhibitor.

In a basic embodiment, therefore, one skilled in the art first identifies a compound having IIb/IIIa inhibitory activity. Compounds having IIb/IIIa inhibitory activity are well known to those skilled in the art, and are readily available, see, e.g., Table 2 and the references incorporated herein in the Background of the Invention. For purposes of this invention, one skilled in the art may use any of these known compounds. Alternatively, one may determine in assays known to those skilled in the art whether a particular compound has IIB/IIIa activity. If the assay is positive, then the scaffold will be useful in the present invention. Assays for IIb/IIIa inhibitory activity are well known in the art. Thus, for example, IIb/IIIa activity can be demonstrated by assessing the ability of compounds to inhibit the binding of the IIb/IIIa receptor to, for example, a known IIb/IIIa ligand, like fibrinogen or fibronectin, or, alternatively, to a known antagonist. (W)93/00095, specifically incorporated herein by reference.) Additionally, the aforementioned binding to ligands can be assessed by one skilled in the art in a platelet aggregation assay.

Many of the existing IIB/IIIa inhibitors contain a specificity determinant which comprises a phenylamidine moiety, which, for purposes of the invention, can serve as a point of orientation for conversion of said IIb/IIIa inhibitor to a VLA-4 inhibitor. In inhibitors which do not have a phenylamidine moiety, the existing basic functionality is converted to a "phantom" phenylamidine moiety, as explained in further detail below. Thus, according to the teachings herein, one can convert virtually any compound having IIb/IIIa activity to a VLA-4 inhibitor by replacing the IIB/IIIa specificity determinant.

The following teaching will enable one skilled in the art to make a claimed VLA-4 inhibitor, using as a starting material any compound which has IIb/IIIa inhibitory activity. Thus, based on the teaching below, one can take the chemical structure of any IIb/IIIa compound, and predict the structure of a compound having VLA-4 inhibitory activity. Applicants have successfully applied this teaching to numerous compounds, and determined that the compounds identified in this manner do in fact have VLA-4 inhibitory activity.

Teaching I:

In certain embodiments, the artisan identifies the chemical structure of a compound having IIb/IIIa activity, such as, for example, the following:

As discussed above, in order to convert this IIb/IIIa structure into a structure which has VLA-4 inhibitory activity, one must replace the IIb/IIIa specificity determinant with a VLA-4 specificity determinant.

Known IIb/IIIa inhibitors frequently have specificity determinants comprising a phenylamidine moiety or other basic functionality. Thus, for example, in the IIb/IIIa inhibitor above (U.S. Pat. No. 5,239,113, claimed herein by reference), the specificity determinant comprises a phenylamidine moiety. To convert this compound to a VLA-4 inhibitory compound, the phenylamidine is "removed" and a VLA-4 specificity determinant is appended.

In the first step of this conversion, for example, the phenyl ring of the phenylamidine moiety in the above compound can be taken to be the inner phenyl ring of a diphenyl urea. In the second step, the amidine functionality is removed and the remainder of the urea is appended. In this example, the bond of connection between the specificity determinant and the integrin scaffold is the amide bond next to the inner phenyl ring of the urea. The steps of this teaching are not limited to amidine-bearing phenyl rings. They can be applied in a likewise manner to, for example, piperazine and piperidine rings bearing amidine functionality.

The compound created via this teaching is a new compound having VLA-4 inhibitory activity. It generally consists of the integrin scaffold of a IIb/IIIa inhibitor and a VLA-4 specificity determinant, i.e. a urea. This compound does not have significant IIb/IIIa inhibitory activity.

Teaching II:

Not all IIb/IIIa inhibitors have a phenylamidine moiety. Thus, to convert a IIb/IIIa compound without a phenylamidine moiety to a VLA-4 inhibitor, the basic functionality can be used as point of reference. For example, in the IIb/IIIa inhibitor below (WO 92/19595, claimed herein by reference), the artisan would use the basic functionality, i.e. the piperidine nitrogen, of the specificity determinant as a point of reference to create, theoretically, a "phantom" phenylamidine.

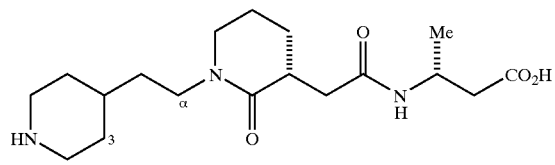

This is done by drawing "phantom" bonds between the 3-position of the piperidine and the carbon alpha to the lactam nitrogen. The "phantom" bonds are shown dashed in the structure below. The orientation of the groups on the "phantom" ring is preferably para.

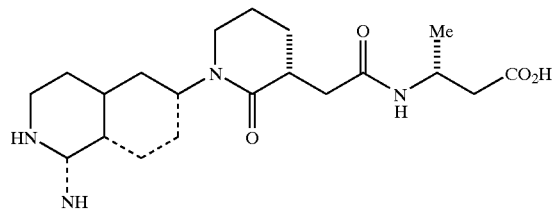

The second step in creating this "phantom" phenylamidine is to remove the unnecessary bonds and atoms to generate a structure having a "phantom" para-substituted phenylamidine, as shown below.

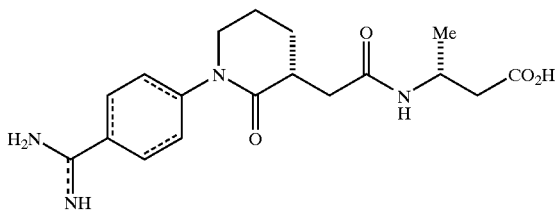

Third, since the "phantom" specificity determinant is comprised of a phenylamidine moiety, the structure of a compound having VLA-4 activity can be drawn following the steps of Teaching I. In this example, the bond of connection between the specificity determinant and the integrin scaffold is that connecting the inner phenyl ring of the urea to the lactam nitrogen.

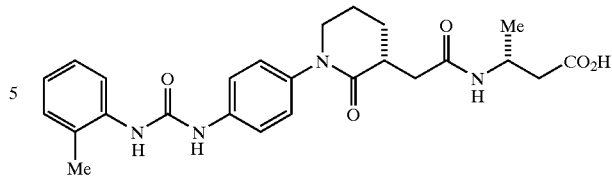

Teaching III:

In other embodiments the original IIb/IIIa compound may have a specificity determinant comprising a guanidine group. As in Teaching II, the basic functionality can be used as a point of reference for converting the IIb/IIIa inhibitor to a VLA-4 inhibitor.

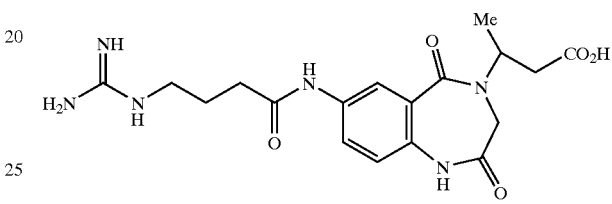

In the structure above (WO 93/08174, claimed herein by reference), the "phantom" phenylamidine is constructed from the internal guanidine nitrogen and the carbon alpha to the amide carbonyl. This construction is chosen such that the groups on the "phantom" ring are in the preferred para orientation. The "phantom" bonds are drawn dashed in the structure below.

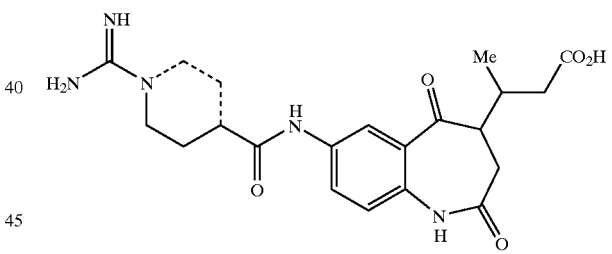

As detailed previously, the amidine functionality is removed and replaced with the remainder of the urea moiety. The bond of connection in this example is the amide bond. In some embodiments it may be desirable to add functionality at or adjacent to the bond of connection. Thus, in this example, an optional methylene is inserted between the urea inner phenyl ring and the amide carbonyl. Thus, the compound having the structure below possesses VLA-4 inhibitory activity without having significant IIb/IIIa activity.

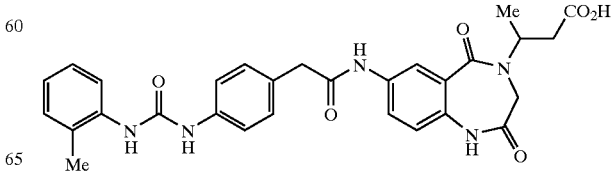

Teaching IV:

In a further embodiment, certain original IIb/IIIa compounds possess a 4,4'-bispiperidyl moiety as a specificity determinant as shown in the structure below (WO 94/14776, herein claimed by reference).

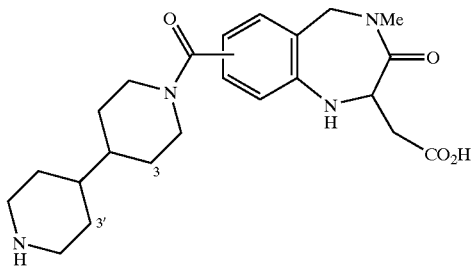

This example is similar to Teaching II; a "phantom" ring is formed between the 3 and 3' carbons of the bispiperidyl system as follows:

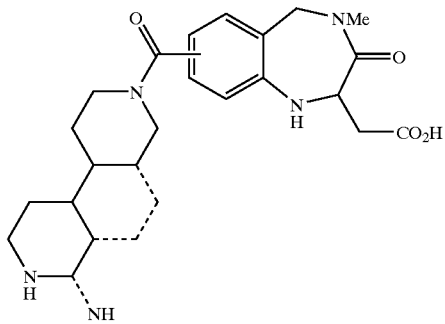

As in previous teachings, the unneeded atoms are removed such that the resultant "phantom" ring is para-substituted.

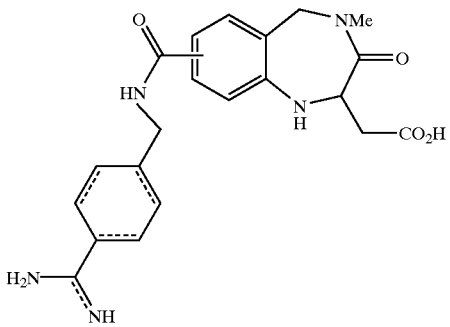

The amidine function is removed and the urea constructed as in Teaching I. In this example, the bond of connection is the amide bond. In some embodiments it may be desirable to modify the functionality at the bond of connection. Thus, in this case, the highlighted amide linkage could be reversed. The compound(s) resulting from this conversion possess(es) inhibitory activity toward VLA-4 without significant IIb/IIIa activity.

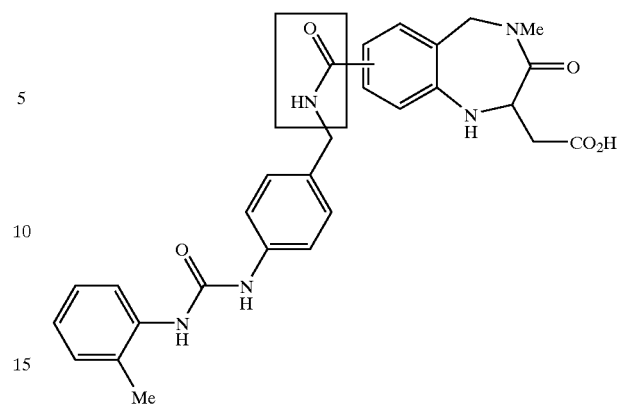

The steps of Teaching IV may be applied to structures having similar IIb/IIIa specificity determinants exemplified by, but not limited to, 4-piperazinylphenyl, 4-pyridyl-piperazinyl, 4-piperidinylpiperazinyl, 4-piperidinylphenyl, and 4-vinylpiperidinyl.

A similar process to that outlined in Teachings I-IV for identifying novel VLA-4 inhibitory compounds can be applied to IIb/IIIa inhibitors that contain functional groups in their specificity determinants such as, for example, amidinophenyl, bispiperidyl, piperidyl, benzylamino, pyridinyl, aminopyridyl, alkylamino, amidinopiperazinyl, guanidino and the like. Thus, these analyses are similar to those specifically illustrated above. Furthermore, application of the above Teachings not only identifies the specificity determinants and integrin scaffolds but, by default, the bond of connection between the two moieties as well. Hence, the specificity determinant portion of a IIb/IIIa inhibitor is clearly distinguishable from the integrin scaffold such that VLA-4 inhibitory compounds will result from the suitable interchange of specificity determinants. VLA-4 inhibitors arising from the analysis herein may be further improved by a lengthening, shortening, reversal or replacement of functionality at or immediately adjacent to the bond of connection between the VLA-4 specificity determinants and the integrin scaffolds. Such connecting functionality includes, but is not limited to $C_1$–$C_3$ alkyl, $C_1$–$C_3$ alkenyl, $C_1$–$C_3$ alkynyl, amide, ester, ether, and thioether. However, to one skilled in the art such changes would be deemed obvious and any alterations would be made on the basis of the compound characteristics desired. Furthermore, although Teachings I-IV all provide for the introduction of a o-methylphenylureidophenyl moiety to comprise the VLA-4 specificity determinant, it will be understood that any VLA-4 specificity determinant can be interchanged with any other as set forth in detail elsewhere in this application. Thus, the teaching above enables one skilled in the art to convert virtually any compound possessing IIb/IIIa inhibitory activity to a VLA-4 inhibitor.

Teaching V:

In another embodiment, any VLA-4 specificity determinant, once identified, can be interchanged with any other such that a new compound possessing VLA-4 inhibitory activity is obtained. For example, the compound below is a VLA-4 inhibitor obtained as described above.

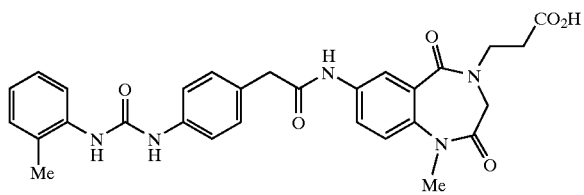

The bond of connection is the amide bond. Thus, the VLA-4 specificity determinant is the o-methylphenylureidophenylacetyl moiety. This can be replaced in its entirety with a different VLA-4 specificity determinant such as, for example, the indolylcarbonylaminophenylacetyl moiety as depicted below. This compound possesses VLA-4 inhibitory activity.

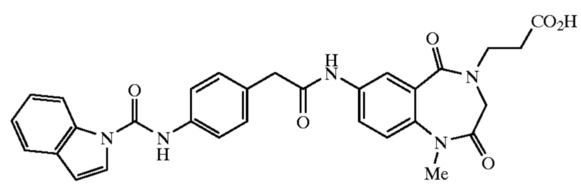

Teaching VI:

In yet another embodiment, the VLA-4 specificity determinant can be replaced and the bond of connection also modified as discussed in Teaching IV above. For example, the o-methylphenylureidophenylacetyl moiety of Teaching V can be replaced with the VLA-4 specificity determinant o-hydroxy-phenylethynylphenylacetyl as shown below. This alternative VLA-4 specificity determinant is disclosed elsewhere in this application. This new compound possesses VLA-4 inhibitory activity.

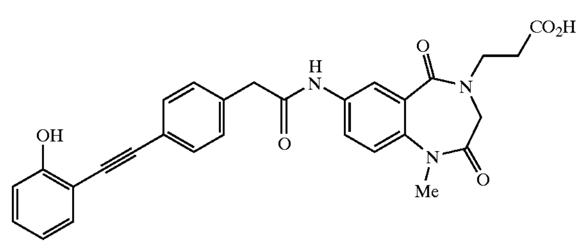

In the second step, the amide bond of connection can be replaced with, for example, an ether linkage as depicted.

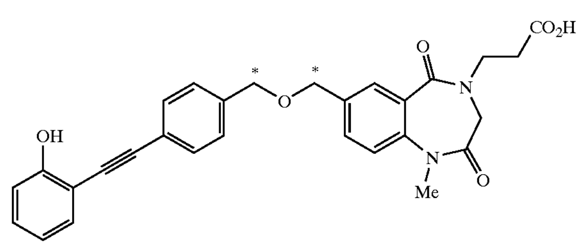

Since such an exchange of functionality can be made at or immediately adjacent to the bond of connection, the oxygen atom of the ether linkage could be located in place of either of the highlighted carbons instead. The compound(s) resulting from this conversion possess(es) VLA-4 inhibitory activity. Thus, Teachings V and VI enable one skilled in the art to both predictably exchange VLA-4 specificity determinants as well as modify functionality at the bond of connection while retaining selective VLA-4 inhibitory activity.

Compositions of the Invention

This invention provides a broad class of novel compounds which are capable of inhibiting VLA-4-mediated cell adhesion by inhibiting the binding of ligands to that receptor. These compounds are represented by formula (I):

A-B (I)

wherein A is a specificity determinant and B is an integrin scaffold. Specifically, A comprises a VLA-4 specificity determinant which does not impart significant IIb/IIIa activity, and B comprises an integrin scaffold, preferably the integrin scaffold from a IIb/IIIa inhibitor. More specifically, the present invention encompasses compounds of Formula (I) and pharmaceutically acceptable derivatives thereof, wherein:

A is a specificity determinant selected from the group consisting of alkyl; aliphatic acyl optionally substituted with N-alkyl- or N-arylamido; aroyl; heterocycloyl; alkyl- or arylsulfonyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl; alkylaminocarbonyl; arylamino carbonyl and aralkylaminocarbonyl optionally substituted with bis(alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl)(aralkyl)aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl)(heterocyclyl)aminocarbonyl; (alkyl)(heterocyclylalkyl)aminocarbonyl; (aralkyl)(heterocyclyl)aminocarbonyl; (aralkyl)(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cycloalkylsulfonyl; arylaroyl, biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl- or alkynyl-aminocarbonyl optionally substituted with aryl; alkenyl- or alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl and heterocyclylalkylsulfonyl; alkenyl, alkynyl, cycloalkyl, aryl-fused cycloalkyl, cycloalkenyl, aryl, aryl-substituted alkyl ("aralkyl"), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy ("aralkoxy"), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylurea-substituted alkyl, N-arylurea-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl and heterocyclylalkyl.

B preferably comprises a scaffold selected from the group consisting of formula IIa, IIb, or IIc,

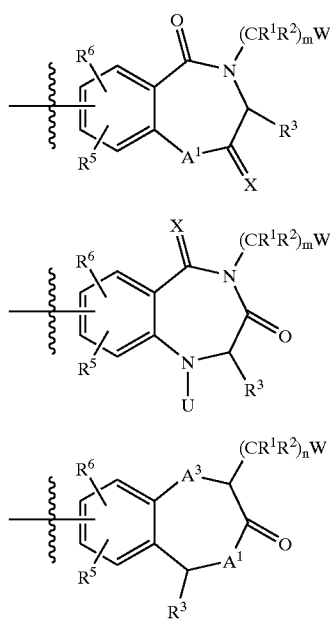

wherein
$A^1$ is selected from the group consisting of $NR^1$, O, S, $(CR^1R^2)_r$, and $N[(CR^1R^2)_m(C\!=\!Y)A^2R^1]$;
$A^2$ is selected from the group consisting of O, $NR^2$, S, and $(CR^1R^2)_r$;
$A^3$ is selected from the group consisting $NR^1$, O, S, and $(CR^1R^2)_r$;
X is selected from the group consisting of $H_2$, O, and S;
Y is $H_2$, or O;
r=0, 1;
n=0–5;
m=1–4;
W is selected from the group consisting of $CO_2H$, $SO_3H$, $PO_4H_2$, tetrazole, and H;
Z is CO, or $(CR^1R^2)_n$;
U is selected from the group consisting of $COR^{12}$, $(CR^1R^2)_nR^{12}$, and $SO_2R^{11}$; $R^1$ and $R^2$ are independently selected from the group consisting of H, alkyl, alkenyl, alkynyl, cycloalkyl, cycloalkenyl, aryl, aralkyl, heterocycle; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide;

$R^3$ is $R^1$, or amino acid side chains;
$R^5$ and $R^6$ are independently selected from the group consisting of H, $OR^1$, halogen, alkyl, $SR^1$, $NZR^{12}$, and $NR^1R^2$;
$R^{11}$ is selected from the group consisting of alkyl, alkenyl, alkynyl, cycloalkyl, cycloalkenyl, aryl, aralkyl, heterocycle; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide; and
$R^{12}$ is selected from the group consisting of H, alkyl, cycloalkenyl, aryl, aralkyl, heterocycle; alkyl optionally substituted with cycloalkyl, heterocycle, alkoxyl, hydroxyl, halogen, aralkoxy, thioalkoxy, carboxy, alkoxycarbonyl, carboxamide, and aralkoxy.

In an alternate preferred embodiment, B comprises a structure of formula IIIa, IIIb or IIIc

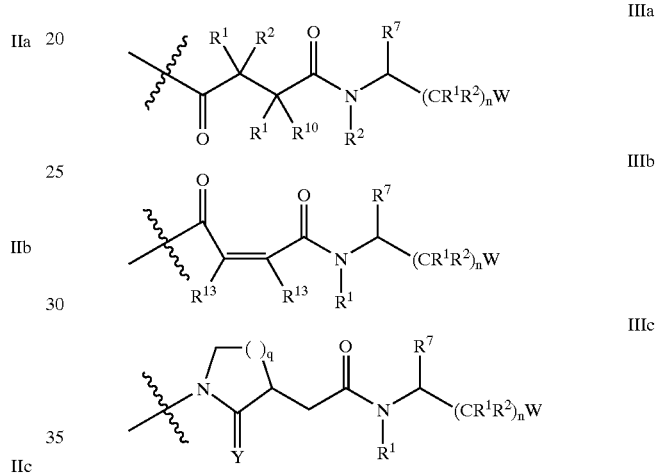

n=0–5;
m=1–4;
q=1 or 2;
r=0 or 1;
Y is $H_2$ or O;
W is selected from the group consisting of $CO_2H$, $SO_3H$, $PO_4H_2$, tetrazole, and H;
Z is CO or $(CR^1R^2)_n$;
$R^1$ and $R^2$ are independently selected from the group consisting of H; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide;
$R^7$ is selected from the group consisting of H; aryl; substituted aryl; aralkyl; alkyl; alkenyl; alkyl optionally substituted with heterocycle, thioalkoxy, carboxy, alkoxycarbonyl, alkoxy, or halogen;
$R^{10}$ is selected from the group consisting of $R^2$, $NHSO_2R^{11}$, $NH_2$, $OR^2$, and $NHZR^{12}$;
$R^{12}$ is selected from the group consisting of H; alkyl; cycloalkenyl; aryl; aralkyl; heterocycle; and alkyl optionally substituted with cycloalkyl, heterocycle, alkoxyl, hydroxyl, halogen, aralkoxy, thioalkoxy, carboxy, alkoxycarbonyl, carboxamide, or aralkoxy;
$R^{13}$ is H or $-\!CH_2(CH_2)_mCH_2\!-\!$;
$R^2$ and $R^7$ may be taken together to form $-\!(CH_2)_m\!-\!$;
$R^2$ and $R^{10}$ may be taken together to form $-\!(CH_2)_m\!-\!$;
$R^{11}$ is selected from the group consisting of alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide.

In yet another alternate preferred embodiment, B is a structure of formula IVa, IVb, or IVc

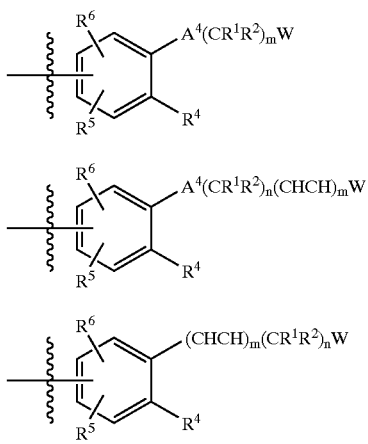

wherein
$A^4$ is selected from the group consisting of $(CR^1R^2)_n$, O, S, $NR^1$, $SO_2NR^1$, $CONR^1$, $CH_2NR^{11}$, $NR^1SO_2$, $CH_2O$, $CH_2NCOR^{11}$, and $CH_2CONR^1$;
n=0–5;
m=1–4;
W is selected from the group consisting of $CO_2H$, $SO_3H$, $PO_4H_2$, tetrazole, and H;
Z is CO, or $(CR^1R^2)_n$;
$R^1$ and $R^2$ are independently selected from the group consisting of H, alkyl, alkenyl, alkynyl, cycloalkyl, cycloalkenyl, aryl, aralkyl, heterocycle; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide;
$R^4$ is selected from the group consisting of H, $OR^1$, $SR^1$, $NR^1R^2$, alkyl, $NZR^1$, $NSO_2R^{11}$, and $CO_2R^1$;
$R^5$ and $R^6$ are independently selected from the group consisting of H, $OR^1$, halogen, alkyl, and $NR^1R^2$; and
$R^{11}$ is selected from the group consisting of alkyl, alkenyl, alkynyl, cycloalkyl, cycloalkenyl, aryl, aralkyl, heterocycle; alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, and carboxamide.

In an alternate preferred embodiment, B comprises a structure of formula Va, or Vb.

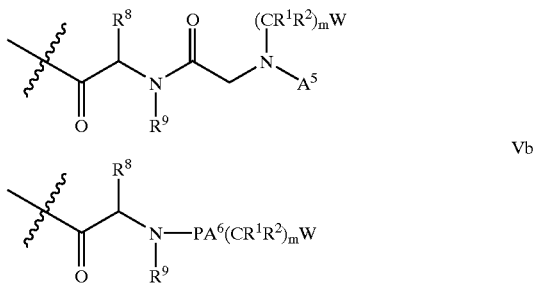

$A^6$ is selected from the group consisting of $NR^1$, O, S, $CR^1(NR^1R^2)$, and $(CR^1R^2)_r$;

$A^5$ is selected from the group consisting of $SO_2R^{11}$, $COR^7$, and $(CR^1R^2)_nR^7$;
n=0–5;
m=1–4;
r=0 or 1;
W is selected from the group consisting of $CO_2H$, $SO_3H$, $PO_4H_2$, tetrazole, and H;
P is CO or $SO_2$;
$R^1$ and $R^2$ are independently selected from the group consisting of H; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide
$R^7$ is selected from the group consisting of H; aryl; substituted aryl; aralkyl; alkyl; alkenyl; alkyl optionally substituted with heterocycle, thioalkoxy, carboxy, alkoxy carbonyl, alkoxy, or halogen;
When $R^8$ is H then $R^9$ is $R^7{}_1$ or $R^8$ and $R^9$ are taken together to form a 4–7 member ring optionally substituted with hydroxyl, $—OR^1$, $—N^1R^1R^2$, $—SR^1$, $SO_2R^{11}$, $—SOR^{11}$;
$R^{11}$ is selected from the group consisting of alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide The chemical groups defined as "A" in formula I are examples of the aforementioned "specificity determinant". The chemical groups defined as "B" in formula I are examples of the aforementioned "integrin scaffold". While specific examples of "integrin scaffolds" from known IIb/IIIa inhibitors are delineated, chemical structural derivatives of these IIb/IIIa inhibitors would be known to one of skill in the art to possess similar IIb/IIIa inhibitory activity. It is also envisioned that "integrin scaffolds" from such IIb/IIIa derivatives or from any compound that can be shown to have IIb/IIIa activity, could be incorporated into VLA-4 inhibitors of the present invention.

A "pharmaceutically acceptable derivative" denotes any pharmaceutically acceptable salt, ester, salt of such ester, amide, or salt of such amide, of a compound of this invention. The invention also includes any other compound which, upon administration to a patient, is capable of providing (directly or indirectly) a compound of this invention (e.g. a pro-drug). The invention also includes metabolites or residues of a compound of this invention characterized by the ability to inhibit, prevent or suppress cell adhesion and cell adhesion-mediated pathologies.

In another preferred embodiment, A is selected from the group consisting of alkyl, aliphatic acyl optionally substituted with N-alkyl- or N-arylamido, aroyl, heterocycloyl, alkyl- and arylsulfonyl, aralkylcarbonyl optionally substituted with aryl, heterocycloalkylcarbonyl, alkoxycarbonyl, aralkyloxycarbonyl, cycloalkylcarbonyl optionally fused with aryl, heterocycloalkoxycarbonyl, alkylaminocarbonyl, arylaminocarbonyl and aralkylaminocarbonyl optionally substituted with bis-(alkylsulfonyl)amino, alkoxycarbonylamino or alkenyl.

More preferably, A is selected from the group consisting of aliphatic acyl, aroyl, aralkylcarbonyl, heterocycloyl, alkoxycarbonyl, aralkyloxycarbonyl and heterocycloalkylcarbonyl. In other embodiments, A is preferably selected from the group consisting of (N-Ar'-urea)-para-substituted aralkylcarbonyl, (N-Ar'-urea)-para-substituted aralkyl and (N-Ar'-urea)-para-substituted aryl. Most preferably, A is selected from the group consisting of (N-Ar'-urea)-para-substituted phenylmethylcarbonyl, (N-Ar'-urea)-para-substituted phenylmethyl and (N-Ar'-urea)-para-substituted phenyl.

Examples of specific preferred compounds of this invention are provided in Table 2.

Examples of more preferred compounds include compound described in Table 1.

The most preferred compounds are those described in Table 3.

Furthermore, the preferred compounds have an $IC_{50}$ of about 1 pM to about 10 μM as measured by a VLA-4 binding assay. More preferred inhibitors have an $IC_{50}$ of less than about 100 nM, more preferably about 1 pM to about 100 nM, and most preferably, about 1 pM to about 10 nM.

Novel IIb/IIIa Inhibitors and Methods of Making them

In other embodiments, applicants have discovered that they can successfully convert novel VLA-4 inhibitors having an integrin scaffold for which no IIb/IIIa precedent exists into novel IIb/IIIa inhibitors. Applicants have thus further demonstrated the portability of IIb/IIIa and VLA-4 scaffolds by creating novel IIb/IIIa inhibitors, replacing the specificity determinant of a novel VLA-4 inhibitor with a IIb/IIIa specificity determinant. Specifically, VLA-4 inhibitors having novel scaffolds, such as the peptoid scaffolds, can be converted to novel IIb/IIIa inhibitors by replacing the VLA-4 specificity determinant with a IIb/IIIa specificity determinant. Thus, for example, one has a compound of Formula I, wherein A is a VLA-4 specificity determinant, and B is a VLA-4 scaffold, preferably comprising a peptoid. One then replaces the original A with a specificity determinant having IIb/IIIa activity, thereby creating a novel compound having IIb/IIIa inhibitory activity.

This concept is demonstrated by compound A, whose structure is shown below:

Compound A

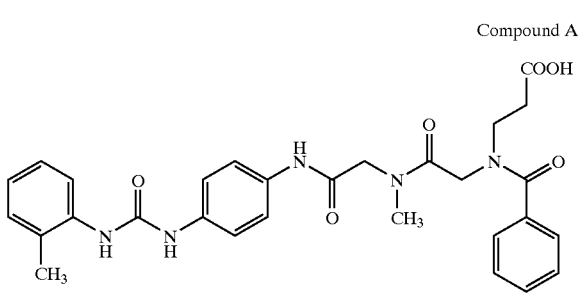

Compound A, a compound having VLA-4 inhibitory activity, comprises a specificity determinant which does not impart significant IIb/IIIa activity, and an integrin scaffold as illustrated. No examples of this integrin scaffold are reported in IIb/IIIa literature. Replacing the VLA-4 specificity determinant with a IIb/IIIa specificity determinant such as bis-piperidinyl, results in a compound such as Compound B, which is Compound B

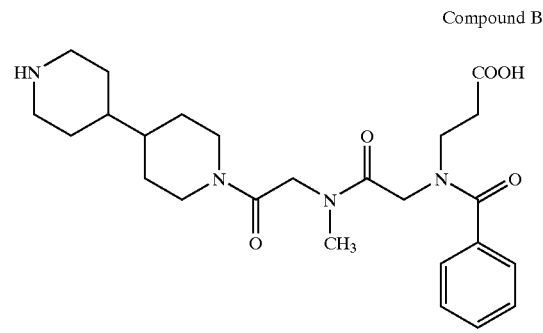

a potent IIb/IIIa inhibitor.

Thus, in one preferred embodiment, compounds represented by PB-1 and PB-2 are also claimed as novel IIb/IIIa inhibitors derived by combining a novel VLA4 scaffolds with known IIb/IIIa specificity determinants, where A is any Iib/IIIa specificity determinant such as those exemplified in table-2.

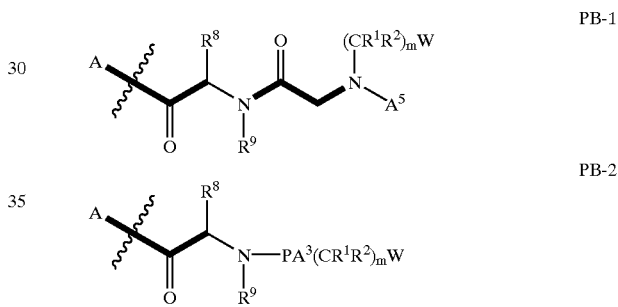

where A is any IIb/IIIa specificity determinant such as those exemplified in table-2.

$A^3$ is selected from the group consisting of $NR^1$, O, S, and $(CR^1R^2)_r$;

$A^5$ is selected from the group consisting of $SO_2R^{11}$, $COR^7$, and $(CR^1R^2)_nR^7$;

n=0–5;

m=1–4;

r=0, 1;

W is selected from the group consisting of $CO_2H$, $SO_3H$, $PO_4H_2$, tetrazole, and H;

P is selected from the group consisting of CO, $SO_2$;

$R^1$ and $R^2$ are independently selected from the group consisting of H; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, or alkoxycarbonyl, carboxamide;

$R^7$ is selected from the group consisting of H; aryl; substituted aryl; aralkyl; alkyl; alkenyl; and alkyl optionally substituted with heterocycle, thioalkoxy, carboxy, alkoxy carbonyl, alkoxy, or halogen;

$R^{15}$ and $R^{16}$ are independently H or methyl;

$R^{11}$ is selected from the group consisting of alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide.

This conversion demonstrates that new IIb/IIIa inhibitors may now be designed based on integrin scaffolds discovered from VLA-4 inhibitors. Thus, VLA-4 inhibitors of the invention are a new source of integrin scaffolds useful for creating novel IIb/IIIa inhibitors.

For ease of discussion, applicants have exemplified the pharmaceutical preparations and methods of treatment herein as they refer to the VLA-4 inhibitors of the invention. However, applicants claimed invention is intended to encompass the same preparations and methods of treatment disclosed herein comprising novel IIb/IIIa inhibitors instead of, or in addition to, the claimed VLA-4 inhibitors.

TABLE 1

Structure-Activity 9    216 Compounds

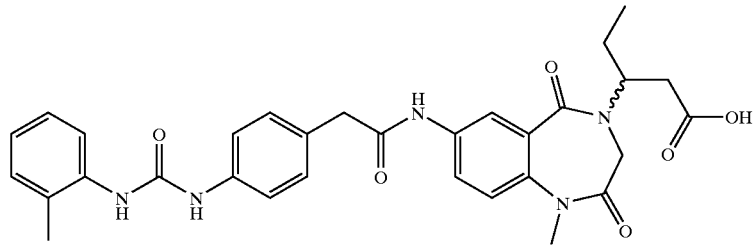

Name: BX60    Act: 0.103

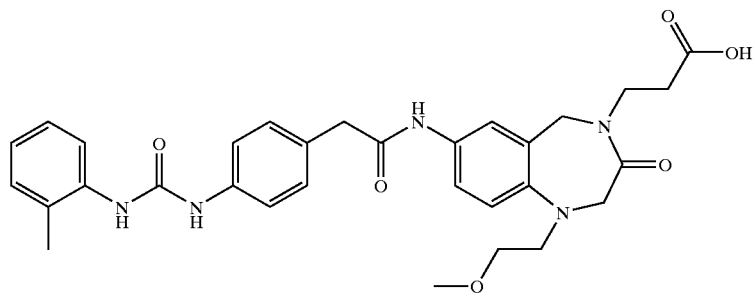

Name: BX61    Act: 0.099333

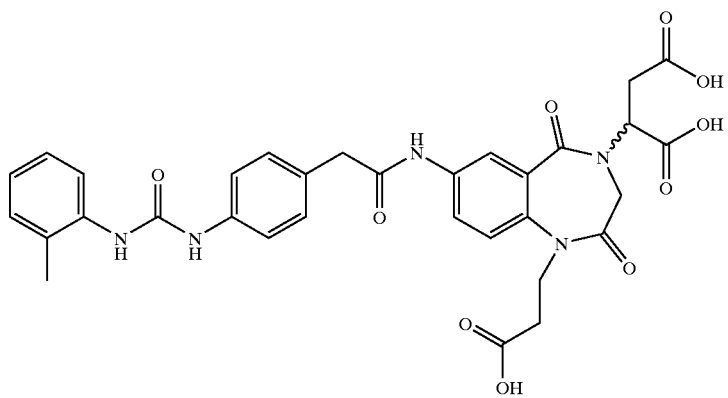

Name: BX62    Act: 0.095

TABLE 1-continued
| Structure-Activity 9 | 216 Compounds |
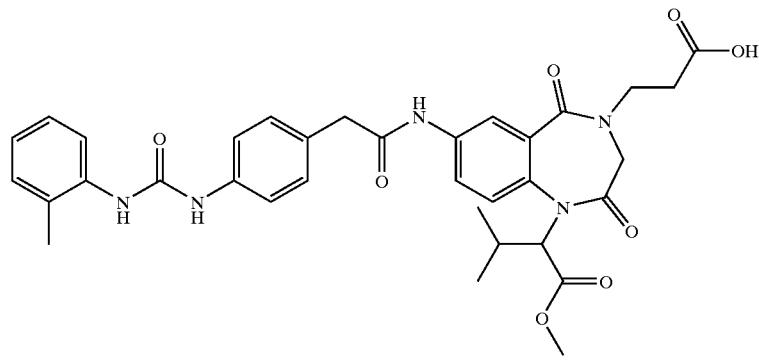
Name: BX63    Act: 0.075
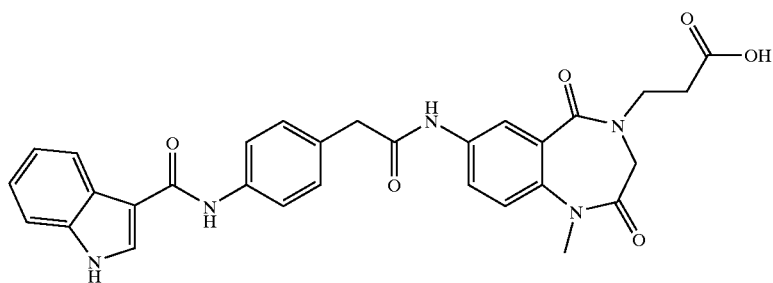
Name: BX64    Act: 0.074
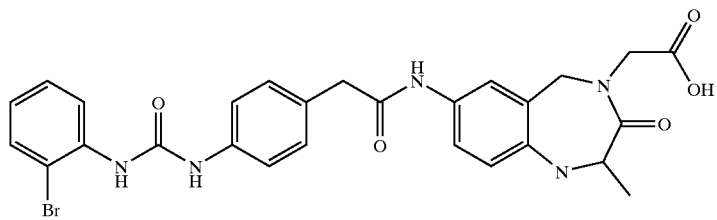
Name: BX65    Act: 0.065
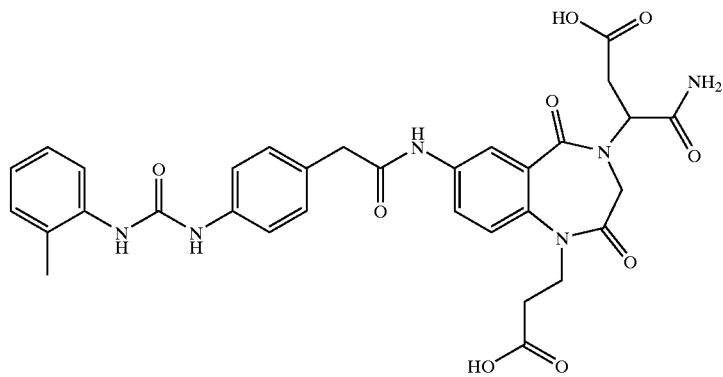
Name: BX66    Act: 0.064

TABLE 1-continued
| Structure-Activity 9 | 216 Compounds |
|---|---|
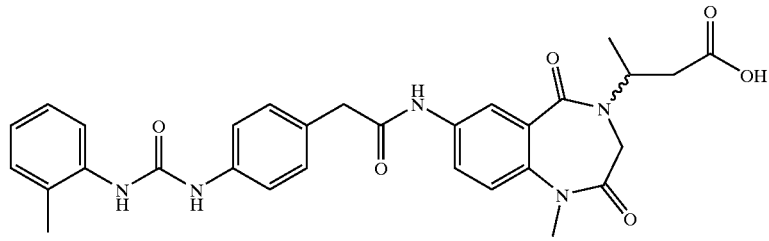
Name: BX67   Act: 0.0625
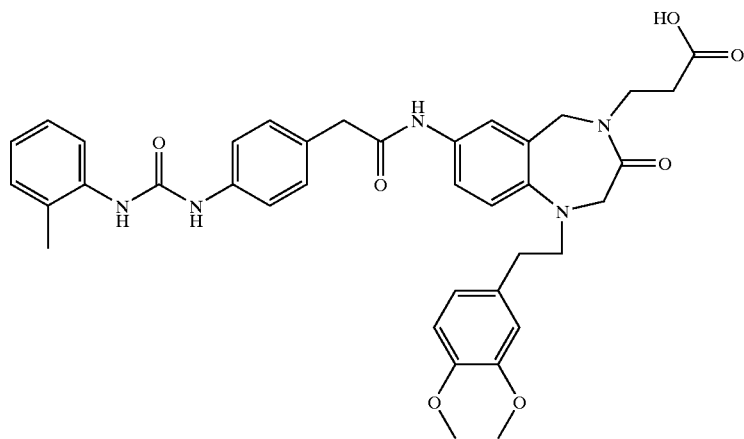
Name: BX68   Act: 0.033
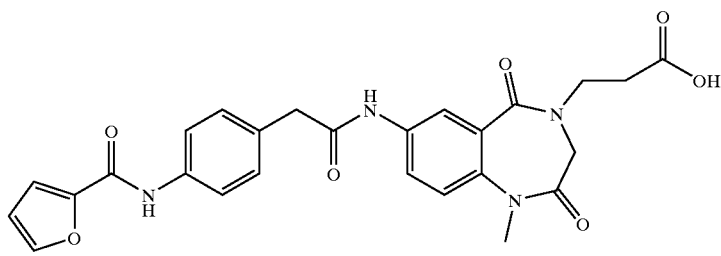
Name: BX12   Act: 6.10333
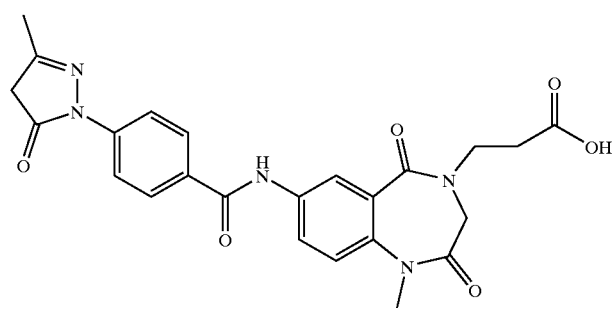
Name: BX13   Act: 5.865

TABLE 1-continued
| Structure-Activity 9 | 216 Compounds |
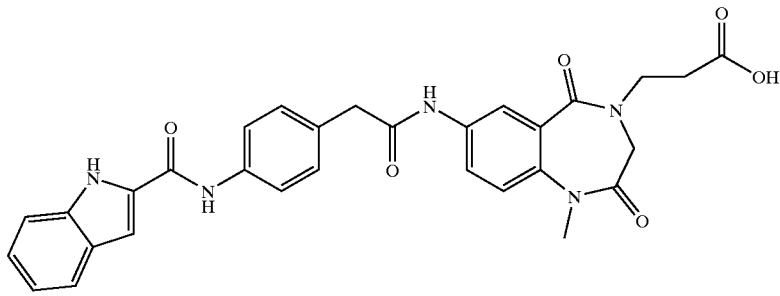
Name: BX14              Act: 5.355
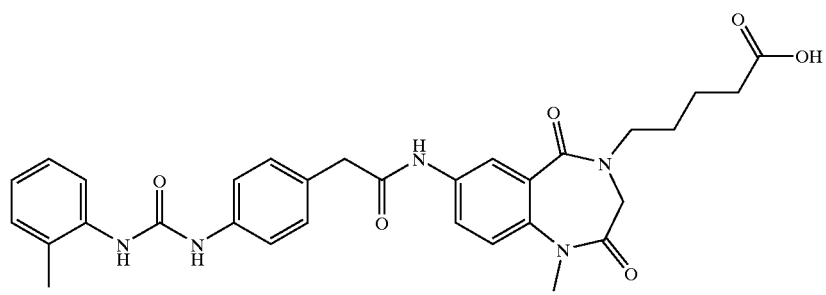
Name: BX15              Act: 5.3
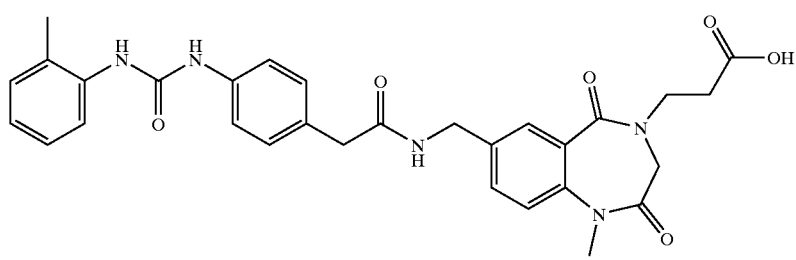
Name: BX16              Act: 5.125
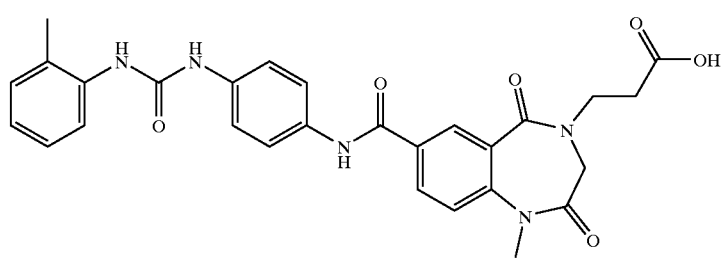
Name: BX17              Act: 4.97667
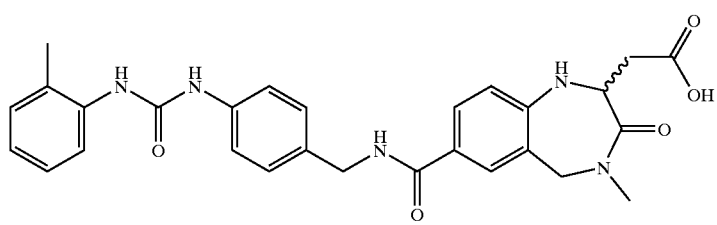
Name: BX18              Act: 4.43

TABLE 1-continued
| Structure-Activity 9 | 216 Compounds |
|---|---|
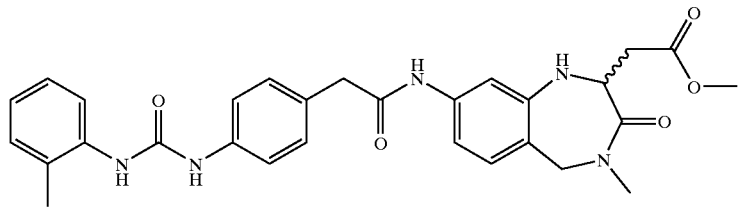
Name: BX19  Act: prodrug
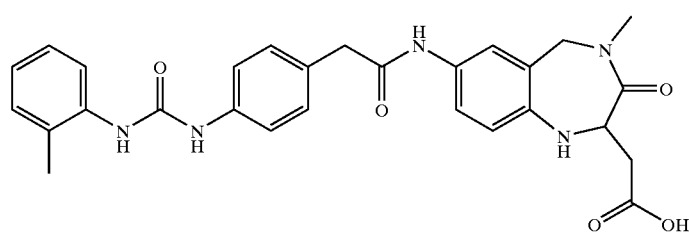
Name: BX22  Act: 3.315
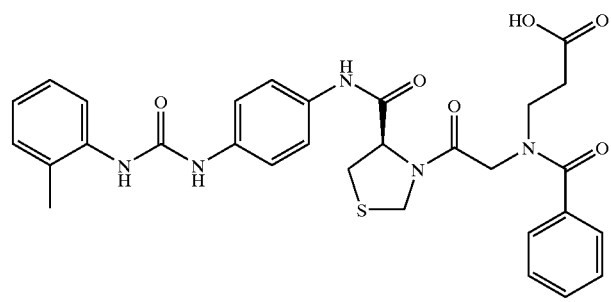
Name: AX39  Act: 0.06
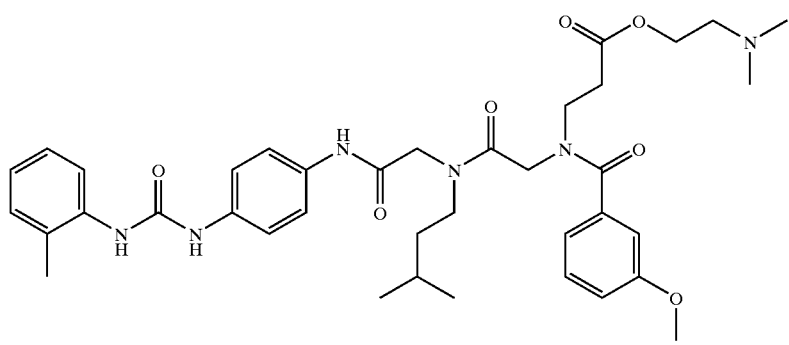
Name: AX40  Act: prodrug TABLE 1-continued
| Structure-Activity 9 | 216 Compounds |
|---|---|
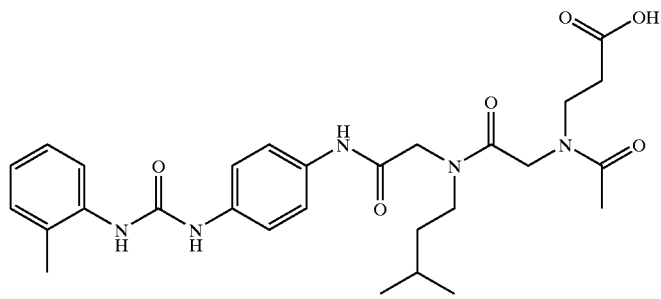
Name: AX41  Act: 0.055
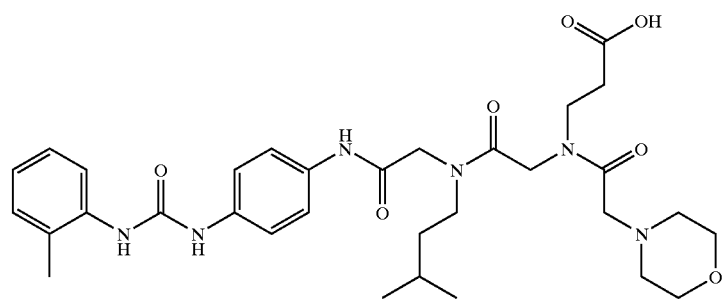
Name: AX42  Act: 0.052
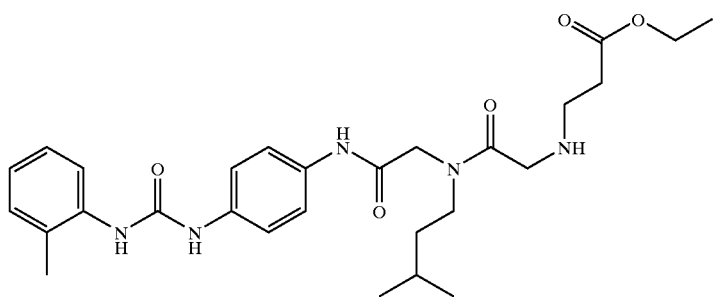
Name: ZX1  Act: prodrug
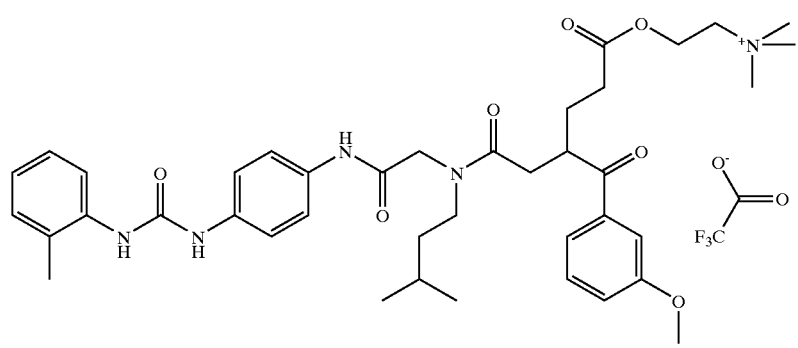
Name: ZX2  Act: prodrug TABLE 1-continued
| Structure-Activity 9 | 216 Compounds |
|---|---|
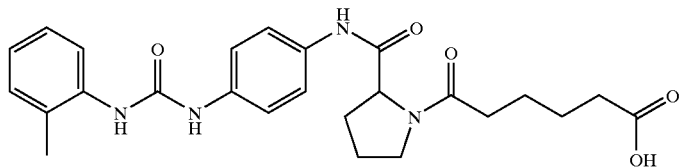
Name: CX1   Act: 13.468
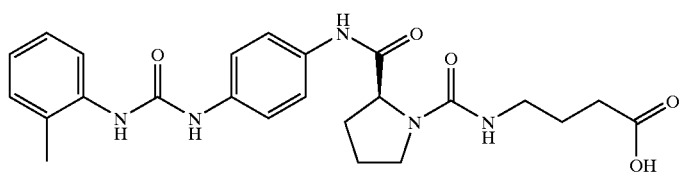
Name: CX2   Act: 8.94
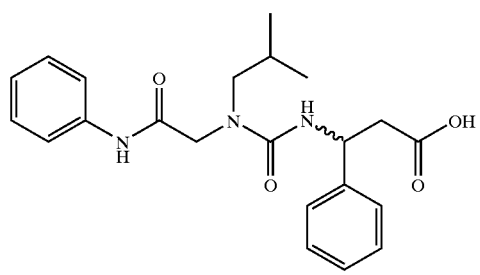
Name: CX3   Act: 3.4
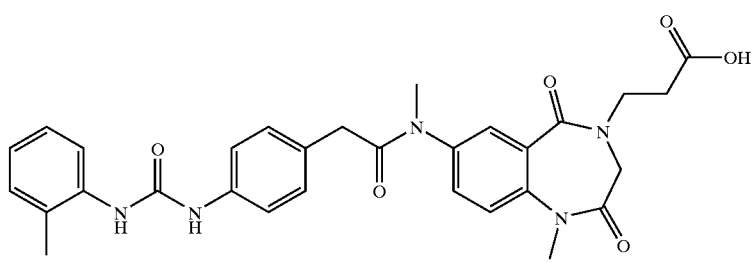
Name: BX23   Act: 3.24
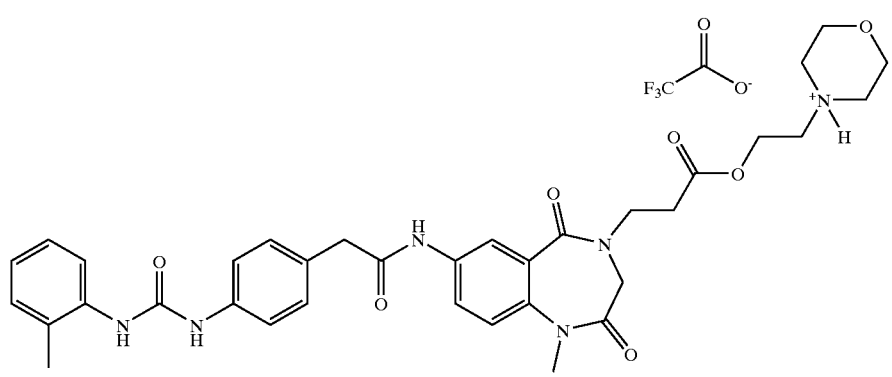
Name: BX24   Act: prodrug TABLE 1-continued
| Structure-Activity 9 | 216 Compounds |
|---|---|
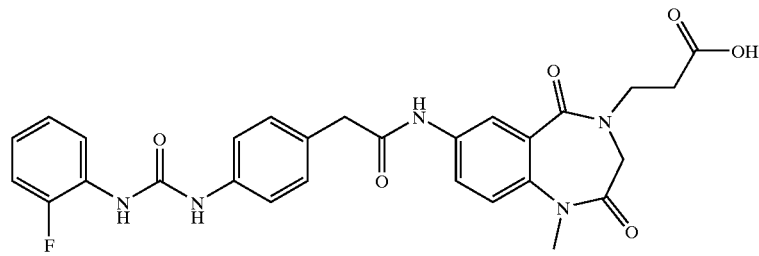
Name: BX25    Act: 2.43
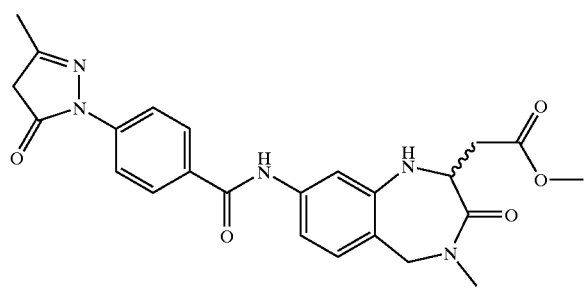
Name: BX27    Act: prodrug
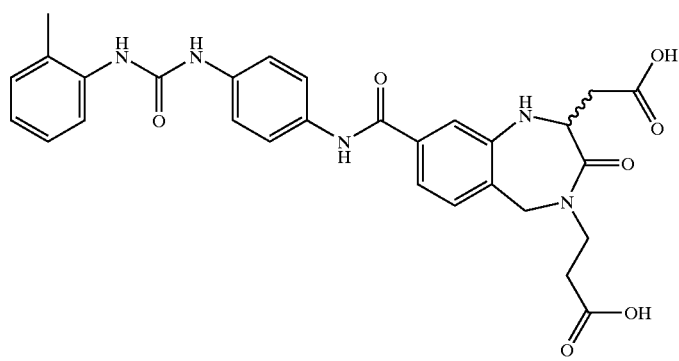
Name: BX28    Act: 1.87
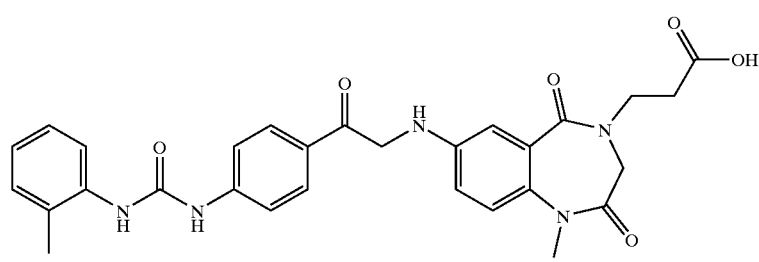
Name: BX29    Act: 1.825

TABLE 1-continued
| Structure-Activity 9 | 216 Compounds |
|---|---|
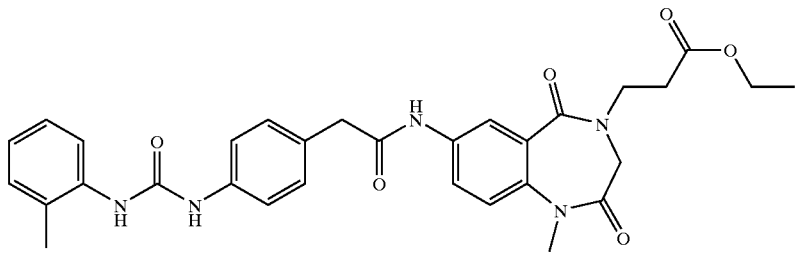
Name: BX30    Act: prodrug
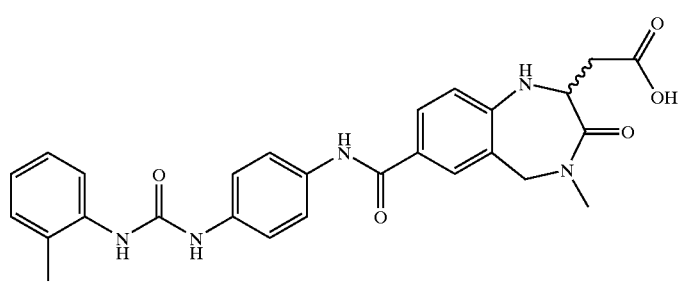
Name: BX31    Act: 1.285
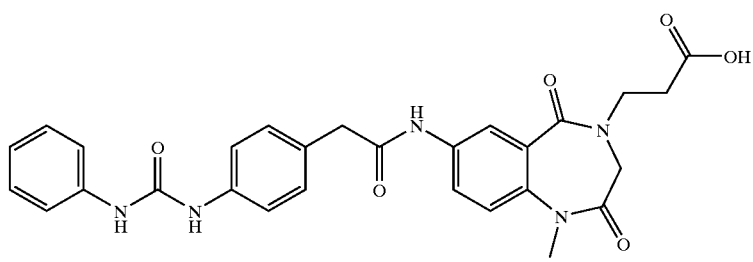
Name: BX32    Act: 0.959
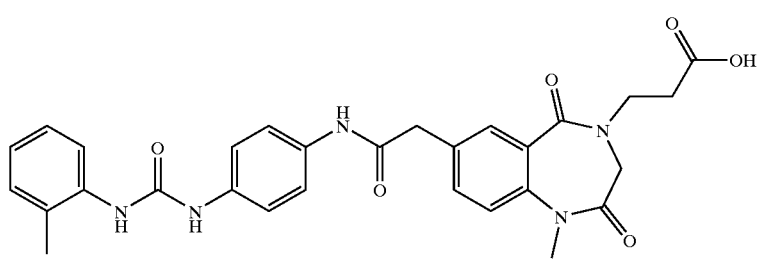
Name: BX33    Act: 0.8855
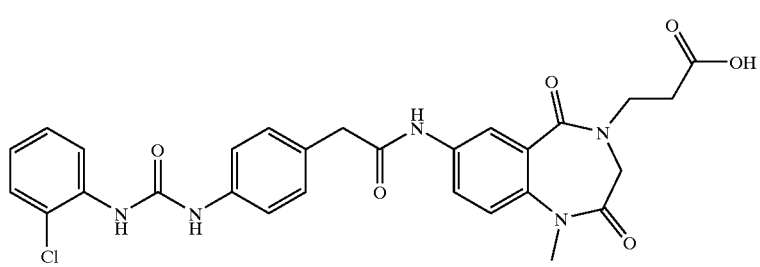
Name: BX34    Act: 0.7235

TABLE 1-continued
| Structure-Activity 9 | 216 Compounds |
|---|---|
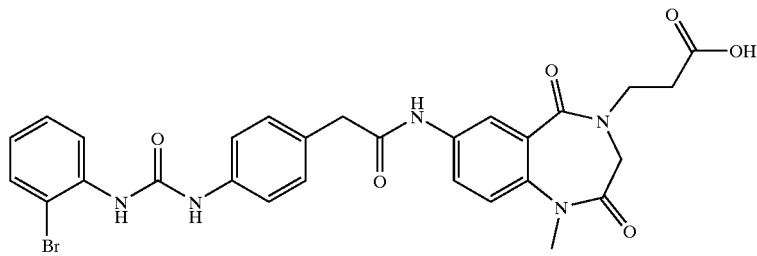
Name: BX35                Act: 0.6715
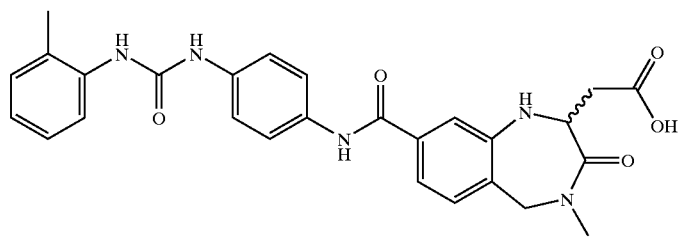
Name: BX36                Act: 0.646
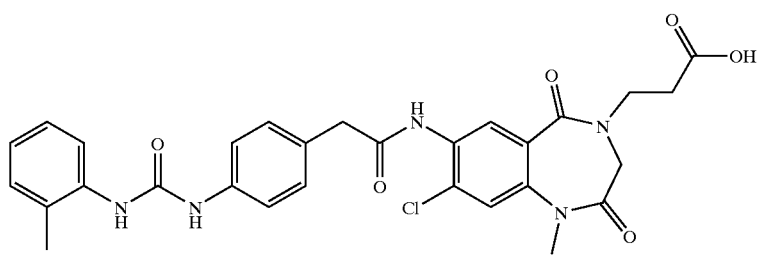
Name: BX37                Act: 0.6435
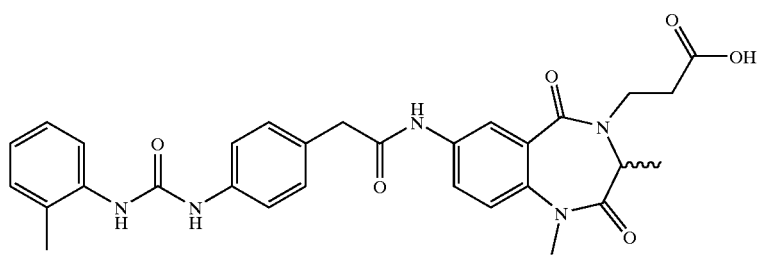
Name: BX38                Act: 0.55

TABLE 1-continued
| Structure-Activity 9 | 216 Compounds |
|---|---|
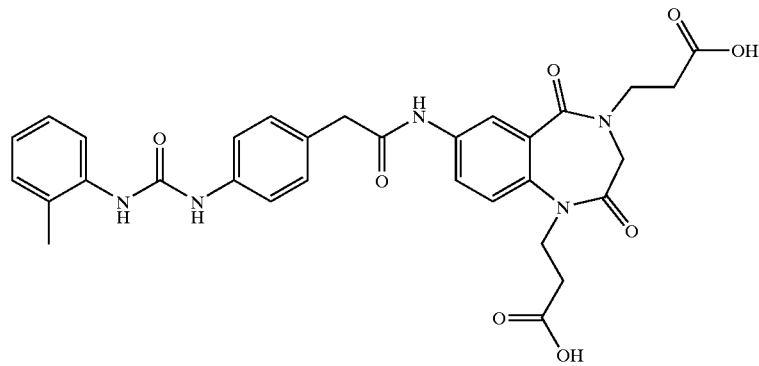
Name: BX39  Act: 0.48
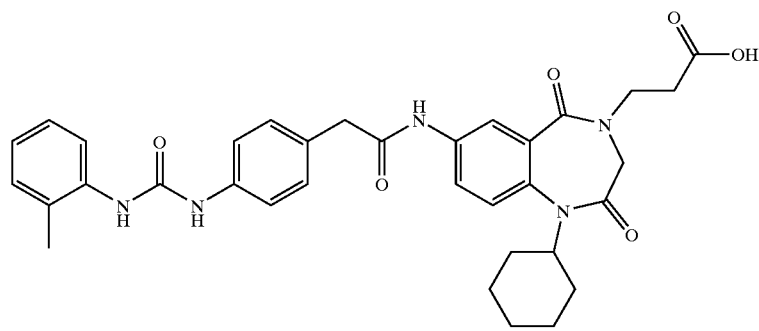
Name: BX40  Act: 0.438
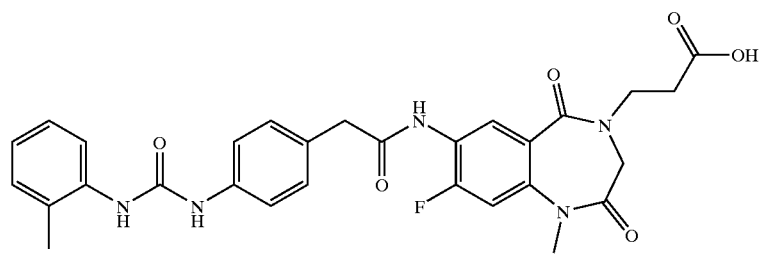
Name: BX41  Act: 0.381
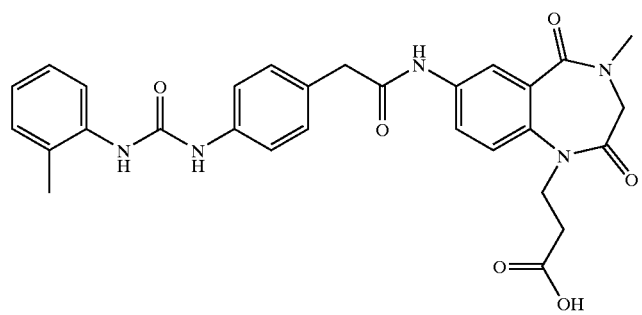
Name: BX42  Act: 0.3255

TABLE 1-continued
Structure-Activity 9      216 Compounds
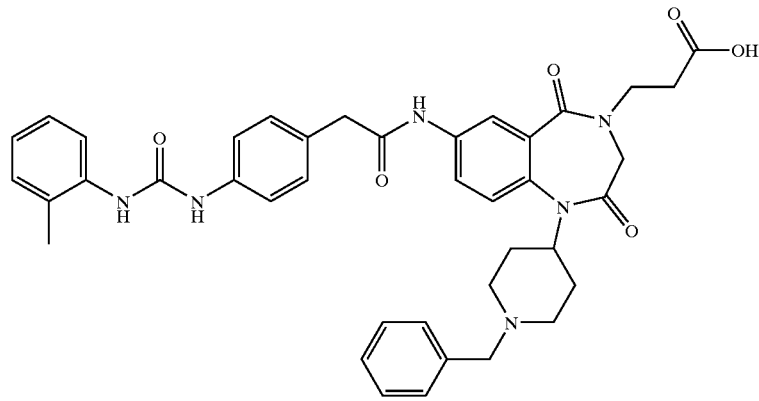
Name: BX43                Act: 0.271333
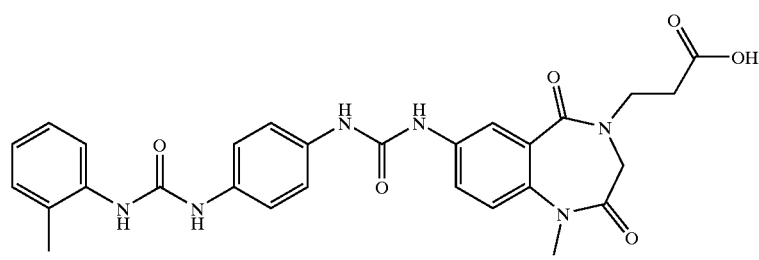
Name: BX44                Act: 0.256667
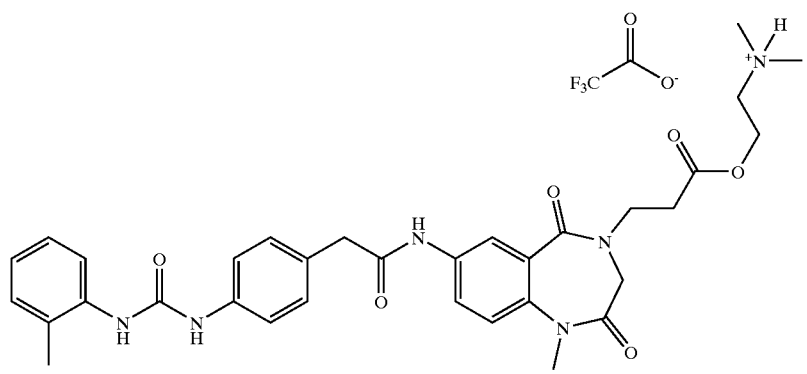
Name: BX45                Act: prodrug
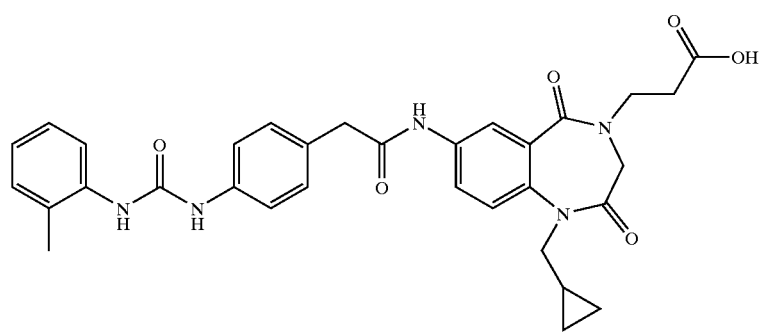
Name: BX46                Act: 0.194

TABLE 1-continued
| Structure-Activity 9 | 216 Compounds |
|---|---|
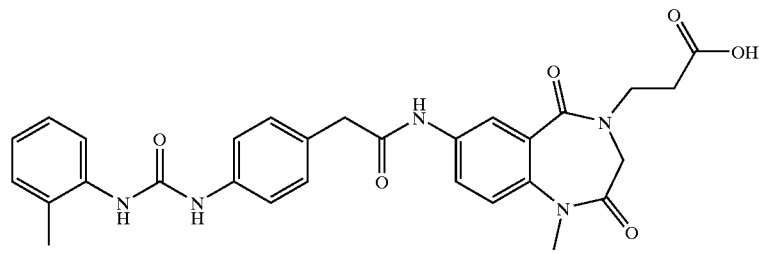
Name: BX47  Act: 0.1774
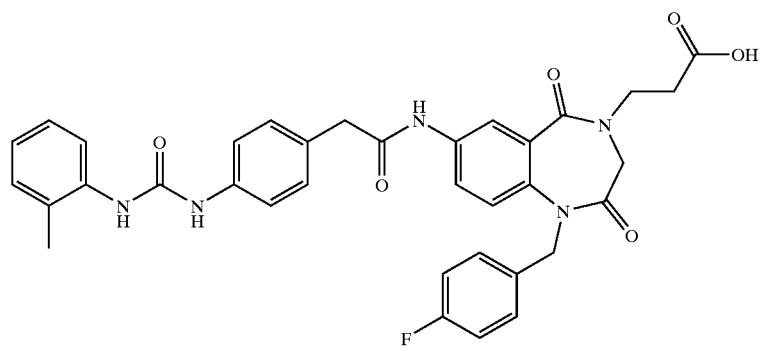
Name: BX48  Act: 0.166333
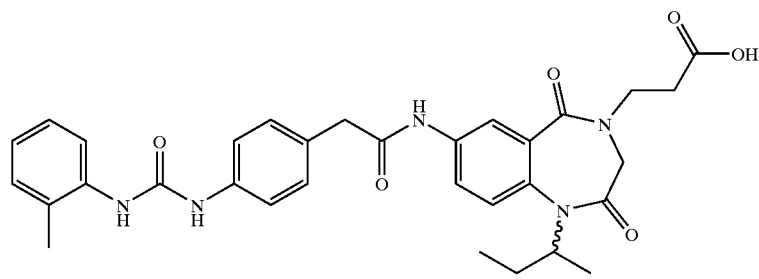
Name: BX49  Act: 0.163
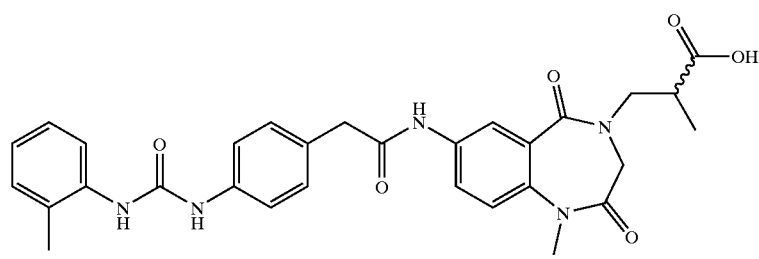
Name: BX50  Act: 0.152333

TABLE 1-continued
| Structure-Activity 9 | 216 Compounds |
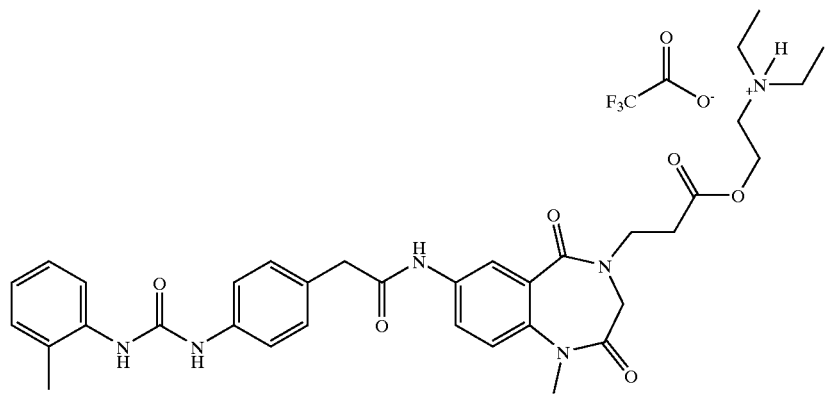
Name: BX51  Act: prodrug
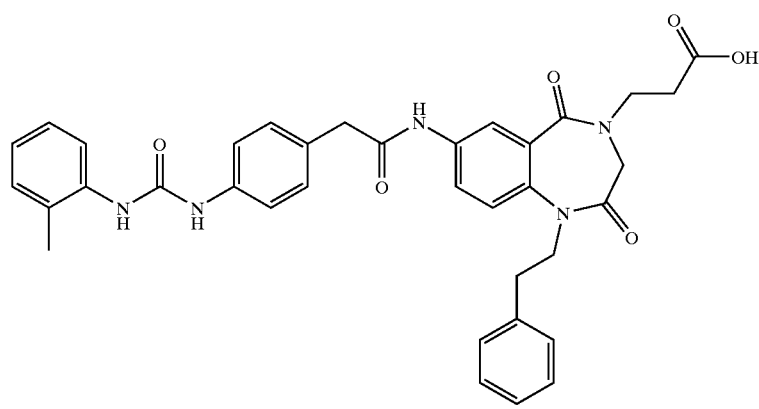
Name: BX52  Act: 0.1375
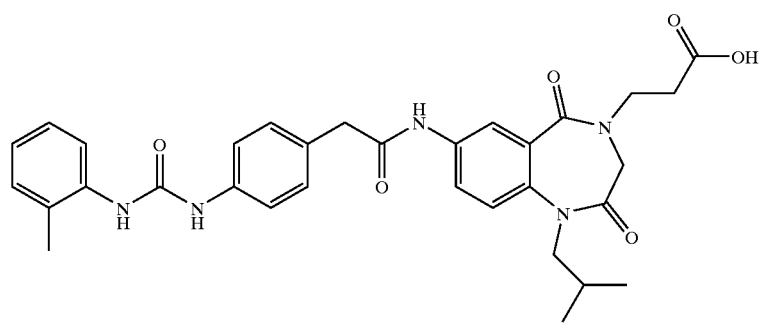
Name: BX53  Act: 0.129

TABLE 1-continued
| Structure-Activity 9 | 216 Compounds |
|---|---|
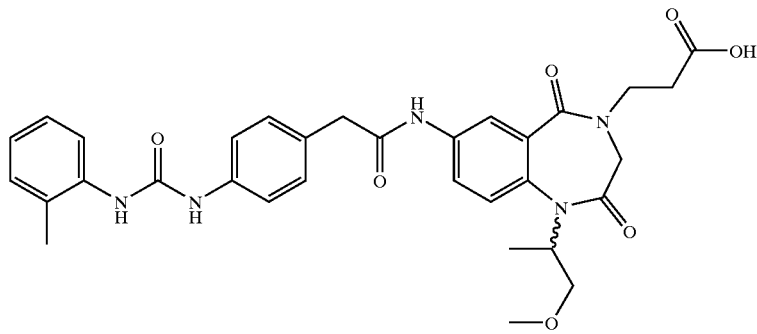
Name: BX54　　　　　Act: 0.1275
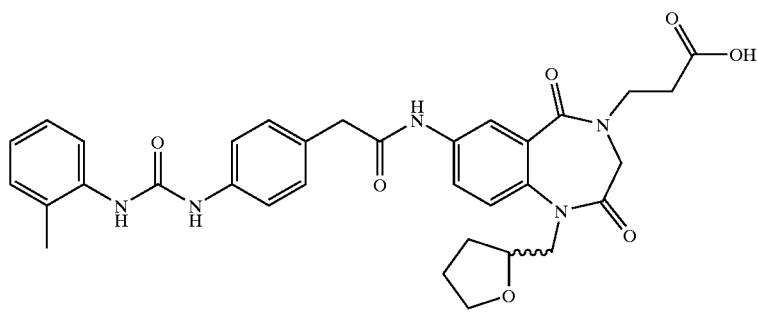
Name: BX55　　　　　Act: 0.1195
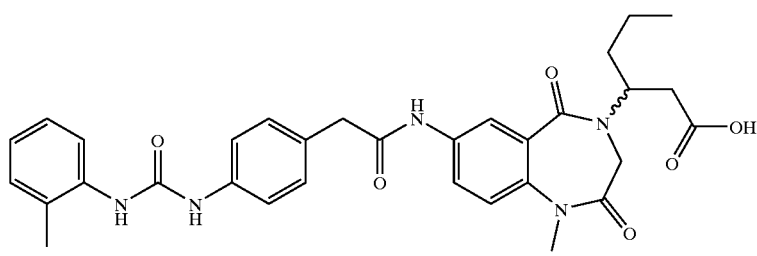
Name: BX56　　　　　Act: 0.119
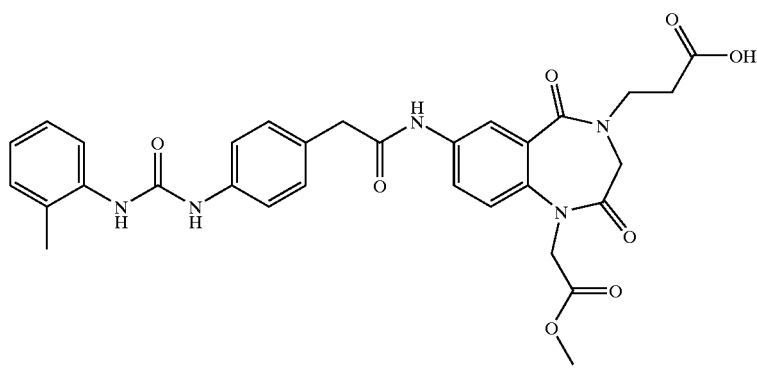
Name: BX57　　　　　Act: 0.1175

TABLE 1-continued
| Structure-Activity 9 | 216 Compounds |
|---|---|
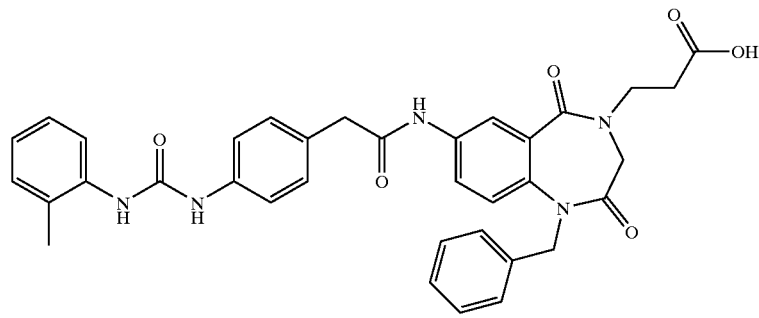
Name: BX58   Act: 0.1155
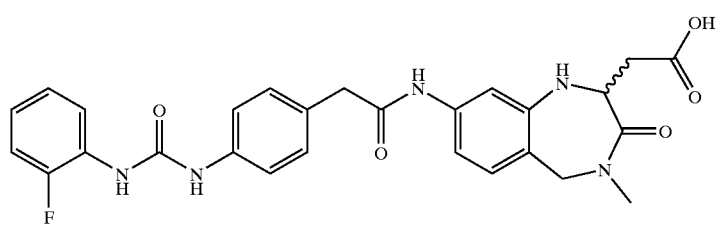
Name: BX59   Act: 0.107
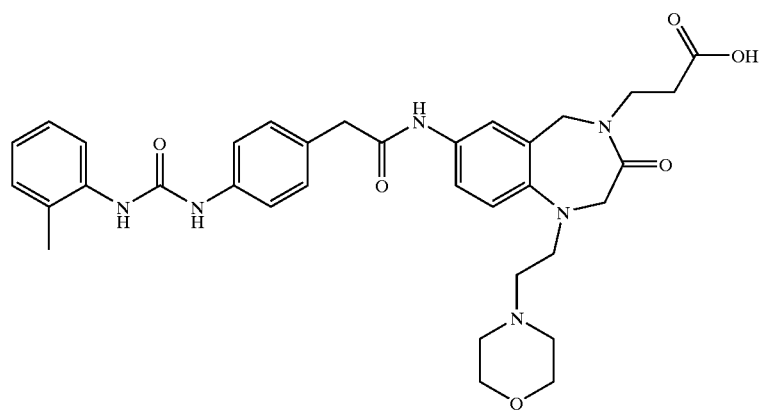
Name: BX69   Act: 0.0315
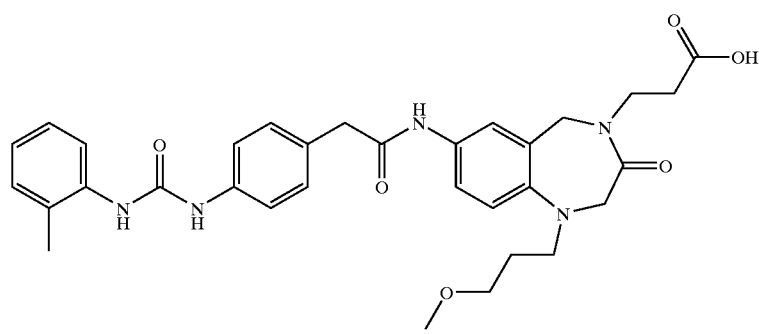
Name: BX70   Act: 0.0305

TABLE 1-continued
| Structure-Activity 9 | 216 Compounds |
|---|---|
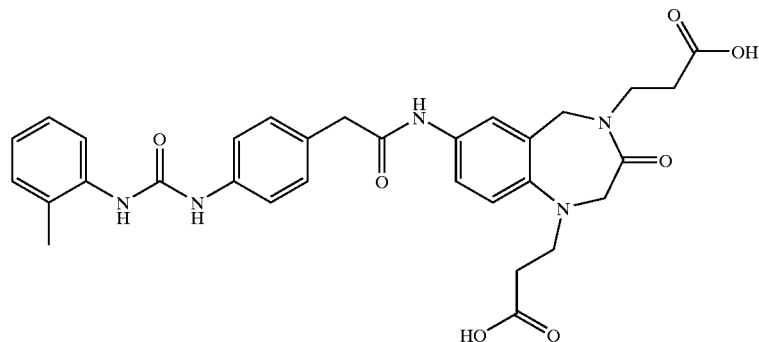
Name: BX71  Act: 0.0205
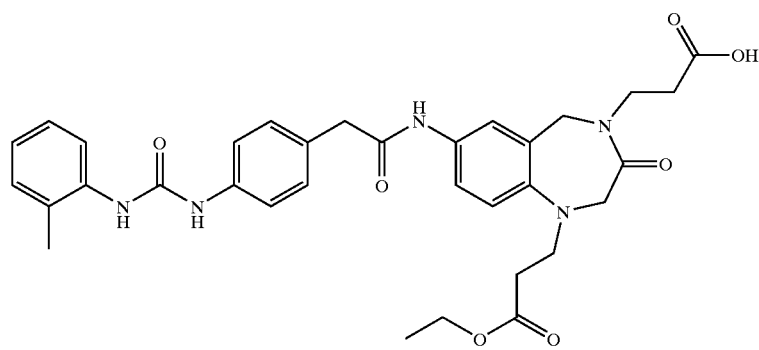
Name: BX72  Act: 0.0125
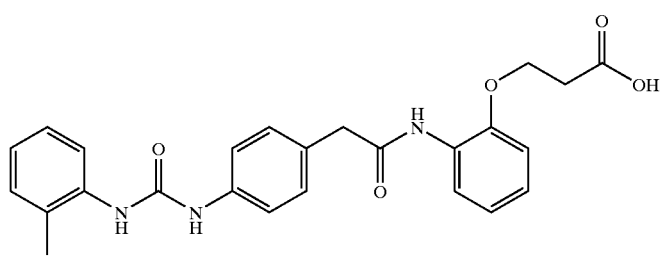
Name: UX1  Act: 4.505
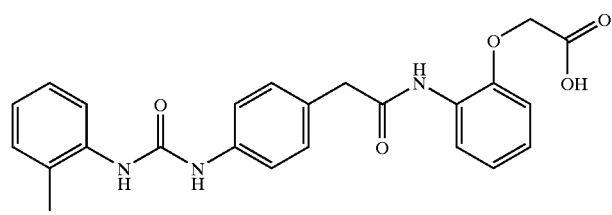
Name: UX2  Act: 1.3

TABLE 1-continued
| Structure-Activity 9 | 216 Compounds |
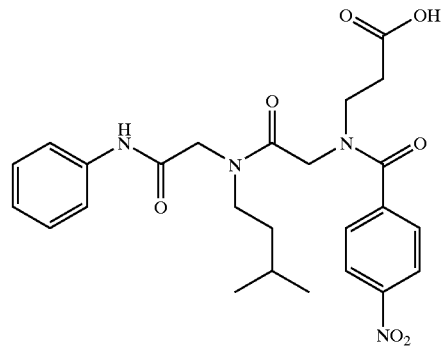
Name: AX1        Act: 18.333
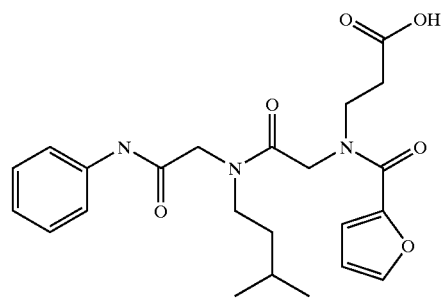
Name: AX2        Act: 1
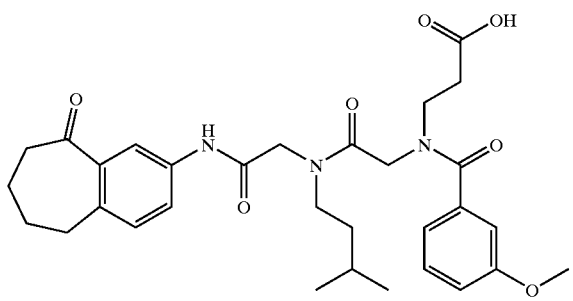
Name: AX3        Act: 15.3
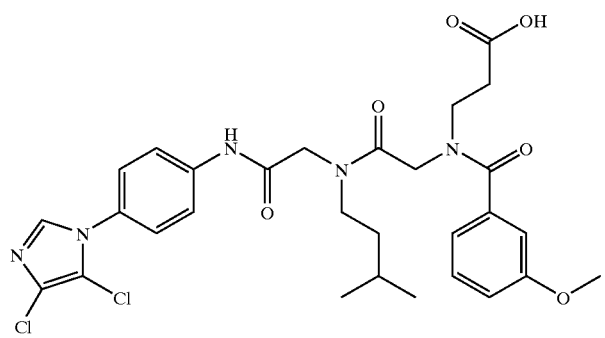
Name: AX4        Act: 15.2

TABLE 1-continued
| Structure-Activity 9 | 216 Compounds |
|---|---|
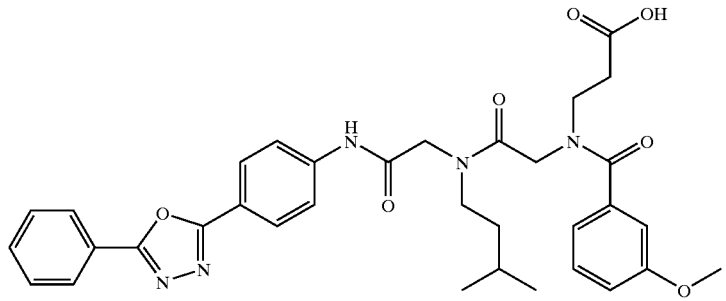
Name: AX5    Act: 14.35
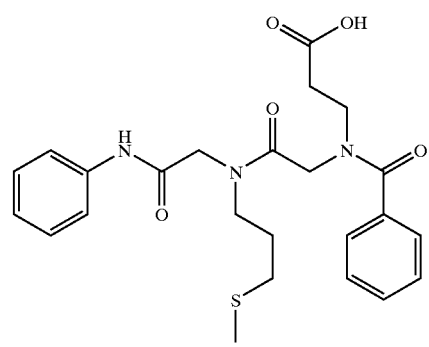
Name: AX6    Act: 13.5
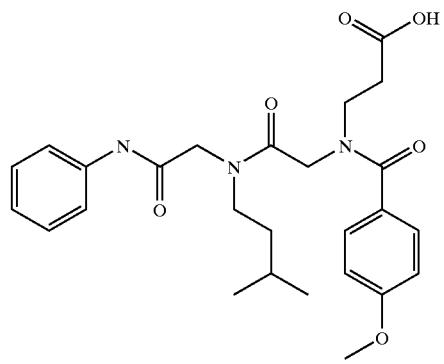
Name: AX7    Act: 11.5
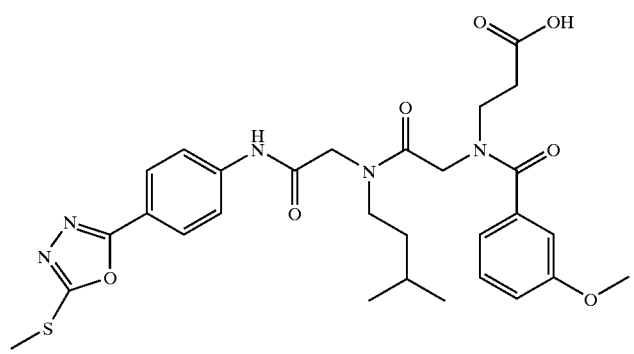
Name: AX8    Act: 9.43

TABLE 1-continued
| Structure-Activity 9 | 216 Compounds |
|---|---|
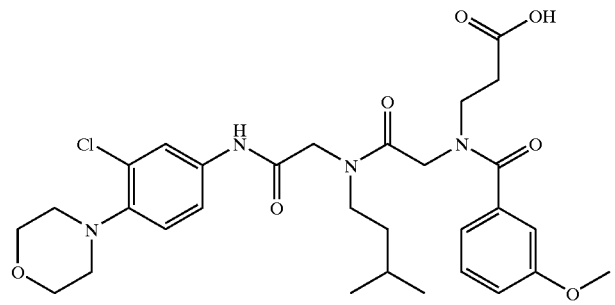
Name: AX9         Act: 7.38
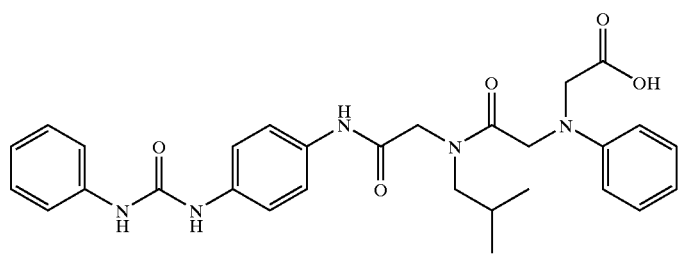
Name: AX10        Act: 6
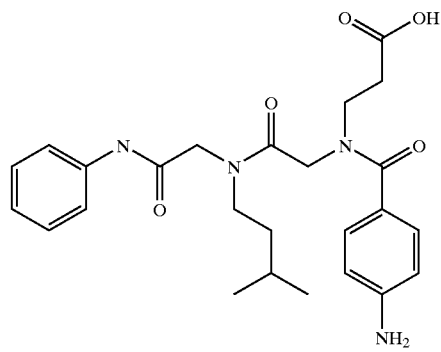
Name: AX11        Act: 6
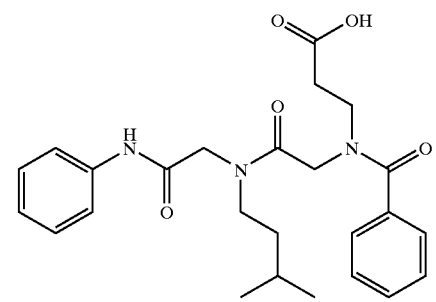
Name: AX12        Act: 4.125

TABLE 1-continued
| Structure-Activity 9 | 216 Compounds |
|---|---|
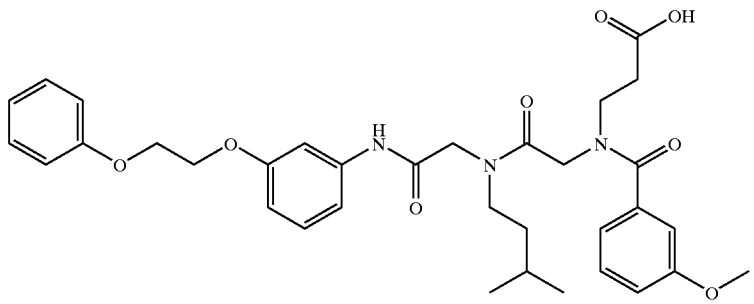
Name: AX13　　　　Act: 3.16
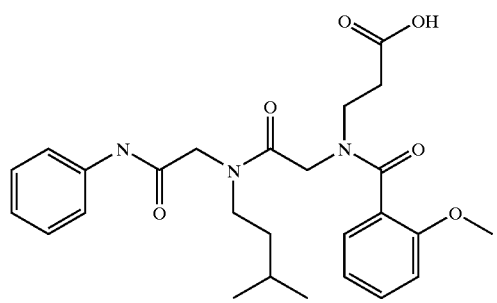
Name: AX14　　　　Act: 3
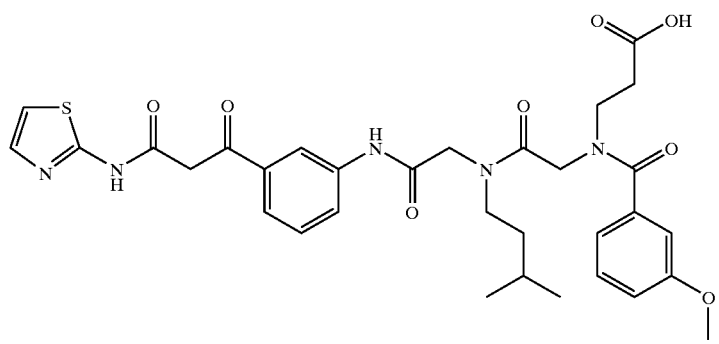
Name: AX15　　　　Act: 2.41
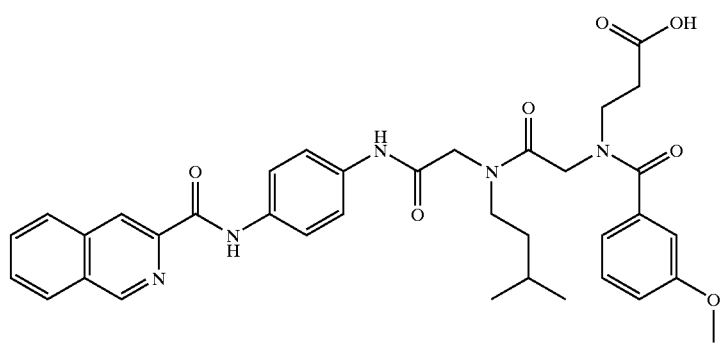
Name: AX16　　　　Act: 2.34

TABLE 1-continued
| Structure-Activity 9 | 216 Compounds |
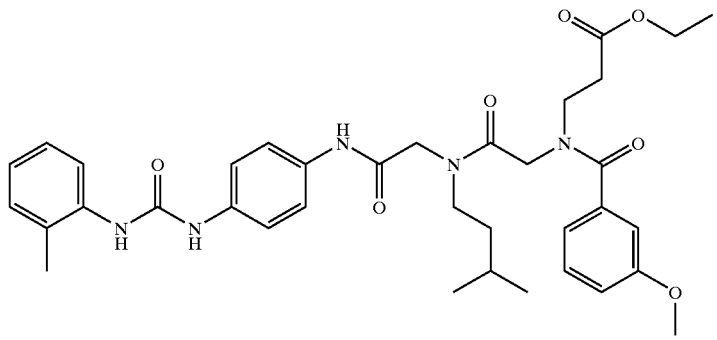
Name: AX17　　　　Act: prodrug
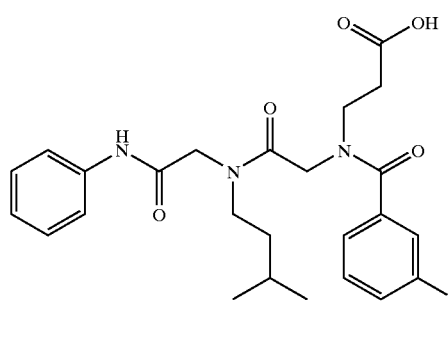
Name: AX18　　　　Act: 1.4
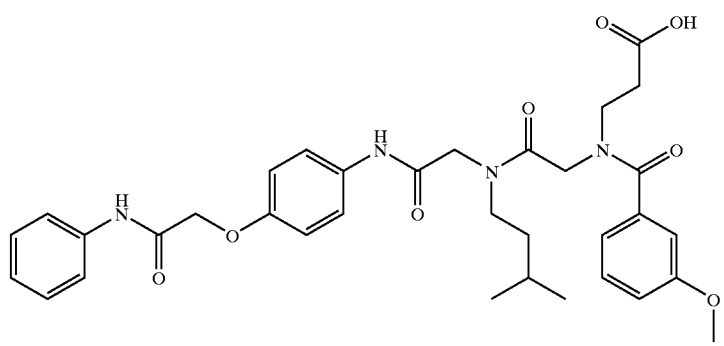
Name: AX19　　　　Act: 1.19
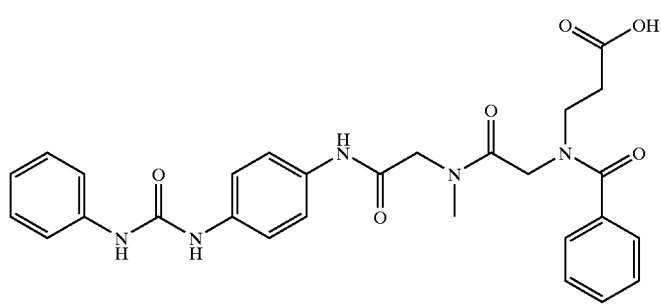
Name: AX20　　　　Act: 1.15

TABLE 1-continued
| Structure-Activity 9 | 216 Compounds |
|---|---|
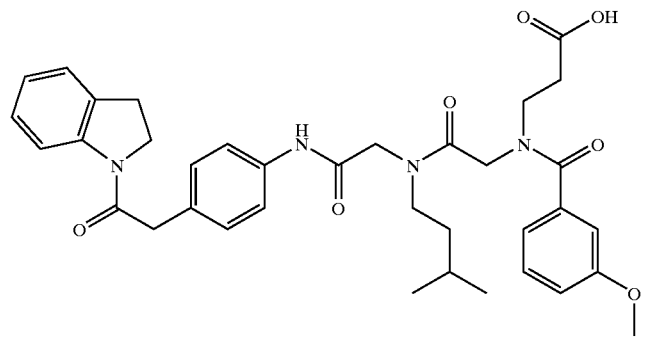
Name: AX21  Act: 0.761
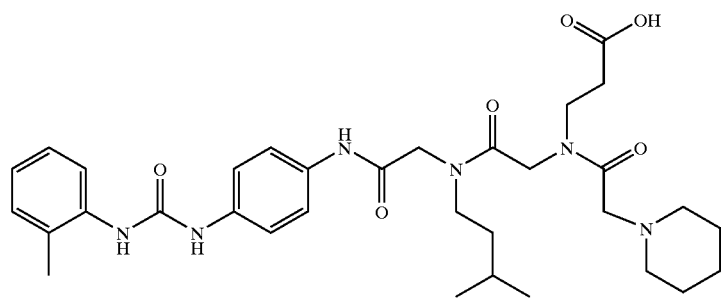
Name: AX22  Act: 0.6365
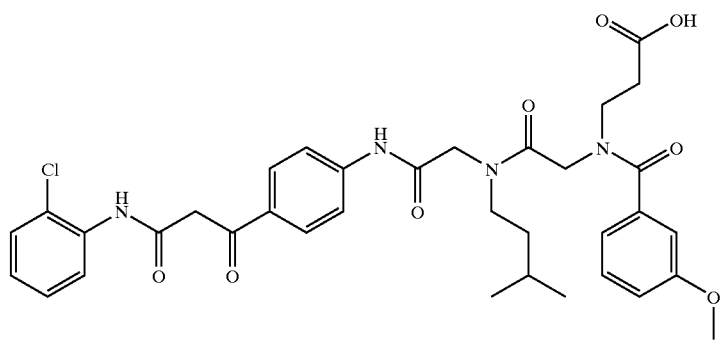
Name: AX23  Act: 0.563
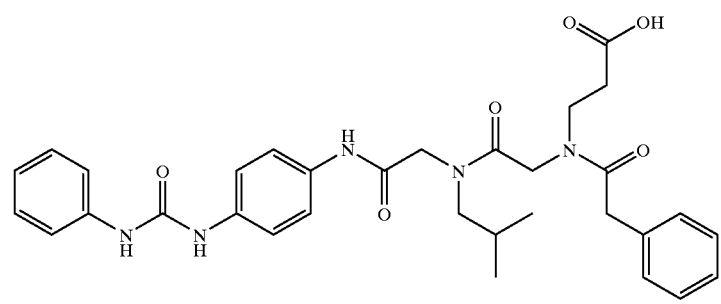
Name: AX24  Act: 0.3

TABLE 1-continued
Structure-Activity 9    216 Compounds
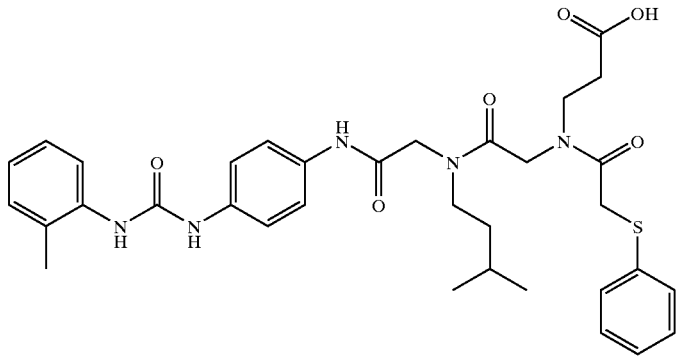
Name: AX25    Act: 0.2455
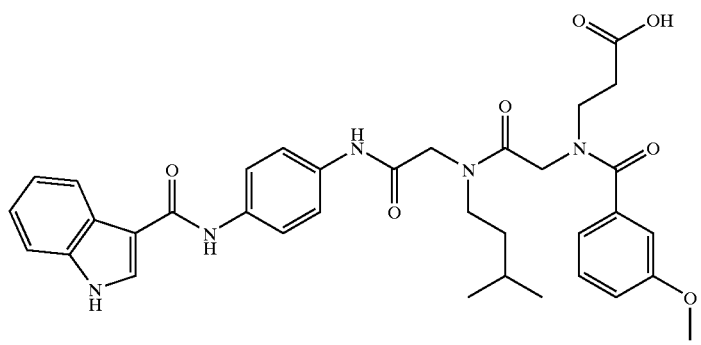
Name: AX26    Act: 0.241
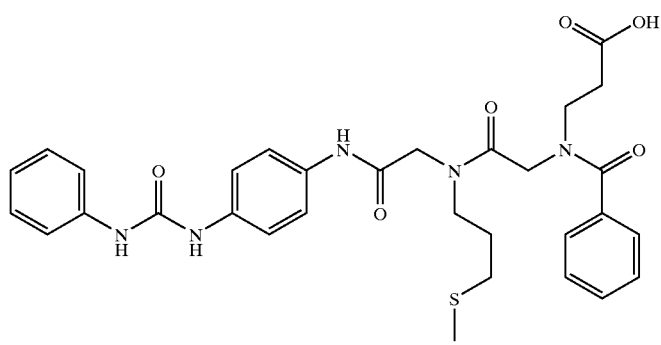
Name: AX27    Act: 0.2
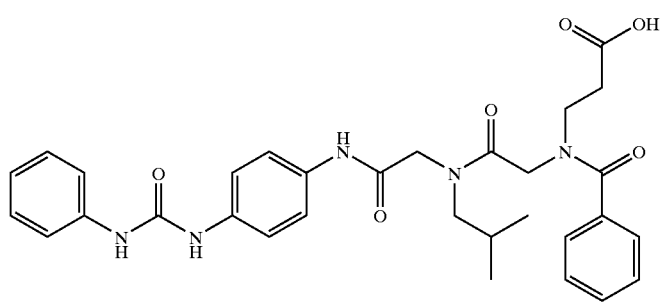
Name: AX28    Act: 0.15

TABLE 1-continued

| Structure-Activity 9 | 216 Compounds |

Name: AX29  Act: 0.109

Name: AX30  Act: prodrug

Name: AX31  Act: prodrug

Name: AX32  Act: 0.0975

TABLE 1-continued
| Structure-Activity 9 | 216 Compounds |
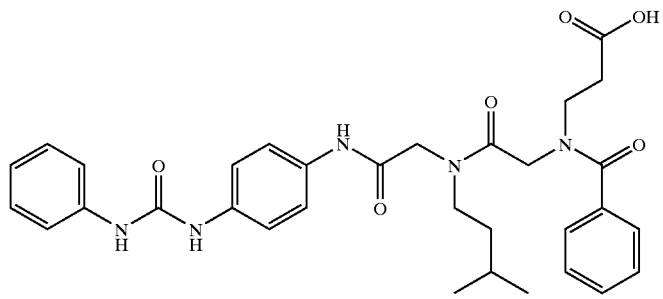
Name: AX33   Act: 0.095
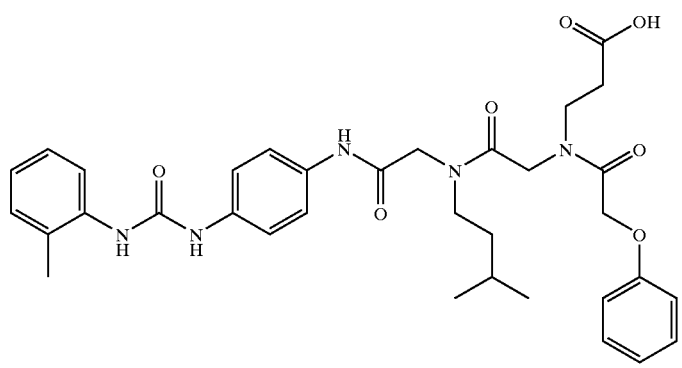
Name: AX34   Act: 0.092
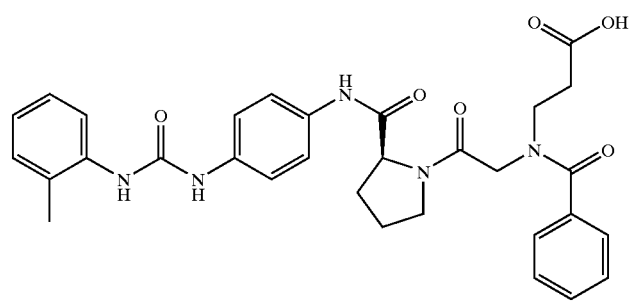
Name: AX35   Act: 0.085
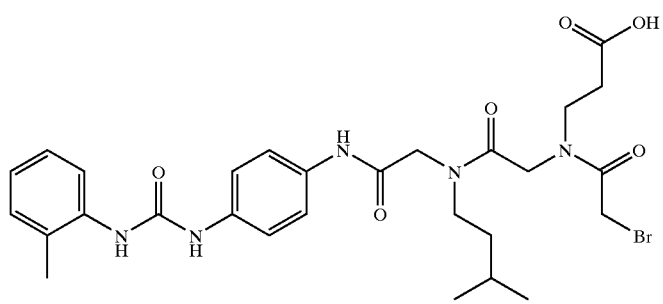
Name: AX36   Act: 0.06325

TABLE 1-continued
| Structure-Activity 9 | 216 Compounds |
|---|---|
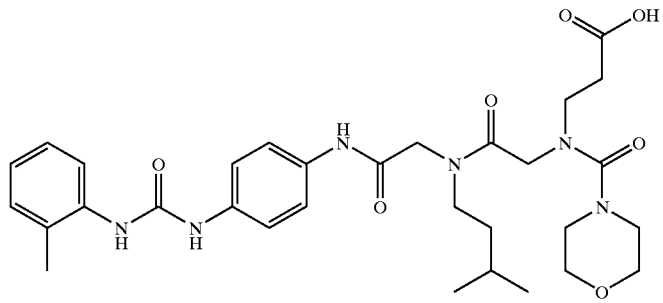
Name: AX37         Act: 0.0605
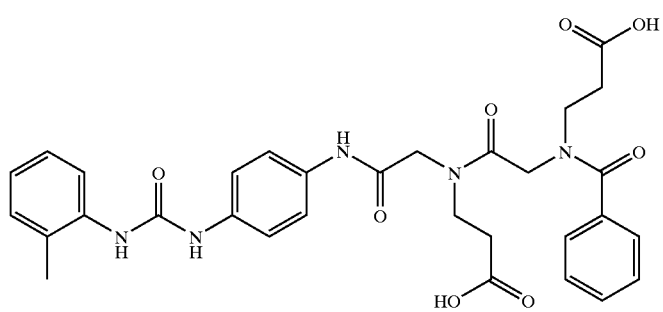
Name: AX38         Act: 0.06
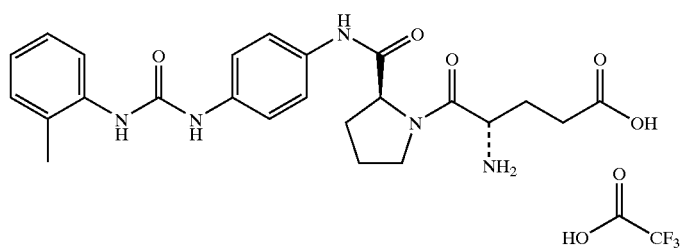
Name: CX4          Act: 2.615
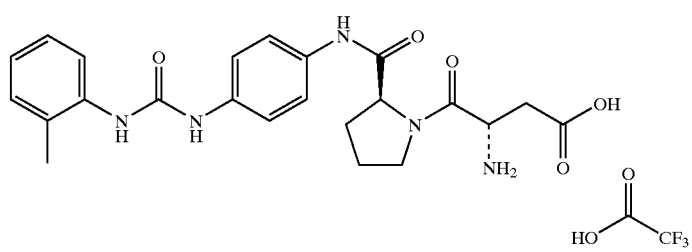
Name: CX5          Act: 1.615
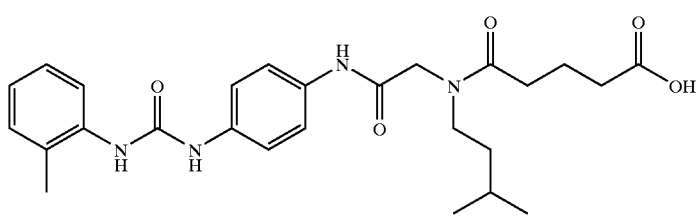
Name: CX6          Act: 1.157

TABLE 1-continued
| Structure-Activity 9 | 216 Compounds |
| --- | --- |
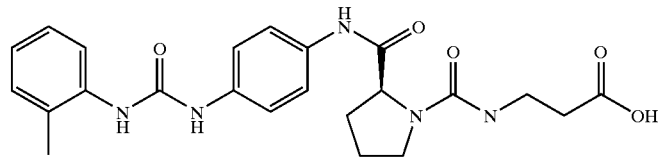
Name: CX7                Act: 0.9
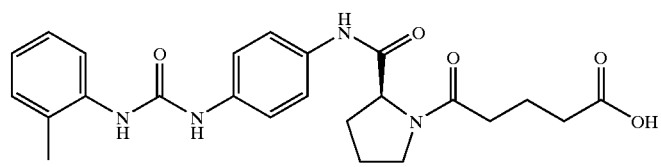
Name: CX8                Act: 0.4805
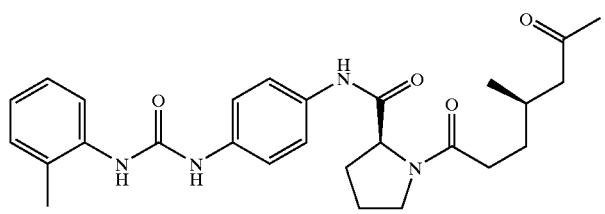
Name: CX9                Act: 0.332
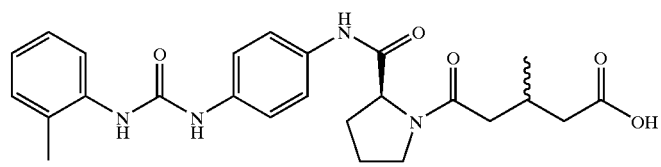
Name: CX10               Act: 0.2585
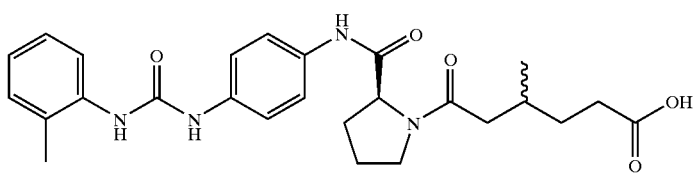
Name: CX11               Act: 0.1435
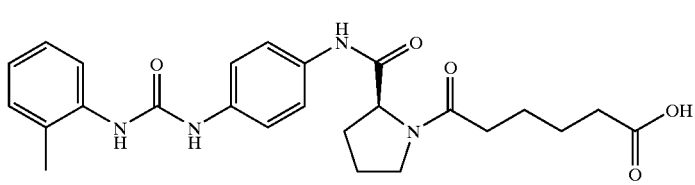
Name: CX12               Act: 0.0605

TABLE 1-continued
| Structure-Activity 9 | 216 Compounds |
|---|---|
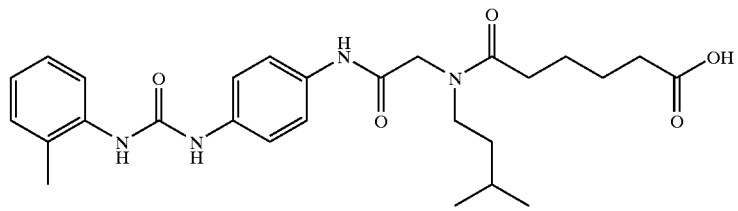
Name: CX13  Act: 0.0525
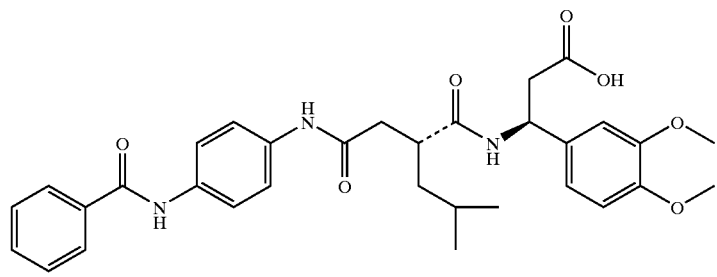
Name: SX3  Act: 11.65
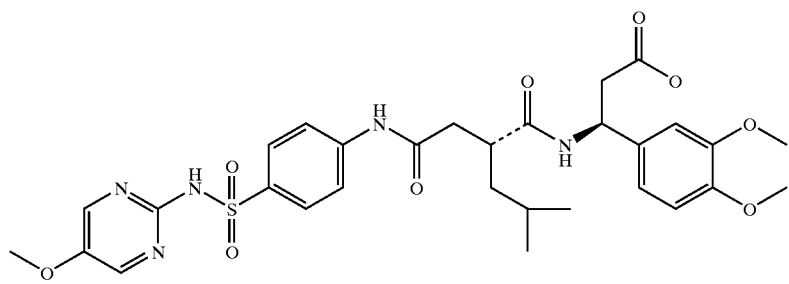
Name: SX4  Act: 11.3
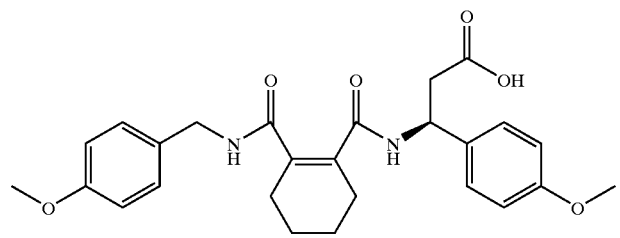
Name: SX5  Act: 7.6
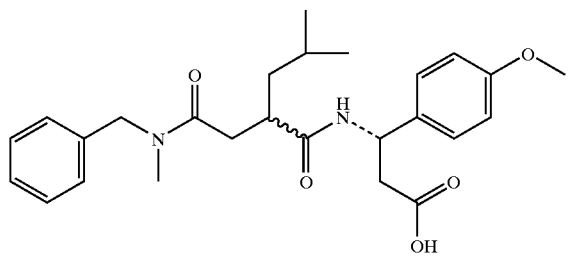
Name: SX6  Act: 6.75

TABLE 1-continued
Structure-Activity 9    216 Compounds
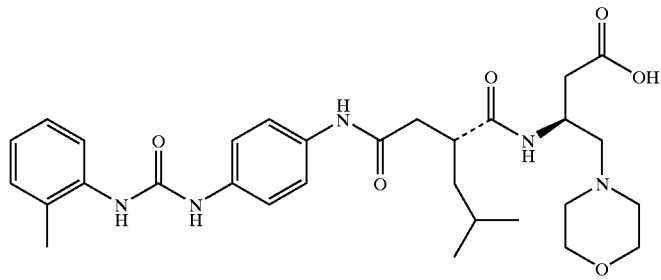
Name: SX7              Act: 5.98333
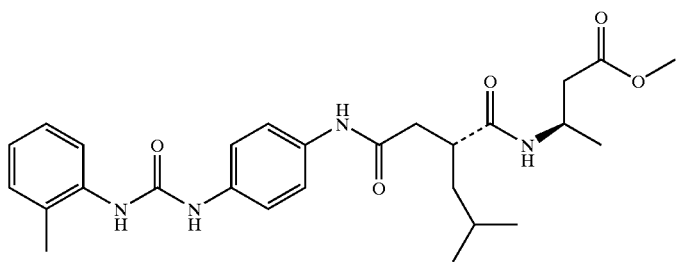
Name: SX8              Act: prodrug
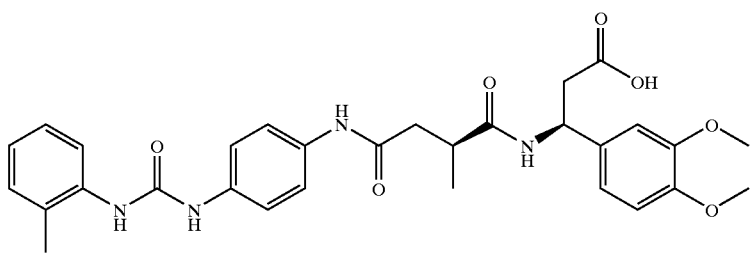
Name: SX9              Act: 5.125
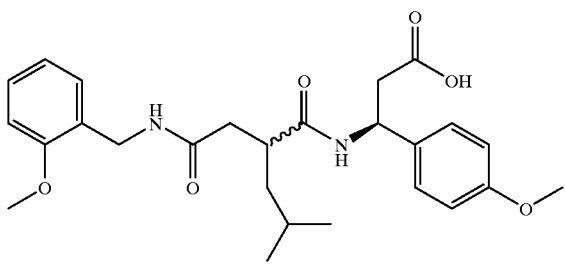
Name: SX10             Act: 5
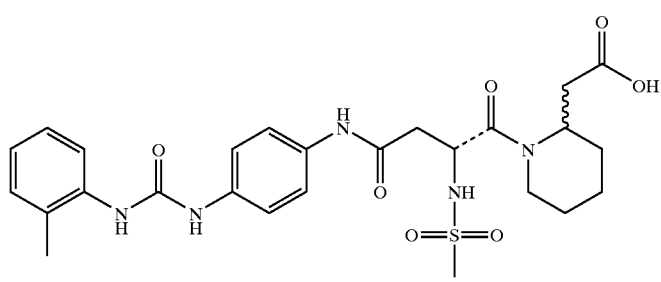
Name: SX12             Act: 3.5

TABLE 1-continued
| Structure-Activity 9 | 216 Compounds |
|---|---|
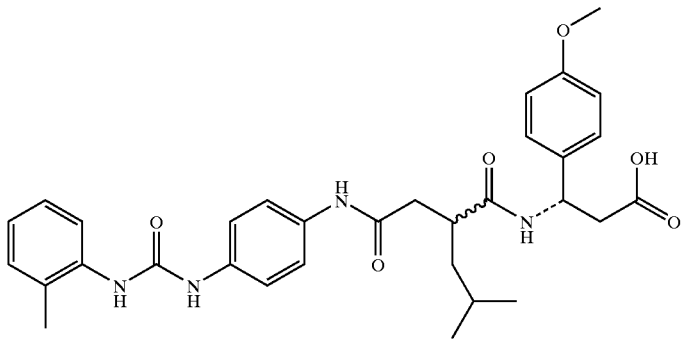
Name: SX13          Act: 3.485
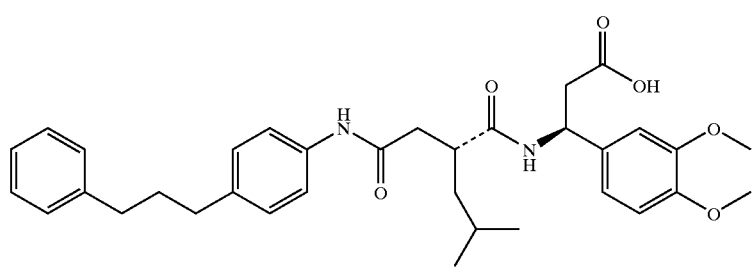
Name: SX14          Act: 3.245
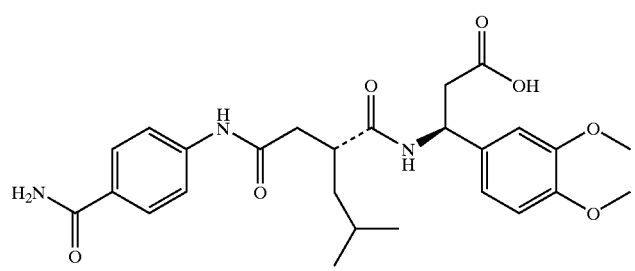
Name: SX15          Act: 2.995
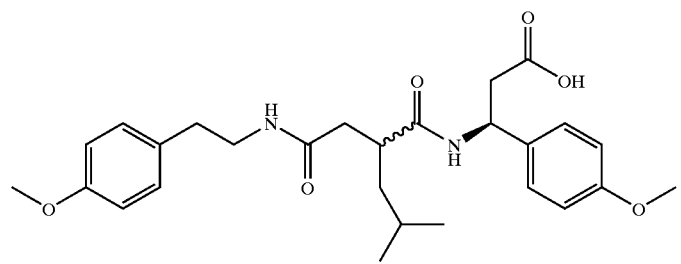
Name: SX16          Act: 2.5

TABLE 1-continued
| Structure-Activity 9 | 216 Compounds |
|---|---|
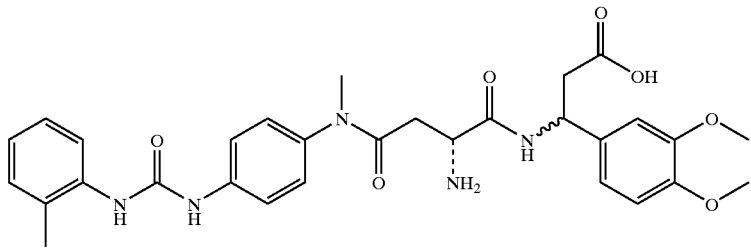
Name: SX17                Act: 2.31
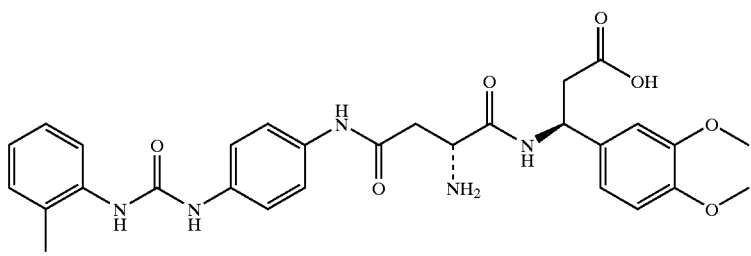
Name: SX19                Act: 1.94
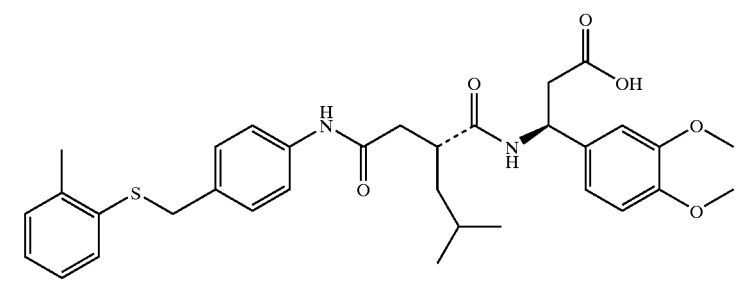
Name: SX20                Act: 1.76667
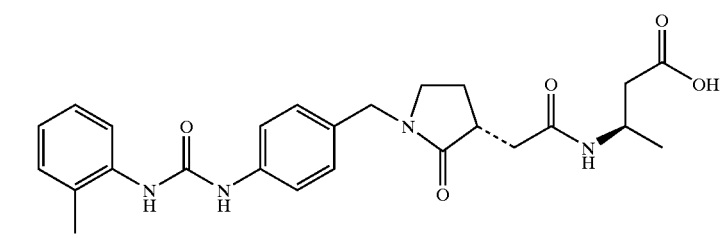
Name: SX21                Act: 1.74
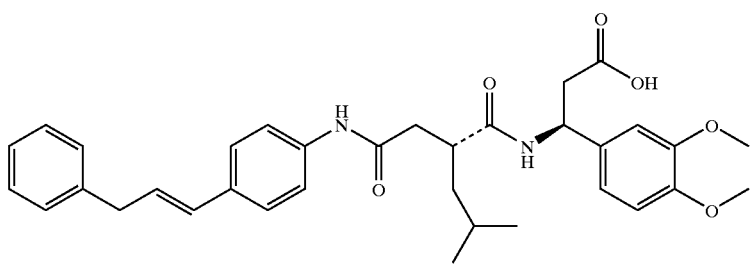
Name: SX22                Act: 1.47

TABLE 1-continued
Structure-Activity 9     216 Compounds
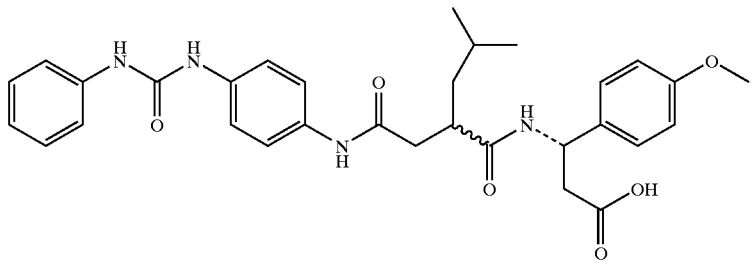
Name: SX23              Act: 1.32667
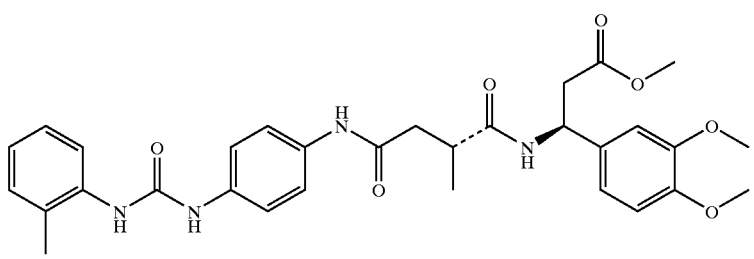
Name: SX24              Act: prodrug
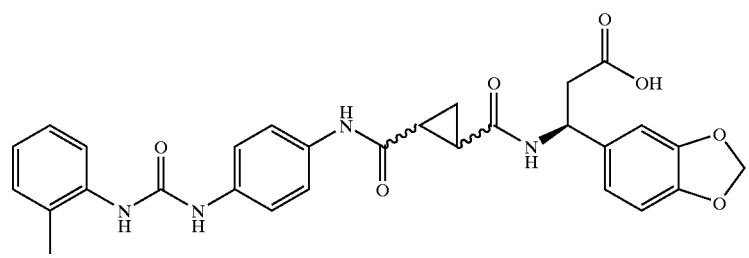
Name: SX25              Act: 0.81
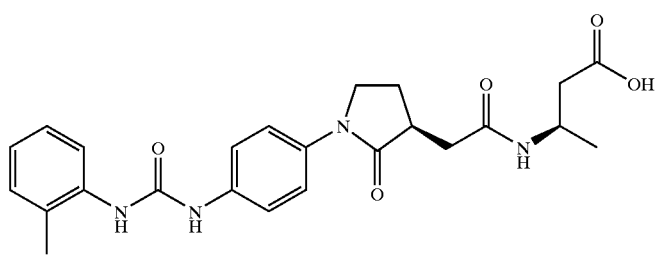
Name: SX26              Act: 0.769
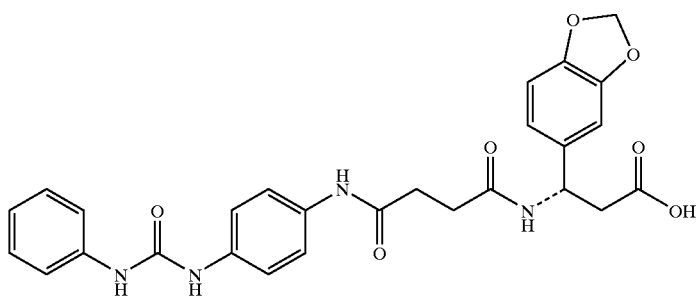
Name: SX27              Act: 0.765

TABLE 1-continued
| Structure-Activity 9 | 216 Compounds |
| --- | --- |
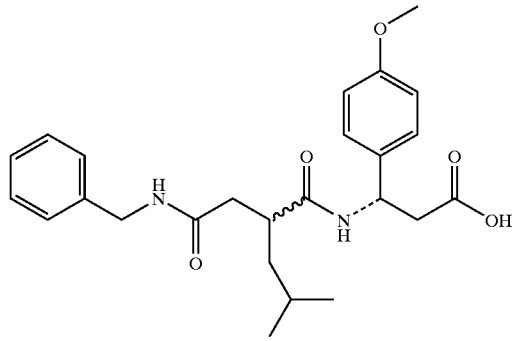
Name: SX28    Act: 0.7175
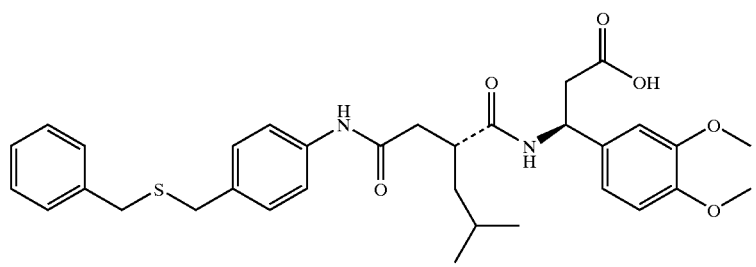
Name: SX29    Act: 0.7005
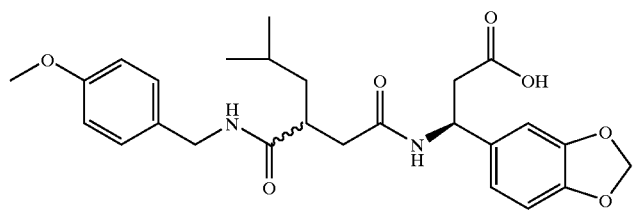
Name: SX30    Act: 0.7
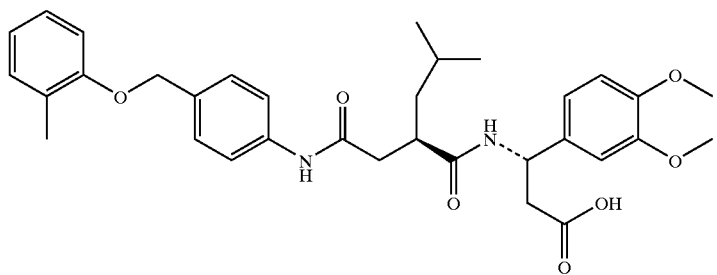
Name: SX31    Act: 0.6795
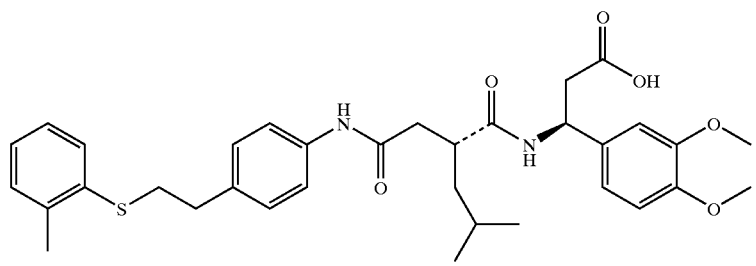
Name: SX32    Act: 0.66

TABLE 1-continued
| Structure-Activity 9 | 216 Compounds |
|---|---|
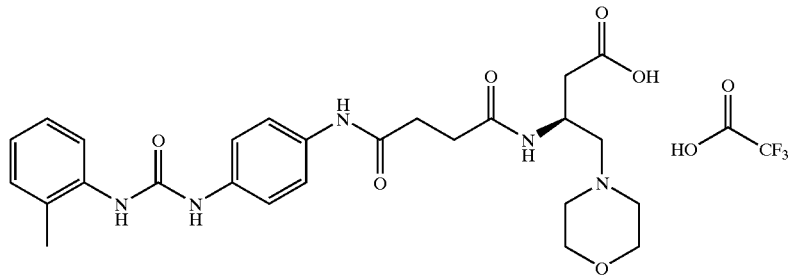
Name: SX33  Act: 0.5135
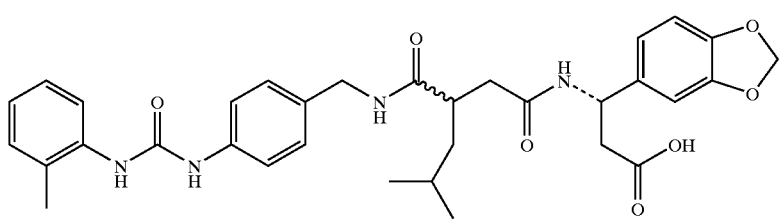
Name: SX34  Act: 0.5
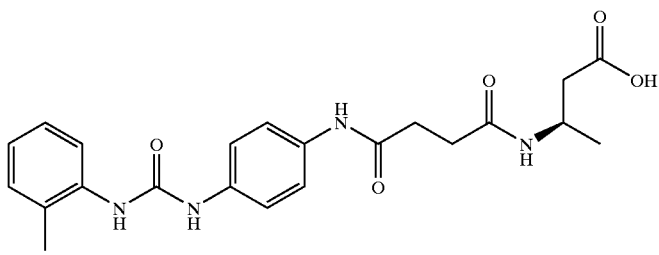
Name: SX35  Act: 0.468
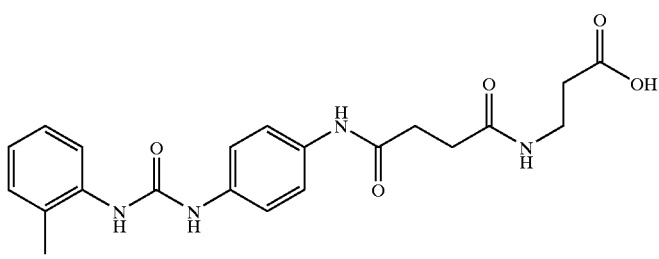
Name: SX36  Act: 0.442
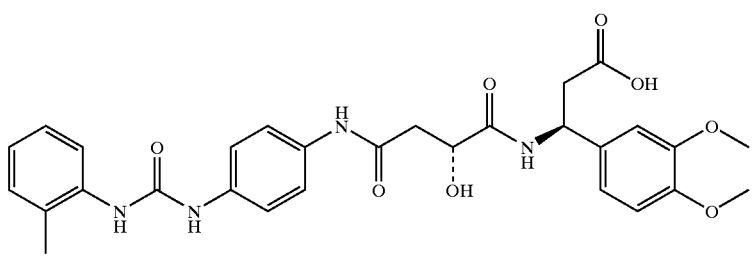
Name: SX38  Act: 0.404

TABLE 1-continued
| Structure-Activity 9 | 216 Compounds |
|---|---|
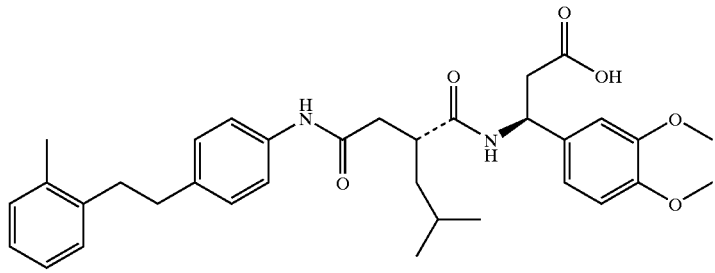
Name: SX39  Act: 0.397
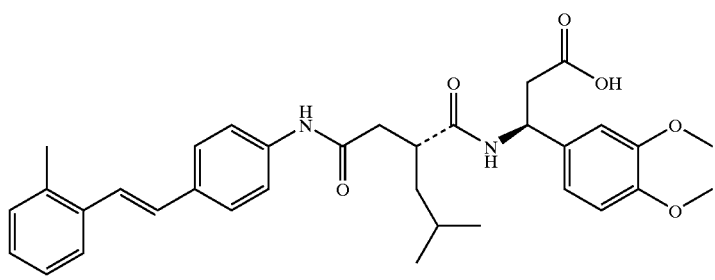
Name: SX40  Act: 0.3725
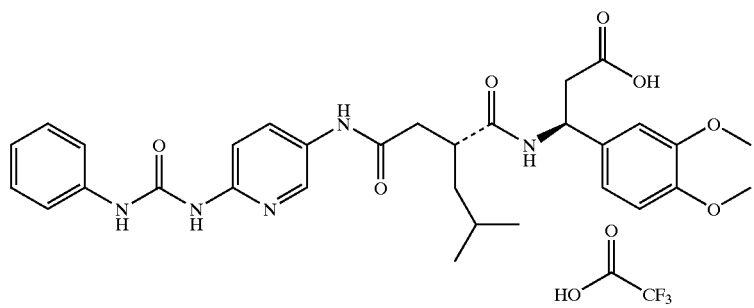
Name: SX41  Act: 0.3095
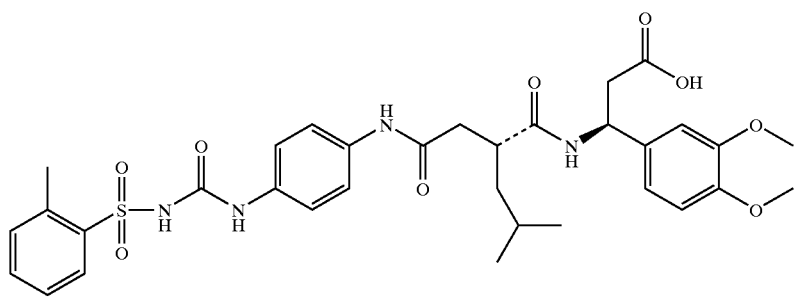
Name: SX42  Act: 0.2975

TABLE 1-continued
Structure-Activity 9     216 Compounds
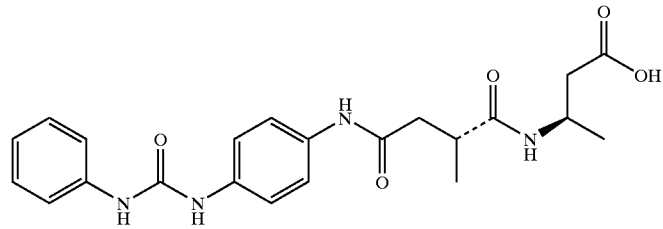
Name: SX43     Act: 0.2405
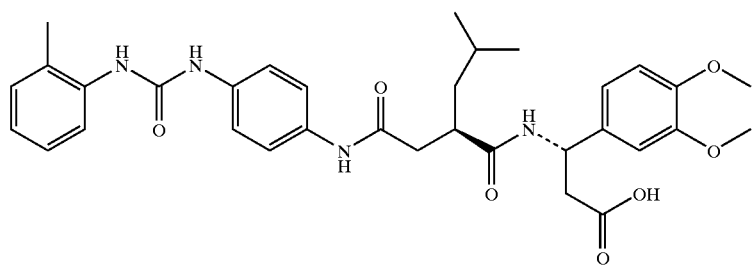
Name: SX44     Act: 0.23333
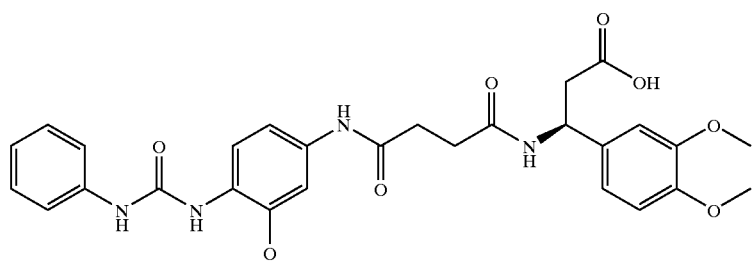
Name: SX45     Act: 0.215667
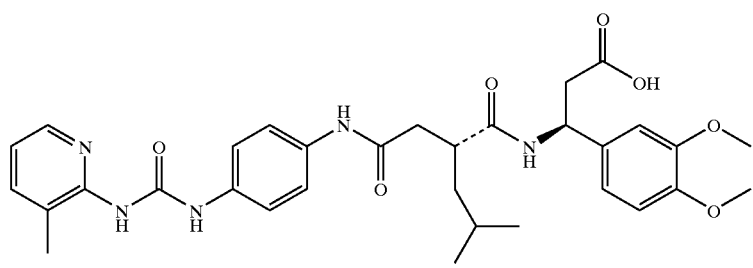
Name: SX46     Act: 0.2005
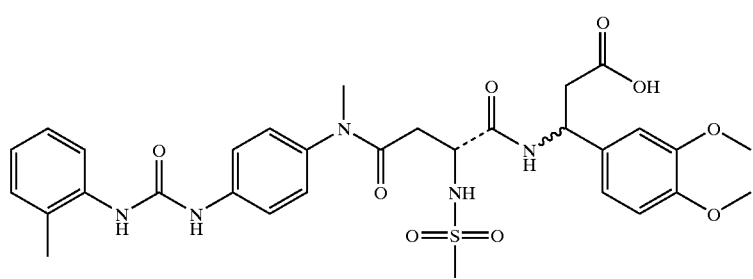
Name: SX47     Act: 0.196

TABLE 1-continued
Structure-Activity 9    216 Compounds
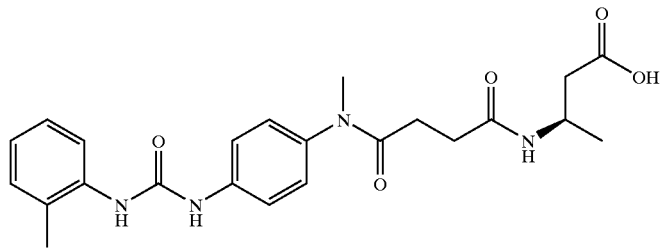
Name: SX48    Act: 0.195
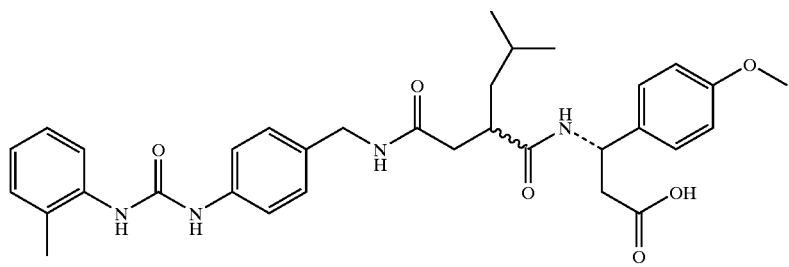
Name: SX49    Act: 0.175
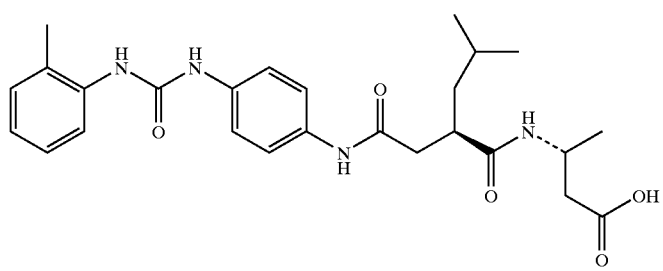
Name: SX50    Act: 0.166667
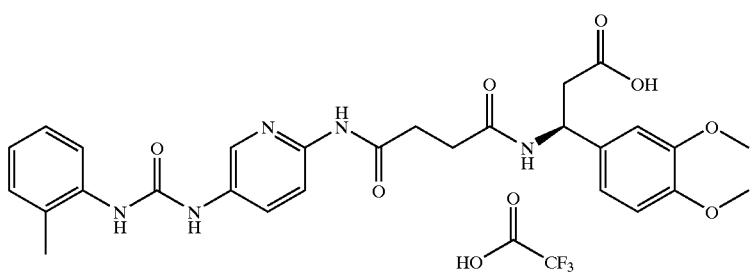
Name: SX51    Act: 0.1425
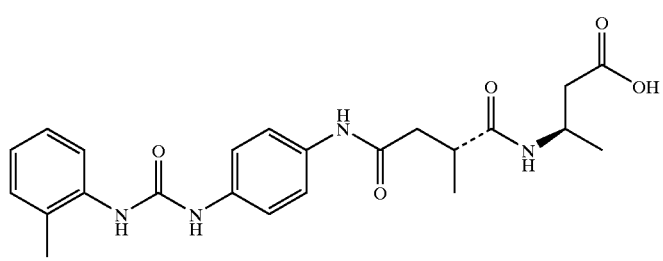
Name: SX52    Act: 0.135

TABLE 1-continued
| Structure-Activity 9 | 216 Compounds |
|---|---|
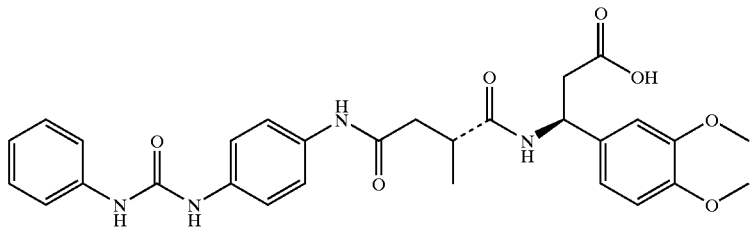
Name: SX53  Act: 0.065
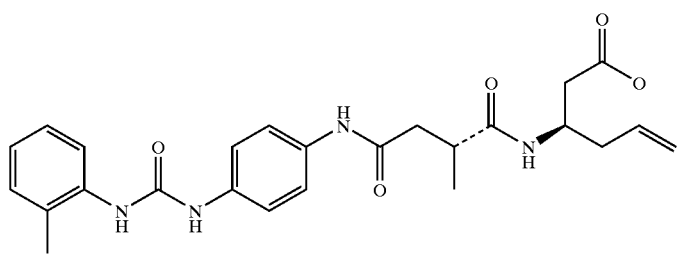
Name: SX54  Act: 0.0585
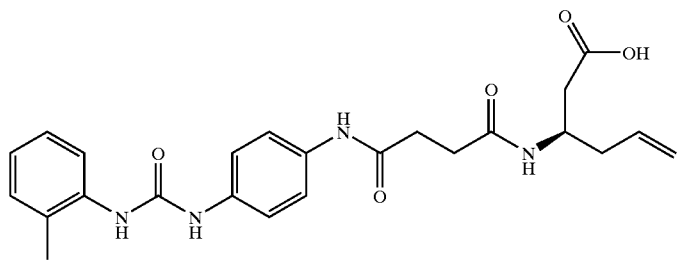
Name: SX55  Act: 0.0575
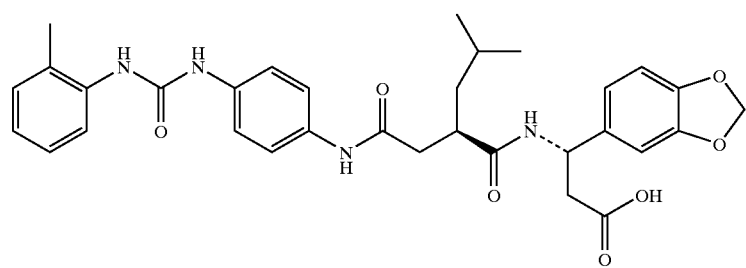
Name: SX56  Act: 0.055
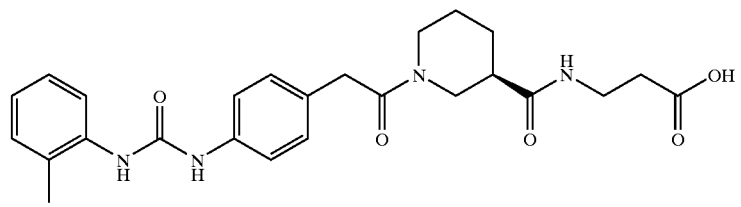
Name: MX1  Act: 0.872

TABLE 1-continued
| Structure-Activity 9 | 216 Compounds |
|---|---|
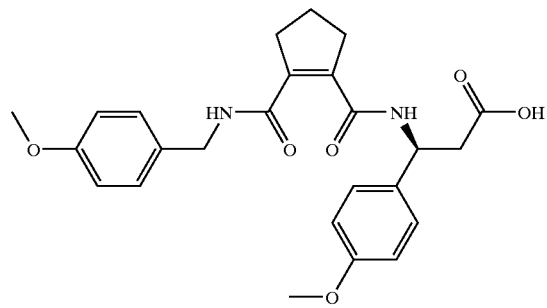
Name: MX2  Act: 0.25
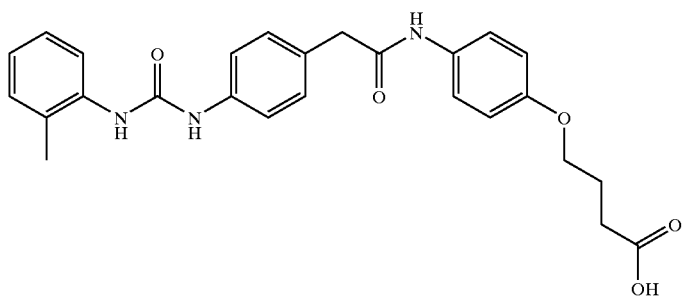
Name: TX1  Act: 3.1
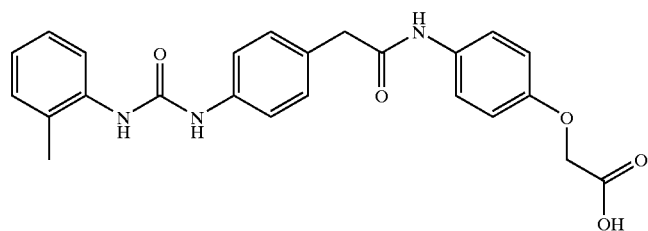
Name: TX2  Act: 2.1
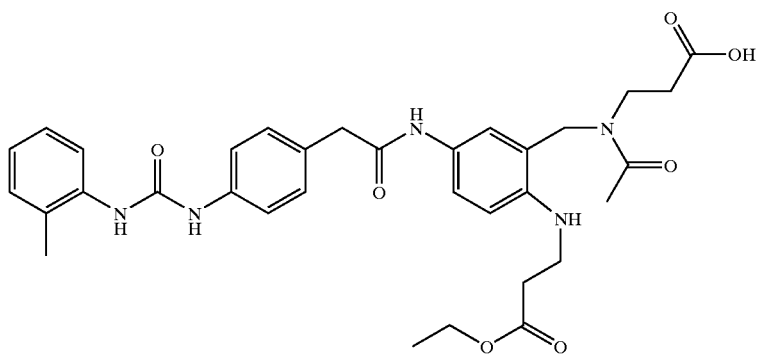
Name: TX3  Act: 0.079

TABLE 1-continued
| Structure-Activity 9 | 216 Compounds |
|---|---|
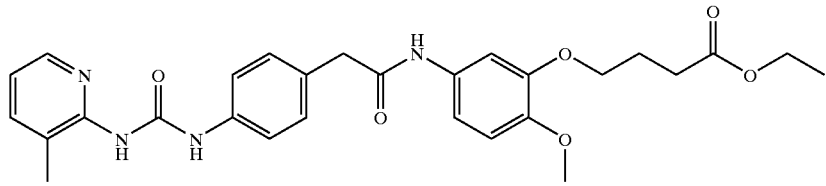
Name: RX1  Act: prodrug
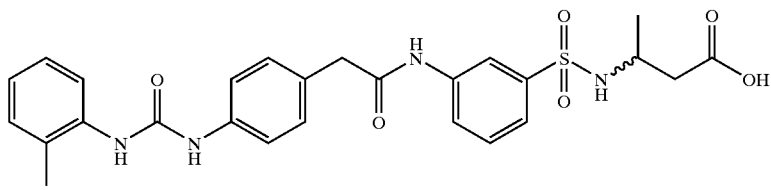
Name: RX2  Act: 10.645
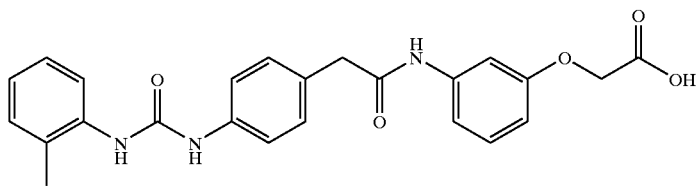
Name: RX3  Act: 8.84
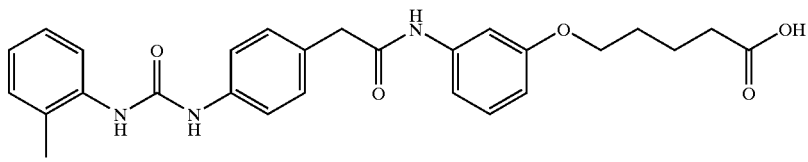
Name: RX4  Act: 4.46
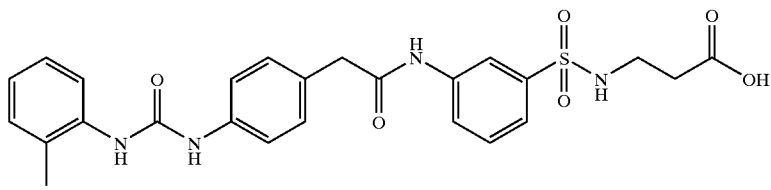
Name: RX5  Act: 3.81
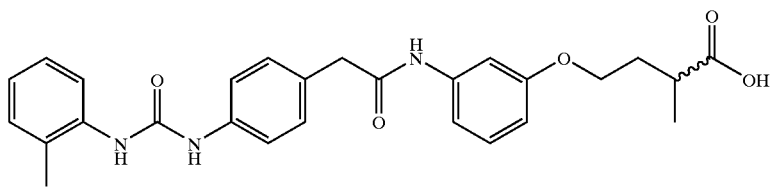
Name: RX6  Act: 2.53

TABLE 1-continued
| Structure-Activity 9 | 216 Compounds |
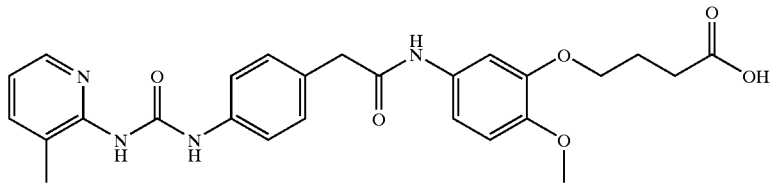
Name: RX7  Act: 2.295
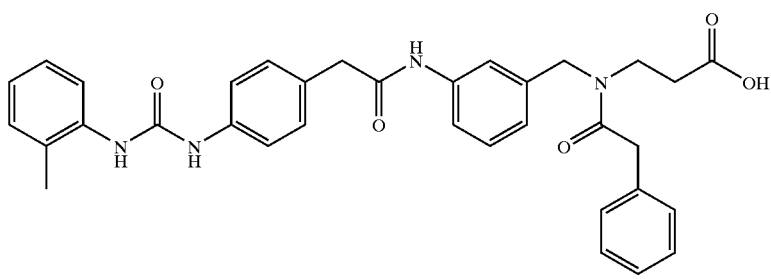
Name: RX8  Act: 2.25
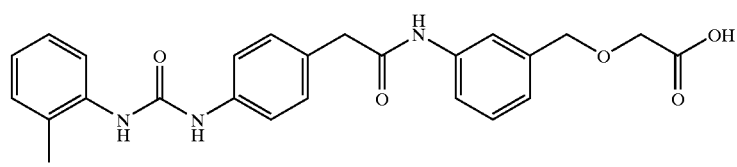
Name: RX9  Act: 2.18
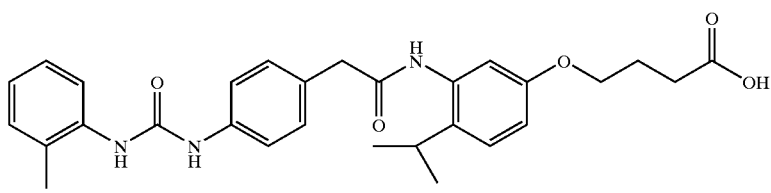
Name: RX10  Act: 2.046
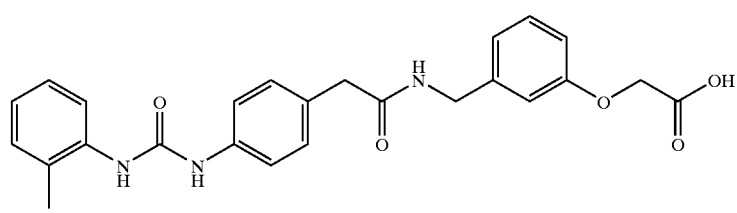
Name: RX11  Act: 1.14
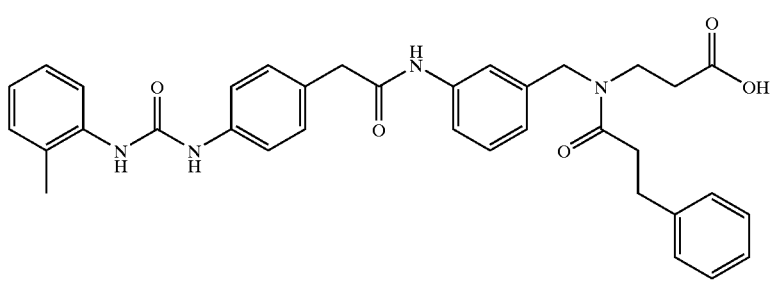
Name: RX12  Act: 1

TABLE 1-continued
| Structure-Activity 9 | 216 Compounds |
|---|---|
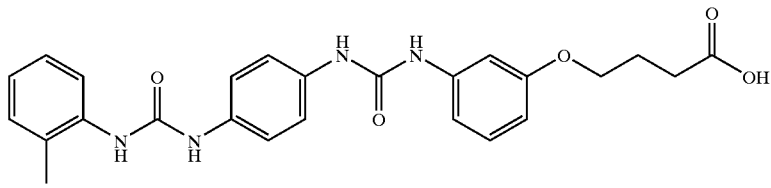
Name: RX13  Act: 0.686333
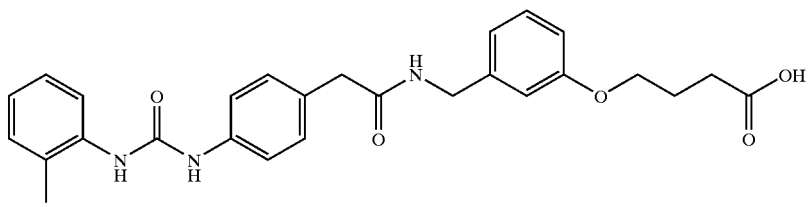
Name: RX14  Act: 0.652
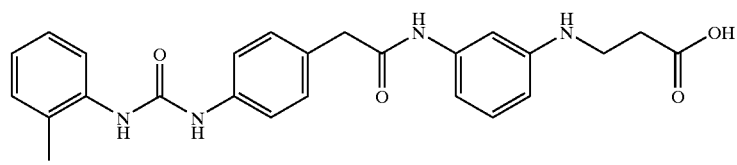
Name: RX15  Act: 0.65
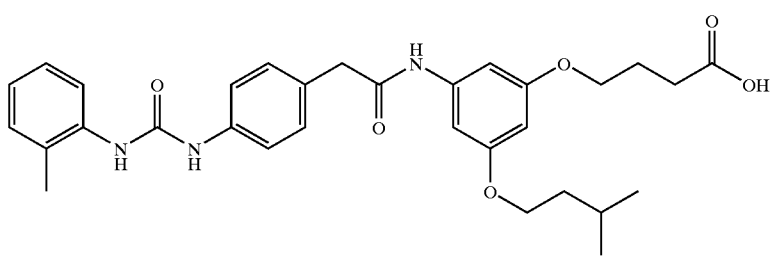
Name: RX16  Act: 0.574
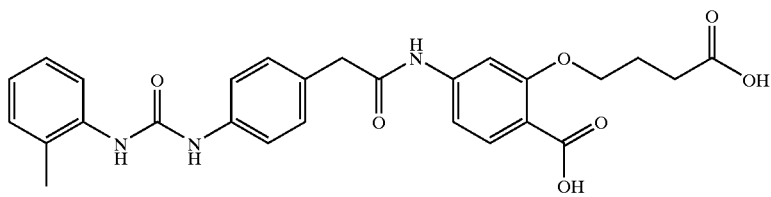
Name: RX17  Act: 0.406
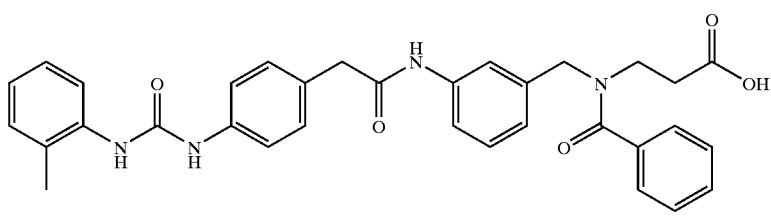
Name: RX18  Act: 0.35

TABLE 1-continued
| Structure-Activity 9 | 216 Compounds |
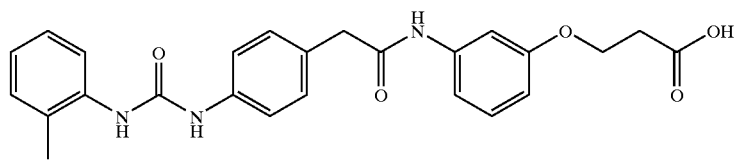
Name: RX19  Act: 0.317
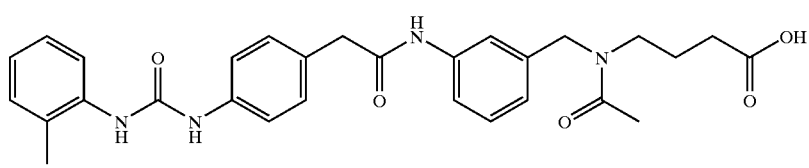
Name: RX20  Act: 0.26
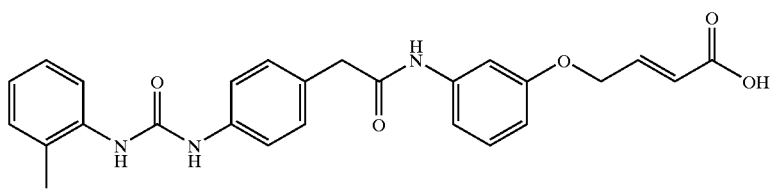
Name: RX21  Act: 0.2575
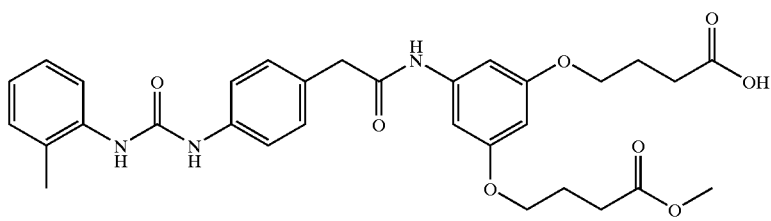
Name: RX22  Act: 0.157
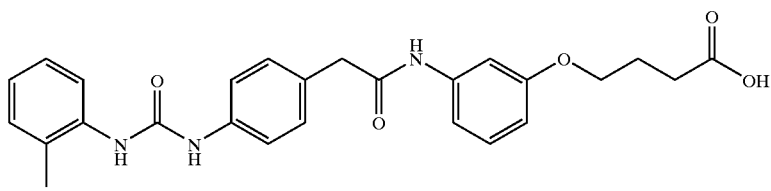
Name: RX23  Act: 0.143667
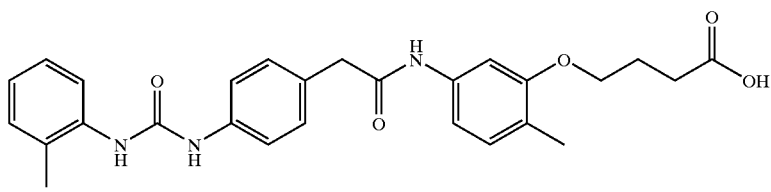
Name: RX24  Act: 0.1355

TABLE 1-continued
| Structure-Activity 9 | 216 Compounds |
| --- | --- |
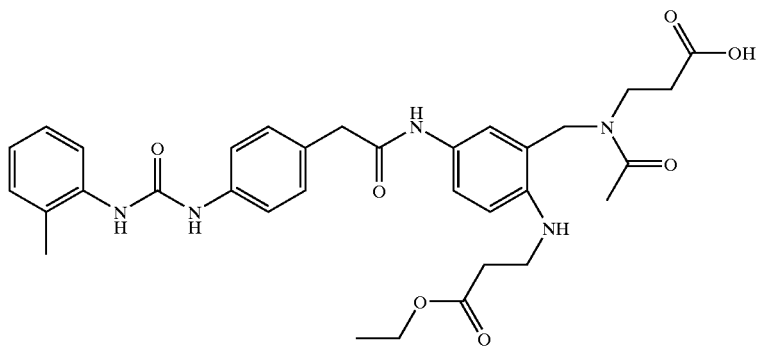
Name: RX25  Act: 0.079
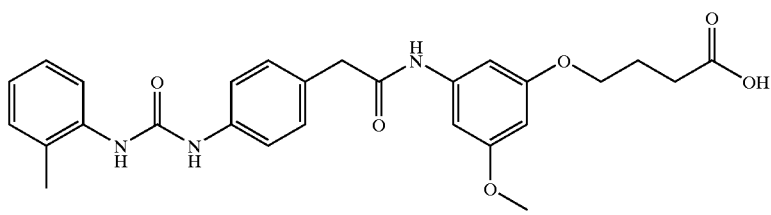
Name: RX26  Act: 0.077666
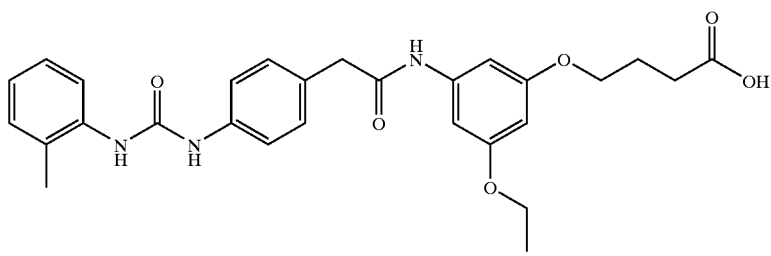
Name: RX27  Act: 0.051
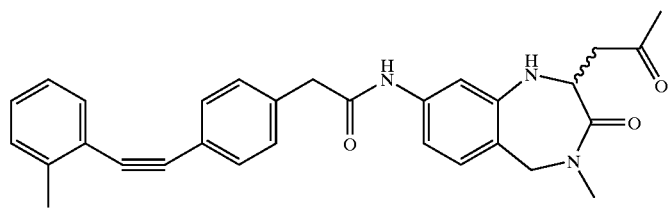
Name: QX1  Act:
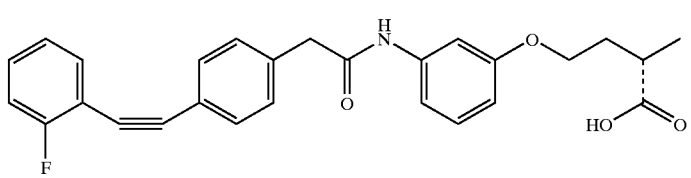
Name: RX29  Act:

TABLE 1-continued
| Structure-Activity 9 | 216 Compounds |
|---|---|
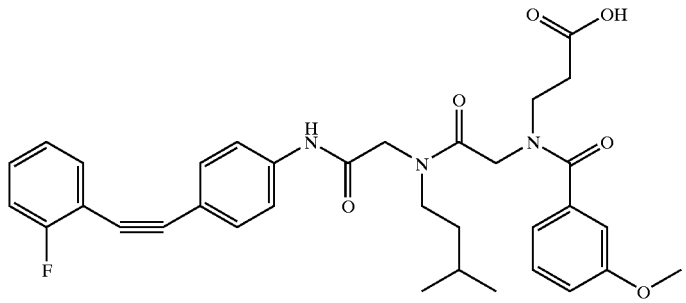
Name: CX14    Act:
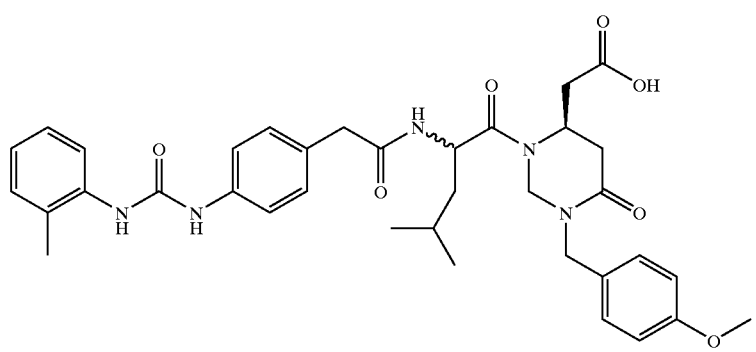
Name: MX3    Act:
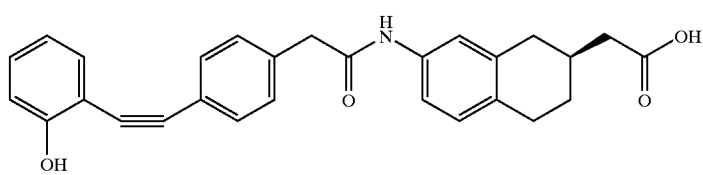
Name: RX30    Act:
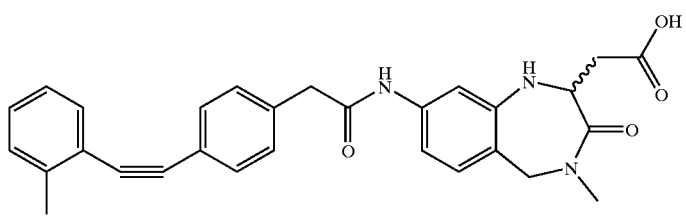
Name: BX73    Act:
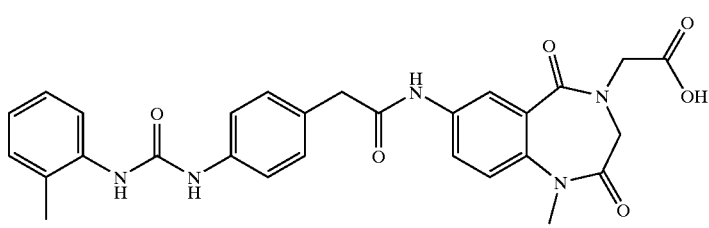
Name: BX1    Act: 19.9333

TABLE 1-continued
| Structure-Activity 9 | 216 Compounds |
|---|---|
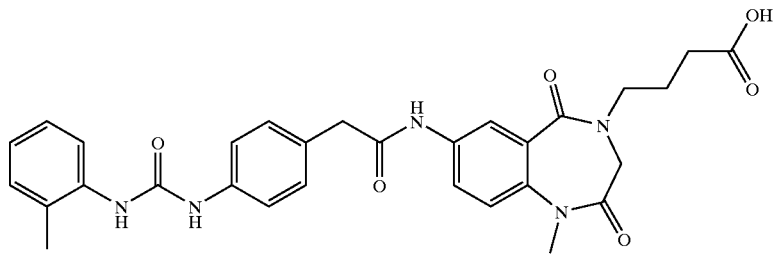
Name: BX3  Act: 17.5
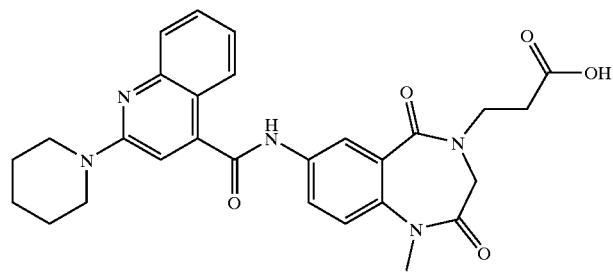
Name: BX4  Act: 17.3
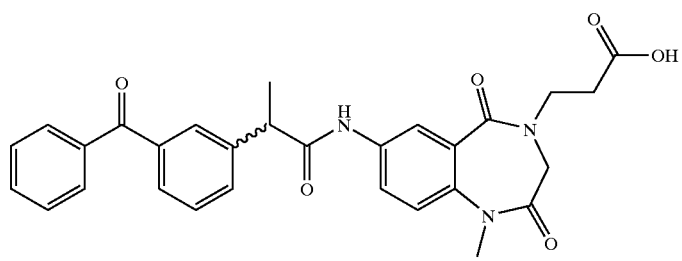
Name: BX5  Act: 17.2
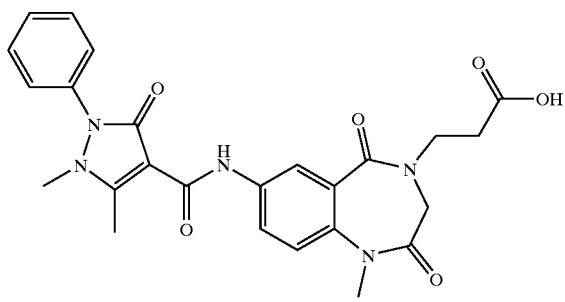
Name: BX6  Act: 15.4

TABLE 1-continued

Structure-Activity 9    216 Compounds

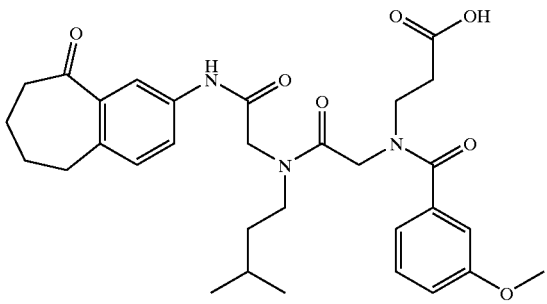

Name: BX7    Act: 15.3

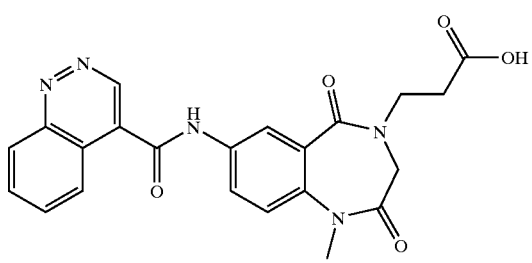

Name: BX9    Act: 13.3

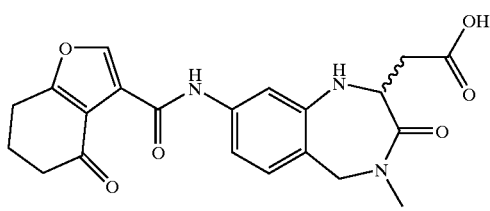

Name: BX10    Act: 11.2775

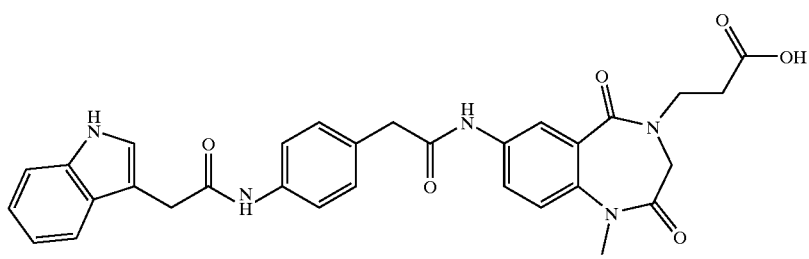

Name: BX11    Act: 9.05

Compounds of this invention may be synthesized using any conventional technique. Preferably, these compounds are chemically synthesized from readily available starting materials, such as α-amino acids and their functional equivalents. Modular and convergent methods for the synthesis of these compounds are also preferred. In a convergent approach, for example, large sections of the final product are brought together in the last stages of the synthesis, rather than by incremental addition of small pieces to a growing molecular chain.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

As used throughout this application, the term "patient" refers to mammals, including humans. And the term "cell" refers to mammalian cells, including human cells.

Once synthesized, the activities and VLA-4 or IIb/IIIa specificities of the compounds according to this invention may be determined and/or confirmed using in vitro and in vivo assays.

For example, the cell adhesion inhibitory activity of these compounds may be measured by determining the concentration of inhibitor required to block the binding of VLA-4-expressing cells to fibronectin- or CS1-coated plates. In this assay microtiter wells are coated with either fibronectin (containing the CS-1 sequence) or CS-1. If CS-1 is used, it must be conjugated to a carrier protein, such as bovine serum albumin, in order to bind to the wells. Once the wells are coated, varying concentrations of the test compound are then added together with appropriately labeled, VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, as well as human peripheral blood lymphocytes (PBLs). These cells are commercially available and may be fluorescently or radioactively labeled if desired.

A direct binding assay may also be employed to quantitate the inhibitory activity of the compounds of this invention. ("DBA") In direct binding assays, for example, a VCAM-IgG fusion protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, the disclosure of which is herein incorporated by reference. The conjugation of that fusion to a marker enzyme can be achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Mass.). Varying concentrations of the test inhibitory compound are then added to the wells followed by addition of VLA-4-expressing cells. The cells, compound and VCAM-IgG enzyme conjugate are mixed together and allowed to incubate at room temperature.

Following incubation, the wells are vacuum drained, leaving behind the cells and any bound VCAM. Quantitation of bound VCAM is determined by adding an appropriate calorimetric substrate for the enzyme conjugated to VCAM-IgG and determining the amount of reaction product. Decreased reaction product indicates increased binding inhibitory activity. The protocol is described more specifically below:

A. Preparation of the Plate for the Assay
1. Block a 96 Well Millipore Multiscreen Assay System Filtration Plate[1] with 200:1/well of Blocking Buffer (1× Phosphate Buffered Saline, 0.1% Tween 20, 1% BSA) for at least 1 hour at room temperature.

[1] Milipore Multiscreen Assay System (Millipore Corporation, Bedford, Mass.) 96 Well Filtration Plate (catalog #MAHV N45 50) Vacuum Source (catalog #XX55 000 00) Vacuum Manifold (catalog #MAVM 096 01) The Millipore Multiscreen Assay System Operating and Maintenance Manual 2. Drain the plate with the vacuum manifold, and wash with 200 μl/well of assay buffer (Tris Buffered Saline, 0.1% BSA, 2 mM glucose, 10 mM HEPES, pH 7.5) draining the plate in between. Repeat twice. Then blot the plate bottom on paper to remove excess buffer.

B. Addition of Assay Reagents to the Plate
3. Prepare a 4 μg/ml VCAMIg-AP solution (Alkaline phosphatase coupled to VCAMIg) in assay buffer and filter with a 0.2: low protein binding syringe filter (Gelman Sciences #4454). From this stock, prepare a 0.4 μg/ml working solution of VCAMIg-AP in assay buffer. Add 25:1 of 0.4 μg/ml VCAMIg-AP to every well.
5. Prepare dilutions of compounds to be tested in assay buffer. Concentrations should be 4× the desired final concentration and run in triplicate. Add 25 μl of the compound dilutions to designated wells.
6. Add 25 μl of assay buffer (in place of test compound) to the total binding (TB) wells and 75 μl of assay buffer to the Non Specific Binding (NSB) wells which additionally do not receive cells.
7. Jurkat cells are centrifuged to remove cell culture media and washed once in assay buffer. Resuspend the washed Jurkat cells to a concentration of $8\times10^6$/ml in assay buffer containing 2 mM $MnCl_2$. Pipeting the mixture up and down to ensure a uniform cell suspension. Add 50:1 of cell suspension to each well except the NSB wells.
8. Gently tap the sides of the plate to mix well contents. Incubate the plate for 60 minutes at room temperature (RT).
C. Assay Color Development
9. Place the plate on the vacuum manifold to drain the well contents. Wash twice with 100 μl/well of wash buffer (assay buffer containing 1 mM $MnCl_2$). Drain the plate and blot on paper towels.
10. Add 10 mg/ml of 4-Nitro phenyl phosphate to Substrate buffer (0.1M glycine, 1 mM $ZnCl_2$, 1 mM $MgCl_2$, pH 10.5). Add 100 μl/well and incubate for exactly 30 minutes at RT.
11. To stop the reaction, add 100 μl/well of 3N NaOH.
12. Read the 96-well plate in a Molecular Devices ELISA platereader at 405 nm. Analyze data with SoftMax software.

In order to assess the VLA-4 inhibitory specificity of the compounds of this invention, assays for other major groups of integrins, i.e., β2 and β3, as well as other 81 integrins, such as VLA-5, VLA-6 and α4β7 can be performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. α4β7 is a recently discovered homolog of VLA-4, which also binds fibronectin and VCAM. Specificity with respect to α4β7 is determined in a binding assay that utilizes the above-described VCAM-IgG-enzyme marker conjugate and a cell line that expresses α4β7, but not VLA-4, such as RPMI-8866 or JY cells.

Once VLA-4 inhibitors are identified, they may be further characterized in in vivo assays. One such assay tests the inhibition of contact hypersensitivity in an animal, such as described by P. L. Chisholm et al., "Monoclonal Antibodies to the Integrin α-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), the disclosures of which are herein incorporated by reference. In these assays, the skin of the animal is sensitized by exposure to an irritant, such as dinitrofluorobenzene, followed by light physical irritation, such as scratching the skin lightly with a sharp edge.

Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear. Swelling is measured using calipers or other suitable instrument to measure ear thickness. In this manner, one may identify those inhibitors of this invention which are best suited for inhibiting inflammation.

Another in vivo assay that may be employed to test the inhibitors of this invention is the sheep asthma assay. This assay is performed essentially as described in W. M. Abraham et al., "α-Integrins Mediate Antigen-induced Late Bronchial Responses and Prolonged Airway Hyperresponsiveness in Sheep", *J. Clin. Invest.*, 93, pp. 776–87 (1994), the disclosure of which is herein incorporated by reference. This assay measures inhibition of Ascaris antigen-induced late phase airway responses and airway hyperresponsiveness in allergic sheep.

The compounds of this invention may also be tested in a platelet aggregation assay.

The compounds of the present invention may be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, tris (hydroxymethyl)methylamine and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds of the present invention may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions.

In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are-not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.1 and about 10 mg/kg body weight per day of the active ingredient compound are useful.

According to another embodiment compositions containing a compound of this invention may also comprise an additional agent selected from the group consisting of corticosteroids, bronchodilators, antiasthmatics (mast cell stabilizers), antiinflammatories, antirheumatics, immunosuppressants, antimetabolites, immunomodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); steroids (inhaled, oral or topical) and interferons (immunomodulators).

According to other embodiments, the invention provides methods for preventing, inhibiting or suppressing cell adhesion-associated inflammation and cell adhesion-associated immune or autoimmune responses. VLA4-associated cell adhesion plays a central role in a variety of inflammation, immune and autoimmune diseases. Thus, inhibition of cell adhesion by the compounds of this invention may be utilized in methods of treating or preventing inflammatory, immune and autoimmune diseases including, but not limited to arthritis, asthma, allergies, adult respiratory distress syndrome, cardiovascular disease, thrombosis or harmful platelet aggregation, allograft rejection, neoplastic disease, psoriasis, multiple sclerosis, CNS inflammation, Crohn's disease, ulcerative colitis, glomerular nephritis and related inflammatory renal disease, diabetes, ocular inflammation (such as uveitis), atherosclerosis, inflammatory and autoimmune diseases. This invention also provides pharmaceutical formulations containing these VLA-4-mediated cell adhesion inhibitors and methods of using the compounds and compositions of the invention for inhibition of cell adhesion. Preferably the diseases to be treated with the methods of this invention are selected from asthma, arthritis, allergies, adult respiratory disress syndrome, cardiovascular disease, thrombosis or harmful platelet aggregation, allograft rejection, neoplastic disease, psoriasis, multiple sclerosis, CNS inflammation, Crohn's disease, ocular inflammation (such as uveitis), artherosclerosis, psoriasis, transplantation rejection, multiple sclerosis, diabetes and inflammatory bowel disease.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

Prep. of AX7

A)

To a solution of β-alanine t-butyl ester (67 mg, 0.124 mmol) in NMP (20 mL) at 0° C. was slowly added a solution of benzyl 2-bromoacetate in NMP (10 mL). The reaction mixture was stirred at 0° C. for 4 h and RT for 6 h. The mixture was diluted with EtOAc (150 mL), washed with water (50 mL×2), sat. NaCl (30 mL) and dried with $Na_2SO_4$. After removal of excess solvent, the residue was purified by flash chromatography using hexanes/EtOAc (1:1) as the eluent to give 210 mg (72%) of the amine. To a solution of this amine (160 mg, 0.55 mmol) in $CH_2Cl_2$ (20 mL) at 5° C. was added p-anisoyl chloride dropwise in the presence of $Et_3N$ (167 mg; 1.65 mmol). After stirring at RT for 18 h, the mixture was diluted with $Et_2O$ (150 mL), washed with 5% citric acid (30 mL), sat. $NaHCO_3$ (30 mL), sat. NaCl (30 mL) and dried with $Na_2SO_4$. After removal of excess solvent, the residue was purified by flash chromatography using hexane/EtOAc (2:1) as the eluent to give 230 mg (98%) of the desired product $^1H$ NMR ($CDCl_3$, 300 MHz, ppm) 7.33 (m, 7 H, Ar), 6.80 (m, 2 H, Ar), 5.15 (s, 2 H, Bn), 4.19 (m, 2 H), 3.79 (s, 3 H, OMe), 2.62 (m, 2 H), 2.55 (m, 2 H), 1.40 (s, 9 H); TLC, hexanes/EtOAc (1:1), $R_f$=0.43.

B)

The compound from step A (170 mg; 0.4 mmol), 10% $Pd(OH)_2$ (140 mg, 0.1 mmol) and EtOAc (30 mL) were stirred at RT under a $H_2$ (1 atm) atmosphere for 18 h. The mixture was filtered and the filtrate was concentrated at reduced pressure to give 100 mg (74%) of the desired compound $^1$H NMR (CDCl$_3$, 300 MHz, ppm) 7.32 (m, 2 H, Ar), 6.88 (m, 2 H, Ar), 4.16 (m, 2 H), 3.79 (s, 3 H, OMe), 3.67 (m, 2 H), 2.56 (m, 2 H), 1.40 (s, 9 H); TLC, 10% MeOH in CH$_2$Cl$_2$, R$_f$=0.09.

C)

The compound from step B (50 mg, 0.148 mmol) in DMF (1.0 mL) was activated with EDC HCl(34 mg, 0.178 mmol) for 15 min. The activated acid was coupled with (33 mg, 0.148 mmol) at RT for 18 h. The mixture was diluted with EtOAc, washed with 5% citric acid, sat. NaHCO$_3$, and dried with Na$_2$SO$_4$. The organic layer was concentrated under reduced pressure to give 67 mg (84%) of the desired compound $^1$H NMR (DMSO-d$^6$, 300 MHz, ppm) 9.60–6.61 (m, 10 H, Ar+NH), 4.25–3.30 (m, 9 H), 3.13–2.48 (m, 4 H), 1.54 (m, 2 H), 1.34 (s, 9 H), 1.18 (m, 1 H), 0.84 (m, 6 H); MS, m/z 540 (C$_{26}$H$_{33}$N$_3$O$_6$ of M$^+$+1 requires 540).

D)

A solution of the compound from step C (67 mg, 0.124 mmol) in CH$_2$Cl$_2$ (5 mL) was treated with TFA (5 mL). The reaction mixture was stirred at RT for 6 h, then concentrated under vacuum. The crude product was purified on a Vydac reverse-phase C18 column (22 mm×25 cm) using a linear gradient of 15% CH$_3$CN/H$_2$O (0.1% TFA) to 40% CH$_3$CN/H$_2$O (0.1% TFA) with a flow rate of 10 mL/min to give AX7 (10.0 mg, 17% isolated yield): $^1$H NMR (DMSO-d$^6$, 300 MHz, ppm) 9.94 (m, 1 H), 7.59–6.91 (m, 9 H), 4.36–4.03 (m, 4 H), 3.76 (s, 3 H, OMe), 3.53–3.11 (m, 4 H), 2.59 (m, 2 H), 1.52–0.71 (m, 9 H); MS, m/z 484 (C$_{26}$H$_{33}$N$_3$O$_6$ of M$^+$+1 requires 484).

Prep. of BX17

A)

To a solution of 2-methylamine-5-iodobenzoic acid (6.93 g; 25 mmol) and Na$_2$CO$_3$ (2.65 g) in water (70 mL) was added dropwise a solution of phosgene in toluene (1.93 M; 20 mL; 38.5 mmol). After stirring at RT for 4 h, the reaction mixture was filtered and the solids were collected. The solids were washed with water (100 mL×2) and dried to afford 5.9 g (78%) of the desired product. A mixture of the above solid (5.33 g, 17.6 mmol), β-alanine ethyl ester hydrochloride (3.07 g; 20 mmol), Et$_3$N (2.23 g, 22 mmol) and 4-dimethyl aminopyridine (50 mg; 0.41 mmol) in DMF (50 mL) was heated at 60° C. for 2 h. The mixture was concentrated in vacuo and the residue was diluted with EtOAc (90 mL), washed with water, sat. NaHCO$_3$, and sat. NaCl and dried with Na$_2$SO$_4$. After removal of excess solvent, 5.7 g (86%) of the desired compound was obtained: $^1$H NMR (CDCl$_3$, 300 MHz, ppm) 7.52–7.46 (m, 2 H, Ar+NH), 6.67 (s, 1 H, NH), 6.40 (d, J=8.7 Hz, 1 H, Ar), 4.14 (q, J=7.2 Hz, 2 H), 3.61 (q, J=6.0 Hz, 2 H), 2.79 (s, 3 H, N—Me), 2.58 (t, J=6.0 Hz, 3 H), 1.24 (t, J=7.1 Hz, 3 H); MS, m/z 399 (C$_{13}$H$_{17}$N$_2$O$_3$I of M$^+$+Na requires 399).

B)

A mixture of the compound from step A (3.76 g; 10 mmol), α-bromoacetyl bromide (3.03 g; 15 mmol), CH$_2$Cl$_2$ (25 mL) and water (25 mL) was stirred at RT for 2 h. After separation, the organic layer was washed with 5% citric acid, and sat. NaHCO$_3$ and dried with Na$_2$SO$_4$. After removal of excess solvent, 4.2 g (85%) of the desired compound was obtained: $^1$H NMR (CDCl$_3$, 300 MHz, ppm) 7.87–7.80 (m, 2 H, Ar), 7.06 (d, J=8.2 Hz, 1 H, Ar), 6.75 (s, 1 H, NH), 4.12 (q, J=7.1 Hz, 2 H), 3.73–3.57 (m, 4 H), 3.14 (s, 3 H, N—Me), 2.56 (t, J=5.8 Hz, 3 H), 1.22 (t, J=7.1 Hz, 3 H).

C)

A mixture of the compound from step B (3.1 g; 6.24 mmol) and Cs$_2$CO$_3$ (3.05 g; 9.36 mmol) in DMF (20 mL) was stirred at RT under nitrogen for 2 h. The mixture was diluted with EtOAc (90 mL), washed with water, 5% citric acid, and sat. NaHCO$_3$ and dried with Na$_2$SO$_4$. After removal of excess solvent, the residue was purified by flash chromatography using hexane/EtOAc (1:2) as the eluent to give 1.65 g (64%) of the desired compound: $^1$H NMR (DMSO-d$^6$, 300 MHz, ppm) 8.29 (d, J=1.8 Hz, 1 H), 7.76 (m, 1 H), 6.90 (d, J=8.6 Hz, 1 H), 4.10 (q, J=7.1 Hz, 2 H), 4.04–3.83 (m, 4 H), 3.32 (s, 3 H, N—Me), 2.77–2.56 (m, 2 H), 1.22 (t, J=7.1 Hz, 3 H); TLC, hexane/EtOAc (1:1), R$_f$=0.22.

D)

A mixture of the compound from step C (100 mg; 0.24 mmol), 2-methyl phenylureaphenylamine (87 mg; 0.36 mmol), PdCl$_2$(PPh$_3$)$_2$ (17 mg; 0.024 mmol) and Bu$_3$N (89 mg, 0.48 mmol) in DMF (10 mL) was heated at 100° C. under CO (1 atm) for 18 h. The mixture was diluted with EtOAc (90 mL), washed with 5% citric acid, and sat. NaHCO$_3$ and dried with Na$_2$SO$_4$. After removal of excess solvent, the residue was purified by flash chromatography using 5% MeOH in CH$_2$Cl$_2$ as the eluent to give 40 mg (30%) of the desired compound: $^1$H NMR (DMSO-d$^6$, 300 MHz, ppm) 9.18 (s, 1 H), 8.55 (s, 1 H), 8.19 (d, J=8.5 Hz, 1 H), 7.69 (s, 1 H), 7.41 (d, J=8.3 Hz, 3 H), 7.24–7.09 (m, 7 H), 4.10 (t, J=7.1 Hz, 2 H), 4.01–3.85 (m, 4 H), 3.36 (s, 3 H, N—Me), 2.70–2.59 (m, 2 H), 2.24 (s, 3 H, Me), 1.22 (t, J=7.1 Hz, 3 H); MS, m/z 580 (C$_{30}$H$_{31}$N$_5$O$_6$ of M$^+$+Na requires 580); TLC, 5% MeOH in CH$_2$Cl$_2$, R$_f$=0.56.

E)

A solution of the compound from step D (20 mg, 0.036 mmol) in MeOH (4 mL) was treated with aqueous LiOH (2N, 2 mL). The reaction mixture was stirred at RT for 2 h, then acidified with TFA (until pH=5–6). The product was purified on a Vydac reverse-phase C18 column (22 mm×25 cm) using a linear gradient of 15% CH$_3$CN/H$_2$O (0.1% TFA) to 27% CH$_3$CN/H$_2$O (0.1% TFA) with a flow rate of 10 mL/min to give BX17 (12.0 mg, 63% isolated yield): $^1$H NMR (DMSO-d$^6$, 300 MHz, ppm) 9.02 (s, 1 H), 8.34 (s, 1 H), 8.16 (d, J=8.5 Hz, 1 H), 7.91–6.90 (m, 11 H), 4.11–3.75 (m, 4 H), 3.33 (s, 3 H, N—Me), 2.88–2.56 (m, 2 H), 2.24 (s, 3 H, Me); MS, m/z 530 (C$_{28}$H$_{27}$N$_5$O$_6$ of M$^+$+1 requires 530)

Prep. of BX31

A)

To a solution of 3-methyl-4-nitrobenzoic acid (3.62 g, 20 mmol) in pyridine (48 mL) at RT was added benzene sulfonyl chloride (7.1 g, 40 mmol). After stirring for 10 min, the mixture was cooled to 5° C. and t-butyl alcohol (4.44 g, 60 mmol) was added. The resulting mixture was stirred at RT for 2 h. The mixture was poured into a mixture of ice and water (200 mL; 1:1). The solids were collected and washed with water (30 mL×3). After drying under vacuum, 4.6 g (97%) of the ester was obtained.

To a solution of the above ester (3.55 g, 15 mmol) in CCl$_4$ (50 mL) at RT was added N-bromosuccinimide (2.94 g, 16.5 mmol) and benzoxyl peroxide (182 mg, 0.75 mmol). The mixture was refluxed for 18 h. After removal of excess solvent, the residue was purified by flash chromatography using hexanes/EtOAc (19:1) as the eluent to give 1.90 g (40%) of the bromide as a yellow oil.

A solution of the bromide (1.57 g, 10 mmol) in CH$_2$Cl$_2$ (20 ml) was added to a solution of methyl amine (2 N in THF; 30 mL; 60 mmol) at RT over a period of 60 min. The resulting mixture was stirred at RT for 18 h and then concentrated in vacuo. The residue was dissolved in CH$_2$Cl2 (80 mL), washed with sat. NaHCO$_3$ (20 mL), and sat. NaCl (20 mL) and dried with Na$_2$SO$_4$. After removal of excess solvent, the residue was purified by flash chromatography using hexanes/EtOAc (1:1) as the eluent to give 810 mg (61%) of the desired compound as light yellow oil $^1$H NMR (CDCl$_3$, 300 MHz, ppm) 8.47 (s, 1 H), 8.15 (d, J=8.0 Hz, 1 H), 7.69 (d, J=8.0 Hz, 1 H), 4.02 (s, 2 H, Bn), 2.43 (s, 3 H, Me), 1.62 (s, 1 H, NH), 1.58 (s, 9 H); TLC, hexanes/EtOAc (1:1), R$_f$=0.27.

B)

A mixture of the compound from step A (810 mg; 3.05 mmol), di-t-butyl dicarbonate (1.33 g, 6.1 mmol) and Et$_3$N (926 mg, 9.15 mmol) in CH$_2$Cl$_2$ (50 mL) was stirred for 18 h. The mixture was diluted with CH$_2$Cl$_2$ (50 mL), washed with 5% citric acid, and sat. NaHCO$_3$ and dried with Na$_2$SO$_4$. After removal of excess solvent, the residue was purified by flash chromatography using hexanes/EtOAc (3:1) as the eluent to give 1.06 g (95%) of the product.

A mixture of protected amine (1.06 g; 2.9 mmol), 10% Pd/C (300 mg, 0.28 mmol) and EtOH (40 mL) was stirred at RT under a H$_2$ (50 psi) atmosphere for 18 h. The mixture was filtered and the filtrate was concentrated at reduced pressure. The residue was purified by flash chromatography using hexanes/EtOAc (4:1) as the eluent to give 620 mg (64%) of the desired compound: $^1$H NMR (CDCl$_3$, 300 MHz, ppm) 7.72–7.65 (m, 2 H, Ar), 6.56 (d, J=8.3 Hz, 1 H, Ar), 5.06 (s, 2 H, NH), 4.32 (s, 2 H, Bn), 2.73 (s, 3 H, Me), 1.55 (s, 9 H), 1.45 (s, 9 H); TLC, hexanes/EtOAc (3:1), R$_f$=0.49.

C)

A mixture of the compound from step B (0.62 g; 1.84 mmol) and dimethyl acetylene dicarboxylate (275 mg; 1.93 mmol) in MeOH (30 mL) was refluxed under a nitrogen atmosphere for 1 h. After removal of excess solvent, 0.85 g (96%) of the adducts was obtained. A mixture of these adducts (0.85 g, 1.78 mmol), 10% Pd/C (300 mg, 0.28 mmol) and EtOH (40 mL) was stirred at RT under a H$_2$ (40 psi) atmosphere for 5 h. The mixture was filtered and the filtrate was concentrated at reduced pressure. The residue was purified by flash chromatography using hexanes/EtOAc (3:1) as the eluent to afford 0.75 g (88%) of reduced product.

A solution of the above reduced product (0.99 g, 2.06 mmol) in CH$_2$Cl$_2$ (30 mL) at RT was treated with TFA (10 mL) The reaction mixture was stirred for 2 h. The mixture was concentrated at reduced pressure to afford 0.68 g (99%) of the desired product as the TFA salt: $^1$H NMR (DMSO-d$^6$, 300 MHz, ppm)8.57 (s, 1 H, NH), 7.89 (s, 1 H, Ar), 7.79 (d, J 9.0 Hz, 1 H, Ar), 6.76 (d, J=8.8 Hz, 1 H, Ar), 6.34 (d, J=8.6 Hz, 1 H, NH), 4.64 (m, 1 H), 3.64 (s, 3 H, Me), 3.61 (s, 3 H, Me), 3.05–2.87 (m, 2 H), 2.43 (s, 3 H, N—Me); MS, m/z 325 (C$_{15}$H$_{20}$N$_2$O$_6$ of M+1 requires 325); TLC, 10% MeOH in CH$_2$Cl$_2$, R$_f$=0.13.

D)

A mixture of the compound from step C (200 mg; 0.62 mmol) and NaOMe (0.5 N; 2.47 mL; 1.23 mmol) in MeOH (30 mL) was refluxed under a nitrogen atmosphere for 5 h. After cooling to 0° C., HCl (1 N, 2 mL) was added. After removal of excess solvent, the residue was purified by flash chromatography using MeOH/CH$_2$Cl$_2$ (1:9) as the eluent to give 110 mg (82%) of the desired acid as a light yellow solid: $^1$H NMR (DMSO-d$^6$, 300 MHz, ppm) 7.58 (s, 1 H, Ar), 7.53 (d, J=8.5 Hz, 1 H, Ar), 6.62 (s, 1 H, NH), 6.56 (d, J=8.5 Hz, 1 H, Ar), 5.45 (d, J=16.4 Hz, 1 H, Bn), 5.16 (s, 1 H), 3.92 (d, J=16.6 Hz, 1 H, Bn), 3.59 (s, 3 H, Me), 2.90 (s, 3 H, Me), 2.76 (m, 2 H); MS, m/z 293 (C$_{14}$H$_{16}$N$_2$O$_5$ of M+1 requires 293); TLC, 10% MeOH in CH$_2$Cl$_2$, R$_f$=0.47.

E)

The acid from step D(45 mg, 0.154 mmol) in DMF (1.0 mL) was activated with EDC.HCl (35.5 mg, 0.185 mmol) for 15 min. The activated acid was coupled with 2-methylphenylureaphenylamine (41 mg, 0.169 mmol) at RT for 72 h. The mixture was diluted with EtOAc, washed with 5% citric acid, and sat. NaHCO3 and dried with Na$_2$SO$_4$. The organic solution was concentrated under reduced pressure to give the desired compound in 82% yield: $^1$H NMR (DMSO-d$^6$, 300 MHz, ppm) 9.70–6.40 (m, 15 H), 5.50 (m, 1 H, Bn), 5.11 (m, 1 H), 3.90 (m, 1 H, Bn), 3.60 (s, 3 H, OMe) 2.92 (s, 3 H, Me), 2.81–2.48 (m, 2 H), 2.23 (s, 3 H, Me); MS, m/z 538 (C$_{28}$H$_{29}$N$_5$O$_5$ of M+Na requires 538).

F)

A solution of the compound from step E (65 mg, 0.13 mmol) in MeOH (3 mL) was treated with aqueous LiOH (2 N, 1 mL). The reaction mixture was stirred at RT for 2 h, then acidified with TFA (until pH=5–6). The product was purified on a Vydac reverse-phase C18 column (22 mm×25 cm) using a linear gradient of 15% CH$_3$CN/H$_2$O (0.1% TFA) to 32% CH$_3$CN/H$_2$O (0.1% TFA) with a flow rate of 10 mL/min to give BX31 (15 mg, 23% isolated yield): $^1$H NMR (DMSO-d$^6$, 300 MHz, ppm) 9.73 (s, 1 H), 8.94 (s, 1 H), 7.89–6.40 (m, 13 H), 5.52 (d, J=16.6 Hz, 1 H), 5.11 (m, 1 H), 3.88 (d, J=16.6 Hz, 1 H), 2.94 (s, 3 H, NMe), 2.82–2.52 (m, 2 H), 2.23 (s, 3 H, Me); MS, m/z 502 (C$_{27}$H$_{27}$N$_5$O$_5$ of M$^+$+1 requires 502)

Prep. of BX36

A)

To a solution of 4-methyl-3-nitrobenzoic acid (10 g, 55 mmol) in pyridine (100 mL) at RT was added benzene sulfonyl chloride (19.4 g, 110 mmol). After stirring for 10 min., the mixture was cooled to 5° C. and t-butyl alcohol (12.2 g, 165 mmol) was added. The resulting mixture was stirred at RT for 2 h. The mixture was poured into a mixture of ice and water (500 mL; 1:1). The solids were collected and washed with water (30 mL×3). After drying under vacuum, 12.5 g (96%) of ester was obtained.

To a solution of the above ester (7.1 g, 30 mmol) in CCl$_4$ (50 mL) at RT was added N-bromosuccinimide (5.88 g, 32 mmol) and benzoyl peroxide (727 mg, 3 mmol). The mixture was refluxed for 18 h. After removal of excess solvent, the residue was purified by flash chromatography using hexanes/EtOAc (19:1) as the eluent to give 8.0 g (91%) of the bromide as a yellow oil. A solution of the bromide (3.16 g, 10 mmol) in CH$_2$Cl$_2$ (20 ml) was added to a solution of methyl amine (2 N in THF; 30 mL; 60 mmol) at RT over a period of 60 min. The resulting mixture was stirred at RT for 18 h and concentrated in vacuo. The residue was dissolved in CH$_2$Cl$_2$ (80 mL), washed with sat. NaHCO$_3$ (20 mL), and sat. NaCl (20 mL) and dried with Na$_2$SO$_4$. After removal of excess solvent, the residue was purified by flash chromatography using hexanes/EtOAc (1:1) as the eluent to give 1.43 g (54%) of the desired amine as a light yellow oil: $^1$H NMR (CDCl$_3$, 300 MHz, ppm) 8.47 (s, 1 H), 8.15 (d, J=8.0 Hz, 1 H), 7.69 (d, J=8.0 Hz, 1 H), 4.02 (s, 2 H, Bn), 2.43 (s, 3 H, Me), 1.62 (s, 1 H, NH), 1.58 (s, 9 H); TLC, 10% MeOH in CH$_2$Cl$_2$, R$_f$=0.49.

B)

A mixture of the compound from step A (1.09 g; 3.45 mmol), di-t-butyl dicarbonate (1.5 g, 6.9 mmol) and Et$_3$N (1.05 g, 10.35 mmol) in CH$_2$Cl$_2$ (50 mL) was stirred for 18 h. The mixture was diluted with CH$_2$Cl$_2$ (50 mL), washed with 5% citric acid, and sat. NaHCO$_3$ and dried with Na$_2$SO$_4$. After removal of excess solvent, the residue was purified by flash chromatography using hexane/EtOAc (3:1) as the eluent to give 1.16 g (92%) of the product.

A mixture of the protected amine (1.16 g; 3.17 mmol), 10% Pd/C (300 mg, 0.28 mmol) and EtOH (40 mL) was stirred at RT under a H$_2$ (50 psi) atmosphere for 18 h. The mixture was filtered and the filtrate was concentrated at reduced pressure. The residue was purified by flash chromatography using hexanes/EtOAc (4:1) as the eluent to give 0.78 g (73%) of the desired compound: $^1$H NMR (CDCl$_3$, 300 MHz, ppm) 7.25–7.0 (m, 3 H, Ar), 4.60 (s, 2 H, NH), 4.34 (s, 2 H, Bn), 2.71 (s, 3 H, Me), 1.54 (s, 9 H), 1.45 (s, 9 H); TLC, hexanes/EtOAc (4:1), R$_f$=0.29.

C)

A mixture of the compound from step B (0.78 g; 2.32 mmol) and dimethyl acetylene dicarboxylate (363 mg; 2.55 mmol) in MeOH (30 mL) was refluxed under a nitrogen atmosphere for 2 h. After removal of excess solvent, 1.05 g (95%) of the adducts was obtained. A mixture of these adducts (1.05 g, 2.2 mmol), 10% Pd/C (300 mg, 0.28 mmol) and EtOH (40 mL) was stirred at RT under a H$_2$ (50 psi) atmosphere for 6 h. The mixture was filtered and the filtrate was concentrated at reduced pressure to afford 0.99 g (94%) of the reduced product.

A solution of the above reduced product (0.99 g, 2.06 mmol) in CH$_2$Cl$_2$ (30 mL) at RT was treated with TFA (15 mL) The reaction was stirred for 4 h. The mixture was concentrated at reduced pressure to afford 0.90 g (99%) of the desired compound as the TFA salt: $^1$H NMR (DMSO-d$^6$, 300 MHz, ppm) 8.63 (s, 1 H), 7.37–7.26 (m, 3 H, Ar), 5.96 (d, J=8.8 Hz, 1H, NH), 4.53 (m, 1 H), 4.15 (m, 2H, Bn), 3.64 (s, 3 H, Me), 3.62 (s, 3 H, Me), 3.04–2.85 (m, 2H), 2.57 (s, 3 H, Me); TLC, 10% MeOH in CH$_2$Cl$_2$, R$_f$=0.22.

D)

A mixture of the compound from step C (550 mg; 1.70 mmol) and NaOMe (0.5 N; 6.8 mL; 3.4 mmol) in MeOH (60 mL) was refluxed under a nitrogen atmosphere overnight. After cooling to 0 $^E$C, HCl (1 N, 5 mL) was added. After removal of excess solvent, the residue was purified by flash chromatography using MeOH/CH$_2$Cl$_2$ (1:9) as the eluent to give 200 mg (40%) of the desired acid as a light yellow solid: $^1$H NMR (DMSO-d$^6$, 300 MHz, ppm) 7.18 (s, 1 H, Ar), 7.04 (s, 2 H, Ar), 6.17 (s, 1 H, NH), 5.47 (t, J=6.6, 1 H), 5.07 (m, 3 H, OMe), 3.89 (d, J=6.6 Hz, 2 H), 3.58 (s, 3 H, Me), 2.89 (s, 3 H, Me), 2.83–2.60 (s, 2 H); MS, m/z 291 (C$_{14}$H$_{16}$N$_2$O$_5$ of M-1 requires 291); TLC, 10% MeOH in CH$_2$Cl$_2$, R$_f$=0.22.

E)

The acid from step D (50 mg, 0.17 mmol) in DMF (0.5 mL) was activated with EDC (39 mg, 0.204 mmol) for 15 min. The activated acid was coupled with 2-methylphenylureaphenylamine (45 mg, 0.188 mmol) at RT for 96 h. The mixture was diluted with EtOAc, washed with 5% citric acid, and sat. NaHCO$_3$ and dried with Na$_2$SO$_4$. The organic solution was concentrated under reduced pressure to give the desired compound in 10% yield: $^1$H NMR (DMSO-d$^6$, 300 MHz, ppm) 9.97–8.57 (m, 2 H), 7.95–6.50 (m, 12 H), 6.10 (m, 1H), 5.50 (m, 1 H, Bn), 4.98 (m, 1 H), 3.90 (m, 1 H, Bn), 3.58 (s, 3 H, OMe), 2.90 (s, 3 H, Me), 2.89–2.55 (m, 2 H), 2.20 (s, 3 H, Me); MS, m/z 538 (C$_{28}$H$_{29}$N$_5$O$_5$ of M+Na requires 538).

F)

A solution of the compound from step E (9.0 mg, 0.017 mmol) in MeOH (3 mL) was treated with aqueous LiOH (2 N, 1 mL). The reaction mixture was stirred at RT for 2 h, then acidified with TFA (until pH=5–6). The product was purified on a Vydac reverse-phase C18 column (22 mm×25 cm) using a linear gradient of 15% CH$_3$CN/H$_2$O (0.1% TFA) to 32% CH$_3$CN/H$_2$O (0.1% TFA) with a flow rate of 10 mL/min to give BX36 (3.0 mg, 35% isolated yield): $^1$H NMR (DMSO-d$^6$, 300 MHz, ppm) 9.98 (s, 1 H), 8.98 (s, 1 H), 7.89–6.92 (m, 12 H), 6.06 (s, 1 H), 5.48 (d, J=6.6 Hz, 1 H), 5.03 (m, 1 H), 3.89 (d, J=6.6 Hz, 1 H), 2.91 (s, 3 H, NMe), 2.75–2.53 (m, 2 H), 2.23 (s, 3 H, Me); MS, m/z 502 (C$_{27}$H$_{27}$N$_5$O$_5$ of M$^+$+1 requires 502)

Preparation of BX47

A. A slurry of N-methylisatoic anhydride (10.12 g, 57.15 mmol) and glycine (4.29 g, 57.17 mmol) in glacial acetic acid (125 mL) was heated at 120° C. for 3.5 h. The reaction solution was then concentrated in vacuo to a thick oil and ether (100 mL) was added. The resulting solids were filtered, rinsed with ether and air dried to give 8.80 g of a tan solid. The solid was slurried with CHCl$_3$ (250 mL) for 1 h. The solution was filtered and the filtrate was concentrated in vacuo to give 7.43 g (68% yield) of a tan solid identified as the desired product: MS (ESP+) 190.9 m/z; $^1$H NMR (CDCl$_3$, 300 MHz, ppm) 3.38 (s, 3H), 3.78–3.83 (m, 2H), 6.85 (br t, 1H), 7.20–7.34 (m, 2H), 7.52–7.58 (m, 1H), 7.88 (dd, J=7.81, 1.65 Hz, 1H).

B. The compound from procedure A (1.52 g, 8.01 mmol), anhydrous CsF (1.22 g, 8.03 mmol), tetraethyl orthosilicate (1.79 mL, 8.03 mmol) and ethyl acrylate (0.96 mL, 8.86 mmol) were slurried in anhydrous THF (8.0 mL) at room temperature for 26 h. The reaction mixture was then filtered through Celite, the filtrate concentrated in vacuo and the resultant solid purified by flash column chromatography (CHCl$_3$ 6 10:1 CHCl$_3$/ether) to give 1.63 g (70% yield) of a light yellow solid identified as the desired product: MS (ESP+) 291 m/z; $^1$H NMR (CDCl$_3$, 300 MHz, ppm) 1.24 (t, J=7.12 Hz, 3H), 2.60–2.78 (m, 2H), 3.37 (s, 3H), 3.94 (ABq, J=14.86 Hz,)L=52.41 Hz, 2H), 3.92 (t, J=7.01 Hz, 2H), 4.13 (q, J=7.10 Hz, 2H), 7.17 (d, J=8.07 Hz, 1H), 7.29 (d, J=8.57 Hz, 1H), 7.50 (dt, J=7.78, 1.67 Hz, 1H), 7.84 (dd, J=7.83, 1.63 Hz, 1H).

C. The compound from procedure B (1.61 g, 5.55 mmol) was dissolved in iced fuming nitric acid (7.4 mL). The reaction solution was allowed to slowly warm to room temperature and after 2 h poured into a mixture of saturated aqueous NaHCO$_3$ (100 mL)/ice (100 g). The slurry was brought to neutral pH with solid NaHCO$_3$. The aqueous solution was extracted with ethyl acetate (4×100 mL). The combined organic phases were washed with water (1×100 mL) and saturated aqueous NaCl (1×100 mL), dried (MgSO$_4$) and concentrated in vacuo to give 1.83 g (98% yield) of a yellow oil identified as the desired product: MS (ESP+) 336, 358 m/z; $^1$H NMR (CDCl$_3$, 300 MHz, ppm) 1.25 (t, J=7.10 Hz, 3H), 2.62–2.81 (m, 2H), 3.42 (s, 3H), 3.90–3.95 (m, 2H), 4.01 (s, 2H), 4.13 (q, J=7.17 Hz, 2H), 7.32 (d, J=9.05 Hz, 1H), 8.33 (dd, J=8.97, 2.70 Hz, 1H), 8.73 (d, J=2.71 Hz, 1H).

D. A slurry of the compound from procedure C (1.82 g, 5.44 mmol) and <10 micron Fe powder (0.91 g, 16.99 mmol) in 2:1 ethanol/water (54 mL) was heated to reflux and glacial acetic acid (0.63 mL, 11.01 mmol) was added. After 2 h the hot reaction mixture was filtered through Celite and the pad washed with hot ethanol (3×50 mL). The filtrate was concentrated in vacuo, dissolved in ethyl acetate (125 mL), washed with saturated aqueous NaHCO$_3$ (2×40 mL), water (1×40 mL) and saturated aqueous NaCl (1×40 mL), dried (MgSO$_4$) and concentrated in vacuo to give a yellow solid. The solid was dissolved in 1:1 CHCl$_3$/THF, passed through a silica gel plug and concentrated in vacuo to give 1.20 g (72% yield) of a yellow foam identified as the desired product: MS (ESP+) 306.1, 328.2 m/z; $^1$H NMR (CDCl$_3$, 300 MHz, ppm)*1.21(t, J=7.13 Hz, 3H), 2.57–2.76 (m, 2H), 3.27 (s, 3H), 3.63 (br s, 1H), 3.87 (t, J=7.25 Hz, 2H), 3.89 (ABq, J=14.69 Hz,)L=77.45 Hz, 2H), 4.10 (q, J=7.12 Hz, 2H), 6.79 (dd, J=8.84, 2.56 Hz, 1H), 6.95(d, J=8.66 Hz, 1H), 7.07 (d, J=2.56 Hz, 1H)

E. 4-o-tolylureidophenylacetic acid (0.57 g, 2.00 mmol), EDC HCl (0.43 g, 2.24 mmol) and the compound from procedure D (0.61 g, 2.00 mmol) were dissolved in anhydrous DMF (10 mL) at room temperature under an atmosphere of nitrogen. After stirring for 3 d the reaction was quenched with water (30 mL). The resultant slurry was stirred for 24 h and filtered. The tan precipitate was washed with 5% aqueous citric acid (2×20 mL), 10% aqueous NaHCO$_3$ (3×20 mL) and water (2×20 mL) and dried in vacuo to give 0.76 g (66% yield) of a tan solid identified as the desired product: MS (ESP+) 572.4, 594.5 m/z; $^1$H NMR (acetone-d$_6$, 300 MHz, ppm) 1.19 (t, J=7.17 Hz, 3H), 2.25 (s, 3H), 2.62–2.68 (m, 2H), 3.31 (s, 3H), 3.64 (s, 2H), 3.78–3.96 (m, 2H), 3.96 (ABq, J=14.87 Hz,)L=86.48 Hz, 2H), 4.07 (q, J=7.08 Hz, 2H), 6.94 (dd, J=8.42, 7.51 Hz, 1H), 7.13 (dd, J=7.90, 5.36 Hz, 2H), 7.27–7.32 (m, 3H), 7.47–7.59 (m, 3H), 7.91–7.94 (m, 3H), 8.40 (s, 1H), 9.46 (s, 1H)

F. 1.0 M sodium trimethylsilanolate/CH$_2$Cl$_2$ (4.0 mL, 4.0 mmol) was added to a solution of the compound from procedure E (0.57 g, 0.99 mmol) in anhydrous THF (100 mL) under an atmosphere of nitrogen at room temperature. After stirring for 5 h the reaction was filtered and the precipatate washed with THF. The precipate was slurried with 1:1 glacial acetic acetic acid/ether (10 mL) for 22 h, filtered, washed with 1:1 glacial acetic acid/ether (3×10 mL) and ether and air dried to give 0.42 g (78% yield) of a white solid identified BX47: MS (ESP+) 544.2, 566.2 m/z; $^1$H NMR (acetone-d$_6$, 300 MHz, ppm)2.14 (s, 3H), 2.56 (t, J=7.10 Hz, 1H), 2.57 (t, J=7.50 Hz, 1H), 3.20 (s, 3H), 3.53 (s, 2H), 3.72–3.77 (m, 2H), 3.87 (ABq, J=15.13 Hz,)L= 75.08 Hz, 2H), 6.82–6.85 (m, 1H), 7.01–7.05 (m, 2H), 7.27 (ABq, J=8.59 Hz,)L=60.76 Hz, 4H), 7.16–7.21 (m, 1H), 7.80–7.84 (m, 3H), 8.28 (s, 1H), 9.34 (s, 1H).

Preparation of RX18

A. Triethylamine (0.35 mL, 2.51 mmol) was added to a slurry of "-bromo-3-nitrotoluene (0.22 g, 1.04 mmol) and β-ethylalanineAHCl (0.19 g, 1.24 mmol) in anhydrous THF (5 mL) under an atmosphere of nitrogen. The reaction was stirred at room temperature for 24 h and at 60 EC for 18 h, cooled to room temprature, diluted with ethyl acetate (50 mL), washed with water (1×15 mL), 5% aqueous NaHCO$_3$ (1×15 mL) and saturated aqueous NaCl (1×15 mL), dried (MgSO$_4$) and concentrated in vacuo to give a yellow oil. The oil was purified by flash column chromatography (2:1 ethyl acetate/hexanes) to give 0.22 g (84% yield) of a yellow oil identified as the desired product: $^1$H NMR (CDCl$_3$, 300 MHz, ppm) 1.24 (t, J=7.16 Hz, 3H), 1.68 (br s, 1H), 2.52 (t, J=6.30 Hz, 2H), 2.88 (t, J=6.31 Hz, 2H), 3.89 (s, 2H), 4.13 (q, J=7.14 Hz, 2H), 7.47 (t, J=7.89 Hz, 1H), 7.66 (d, J=7.52 Hz, 1H), 8.09 (d, J=8.12 Hz, 1H), 8.02 (s, 1H).

B. A solution of the compound from procedure A (0.072 g, 0.28 mmol), anhydrous pyridine (0.035 mL, 0.43 mmol) and benzoyl chloride (0.050 mL, 0.43 mmol) was stirred at 0° C. for 2 h. The reaction solution was then diluted with ethyl acetate (14 mL), washed with 5% aqueous citric acid (2×5 mL), 10% aqueous NaHCO$_3$ (2×5 mL), water (1×5 mL) and saturated aqueous NaCl (1×5 mL), dried (MgSO$_4$) and concentrated in vacuo to give a thick oil. The oil was purified by flash column chromatography (95:5 chloroform/ether) to give 0.089 g (92% yield) of a colorless oil identified as the desired product: $^1$H NMR (CDCl$_3$, 300 MHz, ppm) 1.23 (br s 3H), 2.50 (br s, 1H), 2.72 (br s, 1H), 3.65 (br s, 2H), 4.10 (br s, 2H), 4.73 (br s, 2H), 7.40 (s, 5H), 7.53 (t, J=7.81 Hz, 1H), 7.60 (br s, 1H), 8.00 (br s, 1H), 8.14 (d, J=7.13 Hz, 1H).

C. A slurry of 10% Pd/C (0.016 g, 0.15 mmol) and the compound from procedure B (0.086 g, 0.25 mmol) in 2:1 ethanol/ethyl acetate (1.8 mL) was subjected to an H$_2$ atmosphere (60 psi) at room temperature for 18 h. The reaction was then filtered through Celite, washing the pad extensively with ethyl acetate. The combined washes were concentrated in vacuo to give 0.80 g (95% yield) of an orange oil identified as the desired product: MS (ESP+) 327 m/z; $^1$H NMR (CDCl$_3$, 300 MHz, ppm) the peaks were very broad but consistent with the desired product.

D. A solution of the product from procedure C (0.077 g, 0.24 mmol), 4-o-tolylureidophenylacetic acid (0.075 g, 0.26 mmol), TBTU (0.089 g, 0.28 mmol) and diisopropylethylamine (0.046 mL, 0.26 mL) in NMP (0.60 mL) at room temperature under an atmosphere of nitrogen was stirred for 3 d. It was then diluted with ethyl acetate (25 mL), washed with 5% aqueous citric acid (2×6 mL), 5% aqueous NaHCO$_3$ (2×6 mL), water (1×6 mL) and saturated aqueous NaCl (1×6 mL), dried (MgSO$_4$) and concentrated in vacuo to give a yellow oil. The oil was purified by flash column chromatography (99:1 chloroform/methanol-98:2 chloroform/methanol) to give 0.11 g (78% yield) of a white glass identified as the desired product: MS (ESP+) 593, 615 m/z; $^1$H NMR (CDCl$_3$, 300 MHz, ppm) the peaks were very broad but consistent with the desired product.

E. A solution of the product from procedure D (0.047 g, 0.079 mmol) and lithium hydroxide hydrate (0.021 g, 0.51 mmol) in 2:1 THF/water (3 mL) was stirred at room temperature for 4 h. The reaction was then quenched with glacial acetic acid and concentrated in vacuo to give a white solid. The solid was purified by flash column chromatography (98:1:1 chloroform/methanol/acetic acid-94:5:1 chloroform/methanol/acetic acid) to give, after lyophilization, 0.037 g (82% yield) of a white glass identified as RX18: MS (ESP+) 565, 587 m/z; $^1$H NMR (DMSO-d$_6$, 300 MHz, ppm) 2.23 (F, 3/), 2.48–2.59 (m, 2/), 3.31–3.70 (m, 4/), 4.44 (F, 1/), 4.66 (F, 1/), 6.84–7.56 (m, 16H), 7.83 (d, J=7.55 Hz, 1H), 7.88 (s, 1H), 8.89 (s, 1H), 10.17 (s, 1H).

General Procedure for the Synthesis of 1,4-benzodiazepine-2,5-diones on Solid Support.

Analogs of β-Alanine.

A. Wang resin loaded with Fmoc-protected β-alanine (7.0 g, 2.8 mmol) was treated with 20% piperidine in dimethylformamide (75 mL) for 15 minutes. The resin was then washed with dimethylformamide (3×75 mL), methanol (1×75 mL) and dichloromethane (3×75 mL). B. A solution of 2-fluoro-5-nitrobenzoic acid (5.18 g, 28.0 mmol) and diisopropylcarbodiimide (4.4 mL, 28.0 mmol) in N-methylpyrrolidinone (50 mL) was added to the resin. After the resin was mechanically shaken for over 5 hours, the resin was washed with N-methylpyrrolidinone (3×10 mL) and dichloromethane (3×75 mL). C. The resin was separated into 14 equal(by weight) portions and placed into separate reactors. To each reactor with resin was added a 0.20 M solution (10 mL) of a primary amine in N-methylpyrrolidinone. Some representative primary amines used in this step were: Benzylamine, Phenethylamine, sec-Butylamine, Tetrahydrofurylamine, Glycine methyl ester, β-Alanine ethyl ester, Valine methyl ester, β-Alanine t-butyl ester, 2-Amino 1-methoxypropane, Isobutylamine, (Aminomethyl)cyclopropane, 4-Amino-1-benzylpiperidine, 4-Fluorobenzylamine and cyclohexylamine. Each resin was mechanically shaken for 20 hours. The resins were washed with N-methylpyrrolidinone (3×10 mL) and dichloromethane (2×10 mL). D. Each resin was then treated with 2.0 g (8.86 mmol) of tin(II) chloride dihydrate in 10 mL of 1/1 ethanol/N-methylpyrrolidinone for 1 hour at 80° C. The resins were washed with N-methylpyrrolidinone (2×10 mL), 0.5% solution of sodium bicarbonate in 1/1 water/N-methylpyrrolidinone (5×10 mL), N-methylpyrrolidinone (5×10 mL) and dichloromethane. E.

To each resin was added a mixture of 4-(2-tolylureido)phenylacetic acid (570 mg, 2.0 mmol) and diisopropylcarbodiimide (0.315 mL, 2 mmol) in 5 mL of N-methylpyrrolidinone. The resins were mechanically shaken for 5 hours. Then, each resin was washed with N-methylpyrrolidinone (3×10 mL) and dichloromethane (2×10 mL).

F. To each reactor of resin was added a 0.2 M solution of bromoacetyl bromide in N-methypyrrolidinone (10 mL) and diisopropylethylamine (0.350 mL, 2.0 mmol). After 5 hours of continuously mechanical shaking, each resin was washed with N-methylpyrrolidinone (5×10 mL). G. To each resin was added 0.2 M solution of 1,8-diazabicyclo[5.4.0]undec-7-ene (10 mL). The resins were mechanically shaken for over 5 hours, washed with N-methylpyrrolidinone (3×10 mL), dichloromethane (3×10 mL) and then dried. H. To each resin was added a solution of trifluoroacetic acid/water, 9.5/0.5 (5.0 mL). The resins were shaken for over 30 minutes. The resins were filtered. Each acid solution was collected in a separate 50-mL centrifuge tube. To each tube was added ethyl ether (30 mL). Each tube was spun down for 5 minutes. The ether was discarded. The crude products (pellets) were purified by RP-HPLC to give the corresponding 1,4-benzodiazepine-2,5 diones. Examples: BX58, MS, m/z 620; BX52, MS, m/z 634; BX49, MS, m/z 586; BX40, MS, m/z 612; BX55, MS, m/z 614; BX39, MZ, m/z 602; BX57, MS, m/z 602; BY84, MS, m/z 630; BX63, MS, m/z 644; BX53, MS, m/z 586; BX54, MS, m/z 602; BX46, MS, m/z 584; BX43, MS, m/z 703; BX48, MS, m/z 638.

DL-3-Aminobutyric acid analogs.

Exactly the same procedure as described for the β-Alanine analogs was applied with Fmoc-DL-aminobutyric acid Wang resin (0.476 g, 0.20 mmol). The ratio of resin to solvents and reagents was proportional to that procedure. In step C, a 0.20 M solution of β-alanine t-butyl ester (10 mL) in N-methylpyrrolidinone was added to the resin. After step H was completed, there was obtained BY76, MS, m/z 616.

General Procedures for the Synthesis of Peptoids

Procedure A

1. To 4-nitrophenylisocyanate (60.0 mmol) in $CH_2Cl_2$ (100 mL) was added Aniline or substituted Aniline (60.0 mmol), at RT The reaction mixture was stirred at RT for 1.5 hrs. The solid urea product was filtered, washed with $CH_2Cl_2$ (3×100 mL) and ether (3×100 mL). Then, the urea product was air dryed.

Precursor to E-1:

Yield: 94%; $^1$H NMR (DMSO-$d_6$, 300 MHz, ppm): 8.52 (d,1H), 8.2–8.4 (m, 2H), 7.78–7.9 (m, 4H), 7.06–7.35 (m, 1H), 2.35 (s, 3H) ; MS (FAB): 272.2.

Precursor to E-2:

Yield: 95%; $^1$H NMR (MeOH-$d_4$, 300 MHz, ppm): 8.4 (d,2H), 7.86 (d, 2H), 7.65 (d, 2H), 7.51 (t, 2H), 7.35 (t, 1H); MS (FAB): 258.

2. To the product from step A (15.0 mmol) in ethanol (30 mL), was added tin(II) chloride dihydrate (45.0 mmol, Aldrich) and the resulting mixture was refluxed at 75° C. (using an oil bath) for 2.5 hrs. The reaction mixture was cooled down with an ice bath and 1N HCl was added to acidify the solution. The acidified reaction mixture was washed with EtOAc (3×100 mL). The aqueous extracts were combined and the pH was brought to 10–12, using saturated $K_2CO_3$ solution., This was extracted with EtOAc (3×100 mL). The EtOAc extracts were combined and washed with saturated $NaHCO_3$ solution and dryed over anhydrous $MgSO_4$. Filtration and concentration in vacuo provided pure product.

E-1:

Yield: 85%; $^1$H NMR (DMSO-$d_6$, 300 MHz, ppm): 8.91 (s,1H), 8.09 (s, 1H), 7.92 (d, 1H), 7.15–7.26 (m, 4H), 6.98 (t,1H), 6.6 (d, 2H), 4.82 (s, 2H), 2.32 (s, 3H); MS (FAB): 241.

E-2:

Yield: 88%; $^1$H NMR (MeOH-$d_4$, 300 MHz, ppm): 7.58 (m, 2H) 7.45 (t, 2H), 7.32 (d, 2H), 7.27 (t, 1H), 6.88 (d, 2H); MS (FAB): 227.

Procedure B

1. A solution of 4,4=-bipiperidine dihydrochloride (5.0 g, 20 mmol) in 20 mL of deionized water was brought to pH 8–9 with 5 N NaOH. After the solution was diluted with 240 mL of Ethanol and stirred at RT, Di-t-butyl dicarbonate in 160 mL of Ethanol was added in one portion. The resulting solution was maintained at pH 8–9 with periodic additions of 5 N NaOH. After 3 hrs at RT, the reaction solution was acidified using 1 N HCl. After washing with EtOAc (2×100 mL), the aqueous solution was brought to pH 7 and then washed with EtOAc to extract the mono-Boc product. The organic layer was washed with sat.aq. $NaHCO_3$ (2×100 mL), sat.aq. NaCl (2×100 mL) and dryed over $MgSO_4$. After concentrating the solution in vacuo, 2.5 g (52% yield) of the mono-Boc secondary amine was obtained.

B-1:

$^1$H NMR (MeOH-$d_4$, 300 MHz, ppm): 4.3 (d, 2H), 3.25 (d, 2H) 2.9 (t, 2H), 2.73 (t, 2H), 1.93 (d, 4H), 1.65 (s, 9H), 1.22–1.56 (m,6H); MS (FAB): 268.9; HPLC (Gr A: 5% B to 95% B in 15 mins; C18 column, 100 Å; Buffer B: 0.1% TFA in Acetonitrile; Buffer A: 0.1% TFA in HPLC water): 5.67 min.

Procedure C

1. To the solution of primary amine (1.0 mmol, obtained from procedure A) or to a solution of the secondary amine (1.0 mmol, obtained from procedure B) in NMP (5 mL), EDC (1.1 mmol) was added and quickly followed by the addition of Bromoacetic acid (1.0 mmol) at RT. After the reaction mixture was stirred at RT for over 18 hrs, the reaction was partitioned in EtOAc (15 mL) and deionized water (10 mL). The organic phase was washed with 5% Citric acid (2×10 mL), sat. aq. $NaHCO_3$ (2×10 mL) and sat. aq. NaCl (10 mL). The organic phase was dried ($MgSO_4$ ) and concentrated in vacuo to afford the bromide product:

F-1:

Yield: 84%; $^1$H NMR (MeOH-$d_4$, 300 MHz, ppm): 7.83 (d, 1H), 7.57–7.73 (m, 4H), 7.4 (m, 2H), 7.34 (t, 1H), 4.39 (s, 2H), 2.49 (s, 3H) ; MS (FAB): 362.

F-2:

Yield: 89%; $^1$H NMR (DMSO-$d_6$, 300 MHz, ppm): 7.44–7.61 (bm, 6H), 7.41 (t, 2H), 7.02 (t, 1H), 3.25 (s, 2H); MS (FAB): 348.

F-3:

Yield: 61%; $^1$H NMR (CDCl$_3$, 300 MHz, ppm, rotomers): 4.53 (d, 1H), 3.92–4.12 (m, 4H), 3.82 (d, 1H), 3.0 (t, 1H), 2.4–2.7 (m, 3H), 1.55–1.8 (m, 4H), 1.4 (s, 9H), 0.98–1.33 (bm, 6H); MS (FAB): 382 (Na$^+$ adduct)

2. To a solution of an amine (5 mmol) in NMP (4 mL) at 0° C., a solution of the bromide product from step C1 (1.0 mmol) in NMP (2 mL) was added dropwise. After the reaction mixture was stirred at 0° C. for 30 minutes, the reaction was partitioned in EtOAc (15 mL) and deionized water (10 mL). The organic phase was washed with sat.aq. $NaHCO_3$ (2×10 mL), and sat. aq. NaCl (10 mL). The organic phase was dried ($MgSO_4$) and concentrated in vacuo to afford the secondary amine product.

G-1:

Yield: 78%; $^1$H NMR (MeOH-$d_4$, 300 MHz, ppm): 7.55–8.0 (bm, 6H), 7.4 (m, 2H), 7.24 (m, 1H), 3.61 (s, 2H), 2.9 (t, 2H), 2.52 (s, 3H), 1.9 (m, 1H), 1.69 (m, 2H), 1.23 (d, 6H); MS (FAB): 369.

G-2:
Yield: 80%; $^1$H NMR (MeOH-d$_4$, 300 MHz, ppm): 7.55–7.72 (bm, 6H), 7.49 (t, 2H), 7.21 (t, 1H), 3.59 (s, 2H), 2.84 (t, 2H), 1.89 (m, 1H), 1.64 (q, 2H), 1.12 (d, 6H); MS (FAB): 355.

G-3:
Yield: 75%; $^1$H NMR (MeOH-d$_4$, 300 MHz, ppm): 7.55–7.72 (bm, 6H), 7.49 (m, 2H), 7.21 (t, 1H), 3.59 (s, 2H), 2.95 (t, 2H), 2.8 (t, 2H), 2.5 (s, 3H), 2.29 (s, 3H), 2.05 (m, 2H); MS (FAB): 387.

3. To a solution of the secondary amine (1.0 mmol) from step C2 in NMP (3 mL), EDC (1.1 mmol) was added and quickly followed by the addition of Bromoacetic acid (1.0 mmol) at 0° C. After the reaction mixture was stirred for 3 hrs at 0° C., the reaction was partitioned in EtOAc (15 mL) and deionized water (10 mL). The organic phase was washed with 5% Citric acid (2×10 mL), sat.aq. NaHCO$_3$ (2×10 mL) and sat.aq. NaCl (10 mL). The organic phase was dried (MgSO$_4$) and concentrated in vacuo to afford the N-substituted bromoacetyl product.

H-1;
Yield: 82%; $^1$H NMR (DMSO-d$_6$, 300 MHz, ppm) partial NMR of compound: 9.08 (d, 1H), 7.94 (m,2H), 7.43–7.62 (m, 4H), 7.22 (q, 2H), 7.02 (t, 1H), 4.58 (s, 1H), 4.44 (s, 1H), 4.28 (s, 1H), 4.18 (s, 1H), 2.32 (s, 3H), 1.54–1.75 (m, 2H), 1.38–1.53 (m, 1H), 0.98 (m, 6H).

H-2:
Yield: 72%; $^1$H NMR (CDCl$_3$, 300 MHz, ppm, rotomers): 4.9 (d, 1H), 3.54–3.82 (bm, 6H), 3.4 (d, 1H), 2.49–2.78 (m, 2H), 2.0–2.3 (m, 3H), 1.02–1.43 (bm, 8H), 0.9 (s, 9H), 0.58–0.88 (bm, 6H), 0.49 (m, 6H)

H-3:
Yield: 50%; $^1$H NMR (CDCl$_3$, 300 MHz, ppm, rotomers): 4.9 (d, 1H), 3.54–3.82 (bm, 6H), 3.4 (d, 1H), 2.49–2.78 (m, 2H), 2.3–2.52 (bm, 3H), 2.2 (s, 3H), 1.45–1.72 (m, 4H), 1.3 (s, 9H), 0.8–1.2 (bm,6H).

H-4:
Yield: 45%; $^1$H NMR (CDCl$_3$, 300 MHz, ppm, rotomers): 4.5 (d, 1H), 3.9–4.1 (m, 6H), 3.6 (d, 1H), 2.75–3.0 (bm, 1H), 2.4–2.6 (m, 3H), 1.48–1.71 (bm, 4H), 1.3 (s, 9H), 0.9–1.25 (bm, 6H).

4.a. To a solution of β-alanine t-butyl ester hydrochloride (5 mmol, SIGMA) in CH$_2$Cl$_2$ (20 mL) was added triethylamine (5 mmol) at RT After the solution was stirred at RT for 15 mins, the precipitate formed was filtered and the CH$_2$Cl$_2$ was removed in vacuo to give the free amine, β-alanine t-butyl ester.

4.b. To the $-alanine t-butyl ester (5 mmol) from step 4.a (5 mmol) in NMP (10 mL) at 0° C., was added dropwise a solution of the N-substituted bromoacetyl product from step C3 in NMP (2 mL). After the reaction mixture was stirred for over 18 hrs at 0° C., the reaction was partitioned in EtOAc (15 mL) and deionized water (10 mL). The organic phase was washed with sat.aq. NaHCO$_3$ (2×10 mL)and sat.aq. NaCl (10 mL). The organic phase was dried (MgSO$_4$) and concentrated in vacuo to afford the secondary amine product.

I-1:
Yield: 75%; $^1$H NMR (DMSO-d$_6$, 300 MHz, ppm): 9.1 (d, 1H), 7.92–8.1 (m, 2H), 7.45–7.61 (m, 4H), 7.25 (m, 2H), 7.04 (t, 1H), 4.1–4.28 (bd, 2H), 3.5 (m, 2H), 2.74–2.91 (m, 3H), 2.44 (m, 3H), 2.32 (s, 3H), 1.55–2.1 (m, 3H), 1.5 (s, 9H), 0.99 (m, 6H); MS (FAB): 554.

I-2:
Yield: 45%; $^1$H NMR (CDCl$_3$, 300 MHz, ppm, rotomers): 4.6 (d, 1H), 3.9–4.2 (m, 6H), 3.63–3.9 (m, 3H), 3.25 (m,1H), 2.89–3.04 (m, 2H), 2.4–2.7 (m, 5H), 1.0–1.85 (bm, 28H); MS (FAB): 511.4.

I-3:
Yield: 50%; $^1$H NMR (CDCl$_3$, 300 MHz, ppm, rotomers): 4.55 (d, 1H), 4.0–4.3 (m, 4H), 3.5–3.85 (m, 4H), 2.85–3.18 (m, 5H), 2.48–2.71 (m, 5H), 1.0–1.85 (bm, 28H); MS (FAB): 525.4.

I-4:
Yield: 60%; $^1$H NMR (CDCl$_3$, 300 MHz, ppm, rotomers): 3.75–4.62 (m, 8H), 3.25 (m, 1H), 2.9 (m, 2H), 2.49–2.75 (m, 5H), 1.0–1.85 (bm, 32H), 0.9 (m, 6H); MS (FAB): 581.5.

Procedure D

1. To a stirred solution of Boc-L-Proline or Boc-L-substituted Proline (10 mmol) and EDC (11 mmol) in NMP (10 mL) at RT, was added amine E-1 (10 mmol) obtained from procedure A. After the solution was stirred for over 18 hrs, the reaction was partitioned in EtOAc (100 mL) and deionized water (60 mL). The organic phase was washed with 5% Citric acid (2×60 mL), sat.aq. NaHCO$_3$, and sat.aq. NaCl (50 mL). The organic phase was dried (MgSO$_4$) and concentrated in vacuo to afford the coupled product.

Precursor to J-1:
Yield: 70%; $^1$H NMR (MeOH-d$_4$, 300 MHz, ppm): 7.82 (d, 1H), 7.56–7.77 (m, 4H), 7.4 (m, 2H), 7.22 (t, 1H), 4.4–4.6 (m, 1H), 3.6–3.85 (m, 2H), 2.5 (s, 3H), 2.0–2.33 (m, 4H), 1.5–1.75 (bd, 9H); MS (FAB): 439.2.

2. To the product of step D1, a solution of 75% TFA in CH$_2$Cl$_2$ (25 mL) was added slowly at 0° C. After the mixture was stirred at 0° C. for approximately 2 hrs, the reaction was concentrated in vacuo. The product was redissolved in CH$_2$Cl$_2$, concentrated two more times and placed under high vacuum to remove final traces of TFA. Then, the solid residue was triturated in ether for over 18 hrs, filtered and air-dryed. (quantitative yield).

J-1:
Yield: 80%; $^1$H NMR (MeOH-d$_4$, 300 MHz, ppm): 7.82 (d, 1H), 7.6–7.8 (m, 4H), 7.82–7.93 (q, 2H), 7.74 (t, 1H), 4.58 (m, 1H), ~3.6 (m, 2H), 2.62 (m, 1H), 2.5 (s, 3H), 2.32 (m, 3H); MS (FAB): 339.5.

J-2:
Yield: 75%; $^1$H NMR (MeOH-d$_4$, 300 MHz, ppm): 7.82 (d, 1H), 7.6–7.8 (m, 4H), 7.82–7.93 (q, 2H), 7.74 (t, 1H), 4.58–4.76 (m, 3H), 3.75 (m, 2H), 2.5 (s, 3H); MS (FAB): 358.4 (Na$^+$ adduct).

EXAMPLE 1

AY50

A. The method described in procedure C was followed, using amines E-1 (obtained by using o-Toluidine in procedure A) in step C1 and Isoamylamine in step C2, to obtain the amine product (I-1) in step C4.

B. A stirred solution of the amine prepared in Example 1A (0.9102 mmol, 0.504 g) was treated first with DIEA (0.9102 mmol, 158.6:1) in 20 mL of NMP at 0° C. (under a nitrogen atmosphere), and then Benzoyl choride (0.9102 mmol, 105.7:1) was added dropwise. After the solution was stirred for 4 hrs, the reaction was partitioned in EtOAc (50 mL) and deionized water (40 mL). The organic phase was washed with 5% Citric acid (2×25 mL), sat.aq.NaHCO$_3$ (2×25 mL), and sat.aq. NaCl (25 mL). The organic phase was dried (MgSO$_4$) and concentrated in vacuo to afford the desired compound (350 mg, 59%) as a foam:

$^1$H NMR (CDCl$_3$, 300 MHz, ppm): 6.72–7.55 (brm, 12H), 6.3–6.7 (brd, 1H), 3.8–4.2 (m, 4H), 3.55–3.7 (m, 2H), 3.1–3.5 (brm, 2H), 2.45 (t, 1H), 2.1 (m, 3H), 0.6–1.6 (brm, 19H); MS (FAB): 658.5.

C. To the product from Example 1B (350 mg, 0.5315 mmol), a solution of 25% TFA in CH$_2$Cl$_2$ (5 mL) was added slowly at 0° C. After stirring at 0° C. for 1 hr, the reaction was concentrated in vacuo. The product was redissolved in CH$_2$Cl$_2$, concentrated two more times and placed under high vacuum to remove final traces of TFA. The product was purified by HPLC to give AY50 (260 mg, 91%) as a lyophilized powder:

$^1$H NMR (DMSO-d$_6$, 300 MHz, ppm): 9.7–10.32 (m, 1H), 9.05 (s, 1H), 7.99 (m, 2H), 7.35–7.77 (m, 7H), 7.25 (q, 2H), 7.05 (t, 1H), 4.0–4.55 (brm, 4H), 3.68 (q, 1H), 3.2 (m, 1H), 2.72 (m, 1H), 2.3 (s, 3H), 1.3–1.75 (brm, 4H), 0.77–1.22 (brm, 6H); MS (FAB): 602.5; HPLC (Gr A): 8.72 min.

EXAMPLE 2

AY49

A. The procedure, as described in Example 1B, was performed utilizing the amine (I-1, 0.9102 mmol, 0.504 g) prepared by the procedure described in Example 1A, DIEA (0.9102 mmol, 158.5:1) and m-Anisoyl Chloride (0.9102 mmol, 127.9 ul) to afford the desired product (380 mg, 61% yield) as a foam:

$^1$H NMR (DMSO-d$_6$, 300 MHz, ppm): 9.1 (s, 1H), 7.95 (m, 2H), 7.3–7.65 (m, 5H), 7.23 (m, 2H), 6.83–7.15 (brm, 4H), 4.0–4.5 (brm, 4H), 3.8–3.91 (m, 3H), 3.15–3.22 (m, 4H), 2.5–2.8 (m, 2H), 2.35 (s, 3H), 1.35–1.8 (m, 12H), 0.77–1.22 (brm, 6H); MS (FAB): 710.2 (Na$^+$ adduct).

B. The procedure, as described in Example 1C, was performed utilizing the compound from step B (380 mg, 0.5523 mmol) and 25% TFA in CH$_2$Cl$_2$ (10 mL) to afford AY49 (315.0 mg, 91%) as a lyophilized powder:

$^1$H NMR (DMSO-d$_6$, 300 MHz, ppm): 9.1 (s, 1H), 7.95 (m, 2H), 7.3–7.65 (m, 5H), 7.23 (m, 2H), 6.83–7.15 (brm, 3H), 4.0–4.5 (brm, 4H), 3.8–3.91 (m, 3H), 3.15–3.22 (m, 4H), 2.5–2.8 (m, 2H), 2.35 (s, 3H), 1.35–1.8 (m, 3H), 0.77–1.22 (brm, 6H); MS (FAB): 632.3, 654.2 (Na$^+$ adduct) ; HPLC (Gr A): 9.05 min.

EXAMPLE 3

AY62

A. To a solution of 2,3-dimethoxybenzoic acid (10.9781 mmol, 2.0 g) in CH$_2$Cl$_2$ (20 mL) with a drop of DMF, was added oxalyl chloride (10.9781 mmol, 957.702:1) dropwise at RT After 2 hrs the reaction mixture was concentrated in vacuo to afford 2,3-dimethoxybenzoyl chloride (1.9 g, 90%):

$^1$H NMR (CDCl$_3$, 300 MHz, ppm): 7.52 (m, 1H), 7.12 (d, 2H) 3.89 (s, 3H), 3.88 (s, 3H).

B. The procedure as described in Example 1B was performed utilizing the amine (I-1, 2.0031 mmol, 1.073 g) prepared by the procedure described in Example 1A, DIEA (2.2034 mmol, 383.81:1) and 2,3-dimethoxybenzoyl chloride (2.2034 mmol, 440.677 mg) prepared in Example 3A to afford the desired product (856.0 mg, 51% yield) as a foam:

$^1$H NMR (DMSO-d$_6$, 300 MHz, ppm) partial NMR of compound: 9.1 (s, 1H), 7.9–8.1 (m, 2H), 7.4–7.65 (m, 3H), 6.95–7.3 (brm, 4H), 6.6–6.9 (brm, 1H), 3.7–4.7 (brm, 10H), 2.38 (s, 3H), 1.2–1.8 (brm, 12H), 0.9–1.1 (m, 5H), 0.8 (d, 2H); MS (FAB): 740.4 (Na$^+$ adduct).

C. The procedure as described in Example 1C was performed utilizing the compound from step B (856.0 mg, 1.1922 mmol) and 25% TFA in CH$_2$Cl$_2$ to afford AY62 (786.0 mg, 98%) as a lyophilized powder:

$^1$H NMR (DMSO-d$_6$, 300 MHz, ppm) partial NMR of compound: 9.1 (s, 1H), 7.9–8.1 (m, 2H), 7.4–7.65 (m, 3H), 6.95–7.3 (brm, 4H), 6.6–6.9 (brm, 1H), 3.7–4.7 (brm, 10H), 2.38 (s, 3H), 1.2–1.8 (brm, 12H), 1.18 (t, 3H), 0.89–1.1 (m, 4H), 0.8 (d, 2H); MS (FAB): 662.2, 684.2 (Na$^+$ adduct; HPLC (Gr A): 8.795 min.

EXAMPLE 4

CX13

A. The amine (G-1, 0.271 mmol, 100.0 mg), obtained from step C2 in procedure C using the amines E-1 (obtained by using o-Toluidine in procedure A) in step C1 and Isoamylamine in C2, was added to a stirred solution of Monomethyl adipate (0.271 mmol, 40.15:1) and EDC (0.271 mmol, 51.951 mg) in 4 mL NMP at RT. After the reaction was stirred for over 18 hrs at RT, the reaction was partitioned in EtOAc (15 mL) and deionized water (10 mL). The organic phase was washed with 5% Citric acid (2×10 mL), sat.aq.NaHCO$_3$ (2×10 mL), and sat.aq. NaCl (10 mL). The organic phase was dried (MgSO$_4$) and concentrated in vacuo to afford the desired compound (103 mg, 75% ) as a foam:

$^1$H NMR (CDCl$_3$, 300 MHz, ppm, rotomers): 8.88 (s, 1H), 7.55 (d, 2H), 6.6–7.4 (brm, 7H), 4.0 (m, 2H), 3.62 (s, 3H), 3.43 (m, 1H), 1.9–2.4 (brm, 7H), 1.29–1.8 (brm, 8H), 0.9 (d, 6H); MS (FAB): 511.3.

B. A stirred solution of the compound from step A (103 mg, 0.2034 mmol) in methanol (2 mL) was treated with aq. LiOH (1.0 M, 1.0 mL, 1.0 mmol) at RT for 3 hrs. The reaction was acidified with 1 N HCl and concentrated in vacuo. The crude product was purified by HPLC to afford CX13 (66.0 mg, 65%) as a lyophilized powder:

$^1$H NMR (DMSO-d$_6$, 300 MHz, ppm): 9.9–10.1 (brd, 1H), 9.05 (d, 1H), 7.95 (m, 2H), 7.55 (m, 4H), 7.25 (q, 2H), 7.05 (t, 1H), 4.1–4.25 (brd, 1H), 3.5 (m, 1H), 2.21–2.52 (m, 7H), 1.38–1.71 (m, 7H), 1.2 (t, 1H), 0.95 (m, 6H); MS (FAB): 497.2; HPLC (Gr A): 8.24 min.

EXAMPLE 5

P1

A. The method described in procedure C was followed, using amines E-1 (obtained by using 4,4'-Bipiperidine dihydrochloride in procedure B) in step C1 and Ammonia in step C2, to afford the amine product (I-2) in step C4.

B. To a stirred solution of benzoic acid (0.1351 mmol, 16.5 mg) and EDC (0.1351 mmol, 25.902 mg) in 3 mL of NMP, was added the amine (I-2, 0.1351 mmol, 69.0 mg) prepared by the procedure described in Example 5A. After the solution was stirred for over 18 hrs, the reaction was partitioned in EtOAc (10 mL) and deionized water (5 mL).The organic phase was washed with 5% Citric acid (2×5 mL), sat.aq. NaHCO$_3$ (2×5 mL), and sat.aq. NaCl (5 mL). The organic phase was dryed (MgSO$_4$) and concentrated in vacuo to afford the desired product (35.0 mg, 51%) as a foam.

C. The procedure as described in Example 1C was performed utilizing the compound from step B (35.0 mg, 0.068 mmol) and 25% TFA in CH$_2$Cl$_2$ to obtain P1 (17.0 mg, 55%) as a lyophilized powder:

$^1$H NMR (DMSO-d$_6$, 300 MHz, ppm) partial NMR of compound: 8.4 (m, 1H), 7.9–8.25 (m, 2H), 7.4 (d, 3H), 4.4 (d, 1H), 3.7–4.2 (m, 5H), 2.18–3.12 (m, 4H), 1.6–1.85 (d, 4H), 0.85–1.41 (m, 6H); MS (FAB): 458.8; HPLC (Gr A): 4.1 min.

EXAMPLE 6

P2

A. The method described in procedure C was followed, using amines E-1 (obtained by using 4,4'-bipiperidine dihydrochloride in procedure B) in step C1 and Methylamine in step C2, to obtain the amine product (I-3) in step C4.

B. The procedure as described in Example 5B was performed utilizing the amine (I-3, 0.2835 mmol, 148.8 mg) prepared by procedure described in Example 6A, Benzoic acid (0.2836 mmol, 34.63 mg) and EDC (0.2836 mmol, 54.37 mg) to afford the desired product (84.0 mg, 56% yield) as a foam.

C. The procedure as described in Example 1C was performed utilizing the compound from step B (84.0 mg, 0.158 mmol) and 25% TFA in CH$_2$Cl$_2$ to obtain P2 (49.0 mg, 66%) as a lyophilized powder.

$^1$H NMR (DMSO-d$_6$, 300 MHz, ppm) partial NMR of compound: 8.5 (m, 1H), 8.2 (m, 1H), 7.35–7.6 (m, 4H), 4.1–4.6 (m, 6H), 3.8–4.1 (m, 3H), 2.77–3.2 (m, 7H), 1.7–2.0 (m, 4H), 1.0–1.6 (m, 6H); MS (FAB): 473.2; HPLC (Gr A):, 4.403 min.

EXAMPLE 7

P3

A. The method described in procedure C was followed, using amines E-1 (obtained by using 4,4'-bipiperidine dihydrochloride in procedure B) in step C1 and Isoamylamine in step C2, to afford the amine product (I-4) in step C4.

B. The procedure as described in Example 5B was performed utilizing the amine (I-4, 0.05131 mmol, 29.8 mg) prepared by procedure described in Example 7A, Benzoic acid (0.05131 mmol, 6.2657 mg) and EDC (0.05131 mmol, 9.836 mg) to afford the desired product (15.0 mg, 51% yield) as a foam.

C. The procedure as described in Example 1C was performed utilizing the compound from step B (15.0 mg, 0.0256 mmol) and 25% TFA in CH$_2$Cl$_2$ to obtain P3 (9.0 mg, 67%) as a lyophilized powder:

$^1$H NMR (DMSO-d$_6$, 300 MHz, ppm) partial NMR of compound: 8.5 (m, 1H), 8.2 (m, 1H), 7.33–7.6 (m, 4H), 3.85–4.6 (brm, 6H), 2.8–3.2 (m, 4H), 0.78–2.0 (brm, 19H); MS (FAB): 529.4, 551.3 (Na$^+$ adduct); HPLC (Gr A): 6.27 min.

EXAMPLE 8

CY14

A. To a stirred solution of Mono-methyl adipate (0.2955 mmol, 43.78:1) and EDC (0.2955 mmol, 56.65 mg) in 4 mL NMP at RT, was added the free amine product (J-1, 0.2955 mmol, 100.0 mg), obtained from procedure D using Boc-L-Proline. After the solution was stirred for over 18 hrs, the reaction was partitioned in EtOAc (15 mL) and deionized water. The organic phase was washed with 5% Citric acid (2×10 mL), sat.aq. NaHCO$_3$ (2×10 mL), and sat.aq. NaCl (10 mL). The organic phase was dried (MgSO$_4$) and concentrated in vacuo to afford the desired product (88.2 mg, 62%) as a foam:

$^1$H NMR (CDCl$_3$, 300 MHz, ppm): 7.1–7.52 (brm, 8H), 6.1–6.42 (s, 1H), 4.75 (d, 1H), 3.42–3.68 (m, 5H), 1.94–2.42 (brm, 10H), 1.6–1.8 (m, 4H) ; MS (FAB): 481.4, 503.3 (Na$^+$ adduct)

B. The same procedure as described in Example 4B was performed utilizing the compound from step A (88.2 mg, 0.1832 mmol) and aq. LiOH (1.0 M, 1.0 mL, 1.0 mmol) in MeOH (2 mL) to obtain CY14 (50.8 mg, 60%) as a lyophilized powder:

$^1$H NMR (DMSO-d$_6$, 300 MHz, ppm): 9.9–10.12 (brd, 1H), 9.05 (d, 1H), 7.95 (m, 2H), 7.45–7.61 (m, 4H), 7.24 (q, 2H), 7.05 (t, 1H), 4.45–4.61 (m, 1H), 3.52–3.74 (m, 2H), 1.88–2.44 (brm, 11H), 1.6 (m, 4H); MS (FAB): 467.2, 489.2 (Na$^+$ adduct); HPLC (Gr A): 6.66 min.

EXAMPLE 9

CY17

A. To a solution of tert-butyl diethyl phosphonoacetate (3.0 mmol, 756.75 mg) in 25 mL anhydrous THF, stirred at −75° C. (dry ice/acetone) under a nitrogen atmosphere, was added n-butyl Lithium (3.0 mmol, 1.875 mL) dropwise over a period of 5 mins. After the solution stirred for 1 hr at 0° C., ethyl levulinate (2.7 mmol, 425.7:1) was added under N$_2$ at 0° C. The reaction was gradually warmed up to RT and stirred for 3.5 h. After 3.5 h the reaction mixture was washed with sat.aq. NH$_4$Cl (3×100 mL) and concentrated in vacuo. Then, 100 mL of ether was added to the residue and the ether layer was washed with deionized water (60 mL), and sat.aq. NaCl (2×60 mL). The organic layer was dried (MgSO$_4$) and concentrated in vacuo to afford the crude product. The crude was purified by flash chromatography using 20:1 hexane:EtOAc to afford the orthogonally protected t-Butyl-6-Carboethoxy-3-Methyl-3-Pentenoate (404.0 mg, 54%) as a viscous liquid:

$^1$H NMR (CDCl$_3$, 300 MHz, ppm, isomers): 5.6 (s, 1H), 4.12 (q, 2H), 2.84 (t, 1H), 2.4–2.53 (m, 4H), 2.1 (s, 2H), 1.47 (s, 9H), 1.23 (t, 3H) ; MS (FAB): 264.6 (Na$^+$ adduct) ; HPLC (Gr A): 12.24 min and 12.48 min.

B. The product from Example 9A (0.8277 mmol, 200.3 mg) in 10 mL EtOAc was reduced using 5 mole % of 10% Pd/C (0.04139 mmol, 43.63 mg) in a pressurized hydrogenation container. After 1 hr the reaction mixture was centrifuged for 30 mins. The centrifugation with EtOAc (2×30 mL) was repeated for a further 30 mins. All the organic layers were pooled and concentrated in vacuo to afford t-Butyl-6-Carboethoxy-3-Methyl-3-Pentanoate (150.0 mg, 75%):

$^1$H NMR (CDCl$_3$, 300 MHz, ppm): 4.1 (q, 2H), 2.18–2.4 (m, 3H), 1.88–2.1 (m, 2H), 1.45–1.75 (m, 3H), 1.44 (s, 9H), 1.23 (t, 3H), 0.92 (d, 3H) ; MS (FAB): 266.6 (Na$^+$ adduct).

C. The same procedure as described in Example 4B was performed utilizing t-Butyl-6-Carboethoxy-3-Methyl-3-Pentanoate (150.0 mg, 0.6147 mmol) and aq. LiOH (1.0 M, 1.0 mL, 1.0 mmol) in MeOH (2 mL) obtained the mono-acid product (100 mg, 75%) as a solid:

$^1$H NMR (CDCl$_3$, 300 MHz, ppm): 2.18–2.4 (m, 3H), 1.88–2.1 (m, 2H), 1.45–1.75 (m, 3H), 1.44 (s, 9H), 0.92 (d, 3H); MS (FAB): 239.1 (Na$^+$ adduct).

D. The procedure as described in Example 8A was performed utilizing the acid product from Example 9C (0.0925 mmol, 20.0 mg), the amine (J-1, 0.0925 mmol, 31.30 mg), obtained by using Boc-L-Proline in procedure D, and EDC (0.0925 mmol, 17.73 mg) in NMP (3 mL) to afford the desired compound (39.3 mg, 73%):

$^1$H NMR (CDCl$_3$, 300 MHz, ppm) partial NMR of compound: 7.1–7.8 (brm, 8H), 4.75 (m, 1H), 3.43–3.62 (m, 2H), 1.9–2.6 (brm, 12H), 0.8–1.0 (m, 3H); MS (FAB): 559.3.

E. The procedure as described in Example 1C was performed utilizing the compound from step D (39.3 mg, 0.0703 mmol) and 25% TFA in CH$_2$Cl$_2$ to obtain CY17 (20.2 mg, 60%) as a lyophilized powder:

$^1$H NMR (MeOH-d$_4$, 300 MHz, ppm): 7.81 (d, 1H), 7.52–7.71 (m, 4H), 7.38 (q, 2H), 7.23 (t, 1H), 4.64–4.8 (m, 1H), 3.7–4.0 (m, 2H), 2.05–2.74 (brm, 12H), 1.68–2.0 (m, 2H), 1.05–1.23 (m, 3H); MS (FAB): 481.3, 503.4 (Na$^+$ adduct); HPLC (Gr A): 8.1 min.

EXAMPLE 10

CX12

A. The procedure as described in Example 8A was performed utilizing the amine (J-2, 0.2974 mmol, 100.0 mg), obtained by using Boc-L-Thioproline in procedure D, adipic acid (0.2974 mmol, 43.46 mg) and EDC (0.3569 mmol, 68.414 mg) in NMP (3 mL) to afford the crude acid product. The crude was purified by HPLC to afford CX12 (30.0 mg, 30%) as a lyophilized powder:

$^1$H NMR (DMSO-d$_6$, 300 MHz, ppm): 9.99 (s, 1H), 9.1 (s, 1H), 7.98 (m, 2H), 7.48–7.62 (m, 4H), 7.25 (q, 2H), 7.05 (t, 1H), 4.55–5.05 (m, 4H), 3.22 (m, 1H), 2.41 (m, 6H), 1.6 (m, 4H); MS (FAB): 485.5; HPLC (Gr A): 7.935 min.

EXAMPLE 11

AX41

A. The method described in procedure C was followed, using amine E-1 (obtained by using o-toluidine in procedure A) in step C1 and Isoamylamine in step C2, to obtain the amine (I-1) in step C4.

B. To a stirred solution of amine prepared in Example 11A (0.072 mmol, 39.8 mg) and DIEA (0.0864 mmol, 15.1:1) in NMP (4 mL) at 0° C., was added acetic anhydride (0.0792 mmol, 7.5:1). After the solution was stirred for 4 h at 0° C., the reaction was partitioned in EtOAc (10 mL) and deionized water (5 mL). The organic phase was washed with 5% citric acid (2×5 mL), sat.aq. NaHCO$_3$ (2×5 mL), and sat.aq. NaCl (5 mL). The organic phase was dryed (MgSO$_4$) and concentrated in vacuo to afford the desired compound (20 mg, 50%) as a foam.

C. The procedure described in Example 1C was performed utilizing the compound from step B (20.0 mg, 0.034 mmol) and 25% TFA in CH$_2$Cl$_2$ to afford AX41 (9.0 mg, 50%) as a lyophilized powder:
$^1$H NMR (DMSO-d$_6$, 300 MHz, ppm) partial NMR of compound: 9.76–10.22 (brm, 1H), 9.05 (d, 1H), 7.95 (m, 2H), 7.45–7.65 (m, 4H), 7.24 (q, 2H), 7.03 (t, 1H), 4.1–4.54 (brm, 4H), 2.33 (s, 3H), 2.18 (s, 1H), 1.98 (d, 2H), 1.3–1.8 (brm, 3H), 0.98 (m, 6H); MS (FAB): 540.3; HPLC (Gr A): 7.047 min.

EXAMPLE 12

AY48

A. The method described in procedure C was followed, using amine E-1 (obtained by using o-Toluidine in procedure A) in step C1 and Isoamylamine in step C2, to obtain the amine (I-1) in step C4.

B. The procedure as described in Example 5B was performed utilizing the amine from Example 12A (0.0905 mmol, 50.0 mg), Mono-methyl succinate (0.0905 mmol, 11.96 mg) and EDC (0.09955 mmol, 19.084 mg) to afford the desired compound (30 mg, 50%) as a foam.

C. The procedure as described in Example 1C was performed utilizing the compound from step B (30 mg, 0.045 mmol) and 25% TFA in CH$_2$Cl$_2$ to obtain AY48 (15 mg, 46%) as a lyophilized powder:
$^1$H NMR (DMSO-d$_6$, 300 MHz, ppm) partial NMR of compound: 9.76–10.22 (brm, 1H), 9.05 (d, 1H), 7.95 (m, 2H), 7.45–7.65 (m, 4H), 7.24 (q, 2H), 7.03 (t, 1H), 4.1–4.54 (brm, 4H), 3.18 (s, 3H), 2.33 (s, 3H), 1.3–1.8 (brm, 3H), 0.98 (m, 6H); MS (FAB): 612.4; HPLC (Gr A): 7.998 min.

EXAMPLE 13

AY44

A. The method described in procedure C was followed, using amine E-1 (obtained by using o-Toluidine in procedure A) in step C1 and Isoamylamine in step C2, to obtain the amine (I-1) in step C4.

B. The procedure as described in Example 5B was performed utilizing the amine from Example 12A (0.0398 mmol, 22.0 mg), 3-methoxy propionic acid (0.0398 mmol, 3.7 μl) and EDC (0.04378 mmol, 8.393 mg) to afford the desired compound (15 mg, 59%) as a foam.

C. The procedure as described in Example 1C was performed utilizing the compound from step B (15 mg, 0.0234 mmol) and 25% TFA in CH$_2$Cl$_2$ to obtain AY44 (10 mg, 74%) as a lyophilized powder:
$^1$H NMR (DMSO-d$_6$, 300 MHz, ppm) partial NMR of compound: 9.05 (d, 1H), 7.95 (m, 2H), 7.45–7.65 (m, 4H), 7.24 (q, 2H), 7.03 (t, 1H), 4.1–4.54 (brm, 4H), 3.29 (m, 3H), 2.33 (s, 3H), 1.3–1.8 (brm, 3H), 0.98 (m, 6H); MS (FAB): 584.3, 607.4 (Na$^+$ adduct); HPLC (Gr A): 6.17 min.

Synthesis of SX44

A. To a suspension of 1,4-phenylenediamine (9.15 g, 86 mmol) in dichloromethane (30 mL) was added o-tolyl isocyanate (10.5 mL, 86 mmol). After stirring at room temperature for 30 min the suspension was filtered and washed with dichloromethane (200 mL). Drying under vacuum afforded the desired product as a gray solid (15.8 g, 65.6 mmol. 76%), >99% purity based on HPLC.
$^1$HNMR (d$_6$-dmso): δ 8.61 (1H, s), 7.95 (1H, d), 7.81 (1H, s) 7.30 (2H, m), 7.15 (2H, d), 7.0 (1H, t), 6.61 (2H, d), 4.88 (2H, bs), 2.32 (3H, s).

B. To a solution of (2R)-[(t-Butyloxycarbonyl)methyl]-4-methyl valeric acid (Oxford Asymmetry) (2.4 g, 10.4 mmol) in DMF (20 mL) cooled to 0° C. was added HOBT (2.1 g, 15.5 mmol) followed by EDC (2.4 g, 13.0 mmol) and Hunigs base (5.4 mL, 31.1 mmoL). After stirring for 15 min 2,3-dimethoxy β-phenyl alanine methyl ester hydrochloride (2.9 g, 10.4 mmol) was added. After stirring overnight with warming to room temperature the reaction was worked up by precipitating the product with 60% aqueous bicarbonate. The product was filtered and washed with water, 5% citric acid and brine. The product was dried under vacuum to afford the desired product (4.5 g, 9.9 mmol, 99%), >88% purity based on HPLC as a white powder.
$^1$HNMR (CDCl$_3$): δ 6.81 (3H, m), 6.60 (1H, bd), 5.35 (1H, m), 3.76 (3H, s), 3.75 (3H, s), 3.63 (3H, s), 2.90–2.50 (4H, m), 2.30 (1H, −1.45 (2H, m), 1.40 (9H, s), 1.15 (1H, m), 0.88 (3H, d), 0.82 (3H, s).

C. To a solution of the compound from step B (4.5 g, 9.9 mmol) in dichloromethane (15 mL) was added trifluoroacetic acid (5 mL) and the reaction was stirred at room temperature for 3 h. The solvents were removed in vacuo and the product precipitated out by the addition of ether. Filtration of the solid and drying under vacuum afforded the desired compound (2.9 g, 7.3 mmol, 74%) as a white powder>96% pure based on HPLC.
$^1$HNMR (CDCl$_3$): δ 6.92 (1H, bd), 6.70 (3H, m), 5.35 (1H, m), 3.85 (6H, s), 3.65 (3H, s), 2.95–2.40 (5H, m), 1.55 (2H, m), 1.35 (1H, m), 0.90 (3H, d), 0.87 (3H, d).

D. To a solution of the compound from step C (1.9 g, 4.8 mmol) in DMF (15 mL) was added HBTU (2.1 g, 5.5 mmol) followed by Hunig=s base (2.1 mL, 12.1 mmol) and the compound from step A (1.15 g, 4.8 mmol). After stirring overnight at room temperature the reaction was worked up by precipitation out of 60% aqueous bicarbonate, washed with water, 5% citric acid and brine. Drying under vacuum afforded the desired product (2.9 g, 4.7 mmol, 98%) as a tan solid>87% pure based on HPLC.
$^1$HNMR (CDCl$_3$): δ 9.01–6.81 (15H, m), 5.35 (1H, m) 3.85(3H, s), 3.84 (3H, s), 3.65 (3H, s), 2.90–2.35 (5H, m), 2.33 (3H, s), 1.65–0.90 (3H, m), 0.90 (3H, d). 0.86 (3H, d).

E. To a solution of the compound from step D (2.9 g, 4.6 mmol) in methanol (30 mL) containing DMF (15 mL) was added 2M LiOH (7 mL, 13.8 mmol) and the reaction was stirred overnight at room temperature. The methanol was removed in vacuo and the crude mixture was added dropwise to a 0° C. solution of 1M HCl. The precipitate was filtered and washed with water, methanol/ether (1:9) and ether. The product was dried under vacuum to afford crude SX44 >91% pure based on HPLC. Recrystallization from isopropanol affords pure SX44 as a white solid (1.25 g, 2.1 mmol, 46%) >98% pure based on HPLC.
$^1$HNMR (d$_6$-dmso): * 9.95 (1H, s), 9.11 (1H, s), 8.61 (1H, d), 8.01 (1H, s), 7.95 (1H, d), 7.60 (2H, d), 7.47 (2H, d), 7.24 (2H, m), 7.02 (2H, m), 6.90 (2H, m), 5.25 (1H, m), 3.82 (3H, s), 3.81 (3H, s), 2.98–2.60 (3H, m), 2.46 (2H, m), 2.33 (3H, s), 1.65–1.10 (3H, m), 0.93 (3H, d), 0.84 (3H, s).

ESMS(+): m/z=605

Synthesis of SY62

A. To a solution of (S)-3-(1-Oxopropyl)-4-(phenylmethyl)-2-oxazolidinone (922 mg, 3.95 mmol) in dry THF (40 mL) cooled to −78° C. was added lithium diisopropylamide (2.4 mL, 4.5 mmol, Aldrich 2.0 M) dropwise. The reaction was allowed to at −78° C. for 1 h resulting in a pale yellow solution. t-Butyl bromoacetate (1.74 mL, 11.8 mmol) was then added at once and the reaction was stirred for an additional 15 min at −78° C. then warmed to 0° C. and allowed to proceed an additional 45 min. The reaction was quenched with sat. aqueous ammonium chloride and the THF was removed. The aqueous layer was extracted with dichloromethane (3×50 mL) and the combined organic extracts washed with brine, dried with sodium sulfate and concentrated to afford a thick syrup which when placed in the freezer solidifies to a waxey solid. Trituration with cold hexane affords the desired product (735 mg, 2.11 mmol, 54%) as a white solid in >90% purity by HPLC.

$^1$HNMR (CDCl$_3$): δ 7.40–7.15 (5H, m), 4.65 (1H, m), 4.25–4.0 (3H, m), 3.32 (1 H, dd), 2.83 (1H, dd), 2.76 (1H, dd), 2.37 (1H, dd), 1.41 (9H, s), 1.19 (3H, d).

B. To a 0° C. solution of the compound from step A (350 mg, 1.00 mmol) in THF (15 mL) and water (5 mL) was added 30% hydrogen peroxide (1.10 mL, 10.1 mmol) followed by 2.0 M lithium hydroxide (1.0 mL, 2.0 mmol) and the solution was allowed to stir for 2–3 h until judged complete by HPLC. The reaction was quenched with-excess sodium sulfite and the pH adjusted to ~10 with saturated sodium bicarbonate if neccesary. The THF was removed in vacuo and the aqueous layer wass diluted with water (30 mL) and extracted twice with dichloromethane (30 mL). The aqueous layer was then acidified with 1 M HCl to pH~2 and extracted with ethyl acetate (3×50 mL). The combined organic extracts where washed with brine (30 mL), dried over sodium sulfate and concentrated to afford the desired product (153 mg, 0.81 mmol, 81%) >95% pure based on HPLC as a clear syrup which becomes a waxey solid upon standing in the freezer.

$^1$HNMR (CDCl$_3$): δ 2.88 (1H, m), 2.61 (1H, dd), 2.35 (1H, dd) 1.42 (9H, s), 1.22 (3H, d).

C. Following the procedure used for the synthesis of SX44B, the compound from step B (153 mg, 0.81 mmol) was coupled to 2,3-dimethoxy β-phenyl alanine methyl ester hydrochloride (253 mg, 0.85 mmol) to afford the desired compound (268 mg, 0.6 mmol, 78%) in >85% purity based on HPLC as a white foam.

$^1$HNMR (CDCl$_3$): * 6.81 (3H, m), 6.72 (1H, bd), 5.40 (1H, m) 3.85 (3H, s), 3.84 (3H, s), 3.41 (3H, s), 2.96–2.15 (5H, m), 1.41 (9H, s), 1.14 (3H, d).

D. Following the procedure for SX44C, the compound from step C (268 mg, 0.6 mmol was deprotected to afford desired product (210 mg, 0.59 mmol, 98%) as a thick pale yellow syrup.

$^1$HNMR (CDCl$_3$): δ 6.97 (1H, bd), 5.33 (1H, m), 3.85 (3H, s), 3.84 (3H, s), 3.58 (3H, s), 2.95–2.40 (5H, m), 1.24 (3H, d).

E. Following the procedure for the preparation of SX44D, the compound from step D (210 mg, 0.60 mmol) was coupled to SX44A (168 mg, 0.70 mmol) to afford the desired compound (320 mg, 0.55 mmol, 92%) ~72% pure based on HPLC as a tan solid.

$^1$HNMR (d$_6$-dmso): δ 9.92 (1H, s), 9.42 (1H, br), 8.52 (1H, d), 8.15 (1H, br), 7.92 (1H, d), 7.61 (2H, d), 7.47 (2H, d), 7.25 (2H, m), 7.10–6.85 (4H, m), 5.35 (1H, m), 3.85 (3H, s), 3.84 (3H, s), 3.63 (3H, s), 3.15–2.40 (5H, m), 2.35 (3H, s), 1.12 (3H, d).

F. Following the procedure for the hydrolysis of SX44D, the compound from step E (300 mg, 0.52 mmol) afforded crude SY62 (108 mg) >90% pure based on HPLC. A small amount was purified by HPLC to afford SY62 (8 mg) >99% pure as a white solid.

$^1$HNMR (d$_6$-dmso): δ 9.95 (1H, s), 9.04 (1H, s), 8.46 (1H, d), 7.93 (2H, bm), 7.59 (2H, d), 7.47 (2H, d), 7.24 (2H, m), 7.21–6.89 (4H, m), 5.22 (1H, m), 3.83 (3H, s), 3.8 (3H, s), 2.95–2.65 (5H, m), 2.34 (3H, s), 1.10 (3H, d).

ESMS(−): m/z-H=561

Synthesis of SY60

A. To a solution of succinic anhydride (200 mg, 2.0 mmol) in dichloromethane (5 mL) was added SX44A (482 mg, 2.0 mmol) and the slurry was stirred overnight at room temperature. The solid was filtered and washed with dichloromethane to afford the desired product (630 mg, 1.8 mmol, 92%) as a light gray solid.

$^1$HNMR (D$_6$-dmso): δ 12.25 (1H, br), 9.95 (1H, s), 9.05 (1H, s), 7.95 (2H, m), 7.60 (2H, d), 7.50 (2H, d), 7.25 (2H, m), 7.05 (1H, m), 2.33 (4H, m).

B. To a solution of the compound from step A (192 mg, 0.56 mmol) in DMF (4 mL) was added HBTU (265 mg, 0.70 mmol) followed by Hunig=s base (0.25 mL) and 2,3-dimethoxy-β-phenyl alanine methyl ester (154 mg, 0.56 mmol). After stirring overnight at room temperature the product was precipitated out with 60% aqueous bicarbonate, washed with water, 5% citric acid, brine and dried under vacuum to afford the desired product (100 mg, 0.18 mmol, 32%) as a tan solid>85% pure based on HPLC.

$^1$HNMR (d$_6$-dmso): δ 9.93 (1H, s), 9.10 (1H, s), 8.47 (1H, d), 8.0 (1H, s), 7.95 (1H, d), 7.60 2H, d), 7.46 (2H, d), 7.25 (2H, m), 7.05 (1H, m), 6.92 (2H, m), 5.26 (1H, m), 3.85 (3H, s), 3.84 (3H, s), 3.66 (3H, s), 2.85 (2H, m), 2.55 (2H, m), 2.36 (3H, s).

C. To a solution of the compound from step B (100 mg, 0.18 mmol) in methanol was added 2M LiOH (0.3 mL) and the reaction was stirred at room temperature for 3 h. The methanol was removed and the product precipitated out of 1N HCl. The solid was filtered, washed with water, ether/methanol (9:1), and ether. Drying under vacuum affords SY60 (74 mg, 0.13 mmol, 72%) as a light tan solid>97% pure based on HPLC.

$^1$HNMR (d$_6$-dmso): δ 9.88 (1H, s), 9.05 (1H, s), 8.41 (1H, d), 8.47 (1H, s), 7.90 (1H, d), 7.54 (2H, d), 7.43 (2H, d), 7.20 (2H, m), 6.96 (2H, bm), 6.90 (2H, bm), 5.21 (1H, m), 3.81 (3H, s), 3.80 (3H, s), 2.71 (2H, m), 2.50 (2H, m), 2.30 (3H, s).

ESMS(−): m/z-1=547

Synthesis of RX19

A. To N-t-boc-L-Leucine-N-Hydroxy Succinimide Ester (3.28 g, 0.01 mmol) in DMF (20 ml) at room temperature was added Tyramine (1.37 g, 0.01 mmol) portionwise over 30 minutes with stirring. Following two hours of stirring, the DMF was pumped off under reduced pressure and the residue was taken up in 50 ml of methylene chloride. The organic phase was washed with 5% citiric acid (2×15 ml), H$_2$O (15 ml) and brine (15 ml) dried over MgSO$_4$, filtered, and concentrated to provide the desired compound (3.32 g, 95%) as a white foam.

H$^1$ NMR (CDCl$_3$, 300 MHz, ppm) 7.96 (d, 1H, 8 Hz), 6.93(d, 2H, 8 Hz), 6.73(d, 2H, 8 Hz), 6.53(bs, 1H), 5.09(d, 1H, 8 Hz), 4.02(bs, 1H), 3.47–3.31 (bm, 2H), 2.64(t, 2H, 7 Hz), 1.55(m, 2H), 1.37(s, 9H), 0.84(d, 6H, 6 Hz), m/z 351.

B. A mixture of the compound from step A (1 g, 2.85 mmol) and Bromo-methylacetate (0.45 g, 2.85 mmol) in acetone (15 ml) was refluxed with solid $K_2CO_3$ for 3.5 hours. The reaction mixture was cooled, filtered, and concentrated to yield the desired product (1.09 g, 91%) as an amber gum. $H^1$ NMR($CDCl_3$, 300 MHz, ppm), 7.08 (d, 2H, 8 Hz), 6.81(d, 2H, 8 Hz), 6.14(s, 1H), 4.84 (s, 1H), 4.59(s, 2H), 4.00(s, 1H), 3.78 (s, 3H), 3.78–3.40(bm, 2H), 2.71(t, 2H, 7 Hz), 1.60–1.39 (m, 2H), 0.89(s, 9H), 0.87(d, 6H, 6 Hz); m/z 423.

C. To the compound from step B (353 mg, 0.836 mmol) in 1 ml of $CH_2Cl_2$ cold was added TFA (3 ml) and the mixture was stirred at room temperature for 3 hours. The reaction was concentrated under reduced pressure to provide the desired product which was used without purification. $H^1$ NMR CDCl3, 300 MHz, ppm) 7.59 (bs,3H), 7.24 (m,1H), 7.04 (d, 2H, 9 Hz), 6.77 (d, 2H, 9 Hz), 4.60 (s, 2H, 4.04 (m, 1H), 3.79 (s, 3H), 3.52–3.43 (bm, 2H), 2.75–2.70 (t, 2H, 6 Hz), 1.56 (m, 2H), 1.46 (m, 1H), 0.84 (d, 6H, 6 Hz); m/z 323.

D. A mixture of 2-MPUPA (225 mg, 0.79 mmol), HOBt (169 mg, 1.25 mmol), and EDC (192 mg, 1.00 mmol) was stirred in DMF (5 ml) at room temperature for 1.5 hours. In a separate vial, the compound from step C (0.836 mmol) in DMF (1 ml) cold was neutralized with TEA dropwise (green to litmus) with stirring. The two solutions were combined and stirred at room temparature overnight. The reaction mixture was filtered and the volume reduced by one half under vacuum then dripped into rapidly stirred 5% sodium bicarbonate (50 ml). Following one hour of stirring the solids were collected by filtration, washed with water, and air dried to give the desired compound (140 mg, 35%) as a beige solid. $H^1$ NMR (DMSO, 300 MHz, ppm) 9.06(s, 1H), 8.20(d, 1H, 8 Hz), 8.07(m, 1H), 8.00(s, 1H), 7.94(d, 1H, 8 Hz), 7.47(d, 2H, 9 Hz), 7.27–7.19(m, 6H), 7.03(t, 1H, 7 Hz), 6.92(d, 2H, 9 Hz), 4.84(s, 2H), 4.34–4.31(m, 1H), 3.78(s, 2H), 3.48(d, 1H, 6 Hz), 3.44(s, 3H), 3.37–3.27(m, 2H), 2.72(t, 2H, 7 Hz), 2.33(s, 3H), 1.58–1.46(m, 3H), 0.91(dd, 6H, 6 Hz, 13 Hz); m/z 589.

E. A solution of the compound from step D (24 mg, 0.041 mmol) and 2N LiOH (62 ul, 0.122 mmol)in DMF (1 ml) was stirred at room temperature for 6 hours. The reaction mixture was acidified (red to litmus) with TFA and purified directly by preparative HPLC resulting in RX19 (10 mg, 43%) as a white solid. $H^1$ NMR (DMSO, 300 MHz, ppm) 9.27(s, 1H), 8.18(m, 1H), 8.16(m, 1H), 7.92 (d, 1H, 7 Hz), 7.46(d, 2H, 8 Hz), 7.19–7.03(m, 12H), 6.88(d, 2H, 8 Hz), 4.63(s, 2H), 4.33(m, 1H), 2.69(t, 8 Hz), 2.34(s, 3H), 1.51–1.33(m, 3H), 0.96–0.88(dd, 6H, 6 Hz, 12 Hz), m/z 5.73.

Synthesis of RX23

A. To a stirred solution of m-hydroxyaniline (1.09 g, 0.01 mmol) and HOBt (2.0 g, 0.015 mmol) in DMF (12 ml) at 0° C. was added EDC (2.7 g, 0.014 mmol). The mixture was allowed to warm to room temperature and stirred for 1 hour. Next the reaction was cooled to 0° C. and and 2-MPUPA (2.84 g, 0.01 mmol) was added. Triethylamine was added dropwise until the mixture was basic (green to litmus) and stirring continued overnight at room temperature. Following filtration,the mixture was dripped into 500 ml of vigorously stirring 5% sodium bicarbonate. Following two hours of stirring, the solids were collected by filtration through a coarse sinter glass funnel and washed copiously with $H_2O$. Overnight drying under vacuum gave the desired product (3.2 g, 85%) as an off white solid. $^1H$ NMR (DMSO, 300 MHz, ppm) 7.94(s, 1H), 7.82 (d, 1H 8 Hz), 7.21 (d, 2H, 8 Hz), 7.20–6.90 (m, 7H), 6.42(d, 1H, 7 Hz) 3.53(s, 2H), 2.22(s, 3H); m/z 376.

B. To a stirred solution of the compound from step A (200 mg, 0.53 mmol) and 4-bromo-ethyl butyrate (104 mg, 0.53 mmol) in DMF (1 ml) was added $K_2CO_3$ (120 mg, 1.45 mmol). The slurry was stirred at 70–75° C. for 6 hours, filtered through a sinter glass funnel and dripped into 50 ml of vigorously stirring 5% HCl. The aqueous slurry was extracted with 3×50 ml of EtoAc. The organic phases were combined and washed with brine (25 ml), dried over $MgSO_4$ and concentrated to give the desired compound (150 mg, 57%) as a yellow solid. $^1H$ NMR (DMSO, 300 MHz, ppm) 8.98 (s, 1H) 7.88 (s, 1H), 7.85(d, 1H, 8 Hz), 7.40 (d, 2H, 7 Hz) 7.3–7.1(m, 6H), 6.95(t, 1H, 6 Hz), 6.6(d, 1H, 6 Hz) 4.45(t, 1H, 6 Hz), 4.02(q, 2H, 7 Hz), 3.91(t, 2H, 7 Hz), 3.54(s, 2H), 2.42(t, 2H, 7 Hz), 2.25(s, 3H), 1.94(t, 2H, 7 Hz), 1.15(t, 3H, 7 Hz); m/z 490.

C. To a stirred solution of the compound from step B (150 mg, 0.31 mmol) in DMF (1 ml) at room temperature was added 2N LiOH (385 ul, 0.77 mmol). The mixture was stirred overnight and following acidification with TFA (red to litmus) an aliquot was purified by preparative HPLC to give RX23. $^1$HNMR (DMSO, 300 MHz, ppm) 9.01(s, 1H), 7.91(s, 1H) 7.83 (d, 1H, 8 Hz), 7.39(d, 1H, 8 Hz), 7.29 (s, 1H), 7.23–7.14(m, 5H), 6.92(t, 1H, 8 Hz) 6.6(d, 1H, 8 Hz), 3.92(t, 2H, 7 Hz), 3.54(s, 2H), 2.35(t, 2H, 7 Hz), 2.22 (s, 1H), 1.90(m, 2H); m/z 460.

Synthesis of RX19

A. As described for the synthesis of RX23B utilizing RX23A (119 mg, 0.317 mmol) and 3-Bromo-propionaldehyde dimethylacetal(89 mg, 0.49 mmol) with 250 mg of $K_2CO_3$. The solids were filtered and the DMF was pumped off under high vacuum. Recrystalization from methanol provided the desired product (75 mg, 52%) as a white solid. $H^1$ NMR (DMSO, 300 MHz, ppm) 8.98(s, 1H), 7.88(s, 1H), 7.83(d, 1H, 8 Hz), 7.39(d, 2H, 8 Hz), 7.32(s, 1H), 7.32–7.12(m, 6H), 6.93(t, 1H, 6H), 6.6(m, 1H), 4.53(t, 6H), 3.92(t, 2H, 7H), 3.54(s, 2H), 3.33(s, 3H), 3.24(s, 3H), 2.22(s, 3H), 1.95(q, 2H, 6 Hz, 6 Hz), m/z (M+Na)$^+$ 500.

B. The compound from step A (29 mg, 0.061 mmol) in 2 mL of 50/50 $THF/H_2O$ with a catalytic amount of p-toluenesulfonic was stirred at 40° C. for 4 hours. The reaction mixture was reduced under vacuum and used without purification: m/z 454. The crude residue was taken up in 2 ml of acetone, cooled to 0/in an ice bath and 44 uL of Jones reagent was added. The reaction mixture was allowed to warm to room temparature with stirring overnight. Isopropanol (2 ml) was added and the mixture was stirred an additional 30 minutes, filtered, and concentrated under high vacuum. Preparative HPLC provided RX19 (15.5 mg, 57%) as a tan solid. $H^1$ NMR (DMSO, 300 MHz, ppm) 9.01(s, 1H), 7.9(s, 1H), 7.83(d, 1H, 8 Hz), 7.40 (d, 2H, 8 Hz), 7.31(s, 1H), 7.24–7.09(m, 6H), 6.93(t, 1H, 7 Hz), 6.59(d, 1H, 8 Hz), 4.09(t, 2H, 6 Hz), 3.54(s, 2H), 2.66(t, 2H, 6 Hz), 2.22(s, 3H); m/z 448.

Preparation of BX41

A. To a solution of $Na_2CO_3$ (1.33 g, 12.51 mmol) in $H_2O$ (35 mL) was added portionwise 2-amino-4-fluorobenzoic acid (1.94 g, 12.51 mmol). The mixture was stirred at RT until homogeneous, then cooled in an ice bath. To the cold solution was gradually added phosgene (9.72 mL of a 1.93M solution in toluene, 18.76 mmol). After completing the addition, the reaction was stirred briskly at RT for 2 h. The precipitated solids were collected by suction filtration, rinsed with $H_2O$ (1×35. mL, 1×20 mL), chased with n-hexane, and dried on the filter. There was obtained 2.023 g (89%) of desired product as a white solid: m.p.=228–229° C.; TLC (1:1 $CH_2Cl_2/Et_2O$) $R_f$=0.74; $^1H$ NMR ($CDCl_3$, 300 MHz, ppm) 7.97–7.93 (m, 1H), 6.84–6.79 (m, 2H).

B. Under a stream of dry $N_2$, NaH (0.459 g of a 60% dispersion, 11.48 mmol) was washed with n-hexane (2×10 mL), suspended in anhydrous DMF (55 mL), and cooled in an ice bath. To the cold suspension was added dropwise a solution of the product from part A (1.98 g, 10.93 mmol) in anhydrous DMF (55 mL). After completing the addition, the mixture was stirred at 0° C. for 45 min. To the resulting nearly colorless solution was added MeI (0.71 mL, 11.48 mmol). The reaction was stirred at RT for 2 h until judged complete by TLC analysis. The DMF was removed by rotary evaporation under high vacuum. The syrupy residue was dissolved in EtOAc/$H_2O$, separated, and the organic layer washed with $H_2O$ (1×), brine (1×), and dried ($MgSO_4$). Filtration and concentration provided 2.04 g (96%) of the desired product as a pale yellow solid: TLC (100% $CH_2Cl_2$) $R_f$=0.18; $^1H$ NMR ($CDCl_3$, 300 MHz, ppm) 8.10–8.04 (m, 1H), 6.95–6.89 (m, 1H), 6.84–6.77 (m, 1H), 3.46 (s, 3H).

C. A mixture of the product from part B (2.04 g, 10.45 mmol) and glycine (0.79 g, 10.45 mmol) in glacial AcOH (22 mL) was briskly refluxed under $N_2$. After 18 h, the reaction was judged complete by TLC analysis and cooled to RT. Most of the AcOH was removed by rotary evaporation under high vacuum. The syrupy residue was triturated with $Et_2O$ (20 mL) and stirred briskly at RT for 2 h. The precipitated solids were collected by suction filtration, rinsed with $Et_2O$, and dried on the filter. There was obtained 1.806 g (83%) of the desired product as a white solid: MS (ESP+) 208.9; TLC (100% EtOAc) $R_f$=0.30; $^1H$ NMR ($CDCl_3$, 300 MHz, ppm) 7.84 (br t, 1H), 7.89–7.74 (m, 1H), 6.92–6.86 (m, 1H), 6.83–6.79 (m, 1H), 3.65 (m, 2H), 3.24 (s, 3H).

D. In the manner described for the preparation of BX47, part B, the product of part C above (0.50 g, 2.402 mmol), ethyl acrylate (0.39 mL, 3.60 mmol), anhydrous CsF (0.401 g, 2.642 mmol), and tetraethyl orthosilicate (0.54 mL, 2.40 mmol) were reacted in THF (8 mL) at RT under $N_2$ for 18 h. The crude product was purified by flash chromatography (100% $CH_2Cl_2$ to 10% $Et_2O/CH_2Cl_2$) to provide 0.51 g (69%) of pure product as a white solid: MS (ESP+) 309.2; TLC (10% $Et_2O/CH_2Cl_2$) $R_f$=0.30; $^1H$ NMR ($CDCl_3$, 300 MHz, ppm) 7.83–7.78 (m, 1H), 6.97–6.90 (m, 1H), 6.86–6.82 (m, 1H), 4.08 (q, 2H, J=7.15 Hz), 3.98 (B of AB, 1H, J=14.91 Hz), 3.87–3.80 (m, 3H), 3.30 (s, 3H), 2.74–2.54 (m, 2H), 1.19 (t, 3H, J=7.20 Hz).

E. In the manner described for the preparation of BX47, part C, the product of part D above (0.51 g, 1.68 mmol) was reacted with fuming nitric acid (3 mL) for 18 h. There was obtained 0.49 g (83%) of crude desired product as a foam: MS (ESP+) 354.0; TLC (100% $Et_2O$) $R_f$=0.25; $^1H$ NMR ($CDCl_3$, 300 MHz, ppm) 8.61 (d, 1H, J=8.34 Hz), 7.07 (d, 1H, J=11.83 Hz), 4.11 (q, 2H, J=7.11 Hz), 4.02 (s, 2H), 3.88 (t, 2H, J=6.63 Hz), 3.38 (s, 3H), 2.80–2.57 (m, 2H), 1.23 (t, 3H, J=7.21 Hz).

F. In the manner described for the preparation of BX47, part D, the product of part E above (0.35 g, 0.991 mmol), Fe powder (0.166 g, 2.97 mmol), and glacial AcOH (0.11 mL, 1.98 mmol) were refluxed in 2:1 EtOH/$H_2O$ (10 mL) under $N_2$ for 3 h. There was obtained 0.302 g (94%) of crude desired product as an oil: MS (ESP+) 324.0; TLC (100% EtOAc) $R_f$=0.53; $^1H$ NMR ($CDCl_3$, 300 MHz, ppm) 7.32 (d, 1H, J=9.41 Hz), 6.85 (d, 1H, J=11.8 Hz), 4.51 (br s, 1H), 4.15–4.00 (m, 3H), 3.89–3.79 (m, 3H), 3.29 (s, 3H), 2.78–2.60 (m, 2H), 1.26–1.20 (m, 3H).

G. The product of part F (0.30 g, 0.93 mmol), 4-nitrophenylacetic acid (0.169 g, 0.93 mmol) and EDC (0.269 g, 1.40 mmol) were dissolved in anhydrous DMF and stirred at RT under $N_2$. After 18 h, the reaction was judged complete by TLC and the DMF removed by rotary evaporation under high vacuum. The residue was dissolved in EtOAc/$H_2O$, separated, and the organic layer washed with $H_2O$ (1×) and 5% $NaHCO_3$ (1×). The combined aqueous layers were extracted with EtOAc (2×). The pooled organic layers were washed with brine (1×) and dried ($MgSO_4$). Filtration, evaporation and flash chromatography (100% $CHCl_3$ to 40% THF/$CHCl_3$) provided 0.279 g (61%) of pure desired product as a foam: MS (ESP+) 486.6; TLC (1:1 THF/$CHCl_3$) $R_f$=0.53; $^1H$ NMR ($CDCl_3$, 300 MHz, ppm) 8.54 (d, 2H, J=8.64 Hz), 8.22 (dd, 1H, J=1.90, 6.82 Hz), 7.52 (d, 2H, J=8.68 Hz), 6.89 (d, 1H, J=11.79 Hz), 4.12 (q, 2H, J=7.13 Hz), 4.01 (A of AB, 1H, J=14.98 Hz), 3.87 (s, 2H), 3.92–3.77 (m, 3H), 3.31 (s, 3H), 2.79–2.57 (m, 2H), 1.23 (t, 3H, J=7.13 Hz).

H. In the manner of part F above, the product of part G (0.28 g, 0.574 mmol), Fe powder (0.096 g, 1.722 mmol), and glacial AcOH (66 μL) were refluxed in 2:1 EtOH/$H_2O$ (6 mL) under $N_2$ for 2 h. There was obtained 0.208 g (78%) of crude desired product as a foam: MS (ESP+) 457.3; TLC (1:1 THF/$CHCl_3$) $R_f$=0.38; $^1H$ NMR ($CDCl_3$, 300 MHz, ppm) 8.54 (d, 1H, J=8.64 Hz), 7.53 (br s, 1H), 7.07 (d, 2H, J=8.24 Hz), 6.84 (d, 1H, J=11.70 Hz), 6.73 (d, 2H, J=8.06 Hz), 4.14–4.04 (m, 2H), 3.99 (A of AB, 1H, J=14.92 Hz), 3.88–3.72 (m, 3H), 3.64 (s, 2H), 3.27 (s, 3H), 2.78–2.58 (m, 2H), 1.25–1.20 (m, 3H).

I. A solution of the product of part H (0.21 g, 0.456 mmol) and o-tolyl isocyanate (0.11 mL, 0.89 mmol) in EtOAc (4.5 mL) was refluxed under $N_2$ for 2 h until judged complete by TLC analysis. The reaction was cooled to RT. The precipitated solids were collected by suction filtration, rinsed with EtOAc and dried on the filter to provide 0.159 g (59%) of pure product as an off-white solid: MS (ESP+) 590.2; TLC (1:1 THF/$CHCl_3$) $R_f$=0.50; $^1H$ NMR (DMSO-$d_6$, 300 MHz, ppm) 10.07 (s, 1H), 8.99 (s, 1H), 8.22 (d, 1H, J=8.77 Hz) 7.89 (s, 1H), 7.83 (d, 1H, J=7.96 Hz), 7.42–7.38 (m, 3H), 7.23 (d, 2H, J=8.46 Hz), 7.17–7.10 (m, 2H), 6.92 (t, 1H, J=7.33 Hz), 4.08–3.98 (m, 3H), 3.84–3.76 (m, 2H), 3.70–3.60 (m, 1H), 3.66 (s, 2H), 3.25 (s, 3H), 2.60–2.54 (m, 2H), 2.23 (s, 3H), 1.14 t, (3H, J=7.11 Hz).

J. To a gently refluxing suspension of the product of part I (0.100 g, 0.170 mmol) in anhydrous THF (17 mL) under $N_2$ was added sodium trimethylsilanolate (0.68 mL of a 1.0M solution in $CH_2Cl_2$, 0.678 mmol) The heat was withdrawn and the reaction stirred overnight at RT. The precipitated solids were collected by suction filtration, rinsed with THF, and dried on the filter. The crude product was dissolved in glacial AcOH (1 mL), treated with $Et_2O$ (1 mL), and stirred briskly overnight. The resulting solids were collected, rinsed with 1:1 $Et_2O$/AcOH, and dried on the filter. There was obtained 0.059 g (62%) of BX41 as an off-white solid: MS (ESP+) 584.0 (M+Na) ; $^1H$ NMR (DMSO-$d_6$, 300 MHz, ppm) 10.07 (s, 1H), 9.03 (s, 1H), 8.22 (d, 1H, J=8.71 Hz), 7.93 (s, 1H), 7.82 (d, 1H, J=7.91 Hz), 7.42–7.38 (m, 3H), 7.24 (d, 2H, J=8.36 Hz), 7.17–7.10 (m, 2H), 6.92 (t, 1H, J=7.32 Hz), 4.05 (A of AB, 1H, J=15.1 Hz), 3.83 (B of AB, 1H, J=15.1 Hz), 3.72–3.66 (m, 4H), 3.25 (s, 3H), 2.50–2.46 (m, 2H), 2.23 (s, 3H).

Preparation of BX67

A. In the manner described for the preparation of BX41, part D, 1-methyl-1,4-benzodiazepin-2,5-dione (5.00 g, 26.29 mmol), anhydrous CsF (4.393 g, 28.92 mmol), ethyl crotonate (4.90 mL, 39.44 mL) and tetraethyl orthosilicate (5.86 mL, 26.29 mmol) were reacted in anhydrous THF (88 mL) at RT under $N_2$ for 72 h. The crude product was purified by flash chromatography (100% CH$_2$Cl$_2$ to 25% Et$_2$O/CH$_2$Cl$_2$) to provide 4.04 g (50%) of pure desired product as a white solid: MS (ESP+) 305.4; m.p.=84–86° C.; TLC (1:1 Et$_2$O/CH$_2$Cl$_2$) R$_f$=0.51; $^1$H NMR (CDCl$_3$, 300 MHz, ppm, rotamers) 7.87–7.79 (m, 1H), 7.51–7.45 (m, 1H), 7.28–7.23 (m, 1H), 7.17–7.14 (m, 1H), 5.31–5.22 and 5.19–5.08 (m, 1H), 4.13–4.03 (m, 2H), 3.86–3.73 (m, 2H), 3.35 (s, 3H), 2.85–2.77 and 2.59–2.45 (m, 2H), 1.33 and 1.28 (d, 3H, J=6.9 Hz), 1.24–1.16, (m, 3H).

B. In the manner described for the preparation of BX47, part E, the product of part A above (4.04 g, 13.27 mmol) was reacted with fuming nitric acid (26 mL) for 2 h. Trituration of the crude product with Et$_2$O (45 mL) at −20° C. gave a solid mass which was broken up with a spatula. The suspension was then stirred briskly at RT for 18 h. The solid was collected by suction filtration, washed with Et$_2$O and dried on the filter. There was obtained 4.061 g (88%) of pure product as a faintly yellow powder: MS (ESP+) 350.3; m.p.=104–106° C.; TLC (100% EtOAc) R$_f$=0.76; $^1$H NMR (CDCl$_3$, 300 MHz, ppm, rotamers) 8.75–8.70 (m, 1H), 8.34–8.29 (m, 1H), 7.33–7.30 (m, 1H), 5.24–5.06 (m, 1H), 4.15–4.03 (m, 2H), 3.94–3.78 (m, 2H), 3.41 (s, 3H), 2.85–2.76 and 2.63–2.47 (m, 2H), 1.35 and 1.30 (d, 3H, J=6.9 Hz), 1.27–1.17 (m, 3H).

C. A suspension of the product of part B (4.06 g, 11.62 mmol), Fe powder (1.95 g, 34.87 mmol), and glacial AcOH (1.33 mL, 23.24 mmol) in 2:1 EtOH/H$_2$O (120 mL) was refluxed under N$_2$ for 3 h. The completed reaction was cooled to RT, diluted with H$_2$O (40 mL) and filtered through Celite. The reaction flask and filter cake were washed with EtOAc (4×100 mL). In a separatory funnel, the combined filtrate was washed with 5% NaHCO$_3$ (2×100 mL). The combined aqueous washes were extracted with EtOAc (1×100 mL), and the pooled organics washed with brine (1×100 mL) and dried (MgSO$_4$). Filtration and concentration provided crude product as a foam. This was purified by trituration with Et$_2$O, initially at −20° C. then at reflux for 2 h. After cooling to RT, the solids were collected by suction filtration, rinsed with Et$_2$O, and dried on the filter. There was obtained 3.09 g (83%) of pure product as a peach-colored solid: MS (ESP+) 320.0; m.p.=116–118° C.; TLC (100% EtOAc) R$_f$=0.35; $^1$H NMR (CDCl$_3$, 300 MHz, ppm, rotamers) 7.15–7.08 (m, 1H), 6.96–6.93 (m, 1H), 6.84–6.79 (m, 1H), 5.27–5.05 (m, 1H), 4.27 (br s, 2H), 4.11–4.01 (m, 2H), 3.84–3.62 (m, 2H), 3.26 (s, 3H), 2.81–2.73 and 2.56–2.42 (m, 2H), 1.30–1.24 (d, 3H, J=6.9 Hz), 1.22–1.14 (m, 3H).

D. In the manner described for the preparation of BX41, part G, the product of part C (3.09 g, 9.66 mmol) was condensed with 4-nitrophenylacetic acid (2.10 g, 11.59 mmol) in the presence of EDC (2.78 g, 14.49 mmol) in anhydrous DMF (50 mL) at RT under N$_2$ for 18 h. Crude product was purified by trituration with Et$_2$O at RT. The solid was collected by suction filtration, washed with Et$_2$O (100 mL), and dried on the filter. There was obtained 4.30 g (92%) of desired product as a pale yellow powder: MS (ESP+) 483.3; m.p.= 118–120° C.; TLC (100% EtOAc) R$_f$=0.45; $^1$H NMR (CDCl$_3$, 300 MHz, ppm, rotamers) 8.77 and 8.32 (s, 1H), 8.25 (dd, 1H, J=2.54, 8.99 Hz), 8.19 and 8.17 (d, 2H, J=8.67 and 8.64 Hz, respectively), 7.69 and 7.59 (d, 1H, J=2.60 and 2.56 Hz, respectively), 7.50 and 7.49 (d, 2H, J=8.73 and 8.68 Hz, respectively), 7.15 (d, 1H, J=8.98 Hz), 5.28–5.13 (m, 1H), 4.09 and 3.98 (q, 2H, J=7.12 and 7.13 Hz, respectively), 3.87–3.73 (m, 4H), 3.35 and 3.32 (s, 3H), 2.84–2.75 and 2.54–2.47 (m, 2H), 1.32 and 1.25 (d, 3H, 6.93 and 6.86 Hz, respectively), 1.21 and 1.15 (t, 3H, J=7.23 and 7.12 Hz, respectively).

E. In the manner described in part C above, the product of part D (4.30 9, 8.91 mmol) was reduced with Fe powder (1.49 g, 26.74 mmol) and AcOH (1.02 mL, 17.82 mmol) in refluxing 2:1 EtOH/H2O (90 mL). After an aqueous workup, there was obtained 3.98 g (99%) of crude product as a brittle foam: MS (ESP+) 453.5; TLC (100% EtOAc) R$_f$=0.30; $^1$H NMR (CDCl$_3$, 300 MHz, ppm, rotamers) 8.09 (m, 1H), 7.43–7.38 (m, 1H), 7.10–7.02 (m, 3H), 6.73–6.69 (m, 2H), 5.21–5.08 (m, 1H), 4.13–4.01 (m, 2H), 3.76 (s, 2H), 3.60 (s, 2H), 3.31 and 3.30 (s, 3H), 2.82–2.74 and 2.53–2.46(m, 2H), 1.34–1.15 (m, 6H).

F. In the manner described for the preparation of BX41, part I, the product of part E (3.98 g, 8.8 mmol) was refluxed in EtOAc 90 mL) with o-tolyl isocyanate (2.18 mL, 17.6 mmol) for 3 h. The reaction was cooled to RT and concentrated to roughly one-third of the original volume. The precipitated solids were collected by suction filtration, rinsed with EtOAc (1×25 mL) and dried on the filter. There was obtained 3.77 g (73%) of desired product as an off-white powder: MS (ESP+) 586.4; m.p.=164–166° C.; TLC (1:1 THF/CHCl$_3$) R$_f$=0.45; $^1$H NMR (CDCl$_3$, 300 MHz, ppm, rotamers) 9.02 and 8.90 (br s, 1H), 7.96 and 7.92 (br s, 1H), 7.88–7.84 (m, 1H), 7.68–7.63 (m, 1H), 7.51–7.48 (m, 1H), 7.31 (br s, 1H), 7.03–6.85 (m, 8H), 5.22–5.10 (m, 1H), 4.06–3.92 (m, 2H), 3.75–3.65 (m, 2H), 3.40 (s, 2H), 3.26 and 3.23 (s, 3H), 2.79–2.70 and 2.51–2.44 (m, 2H), 2.06 (s, 3H), 1.30 and 1.22 (d, 3H, J=6.9 Hz), 1.17–1.11 (m, 3H).

G. To a cloudy solution of the product of part F (1.00 g, 1.71 mmol) in CH$_2$Cl$_2$ (7 mL) was gradually added at RT sodium trimethylsilanolate (10.25 mL of a 1.0M solution in CH$_2$Cl$_2$, 10.25 mmol). After stirring overnight at RT, the reaction was concentrated to dryness and the solid residue treated with 1N HCl to pH 2–3. The viscous mixture was diluted with H$_2$O (50 mL) and extracted with 20% Et$_2$O/THF (1×100 mL) The organic extract was washed with H$_2$O (1×25 mL) and brine (2×25 mL) and dried (MgSO$_4$). Filtration and evaporation provided 0.93 g of crude product which was recrystallized from MeCN (25 mL) to give 0.657 g (69%) of BX67 as a beige powder: MS (ESP+) 558.2; m.p.=237–239° C.; TLC (3:1 THF/CHCl$_3$) R$_f$=0.37; $^1$H NMR (DMSO-d$_6$, 300 MHz, ppm, rotamers) 10.46 (s, 1H), 8.99 (s, 1H), 7.95–7.93 (m, 1H), 7.88 (s, 1H), 7.84–7.76 (m, 2H), 7.40 (d, 2H, J=8.56 Hz),7.33 (dd, 1H, J=1.82, 8.93 Hz) 7.23 (d, 2H, J=8.50 Hz), 7.17–7.07 (m, 2H), 6.95–6.90 (m, 1H), 5.03–4.90 (m, 1H), 3.84–3.71 (ABq, 2H), 3.56 (s, 2H), 3.24 and 3.22 (s, 3H), 2.56–2.40 (m, 2H), 2.22 (s, 3H), 1.17 and 1.14 (d, 3H, J=7.0 and 6.80 Hz, respectively).

Preparation of MX3

A. To a solution of Z-Asp(OtBu) (1.00 g, 3.09 mmol) in anhydrous DME (8 mL) at −20° C. under N$_2$ was added, in order, N-methylmorpholine (0.34 mL, 3.09 mmol) and isobutyl chloroformate (0.40 mL, 3.09 mmol). After 5 min, the reaction was filtered through glass wool to remove solids. To the filtrate was added ethereal CH$_2$N$_2$ (ca. 4.64 mmol) at 0° C. After 30 min, excess CH$_2$N$_2$ was removed by bubbling a stream of dry N$_2$ through the reaction for 10 min. The reaction was concentrated to dryness and the residue dissolved in MeOH (16 mL) to which was added a solution of silver benzoate (0.14 g, 0.62 mmol) in Et$_3$N (1.55 mL) at RT. After stirring 30 min, the reaction was evaporated to dryness, the residue dissolved in EtOAc, and this solution passed through a pad of $SiO_2$. The filtrate was washed with 5% $NaHCO_3$ (3×), $H_2O$ (1×), 5% citric acid (3×), and brine (2×), and dried ($MgSO_4$). Filtration and evaporation provided crude product as an oil (0.70 g, 64%): MS (FAB) 348; TLC (20% EtOAc/hexane) $R_f$=0.30; $^1H$ NMR ($CDCl_3$, 300 MHz, ppm) 7.35–7.27 (m, 5H), 5.72 and 5.58 (br d, 1H, 8.9 Hz), 5.10 and 5.06 (s, 2H), 4.60–4.51 and 4.36–4.29 (m, 1H), 3.73 and 3.64 (s, 3H), 2.75–2.47 (m, 4H), 1.40 (s, 9H).

B. A solution of the above product (0.70 g, 1.99 mmol) in MeOH (3 mL) was treated with 1N NaOH (3 mL) at RT. After stirring 1 hr, the reaction was judged complete by TLC analysis. The MeOH was removed by rotary evaporation. The residue was diluted with $H_2O$ and extracted with $Et_2O$ (3×). These extracts were discarded. The aqueous was made acidic (pH 4) by addition of 1M $NaHSO_4$ and extracted with EtOAc (3×). The combined EtOAc extracts were washed with $H_2O$ (1×), and brine (1×), and dried ($MgSO_4$). The product was obtained as an oil (0.52 g, 77%): MS (FAB) 338 (M+H), 360 (M+Na); TLC (1:1 EtOAc/$CHCl_3$) $R_f$=0.13; $^1H$ NMR ($CDCl_3$, 300 MHz, ppm) 7.33–7.28 (m, 5H), 5.77 and 5.63 (d,1H, J=8.7 Hz), 5.11 and 5.07 (s, 2H), 4.63–4.58 and 4.37–4.30 (m, 1H), 2.78–2.50 (m, 4H), 1.40 (s, 9H).

C. A mixture of DCC (1.85 g, 8.95 mmol) and HOBT (1.37 g, 8.95 mmol) in EtOAc (55 mL) was stirred at RT 20 min until homogeneous. The product of part B (3.02 g, 8.95 mmol), 4-methoxybenzylamine (1.17 mL, 8.95 mmol), and N-methylmorpholine (1.97 mL, 17.9 mmol) were then added. After stirring overnight, the reaction was filtered to remove solids and the cake washed with fresh EtOAc (50 mL). The filtrate was washed with $H_2O$ (2×) 5% citric acid (1×) 5% $NaHCO_3$ (1×), and brine (1×), and dried ($MgSO_4$). Flash column chromatography on $SiO_2$ eluting with 100% $CHCl_3$ followed by 10% EtOAc/$CHCl_3$ provided product as a white solid (3.41 g, 83%): mp=100–102° C.; MS (FAB) 457; TLC (9:1 $CHCl_3$/MeOH) $R_f$=0.71; $^1H$ NMR ($CDCl_3$, 300 MHz, ppm) 7.33–7.27 (m, 5H), 7.16 (d, 2H, J=8.6 Hz), 6.82 (d, 2H, J=8.7 Hz), 6.06 (br s, 1H), 5.89 (br d, 1H), 5.04 (s, 2H), 4.31 (d, 2H, J=5.6 Hz), 4.31–4.22 (m, 1H), 3.76 (s, 3H), 2.68–2.44 (m, 4H), 1.39 (s, 9H).

D. A suspension of this product (0.50 g, 1.1 mmol) and Degussa type E101 NE/W 10% Pd/C (0.117 g) in MeOH (20 mL) was hydrogenolyzed under 25 psi $H_2$ for 18 hr. The reaction was filtered through Celite, rinsing with MeOH. The filtrate was evaporated to dryness. The product was obtained as a colorless oil (0.36 g, 100%): MS (FAB) 323; TLC (9:1 $CHCl_3$/MeOH) $R_f$=0.30; $^1H$ NMR ($CDCl_3$, 300 MHz, ppm) 7.58 (br s, 1H), 7.15 (d, 2H, J=8.6 Hz), 6.79 (d, 2H, J=8.6 Hz), 4.30 (d, 2H, J=6.50 Hz), 3.74 (s, 3H), 3.54 (m, 1H), 3.15 (br s, 2H), 2.46–2.29 (m, 4H), 1.40 (s, 9H).

E. The product from part D (0.36 g, 1.1 mmol) and Eschenmoser's salt (0.204 g, 1.1 mmol) were refluxed in MeCN (10 mL) under an inert atmosphere for 42 hr. The reaction was cooled to RT and evaporated to dryness. The residue was diluted with 5% $NaHCO_3$ and extracted with EtOAc (3×). The combined organic extracts were washed with 5% $NaHCO_3$ (1×), $H_2O$ (1×), and brine (1×), and dried ($MgSO_4$). Flash column chromatography with a $CHCl_3$/EtOAc gradient provided the product as an oil (0.19 g, 51%): MS (FAB) 335; TLC (1:1 EtOAc/$CHCl_3$) $R_f$=0.22; $^1H$ NMR ($CDCl_3$, 300 MHz, ppm) 7.16 (d, 2H, J=8.6 Hz), 6.81 (d, 2H, J=8.6 Hz), 4.64 (A of AB, 1H, J=14.6 Hz), 4.27 (B of AB, 1H, J=14.6 Hz), 4.10 (ABq, 2H, J=11.7 Hz), 3.75 (s, 3H), 3.28 (m, 1H), 2.50 (dd, 1H, J=4.4, 17.2 Hz), 2.37 (AB of ABX, 2H, J=15.8 Hz), 2.24 (dd, 1H, J=11.2, 17.2 Hz), 1.99 (br s, 1H), 1.40 (s, 9H).

F. A mixture of o-tolylureidophenylacetic acid (3.53 g, 12.4 mmol), H-Leu-OtBu.HCl (2.78 g, 12.4 mmol), TBTU (3.98 g, 12.4 mmol), and $iPr_2NEt$ (4.32 mL, 24.8 mmmol) in DMF (25 mL) was stirred overnight at RT. The product was precipitated by addition of $H_2O$ (10 mL). The solids were collected by filtration on a medium frit, washing with 2:1 DMF/$H_2O$ (35 mL), $H_2O$ (25 mL), and $Et_2O$ (2×25 mL), and dried on the filter (4.18 g, 74%). All of this product was suspended in $CH_2Cl_2$ (16 mL) and treated with TFA (16 mL) and stirred at RT 2 hr. The reaction was concentrated to a syrup which was evaporated from $CH_2Cl_2$ (2×20 mL). The residue was triturated with $Et_2O$ (100 mL) at RT for 2 hr. The solids were collected by filtration on a medium frit, washing with $Et_2O$ (50 mL), and dried on the filter (3.40 g, 93%): MS (FAB) 398.

H. The product from step G (0.66 g, 1.96 mmol), the product of part F (0.78 g, 1.96 mmol) and EDC (0.410 g, 2.14 mmol) were stirred in NMP (4 mL) at RT for 48 hr. The reaction was poured into EtOAc (60 mL), washed with H2O (8×6 mL), brine (1×), and dried ($MgSO_4$). The desired diastereomer was isolated pure (0.34 g, 24%) by repeated flash column chromatography using 1:1 EtOAc/$CH_2Cl_2$: MS (ESP+) 714.3; TLC (100% EtOAc) $R_f$=0.53; $^1H$ NMR ($CDCl_3$, 300 MHz, ppm) 7.53–7.43 (m, 2H), 7.20–7.00 (m, 9H), 6.80–6.73 (m, 2H), 6.45–6.33 (m, 1H), 5.31–4.58 (m, 4H), 4.21–4.00 (m, 1H), 3.73 (s, 3H), 3.41 (s, 2H), 2.74–2.35 (m, 4H), 2.14 (s, 3H), 1.36 (s, 9H), 1.56–1.05 (m, 3H), 0.88, 0.82, 0.68, 0.63 (4d, 6H total, J=6.17, 6.32, 6.46, 6.37 Hz, respectively).

G. This product (0.34 g, 0.476 mmol) was stirred in TFA (3 mL) at RT for 3 hr. The reaction was concentrated to dryness and the residue evaporated from $CH_2Cl_2$ (3×3 mL). The crude product was triturated with $Et_2O$ at RT, collected by filtration and dried on the filter. The product, MX3, was obtained as a light yellow solid (0.263 g, 84%): MS (ESP+) 680.2 (M+Na) ; $^1H$ NMR ($d^6$-DMSO, 300 MHz, ppm) consistent with structure and indicative of rotamers.

It will be apparent to those skilled in the art that various modifications and variations can be made in the methods and compositions of the present invention without departing from the spirit or scope of the invention. Thus, it is intended that the present invention cover the modifications and variations of this invention provided that they come within the scope of the appended claims and their equivalents.

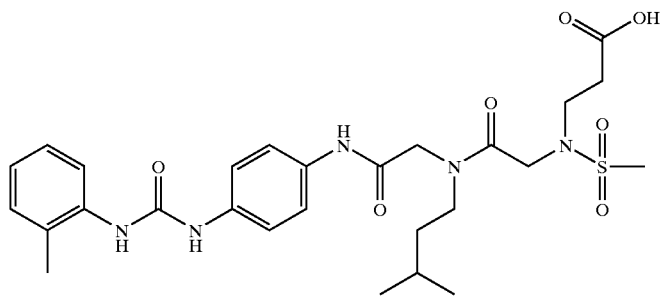
Name: AY46  Act: 0.0225
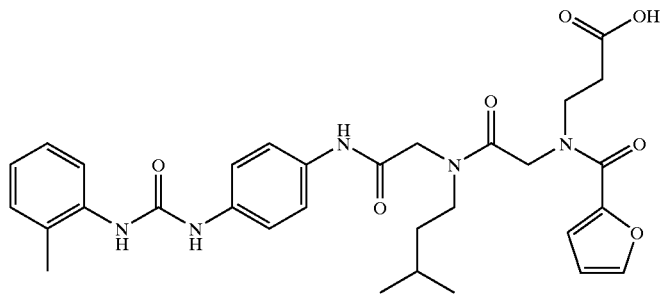
Name: AY47  Act: 0.0195
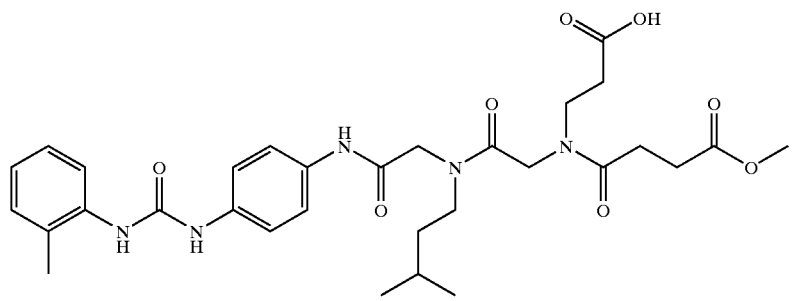
Name: AY48  Act: 0.017

-continued
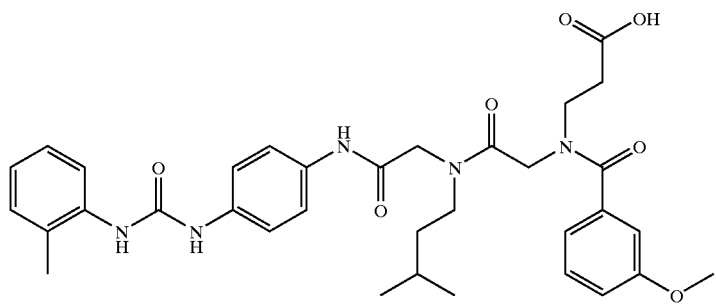
Name: AY49  Act: 0.015
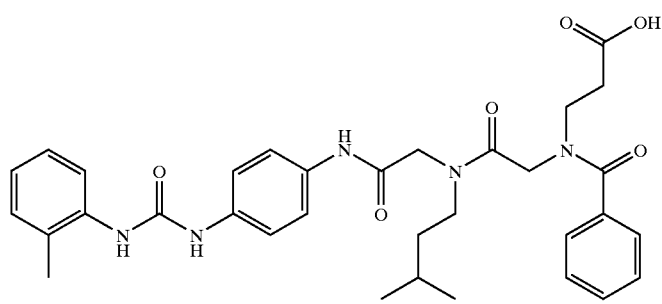
Name: AY50  Act: 0.0125
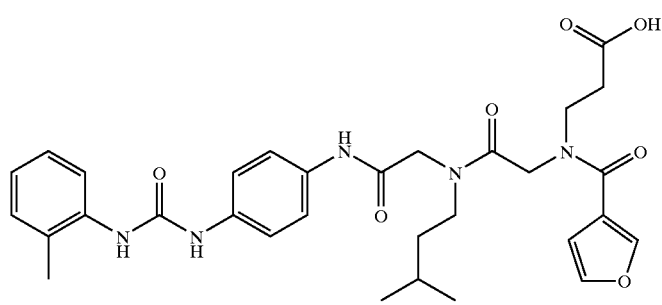
Name: AY51  Act: 0.012

TABLE 3
Structure-Activity 9
52 Compounds
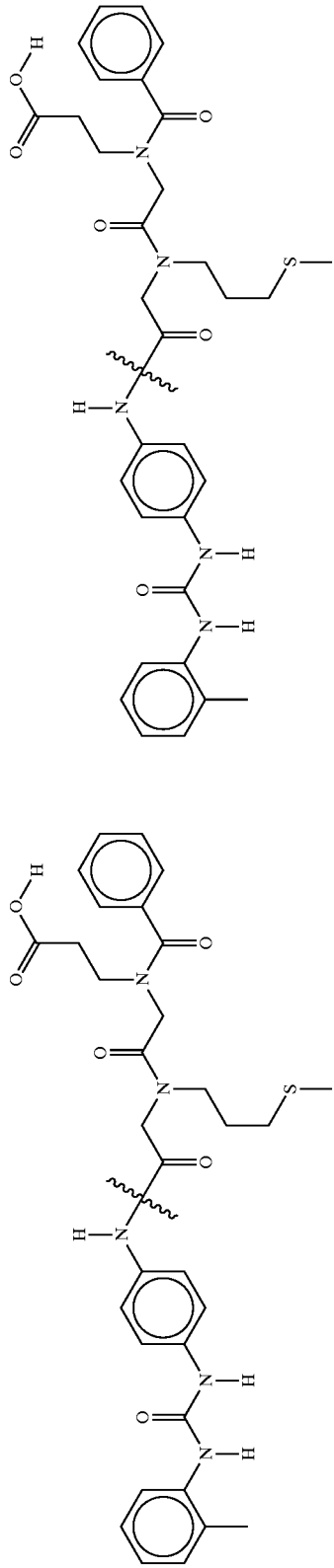
Name: AY43
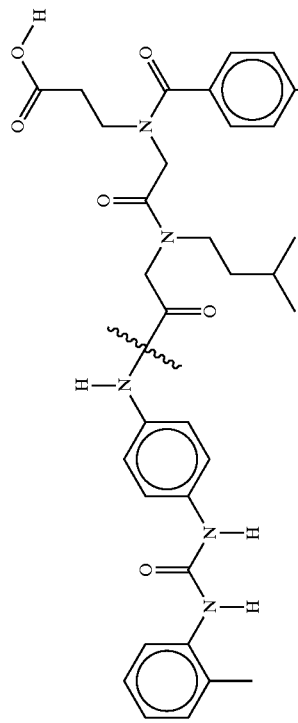
Act: 0.0375 Name: AY44
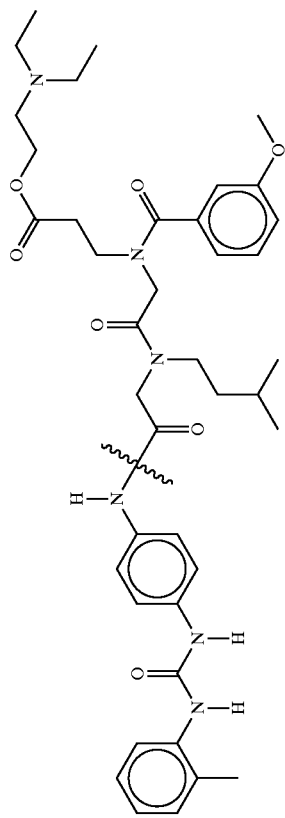
Act: prodrug Name: AY52
Act: 0.011333
Name: AY45

TABLE 3-continued
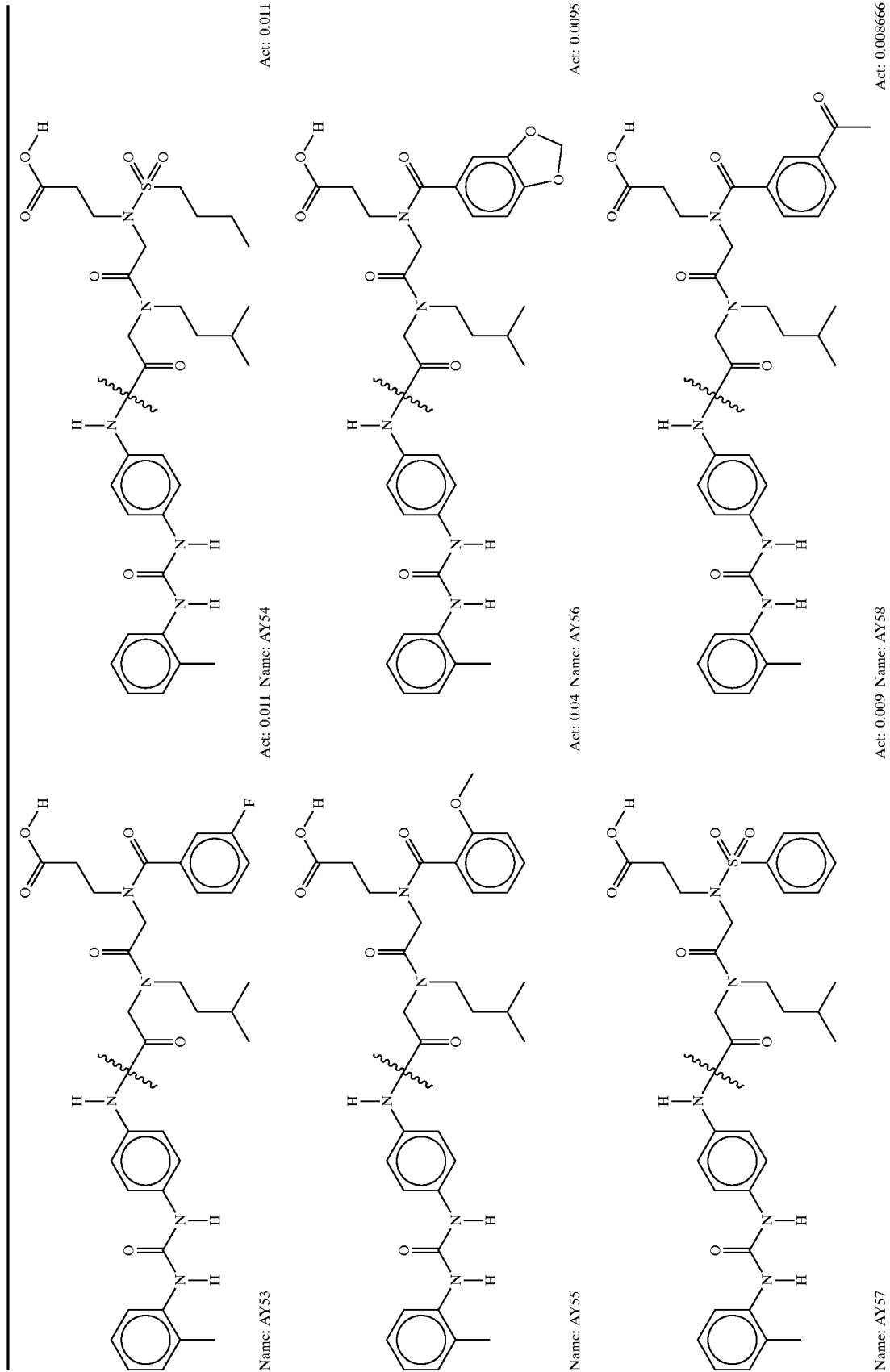

TABLE 3-continued
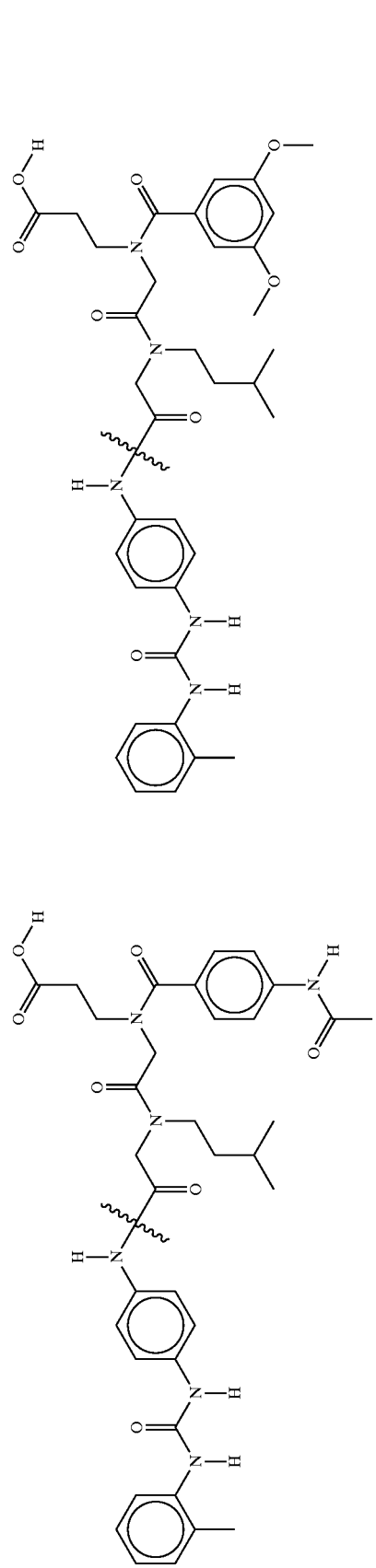
Name: AY59
Name: AY61
Act: 0.007 Name: AY60
Act: 0.006 Name: AY62
Act: 0.006333
Act: 0.0055
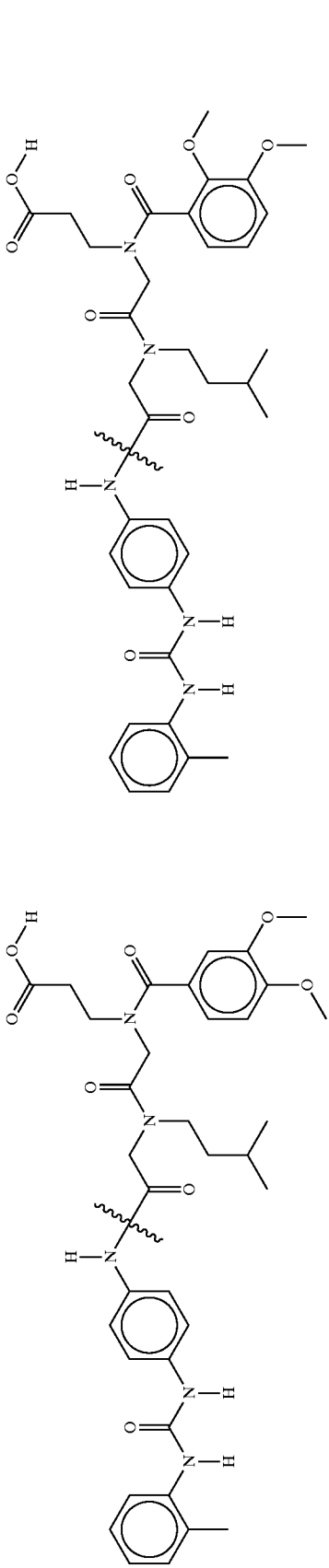

TABLE 3-continued
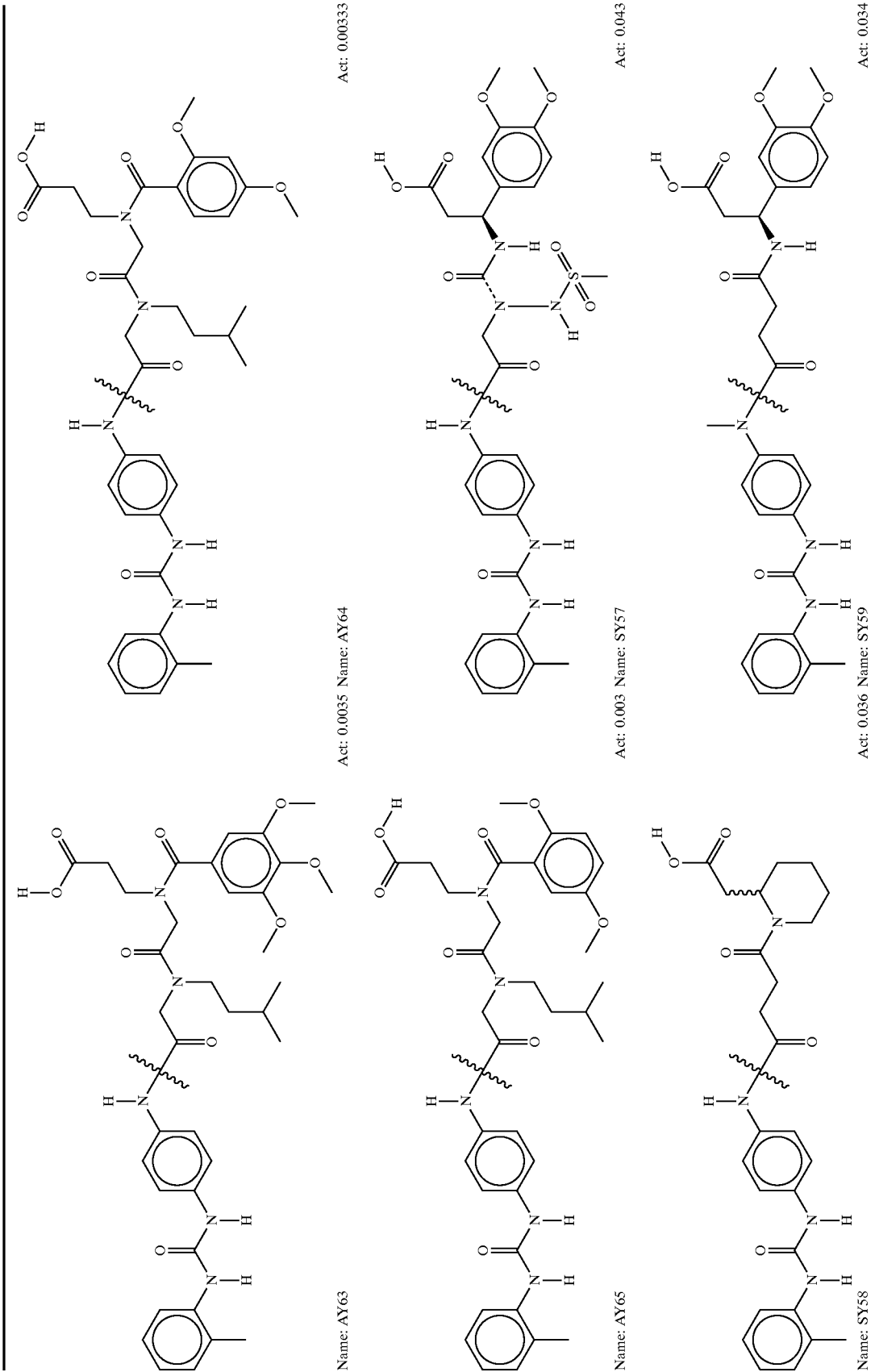

TABLE 3-continued
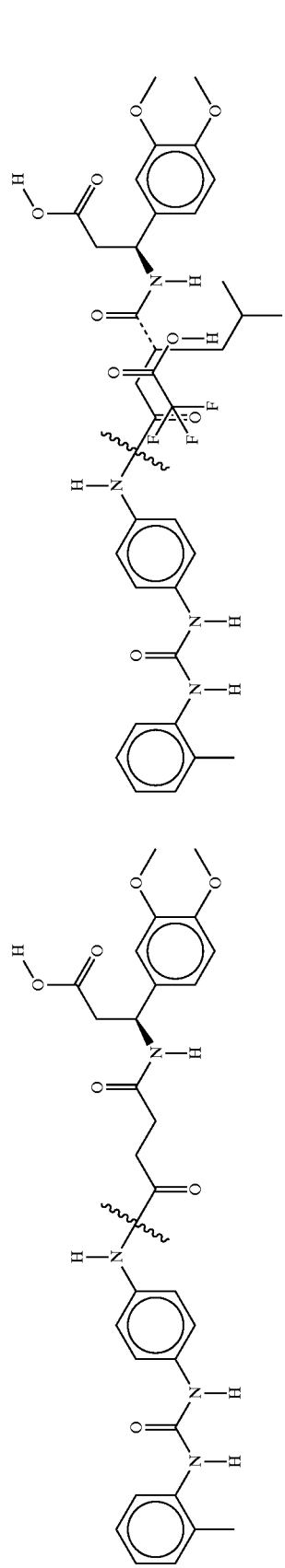
Name: SY60 Act: 0.01625  Name: SY61 Act: 0.0125
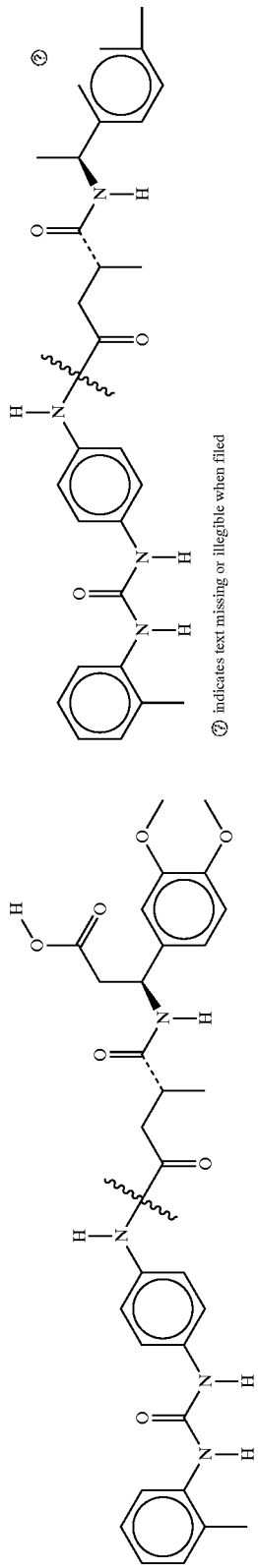
Name: SY62 Act: 0.009666 Name: SY63 Act: 0.0095
Ⓣ indicates text missing or illegible when filed
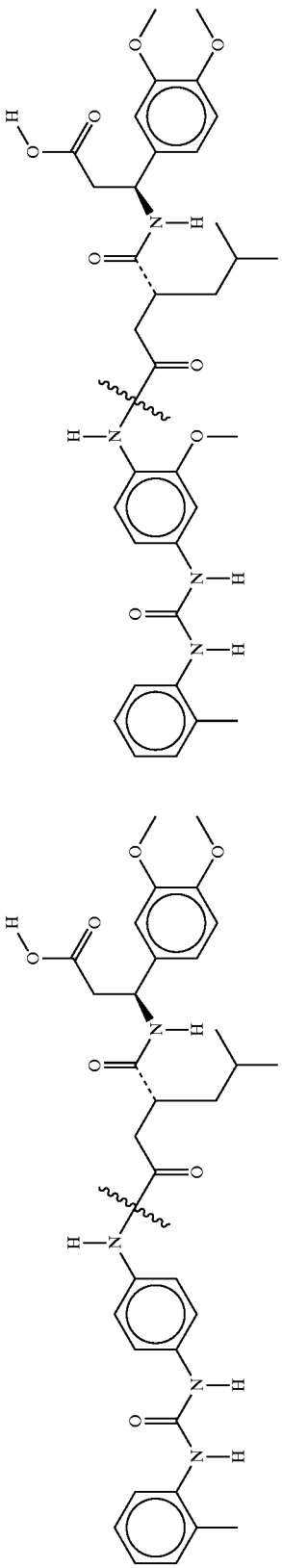
Name: SY64 Act: 0.0055 Name: SY65 Act: 0.004

TABLE 3-continued
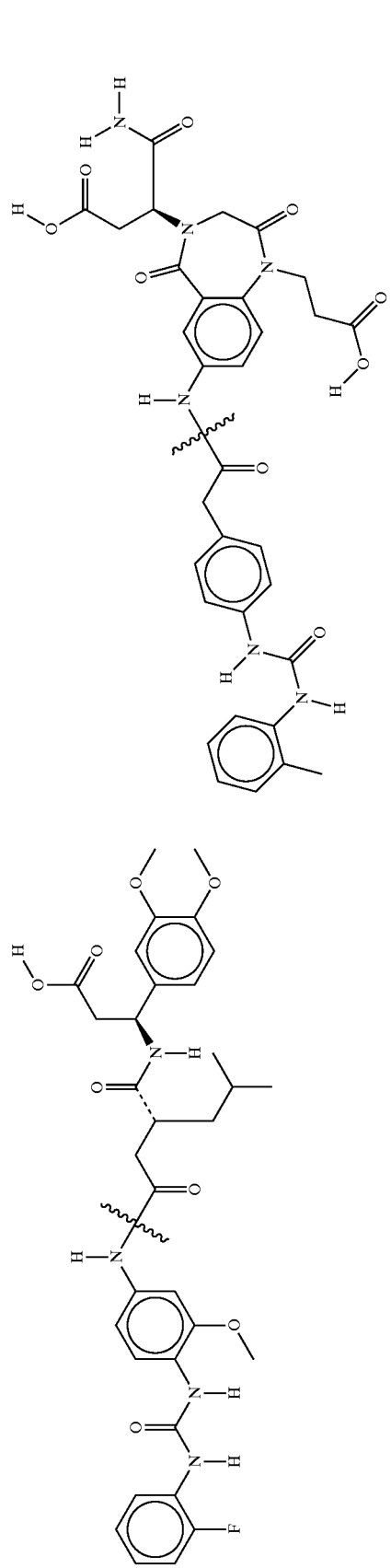
Name: SY66
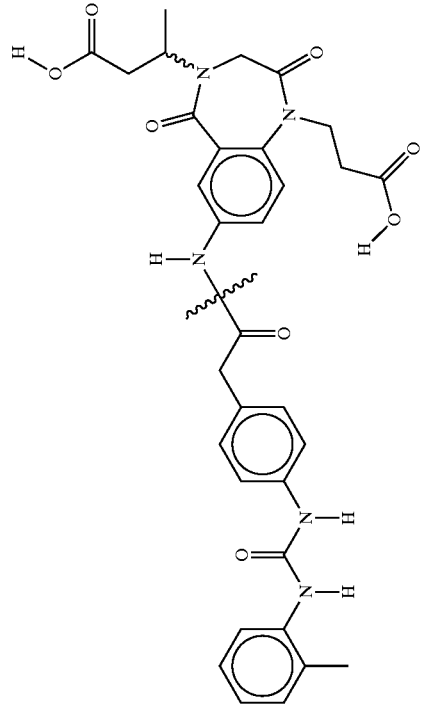
Act: 0.038 Name: BY70
Act: 0.0145 Name: BY76
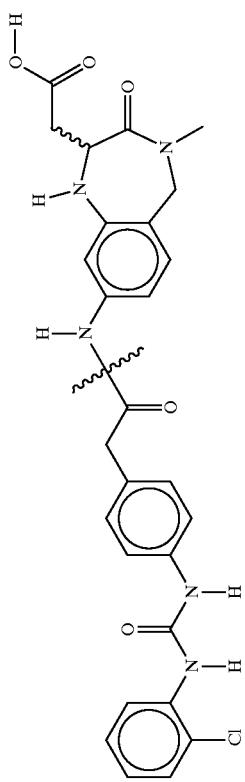
Act: 0.003 Name: BY75
Act: 0.0185

TABLE 3-continued
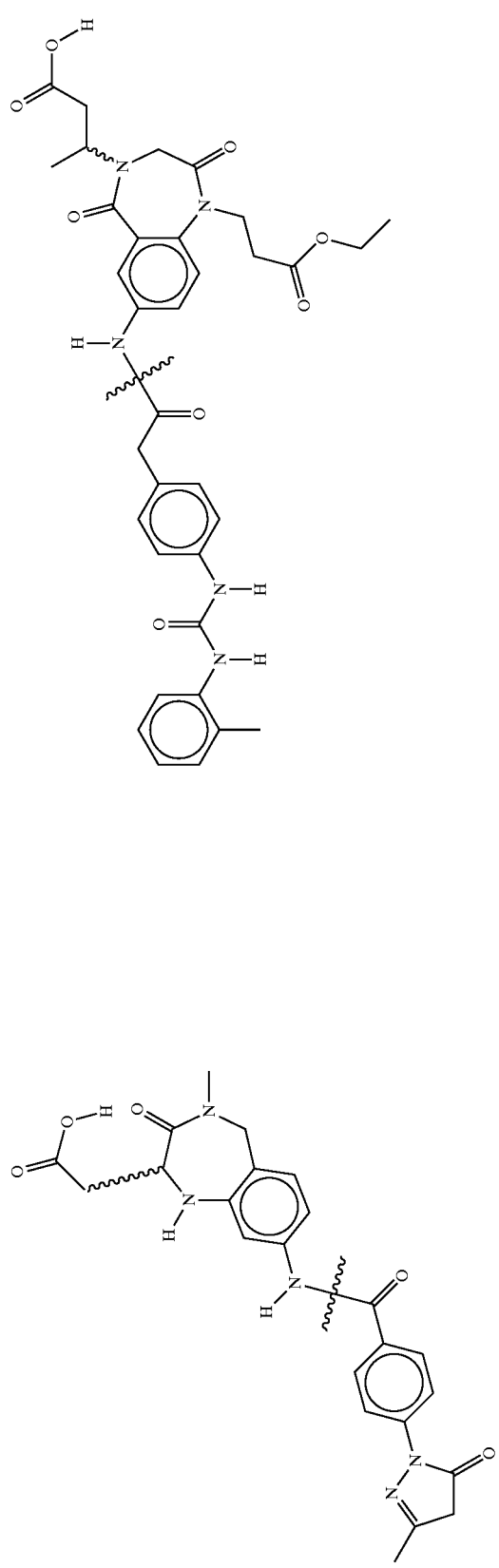
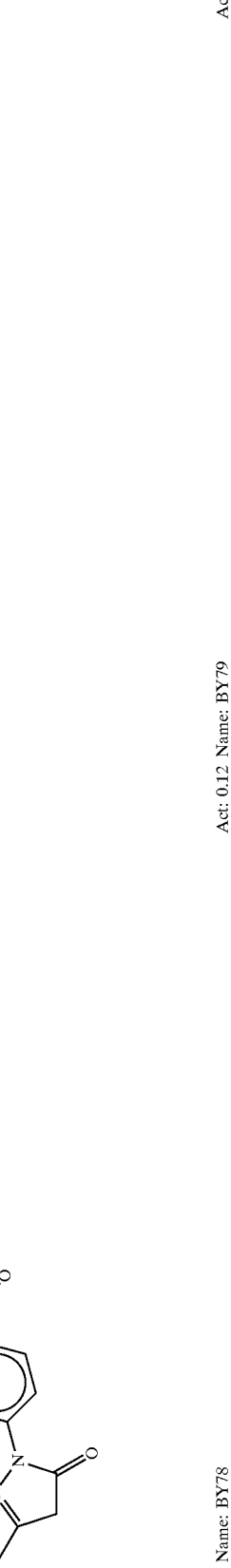
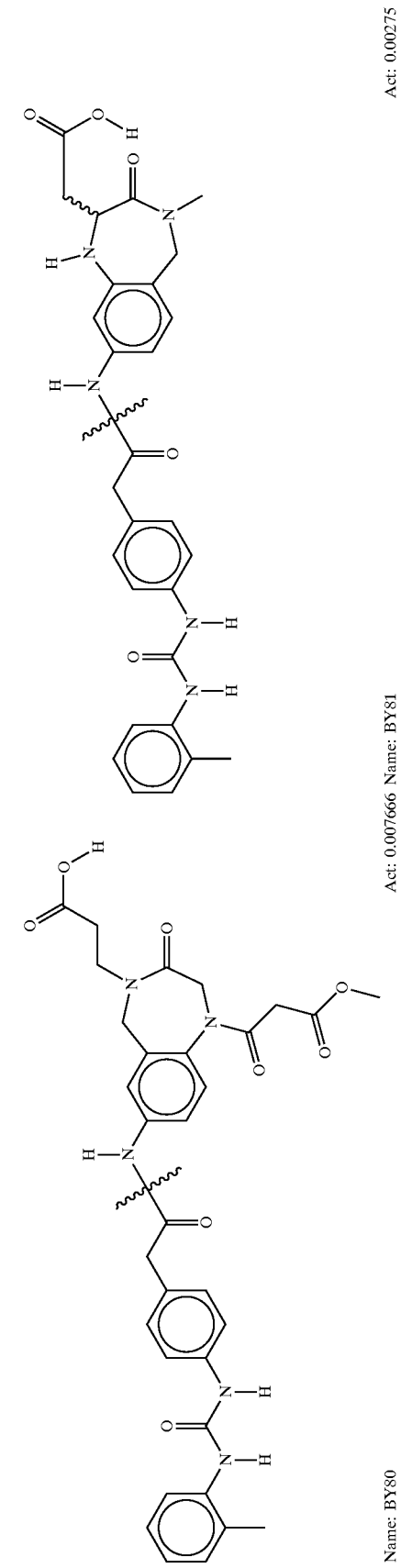
Name: BY78
Name: BY80
Act: 0.12 Name: BY79
Act: 0.01
Act: 0.007666 Name: BY81
Act: 0.00275

TABLE 3-continued
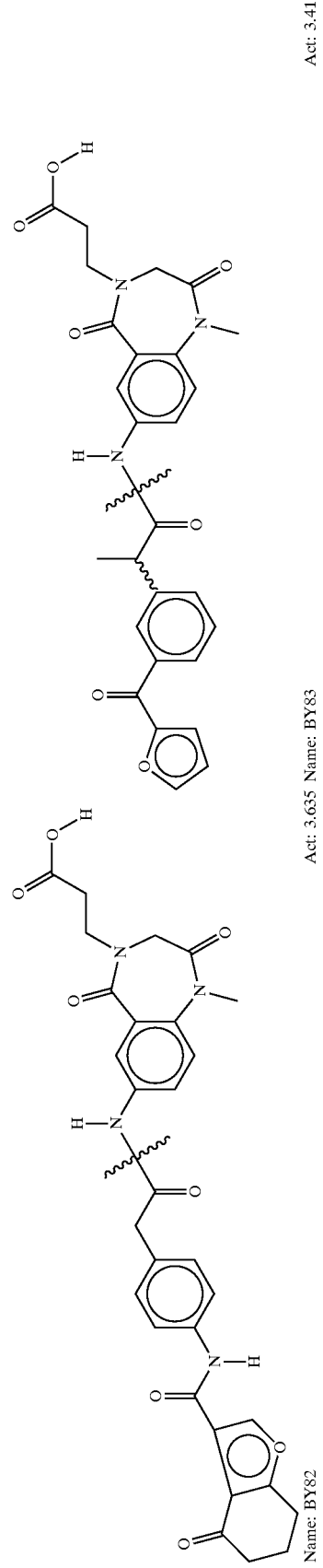
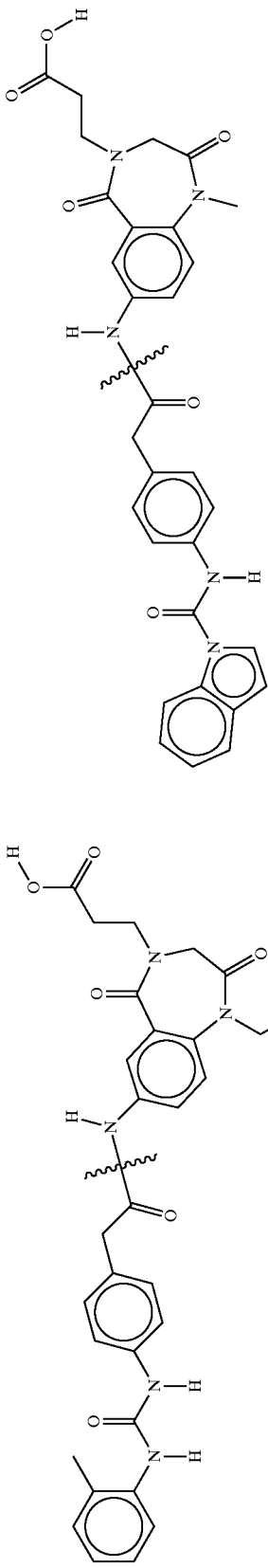
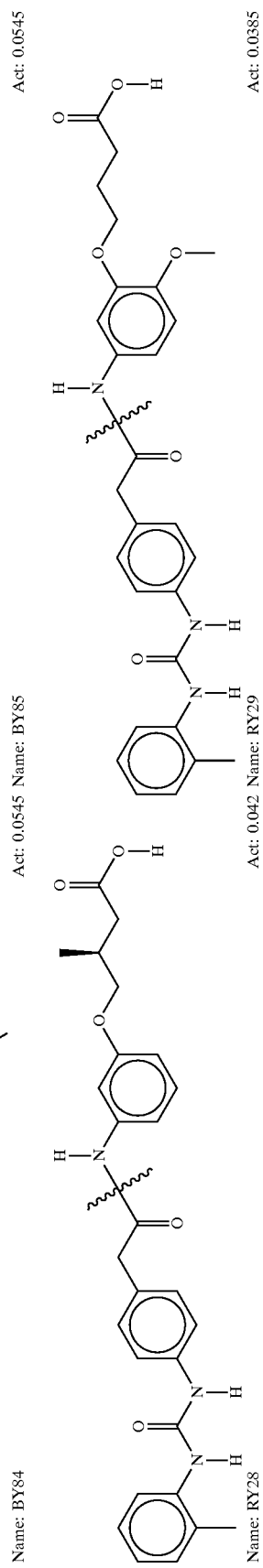

TABLE 3-continued

| Name: RY30 | Act: 0.01 Name: CY14 | Act: 0.036 |
| Name: CY15 | Act: 0.033 Name: CY16 | Act: 0.0065 |
| Name: CY17 | Act: 0.0055 Name: CY18 | Act: 0.002 |
| Company | Patent Number | Preferred Compound | Hybrid Structure |

TABLE 3-continued
| | | | | | |
|---|---|---|---|---|---|
| Merck | EP 478328 | 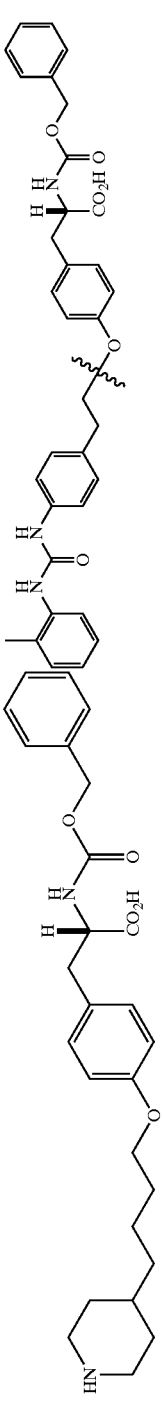 | | | |
| Merck | EP 478363 | 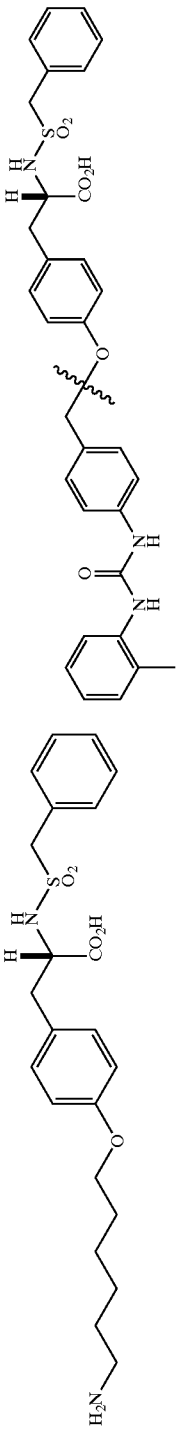 | | | |
| Merck | EP 478362 | 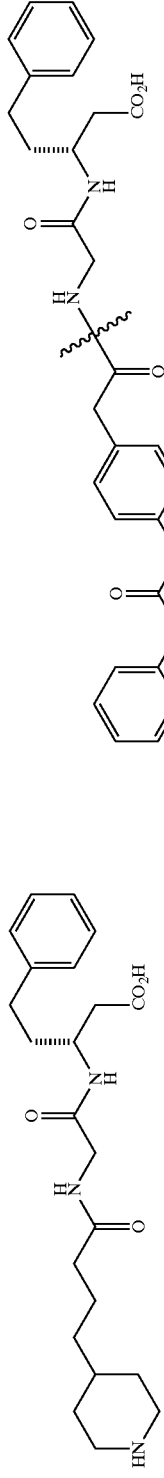 | | | |
| Merck | U.S. Pat. No. 5272158 | 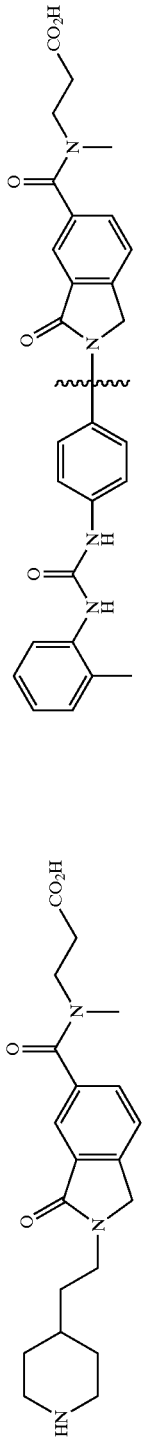 | | | |
| Merck | U.S. Pat. No. 5227490 WO 93/16697 | 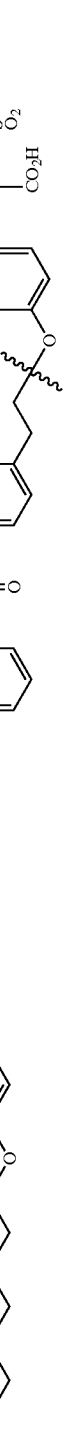 | | | |

TABLE 3-continued

| Merck | U.S. Pat. No. 5294616 | U.S. Pat. No. 5264420 | EP 512829 | EP 512829 |

TABLE 3-continued
| Merck | EP 512831 | 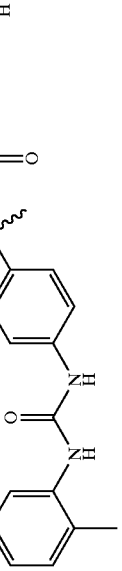 |  |
| Merck | EP 512831 | 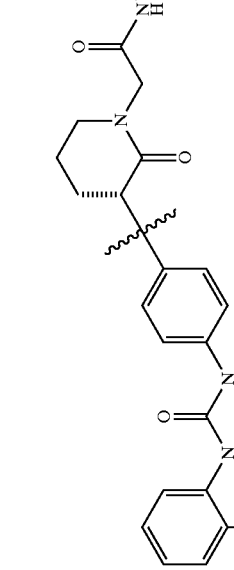 | 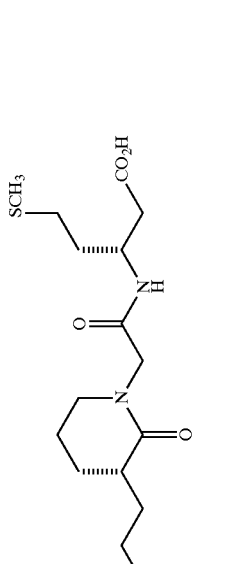 |
| Merck | U.S. Pat. No. 5389631 | 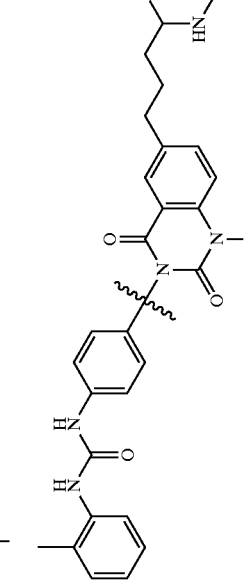 | 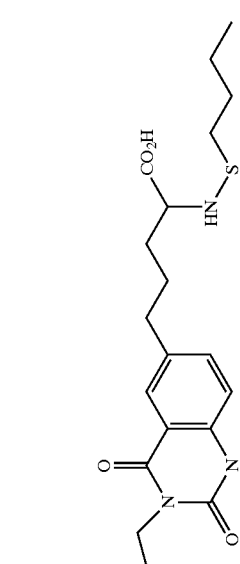 |
| Merck | U.S. Pat. No. 5389631 | 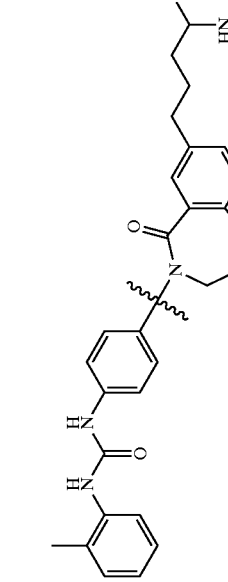 | 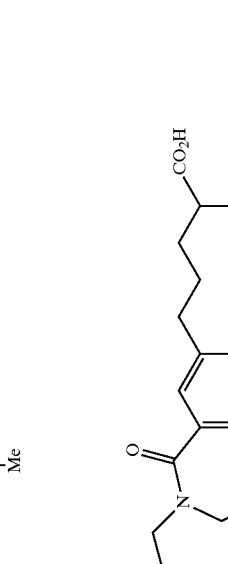 |

TABLE 3-continued
| Merck | U.S. Pat. No. 5340798 | 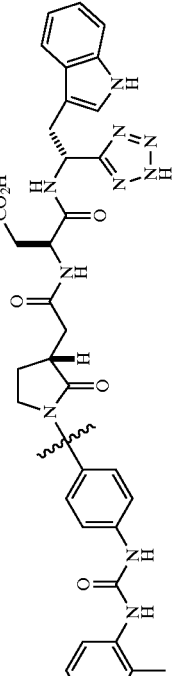 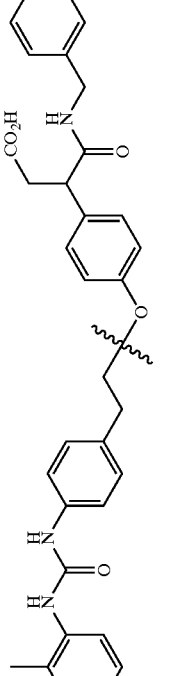 |
| Merck | U.S. Pat. No. 5358956 GB 2271567 | 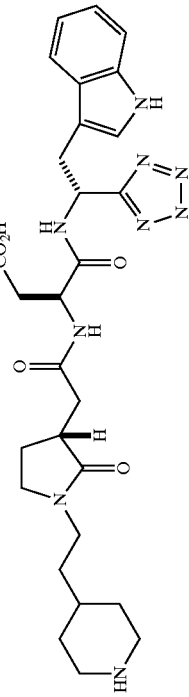 |
| Merck | EP 540334 | 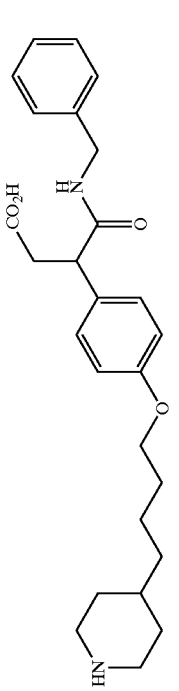 |
| Merck | EP 540334 | 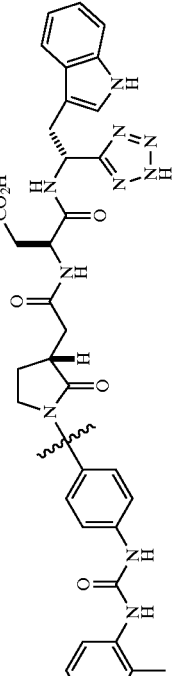 |
| Merck | WO 94/08577 | 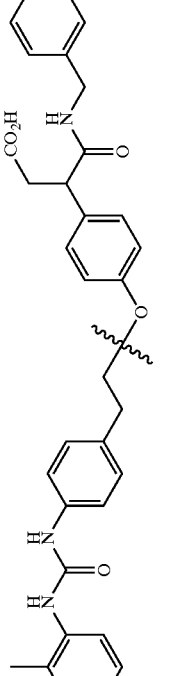 |

TABLE 3-continued
| Merck | U.S. Pat. No. 5334596 WO 94/26745 | 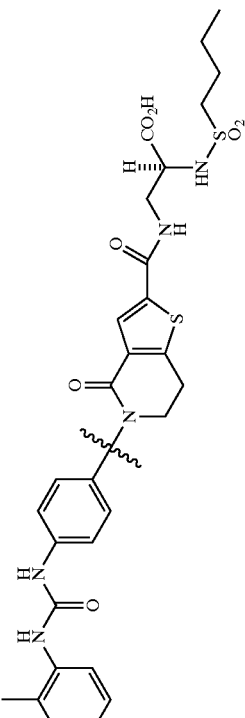 | 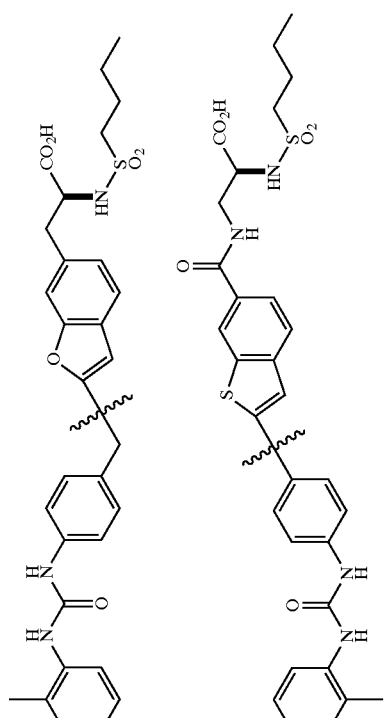 |
| Merck | U.S. Pat. No. 5334596 WO 94/26745 | 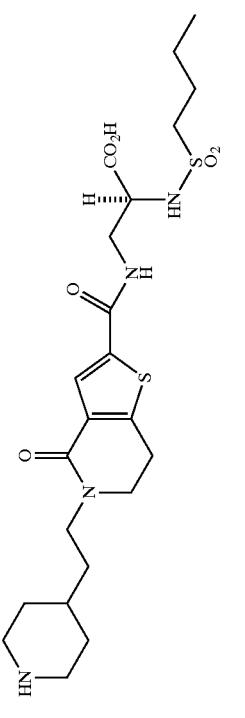 | 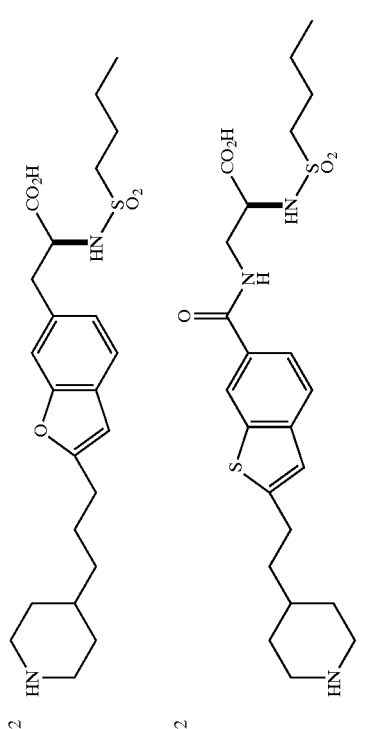 |
| Merck | WO 94/08962 | 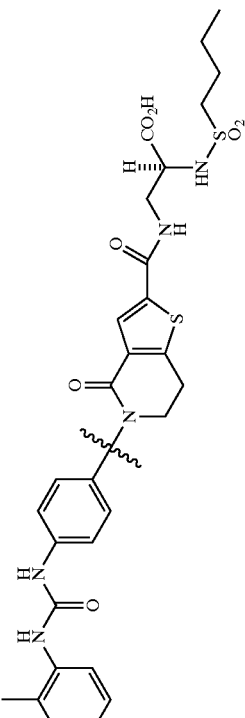 | 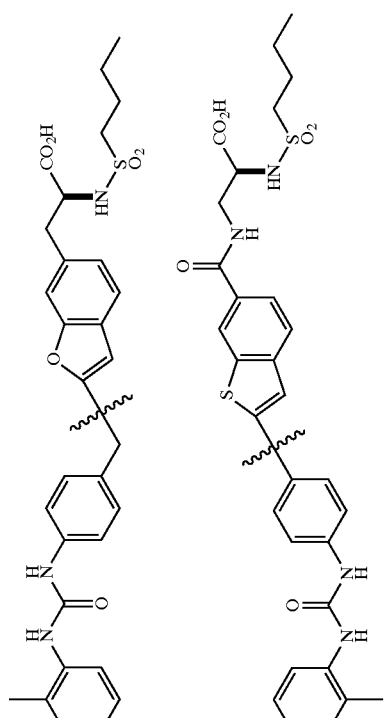 |
| Merck | WO 94/08962 | 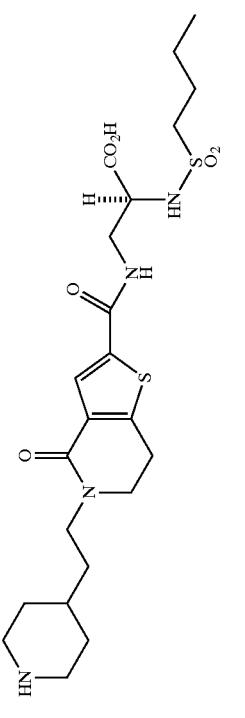 | 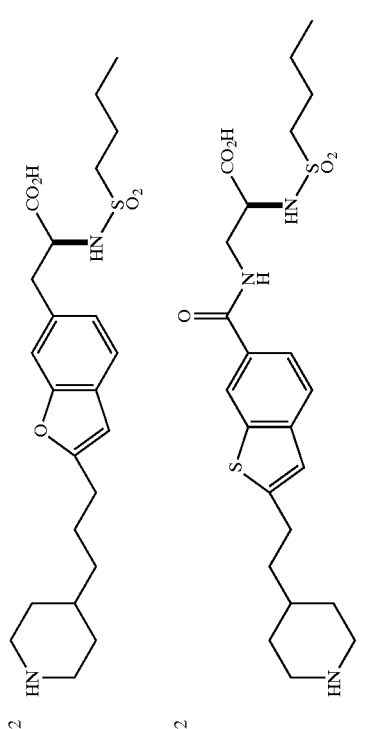 |

TABLE 3-continued

| Merck | WO 94/08962 | | |
| Merck | WO 94/08962 | | |
| Merck | WO 94/22825 | | |
| Merck | WO 94/12181 | | |
| Merck/Germany | EP 608759 | | |

TABLE 3-continued
| | | |
|---|---|---|
| Merck | WO 94/18981 | 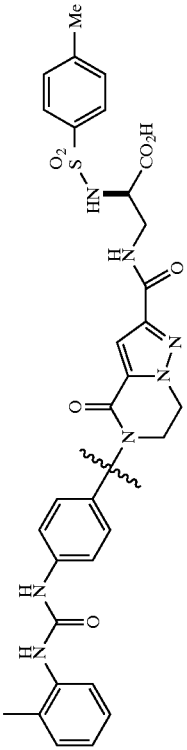 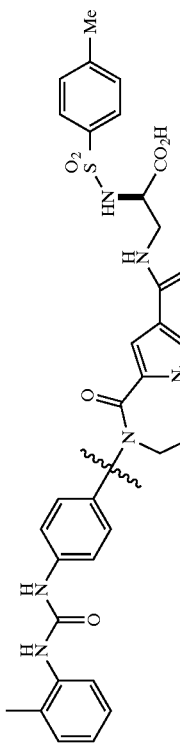 |
| Merck | WO 94/18981 | 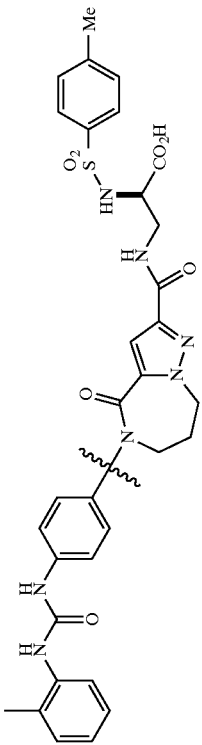 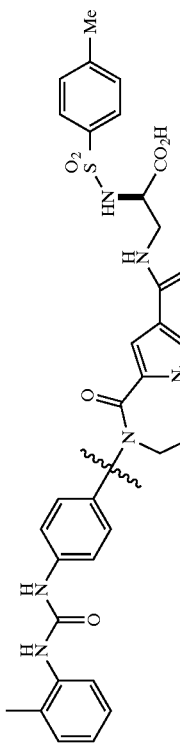 |
| Merck | WO 94/18981 | 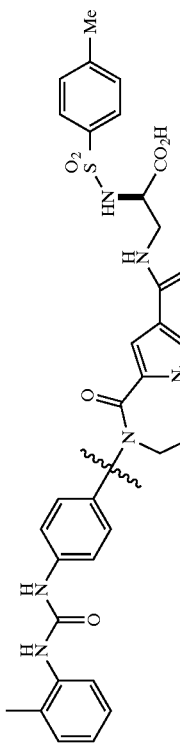 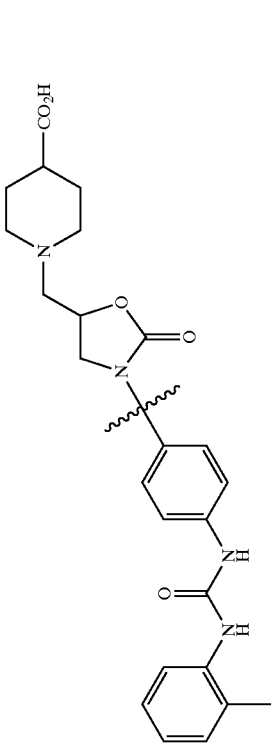 |
| Merck/ Germany | EP 623615 US 5532255 | 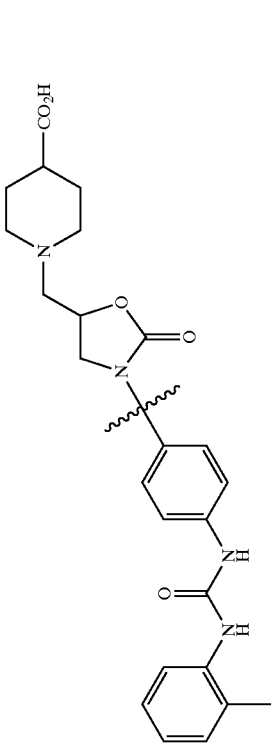 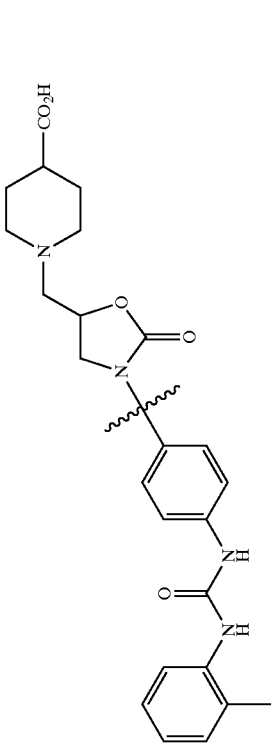 |

TABLE 3-continued

| | |
|---|---|
| Merck/ Germany | EP 645376 |
| Merck/ Germany | EP 668278 |
| Merck | GB 2292558 |
| Merck/ Germany | EP 711770 |

TABLE 3-continued

| Sandoz | EP 560730 | | |
| Genentech | U.S. Pat. No. 5250679 | | |
| Genentech | WO 93/08174 | | |

TABLE 3-continued
| | | |
|---|---|---|
| Genentech | U.S. Pat. No. 5403836 | 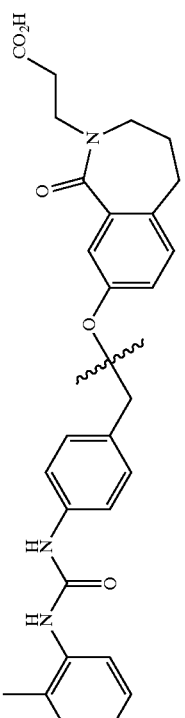 |
| Monsanto | U.S. Pat. No. 4879313<br>EP 352249 | 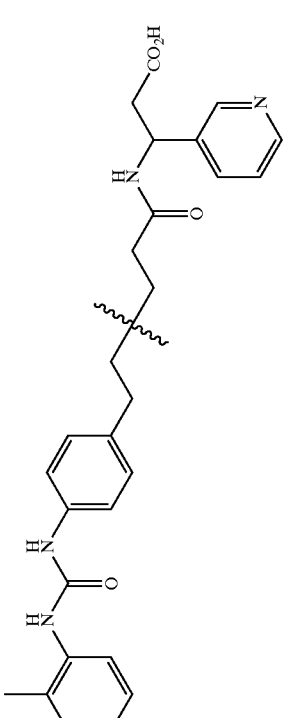 |
| Searle | U.S. Pat. No. 5220050 | 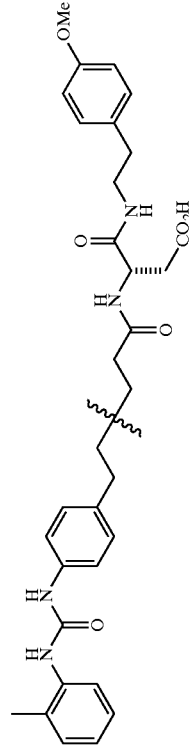 |
| Monsanto | U.S. Pat. No. 5239113<br>WO 93/07867<br>EP 542708 | 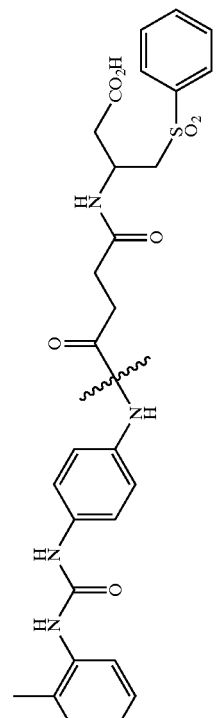 |

TABLE 3-continued

| | | | | |
|---|---|---|---|---|
| Searle | U.S. Pat. No. 5272162 WO 94/01396 | | | |
| Searle | U.S. Pat. No. 5344957 | | | |
| Searle | WO 93/12074 | | | |
| Monsanto | U.S. Pat. No. 5314902 | | | |

TABLE 3-continued

| | | |
|---|---|---|
| Searle Monsanto | WO 93/16038 | |
| Searle | WO 94/00424 | |
| Searle Monsanto | WO 94/18162 | |
| Searle Monsanto | WO 94/21602 | |

TABLE 3-continued

| | | |
|---|---|---|
| Searle | WO 94/22820 | |
| DuPont Merck | U.S. Pat. No. 5523302 | |
| DuPont Merck | U.S. Pat. No. 5446056 | |
| DuPont Merck | WO 95/18111 | |

TABLE 3-continued
| | | |
|---|---|---|
| Thomae | EP 718287 | 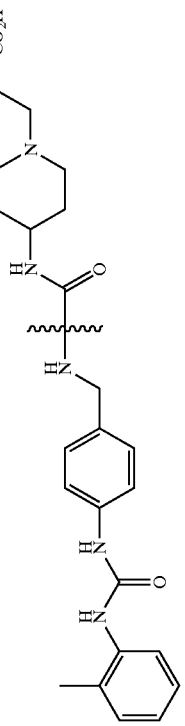 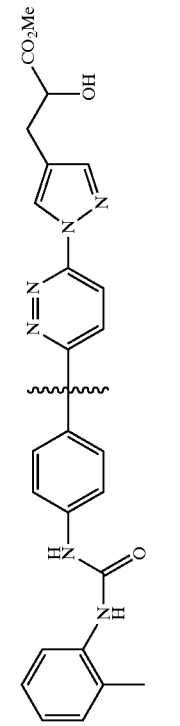 |
| Thomae | DE 4446301 | 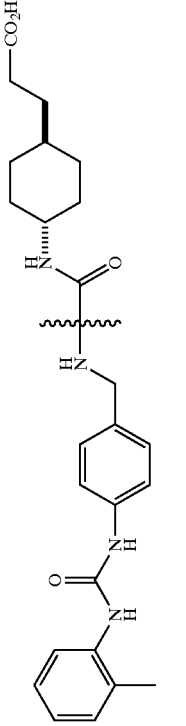 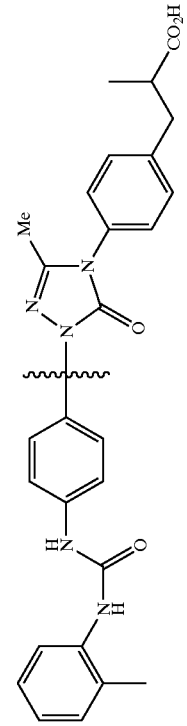 |
| Thomae | EP 525629 | 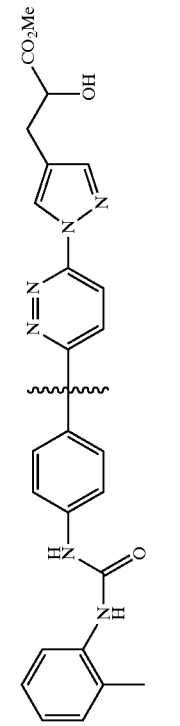 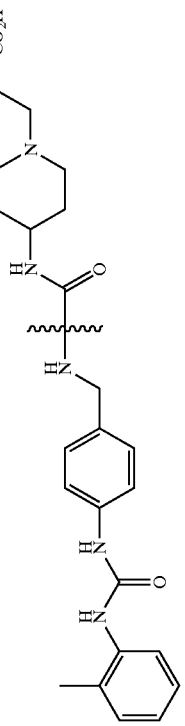 |
| Thomae | EP 587134 | 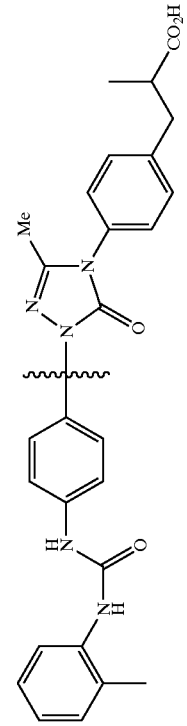 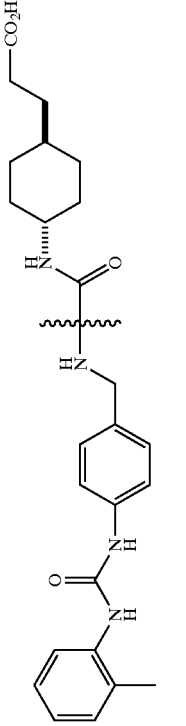 |
| Thomae | EP 604800 | 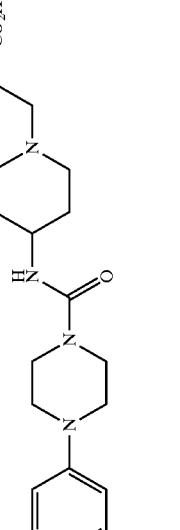 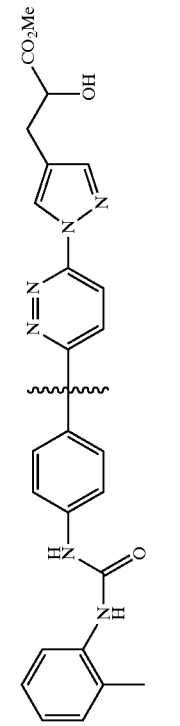 |

TABLE 3-continued

| | | |
|---|---|---|
| Thomae | EP 503548 | |
| Hoffman LaRoche | EP 505868 | |
| Hoffman LaRoche | U.S. Pat. No. 5399585 | |
| Hoffman LaRoche | U.S. Pat. No. 5256812 | |

TABLE 3-continued

| Hoffman LaRoche | U.S. Pat. No. 5084466 EP 381033 |
| Rhone-Poulenc | WO 93/11759 U.S. Pat. No. 5258398 |
| Takeda | EP 614664 |

TABLE 3-continued

| Takeda | EP 529858 |
| Cassella (Hoechst) | |
| Glaxo | EP 537980 WO 93/08181 |
| Glaxo | EP 542363 WO 93/10091 |
| Glaxo | WO 96/20192 |

TABLE 3-continued
| | | |
|---|---|---|
| Glaxo | WO 93/22303 | 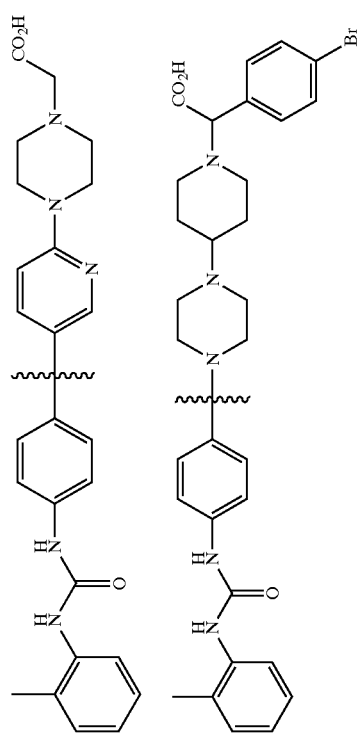 |
| Glaxo | WO 93/14077 | 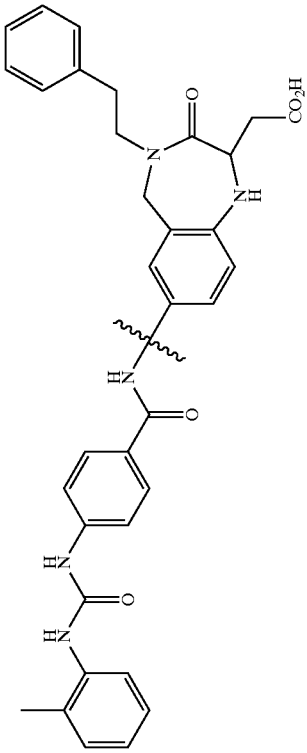 |
| Smith-Kline Beecham | WO 93/00095 | 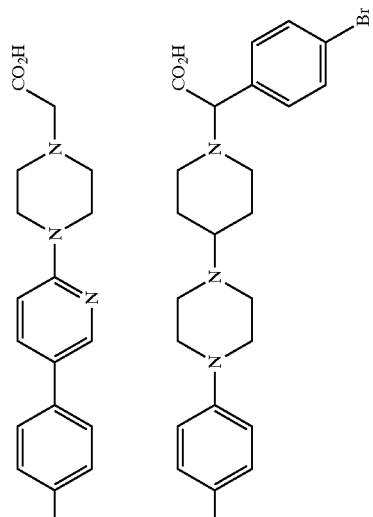 |
| Smith-Kline Beecham | WO 94/12478 | 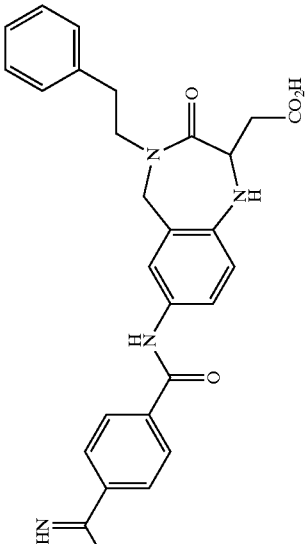 |

TABLE 3-continued
| Smith-Kline Beecham | WO 94/14776 | 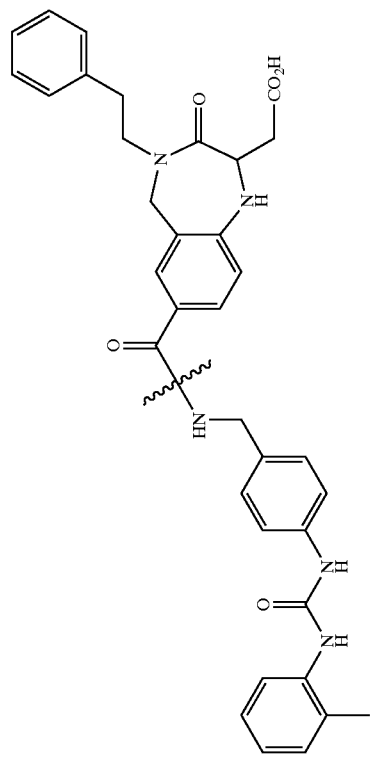 |
| Smith-Kline Beecham | WO 94/22444 | 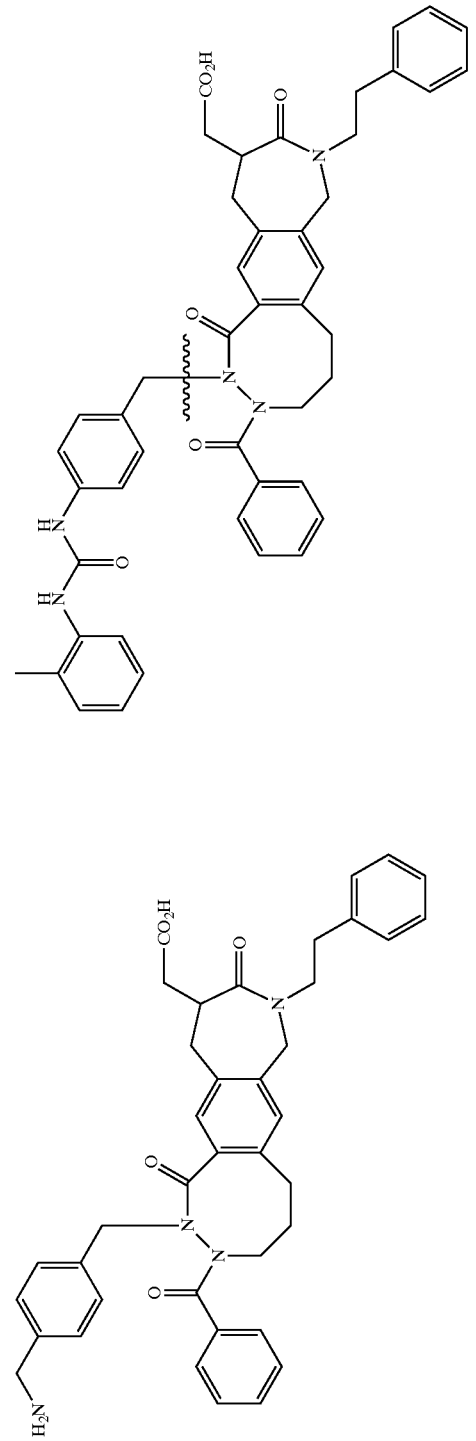 |

TABLE 3-continued

| Smith-Kline Beecham | WO 94/29273 |
| Smith-Kline Beecham | WO 94/29273 |
| Smith-Kline Beecham | WO 95/18619 |
| Smith-Kline Beecham | WO 95/18619 |

TABLE 3-continued
| | | | |
|---|---|---|---|
| Smith-Kline Beecham | WO 96/19223 | 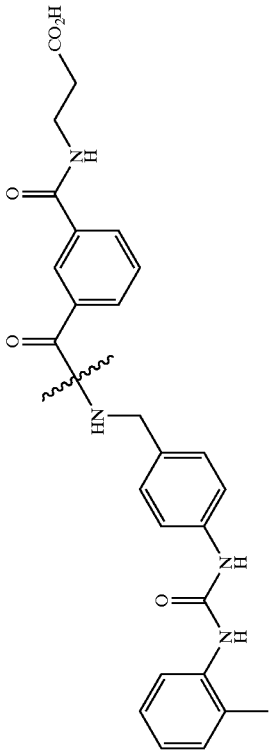 | 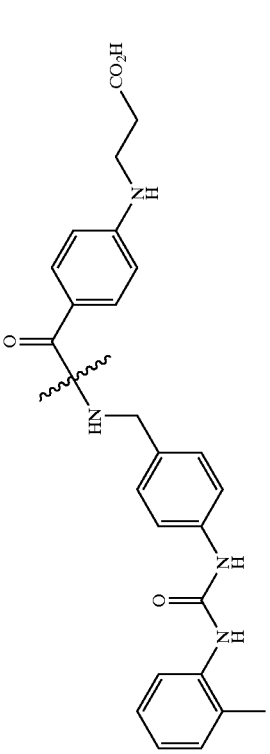 |
| Smith-Kline Beecham | WO 96/19221 | 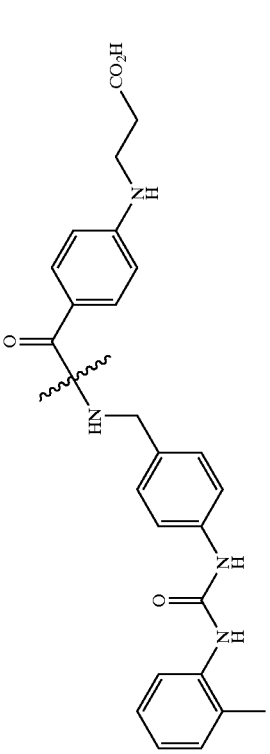 | 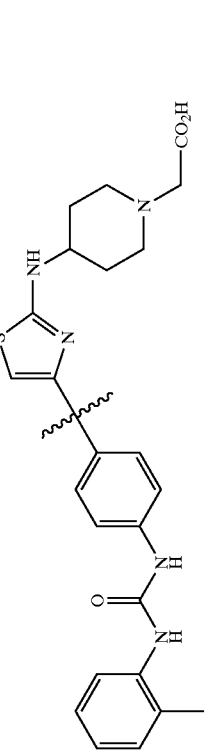 |
| Smith-Kline Beecham | WO 96/19222 | 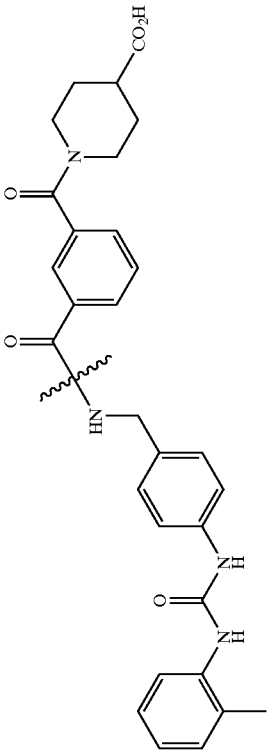 | 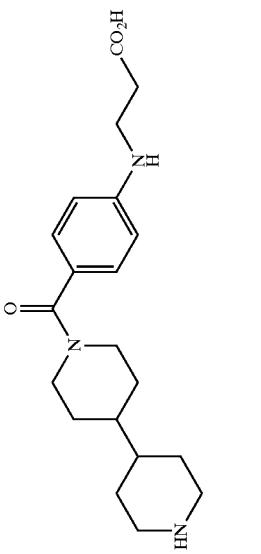 |
| Sanofi | EP 719775 | 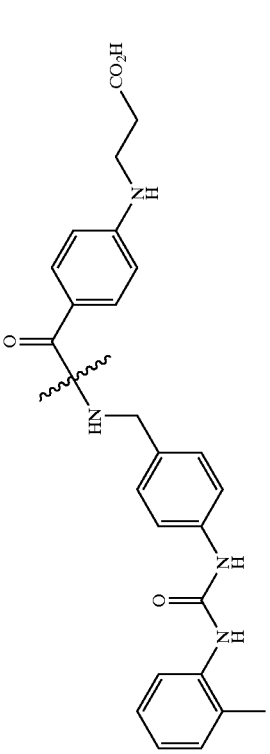 | 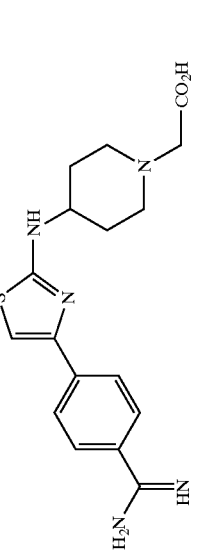 |

TABLE 3-continued

| Eli Lilly | EP 635492 | | |
| Eli Lilly | EP 635492 | | |
| Eli Lilly | EP 655439 | | |
| Ortho | WO 95/25091 | | |

TABLE 3-continued
| | | | |
|---|---|---|---|
| Zeneca | WO 94/22834 | 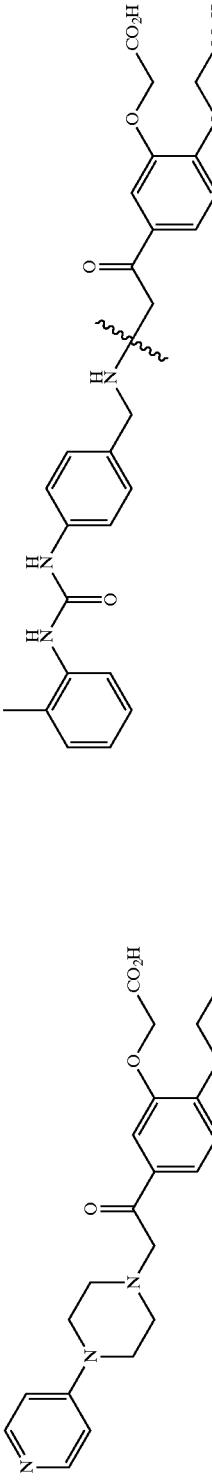 | 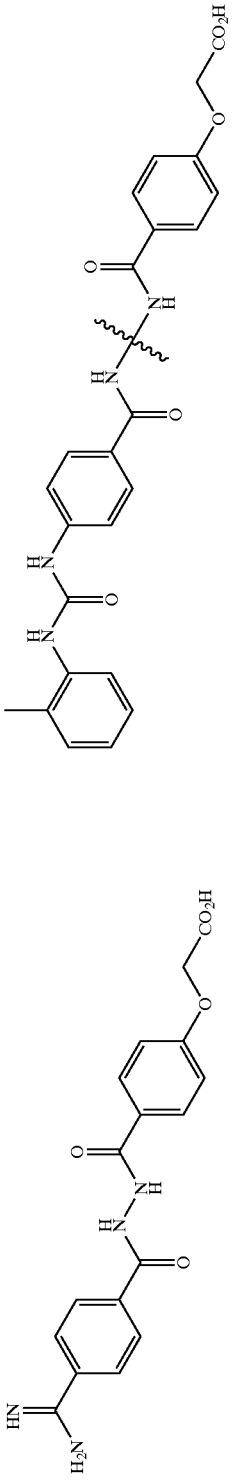 |
| Zeneca | EP 632016 | 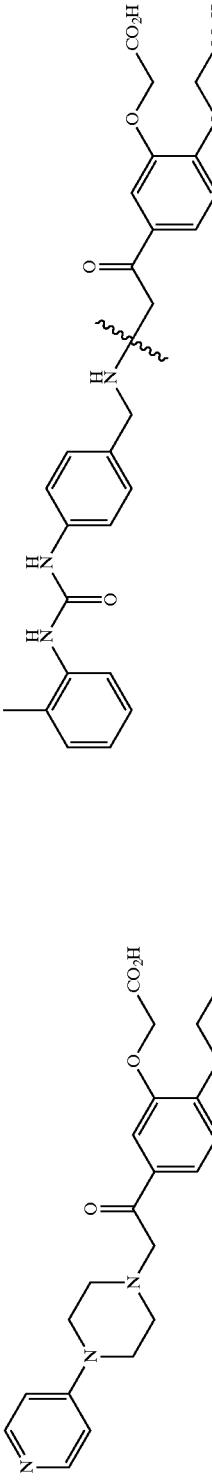 | 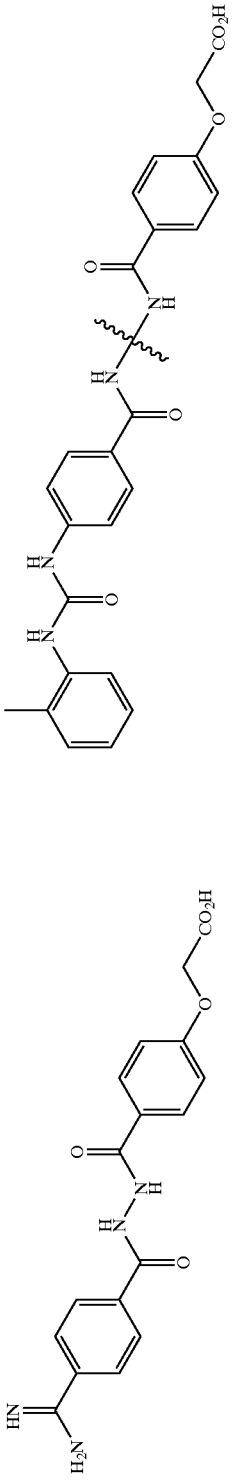 |
| Zeneca | U.S. Pat. No. 5463011<br>U.S. Pat. No. 5494922<br>(CIP) | 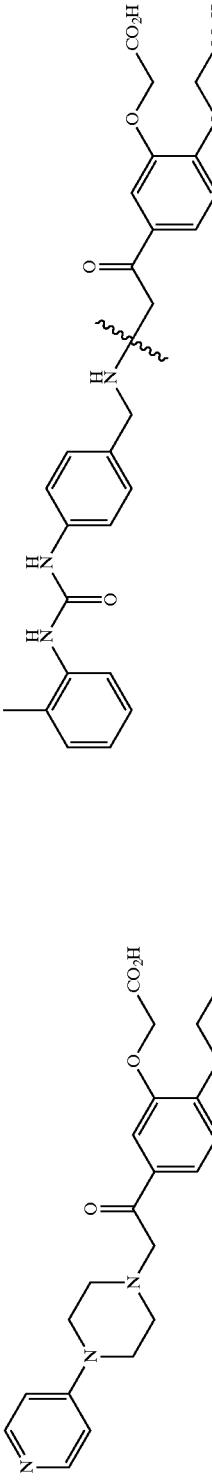 | 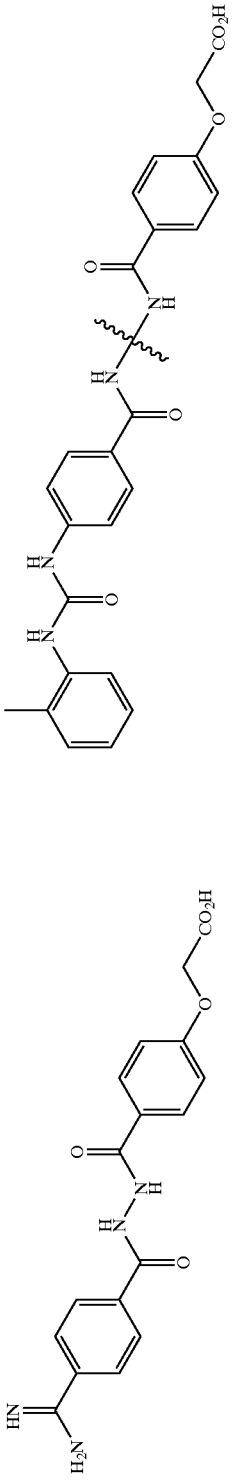 |

TABLE 3-continued
| | | |
|---|---|---|
| Eli Lilly WO 96/22288 | 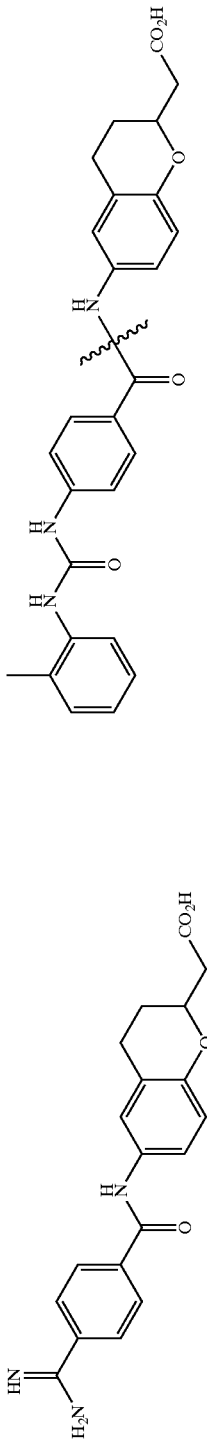 | |
| Fujisawa WO 96/29309 | 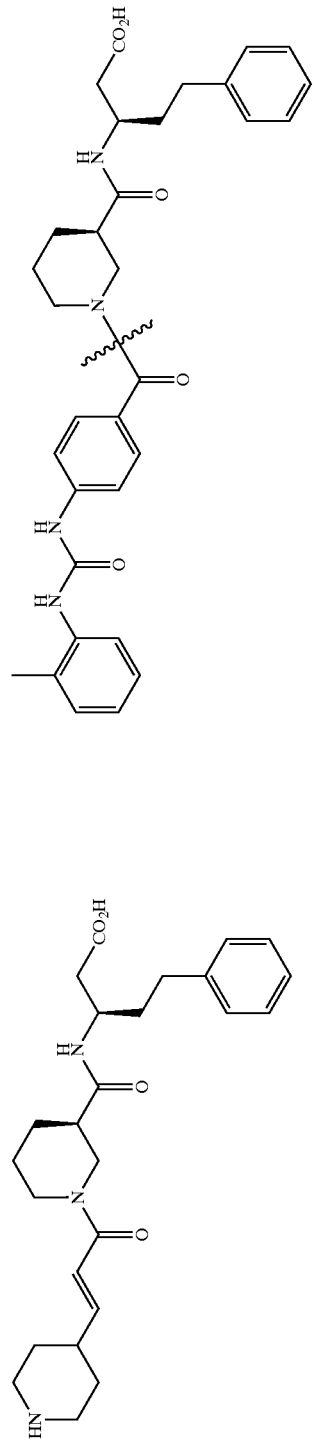 | |
| Merck/ Germany EP 727425 | 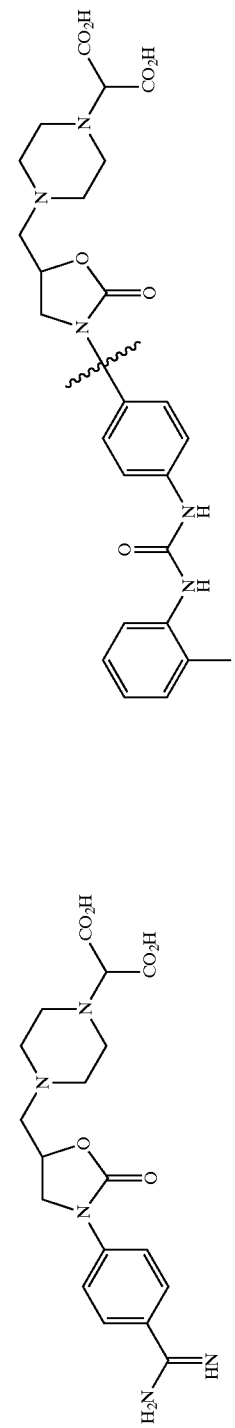 | |

What we claim is:
1. A cell adhesion inhibitor having Formula (I)

A—B     (I), wherein A comprises a VLA-4 specificity determinant which does not impart significant IIb/IIIa activity and is selected from the group consisting of alkyl; aliphatic acyl optionally substituted with N-alkyl- or N-arylamido; aroyl; heterocycloyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl; alkylaminocarbonyl optionally substituted with bis(alkylsulfonyl)amino, alkoxycarbonylamino or alkenyl; arylaminocarbonyl optionally substituted with bis(alkylsulfonyl)amino, alkoxycarbonylamino or alkenyl; aralkylaminocarbonyl optionally substituted with bis(alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl)(aralkyl) aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl)(heterocyclyl) aminocarbonyl; (alkyl)(heterocyclylalkyl)aminocarbonyl; (aralkyl)(heterocyclyl)aminocarbonyl; (aralkyl)(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cycloalkylalkylsulfonyl; arylaroyl; biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl-aminocarbonyl optionally substituted with aryl; alkynyl-aminocarbonyl optionally substituted with aryl; alkenyl-aminosulfonyl optionally substituted with aryl; alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl; heterocyclylalkylsulfonyl; alkenyl; alkynyl; cycloalkyl; aryl-fused cycloalkyl; cycloalkenyl; aryl; aryl-substituted alkyl; aryl-substituted alkenyl; aryl-substituted alkynyl; cycloalkyl-substituted alkyl; cycloalkenyl substituted cycloalkyl; biaryl; alkoxy; alkenoxy; alkynoxy; aryl-substituted alkoxy; aryl-substituted alkenoxy; aryl-substituted alkynoxy; alkylamino; alkenylamino; alkynylamino; aryl-substituted alkylamino; aryl-substituted alkenylamino; aryl-substituted alkynylamino; aryloxy; arylamino; N-alkylurea-substituted alkyl; N-arylurea-substituted alkyl; alkylcarbonylamino-substituted alkyl; aminocarbonyl-substituted alkyl; heterocyclyl; heterocyclyl-substituted alkyl; heterocyclyl-substituted amino; carboxyalkyl substituted aralkyl; oxocarbocyclyl-fused aryl; arylurea-substituted arylalkylcarbonylamino; heteroarylamido-substituted arylalkylcarbonylamino; and arylurea-substituted arylurea, and B is of Formula IIIa

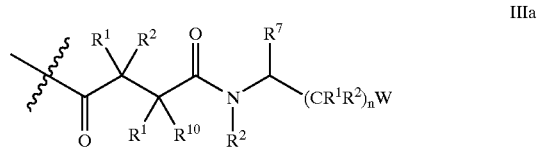

IIIa wherein
n=0–5;
W is selected from the group consisting of $CO_2H$, $SO_3H$, $PO_4H_2$, tetrazole, and hydrogen; each of $R^1$ and $R^2$, independently, is selected from the group consisting of hydrogen; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide;
$R^7$ is selected from the group consisting of hydrogen, aryl; aralkyl, alkenyl; and alkyl optionally substituted with heterocycle, thioalkoxy, carboxy, alkoxycarbonyl, alkoxy, or halogen; and
$R^{10}$ is selected from the group consisting of $R^2$, $NHSO_2R^{11}$, $NH_2$, $OR^2$, and $NHZR^{12}$, where $R^{11}$ is selected from the group consisting of alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide; $R^{12}$ is selected from the group consisting of hydrogen; cycloalkenyl; aryl; aralkyl; heterocycle; and alkyl optionally substituted with cycloalkyl, heterocycle, alkoxyl, hydroxyl, halogen, aralkoxy, thioalkoxy, carboxy, alkoxycarbonyl, carboxamide, or aralkoxy; and Z is CO or $(CR^1R^2)_n$;
provided that $R^2$ and $R^7$ or $R^2$ and $R^{10}$ may be taken together to form —$(CH_2)_m$—, where m=1–4.

2. A cell adhesion inhibitor of claim 1 selected from the group consisting of the compounds:
3-(3,4-dimethoxyphenyl)-3-(4-methyl-(2-(4-(benzoylamino)phenylcarbamoyl)methyl)pentanoylamino)propionic acid;
3-(3,4-dimethoxyphenyl)-3-(4-methyl-(2-(4-(4-(methoxy)pyrmdin-2-yl -aminosulfonyl)phenylcarbamoyl)methyl)pentanoylalmino)propionic acid;
3-{2-[(benzyl-methyl-carbamoyl)-methyl]-4-methyl-pentanoylamino}-3-(4-methoxy-phenyl)-propionic acid;
3-(4-methyl-2-{[4-(3-o-tolyl-ureido)-phenylcarbamoyl]-methyl}-pentanoylamino)-4-morpholin-4-yl-butyric acid;
3-(4-methyl-2-{[4-(3-o-tolyl-ureido)-phenylcarbamoyl]-methyl}-pentanoylamino)-butyric acid methyl ester;
3-(3,4-dimethoxy-phenyl)-3-{2-methyl-3-[4-(3-o-tolyl-ureido)-phenylcarbamoyl]-propionylamino}-propionic acid;
3-{2-[(2-methoxy-benzylcarbamoyl)-methyl]-4-methyl-pentanoylamino}-3-(4-methoxy-phenyl)-propionic acid;
(1-{2-methanesulfonylamino-3-[4-(3-o-tolyl-ureido)-phenylcarbamoyl]-propionyl}-piperidin-2-yl)-acetic acid;
3-(4-methoxy-phenyl)-3-(4-methyl-2-{[4-(3-o-tolyl-ureido)-phenylcarbamoyl]-methy1}-pentanoylamino)-propionic acid;

3-(3,4-dimethoxy-phenyl)-3-(4-methyl-2-{[4-(3-phenyl-propyl)-phenylcarbamoyl]-methyl}-pentanoylamino)-propionic acid;

3-{2-[(4-carbamoyl-phenylcarbamoyl)-methyl]-4-methyl-pentanoylamino}-3-(3,4-dimethoxy-phenyl)-propionic acid;

3-(4-methoxy-phenyl)-3-(2-{[2-(4-methoxy-phenyl)-ethylcarbamoyl]-methyl}-4-methyl-pentanoylamino)-propionic acid;

3-{2-amino-3-[4-(3-o-tolyl-ureido)-phenylmethylcarbamoyl]-propionylamino}-3-(3,4-dimethoxy-phenyl)-propionic acid;

3-{2-amino-3-[4-(3-o-tolyl-ureido)-phenylcarbamoyl]-propionylamino}-3-(3,4-dimethoxy-phenyl)-propionic acid;

3-[4-methyl-2-((4-o-tolylsulfanylmethyl-phenylcarbamoyl)methyl)-pentanoylamino]3-(3,4-dimethoxy-phenyl)-propionic acid;

3-(3,4-dimethoxy-phenyl)-3-(4-methyl-2-{[4-(3-phenyl-propenyl)-phenylcarbamoyl]-methyl}-pentanoylamino)-propionic acid;

3-(4-methoxy-phenyl)-3-(4-methyl-2-{[4-(3-phenyl-ureido)-phenylcarbamoyl]-methyl}-pentanoylamino)-propionic acid;

3-(3,4-dimethoxy-phenyl)-3-{2-methyl-3-[4-(3-o-tolyl-ureido)-phenylcarbamoyl]-propionylamino}-propionic acid methyl ester;

3-benzo[1,3]dioxol-5-yl-3-({2-[4-(3-o-tolyl-ureido)-phenylcarbamoyl]-cyclopropanecarbonyl}-amino)-propionic acid, 3-benzo[1,3]dioxol-5-yl-3-{3-[4-(3-phenyl-ureido)-phenylcarbamoyl]-propionylamino}-propionic acid;

3-[2-(benzylcarbamoyl-methyl)-4-methyl-pentanoylamino]-3-(4-methoxy-phenyl)-propionic acid;

3-{2-[4-benzylsulfanylmethyl-phenylcarbamoyl)-methyl]-4-methyl-pentanoylamino}-3-(3,4-dimethoxy-phenyl)-propionic acid, 3-benzo[1,3]dioxol-5-yl-3-[3-(4-methoxy-benzylcarbamoyl)-5-methyl-hexanoylamino]-propionic acid;

3-(3,4-dimethoxy-phenyl)-3-{4-methyl-2-[(4-o-tolyloxymethyl-phenylcarbamoyl)-methyl]-pentanoylamino}-propionic acid;

3-(3,4-dimethoxy-phenyl)-3-(4-methyl-2-{[4-(2-o-tolylsulfanyl-methyl)-phenylcarbamoyl]-methyl}-pentanoylamino)-propionic acid;

4-morpholin-4-yl-3-{3-[4-(3-o-tolyl-ureido)-phenylcarbamoyl]-propionylamino}-butyric acid;

3-benzo[1,3]dioxol-5-yl-3-(5-methyl-3-{[4-(3-o-tolyl-ureido)-benzyl]-carbamoyl}-hexanoylamino)-propionic acid;

3-{3-[4-(3-o-tolyl-ureido)-phenylcarbamoyl]-butyric acid;

3-{3-[4-(3-o-tolyl-ureido)-phenylcarbamoyl]-propionylamino}-propionic acid;

3-(3,4-dimethoxy-phenyl)-3-{2-hydroxy-3-[4-(3-o-tolyl-ureido)-phenylcarbamoyl]-propionylamino}-propionic acid;

3-(3,4-dimethoxy-phenyl)-3-(4-methyl-2-{[4-(2-o-tolyl-ethyl)-phenylcarbamoyl]-methyl}-pentanoylamino)-propionic acid, 3-(3,4-dimethoxy-phenyl)-3-(4-methyl-2-{[4-(2-o-tolyl-vinyl)-phenylcarbamoyl]-methyl}-pentanoylamino)-propionic acid;

3-(3,4-dimethoxy-phenyl)-3-{2-([6-(3-phenyl-ureido)-pyridin-3-ylcarbamoyl]methyl)-4-methylpentanoylamino}-propionic acid;

3-(3,4-dimethoxy-phenyl)-3-[4-methyl-2-(4-[3-(o-tolylsulfonyl)-ureido]-phenylcarbamoyl}-methyl)-pentanoylamino]-propionic acid;

3-{3-[4-(3-phenyl-ureido)-phenylcarbamoyl]-2-methylpropionylamino}-butyric acid;

3-(3,4-dimethoxy-phenyl)-3-(4-methyl-2-{[4-(3-o-tolyl-ureido)-phenylcarbamoyl]-methyl}-pentanoylamino)-propionic acid;

3-(3,4-dimethoxy-phenyl)-3-{3-[3-hydroxy-4-(3-phenyl-ureido)-phenylcarbamoyl]-propionylamino}-propionic acid;

3-(3,4-dimethoxy-phenyl)-3-[4-methyl-2-({4-[3-(3-methyl-pyridin-2-yl)-ureido]-phenylcarbamoyl}-methyl)-pentanoylaminol]-propionic acid;

3-(3,4-dimethoxy-phenyl)-3-(2-methanesulfonylamino-3-{methyl-[4-(3-o-tolyl-ureido)-phenyl]-carbamoyl}-propionylamino)-propionic acid;

3-(3-{methyl-[4-(3-o-tolyl-ureido)-phenyl]-carbamoyl}-propionylamino)-butyric acid; 3-(4-methoxyphenyl)-3-(4-methyl-2-[((4-(3-o-tolyl-ureido)benzyl)carbamoyl)methyl]pentanoylamino)propionic acid;

3-(4-methyl-2-{[4-(3-o-tolyl-ureido)-phenylcarbamnoyl]-methyl}-pentanoylamino)-butyric acid;

3-(3,4-dimethoxy-phenyl)-3-{3-[5-(3-o-tolyl-ureido)-pyridin-2-ylcarbamoyl]-propionylamino}-propionic acid;

3-{2-methyl-3-[4-(3-o-tolyl-ureido)-phenylcarbamoyl]-propionylamino}-butyric acid;

3-(3,4-dimethoxy-phenyl)-3-{2-methyl-3-[4-(3-phenyl-ureido)-phenylcarbamoyl]-propionylamino}-propionic acid;

3-{2-methyl-3-[4-(3-o-tolyl-ureido)-phenylcarbamoyl]-propionylamino}-hex-5-enoic acid;

3-{3-[4-(3-o-tolyl-ureido)-phenylcarbamoyl]-propionylamino}-hex-5-enoic acid;

3-benzo[1,3]dioxol-5-yl-3-(4-methyl-2-{[4-(3-o-tolyl-ureido)-phenylcarbamoyl]-methyl}-pentanoylamino)-propionic acid;

(1-(3-(4-(3-o-tolyl-ureido)phenylcarbamoyl)propionyl)piperidin-2-yl)acetic acid;

3-(3,4-dimethoxy-phenyl)-3-(3-{methyl-[4-(3-o-tolyl-ureido)-phenyl]-carbamoyl}-propionylamino)-propionic acid, 3-(3,4-dimethoxy-phenyl)-3-{3-[4-(3-o-tolyl-ureido)-phenylcarbamoyl]-propionylamino}-propionic acid, 3-(3,4-dimethoxy-phenyl)-3-{4-methyl-2-([4-(3-o-tolyl-ureido)-phenylcarbamoyl]methyl)-pentanoylamino}-propionic acid;

3-benzo[1,3]dioxol-5-yl-3-{2-methyl-3-[4-(3-o-tolyl-ureido)-phenylcarbamoyl]-propionylamino}-propionic acid;

3-(3,4-dimethoxy-phenyl)-3-(4-methyl-2-{[4-(3-o-tolyl-ureido)-phenylniethylcarbamoyl]-methyl}-pentanoylamino)-propionic acid;

3-(3,4-dimethoxy-phenyl)-3-(2-{[2-methoxy-4-(3-o-tolyl-ureido)-phenylcarbamoyl]-methyl}-4-methyl-pentanoylamino)-propionic acid; and 3-(3,4-dimethoxy-phenyl)-3-(2-{[3-methoxy-4-(3-o-fluorophenyl-ureido)-phenylcarbamoyl]-methyl}-4-methyl-pentanoylamino)-propionic acid.

3. A cell adhesion inhibitor of claim 2 selected from the group consisting of the following compounds:

3-benzo[1,3]dioxol-5-yl-3-{2-methyl-3-[4-(3-o-tolyl-ureido)-phenylcarbamoyl-propionylamino}-propionic acid;

3-(3,4-dimethoxy-phenyl)-3-(4-methyl-2-{[4-(3-o-tolyl-ureido)-phenylmethylcarbamoyl]-methyl}-pentanoylamino)-propionic acid; and 3-(3,4-dimethoxy-phenyl)-3-(2-{[3-methoxy-4-(3-o-fluorophenyl-ureido)-phenylcarbamoyl]-methyl}-4-methyl-pentanoylamino)-propionic acid.

4. A cell adhesion inhibitor of claim 2 selected from the group consisting of following compounds:
3-(3,4-dimethoxy-phenyl)-3-[4-methyl-2-({4-[3-(o-tolyl-sulfonyl)-ureido]-phenylcarbamoyl}-methyl)-pentanoylamino]-propionic acid;
3-(3,4-dimethoxy-phenyl)-3-(4-methyl-2-{[4-(3-o-tolyl-ureido)-phenylcarbamoyl]-methyl}-pentanoylamino)-propionic acid;
3-(3,4-dimethoxy-phenyl)-3-{3-[3-hydroxy-4-(3-phenyl-ureido)-phenylcarbamoyl]-propionylamino}-propionic acid;
3-(3,4-dimethoxy-phenyl)-3-[4-methyl-2-({4-[3-(3-methyl-pyridin-2-yl)-ureido]-phenylcarbamoyl}-methyl)-pentanoylamino]-propionic acid;
3-(3-{methyl-[4-(3-o-tolyl-ureido)-phenyl]-carbamoyl}-propionylamino)-butyric acid;
3-(4-methoxyphenyl)-3-(4-methyl-2-[((4-(3-o-tolyl-ureido)benzyl)carbamoyl)methyl]pentanoylamino)propionic acid;
3-(4-methyl-2-{[4-(3-o-tolyl-ureido)-phenylcarbamoyl]-methyl}-pentanoylamino)-butyric acid;
3-(3,4-dimethoxy-phenyl)-3-{3-[5-(3-o-tolyl-ureido)-pyridin-2-ylcarbamoyl]-propionylamino}-propionic acid;
3-{2-methyl-3-[4-(3-o-tolyl-ureido)-phenylcarbamoyl]-propionylamino}-butyric acid; and
3-(3,4-dimethoxy-phenyl)-3-{2-methyl-3-[4-(3-phenyl-ureido)-phenylcarbamoyl]-propionylamino}-propionic acid.

5. The cell adhesion inhibitor according to claim 1, wherein A is selected from the group consisting of alkylamino; alkenylamino; alkynylanmino; aryl-substituted alkylamino; aryl-substituted alkenylamino; aryl-substituted alknylamino; arylamino; N-alkylurea-substituted alkyl; N-arylurea-substituted alkyl; arylurea-substituted arylalkylcarbonylamino; heteroarylamido-substituted arylalkylcarbonylamino; and arylurea-substituted arylurea.

6. The cell adhesion inhibitor according to claim 1, wherein A is selected from the group consisting of alkylamino; arylamino; aryl-substituted alkylamino; heterocyclyl; and heterocyclyl-substituted amino.

7. The cell adhesion inhibitor according to claim 1, wherein A is selected from the group consisting of aryl-substituted alkylamino; aryl-substituted alkenylamino; aryl-substituted alkynylamino; arylamino; N-alkylurea-substituted alkyl; N-arylurea-substituted alkyl; arylurea-substituted arylalkylcarbonylamino; heteroarylamido-substituted arylalkylcarbnylamino; and arylurea-substituted arylurea.

8. The cell adhesion inhibitor according to claim 1, wherein A is (N-Ar'-urea)-para-substituted arylamino or (N-Ar'-urea)-para-substituted aralkylamino.

9. The cell adhesion inhibitor according to claim 1 wherein each of $R^1$ and $R^2$, independently, is selected from the group consisting of hydrogen, aryl, and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide.

10. The cell adhesion inhibitor according to claim 1 wherein $R^7$ is selected from the group consisting of aryl, aralkyl, alkenyl, and alkyl optionally substituted with heterocycle.

11. The cell adhesion inhibitor according to claim 1 wherein $R^{10}$ is selected from the group consisting of $R^2$, $NHSO_2R^{11}$, $NH_2$, and $OR^2$.

12. The cell adhesion inhibitor according to claim 1 wherein W is $CO_2H$.

13. The cell adhesion inhibitor according to claim 1 wherein $R^{11}$ is selected from the group consisting of alkenyl; alkynyl; aryl; aralkyl; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide.

14. The cell adhesion inhibitor according to claim 1, wherein A is selected from the group consisting of alkylamino; arylamino; aryl-substituted alkylamino; heterocyclyl; and heterocyclyl-substituted amino, each of $R^1$ and $R^2$, independently, is selected from the group consisting of hydrogen, aryl, and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide, and $R^7$ is selected from the group consisting of aryl, aralkyl, alkenyl, and alkyl optionally substituted with heterocycle.

15. The cell adhesion inhibitor according to claim 1, wherein A is selected from the group consisting of alkylamino; arylamino; aryl-substituted alkylamino; heterocyclyl; and heterocyclyl-substituted amino, $R^7$ is selected from the group consisting of aryl, aralkyl, alkenyl, and alkyl optionally substituted with heterocycle and $R^{10}$ is selected from the group consisting of $R^2$, $NHSO_2R^{11}$, $NH_2$, and $OR^2$.

16. The cell adhesion inhibitor according to claim 1, wherein A is selected from the group consisting of alkylamino; arylamino; aryl-substituted alkylamino; heterocyclyl; and heterocyclyl-substituted amino, each of $R^1$ and $R^2$, independently, is selected from the group consisting of hydrogen, aryl, and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide, and $R^{10}$ is selected from the group consisting of $R^2$, $NHSO_2R^{11}$, $NH_2$, and $OR^2$.

17. A pharmaceutical composition comprising:
  (a) the cell adhesion inhibitor of claim 1 in an amount effective for the prevention, inhibition or suppression of cell adhesion; and
  (b) a pharmaceutically acceptable carrier.

18. The cell adhesion inhibitor according to claim 1, wherein said inhibitor has an $IC_{50}$ of about 1 pM to about 10 µM, as measured by a VLA-4 direct binding assay comprising the steps of conjugating a VCAM-IgG fusion protein to a alkaline phosphatase marker enzyme, contacting the fusion protein-marker enzyme conjugate with said inhibitor and Jurkat cells, colorizing the marker enzyme conjugated to the fusion protein, and determining the amount of cell-bound fusion protein.

19. The cell adhesion inhibitor according to claim 18, wherein said inhibitor has an $IC_{50}$ of about 1 pM to about 100 nM.

20. The cell adhesion inhibitor according to claim 19, wherein said inhibitor has an $IC_{50}$ of about 1 pM to about 10 nM.

21. A cell adhesion inhibitor having Formula (I)

$$A—B \qquad (I),$$

wherein A is selected from the group consisting of alkyl; aliphatic acyl optionally substituted with N-alkyl- or N-arylamido; aroyl; heterocycloyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl; alkylaminocarbonyl optionally substituted with bis(alkylsulfonyl)amino, alkoxycarbonylamino or alkenyl; arylaminocarbonyl optionally substituted with bis(alkylsulfonyl)amino, alkoxycarbonylamino or alkenyl; aralkylaminocarbonyl optionally substituted with bis (alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl)(aralkyl) aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl) (heterocyclyl) aminocarbonyl; (alkyl)(heterocyclylalkyl) aminocarbonyl; (aralkyl)(heterocyclyl)aminocarbonyl; (aralkyl)(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cylcoalkylalkylsulfonyl; arylaroyl; biarylsulfonyl; alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl-aminocarbonyl optionally substituted with aryl; alkynyl-aminocarbonyl optionally substituted with aryl; alkenyl-aminosulfonyl optionally substituted with aryl; alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl; heterocyclylalkylsulfonyl; alkenyl; alkynyl; cycloalkyl; aryl-fused cycloalkyl, cycloalkenyl; aryl; aryl-substituted alkyl; aryl-substituted alkenyl; aryl-substituted alkynyl; cycloalkyl-substituted alkyl; cycloalkenyl-substituted cylcoalkyl; biaryl; alkoxy; alkenoxy; alkynoxy; aryl-substituted alkoxy; aryl-substituted alkenoxy; aryl-substituted alkynoxy; alkylamino; alkenylamino; alkynylamino; aryl-substituted alkylamino; aryl-substituted alkenylamino; aryl-substituted alkynylamino; aryloxy; arylamino; N-alkylurea-substituted alkyl; N-arylurea-substituted alkyl; alkylcarbonylamino-substituted alkyl; aminocarbonyl-substituted alkyl; heterocyclyl; heterocyclyl-substituted alkyl; heterocyclyl-substituted amino; carboxyalkyl substituted aralkyl; oxocarbocyclyl-fused aryl; arylurea-substituted arylalkylcarbonylamino; heteroarylamido-substituted arylalkylcarbonylamino; and arylurea-substituted arylurea, and B is of Formula IIIa

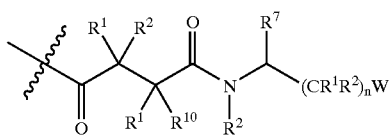

IIIa wherein n=0–5;

W is selected from the group consisting of $CO_2H$, $SO_3H$, $PO_4H_2$, tetrazole, and hydrogen;

each of $R^1$ and $R^2$, independently, is selected from the group consisting of hydrogen; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide;

$R^7$ is selected from the group consisting of hydrogen, aryl; aralkyl, alkenyl; and alkyl optionally substituted with heterocycle, thioalkoxy, carboxy, alkoxycarbonyl, alkoxy, or halogen; and $R^{10}$ is selected from the group consisting of $R^2$, $NHSO_2R^{11}$, $NH_2$, $OR^2$, and $NHZR^{12}$, where $R^{11}$ is selected from the group consisting of alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide; $R^{12}$ is selected from the group consisting of hydrogen; cycloalkenyl; aryl; aralkyl; heterocyle; and alkyl optionally substituted with cycloalkyl, heterocycle, alkoxyl, hydroxyl, halogen, aralkoxy, thioalkoxy, carboxy, alkoxycarbonyl, carboxamide, or aralkoxy; and Z is CO or $(CR^1R^2)_n$;

provided that $R^2$ and $R^7$ or $R^2$ and $R^{10}$ may be taken together to form $—(CH_2)_m—$, where m=1–4; further provided that A contains at least one cyclic moiety.

22. The cell adhesion inhibitor of claim 21, wherein A contains at least two cyclic moieties.

23. The cell adhesion inhibitor of claim 21, wherein A contains a urea group.

24. A cell adhesion inhibitor having Formula (I)

A—B    (I), wherein A comprises a VLA-4 specificity determinant which does not impart significant IIb/IIIa activity and is selected from the group consisting of alkyl; aliphatic acyl optionally substituted with N-alkyl- or N-arylamido; aroyl; heterocycloyl; aralkylcarbonyl optionally substituted with aryl; heterocycloalkylcarbonyl; alkoxycarbonyl; aralkyloxycarbonyl; cycloalkylcarbonyl optionally fused with aryl; heterocycloalkoxycarbonyl; alkylaminocarbonyl optionally substituted with bis(alkylsulfonyl)amino, alkoxycarbonylamino or alkenyl; arylaminocarbonyl optionally substituted with bis(alkylsulfonyl)amino, alkoxycarbonylamino or alkenyl; aralkylaminocarbonyl optionally substituted with bis (alkylsulfonyl)amino, alkoxycarbonylamino or alkenyl; alkylsulfonyl; aralkylsulfonyl; arylsulfonyl; cycloalkylsulfonyl optionally fused with aryl; heterocyclylsulfonyl; heterocyclylalkylsulfonyl; aralkoxycarbonyl; aryloxycarbonyl; cycloalkyloxycarbonyl; heterocyclyloxycarbonyl; heterocyclylalkoxycarbonyl; mono- or di-alkylaminocarbonyl optionally substituted with aryl; (alkyl)(aralkyl) aminocarbonyl; mono- or di-aralkylaminocarbonyl; mono- or di-arylaminocarbonyl; (aryl)(alkyl)aminocarbonyl; mono- or di-cycloalkylaminocarbonyl; heterocyclylaminocarbonyl; heterocyclylalkylaminocarbonyl; (alkyl) (heterocyclyl) aminocarbonyl; (alkyl)(heterocyclylalkyl) aminocarbonyl; (aralkyl)(heterocyclyl)aminocarbonyl; (aralkyl),(heterocyclylalkyl)aminocarbonyl; alkenoyl optionally substituted with aryl; alkenylsulfonyl optionally substituted with aryl; alkynoyl optionally substituted with aryl; alkynylsulfonyl optionally substituted with aryl; cycloalkenylcarbonyl; cycloalkenylsulfonyl; cycloalkylalkanoyl; cylcoalkylalkylsulfonyl; arylaroyl; biarylsulfonyl;

alkoxysulfonyl; aralkoxysulfonyl; alkylaminosulfonyl; aryloxysulfonyl; arylaminosulfonyl; N-arylurea-substituted alkanoyl; N-arylurea-substituted alkylsulfonyl; cycloalkenyl-substituted carbonyl; cycloalkenyl-substituted sulfonyl; alkenoxycarbonyl optionally substituted with aryl; alkenoxysulfonyl optionally substituted with aryl; alkynoxycarbonyl optionally substituted with aryl; alkynoxysulfonyl optionally substituted with aryl; alkenyl-aminocarbonyl optionally substituted with aryl; alkynyl-aminocarbonyl optionally substituted with aryl; alkenyl-aminosulfonyl optionally substituted with aryl; alkynyl-aminosulfonyl optionally substituted with aryl; acylamino-substituted alkanoyl; acylamino-substituted alkylsulfonyl; aminocarbonyl-substituted alkanoyl; carbamoyl-substituted alkanoyl; carbamoyl-substituted alkylsulfonyl; heterocyclylalkanoyl; heterocyclylaminosulfonyl; carboxyalkyl-substituted aralkoyl; carboxyalkyl-substituted aralkylsulfonyl; oxocarbocyclyl-fused aroyl; oxocarbocyclyl-fused arylsulfonyl; heterocyclylalkanoyl; N',N'-alkyl, arylhydrazinocarbonyl; aryloxy-substituted alkanoyl; heterocyclylalkylsulfonyl; alkenyl; alkynyl; cycloalkyl; aryl-fused cycloalkyl, cycloalkenyl; aryl; aryl-substituted alkyl; aryl-substituted alkenyl; aryl-substituted alkynyl; cycloalkyl-substituted alkyl; cycloalkenyl-substituted cylcoalkyl; biaryl; alkoxy; alkenoxy; alkynoxy; aryl-substituted alkoxy; aryl-substituted alkenoxy; aryl-substituted alkynoxy; alkylamino; alkenylamino; alkynylamino; aryl-substituted alkylamino; aryl-substituted alkenylamino; aryl-substituted alkynylamino; aryloxy; arylamino; N-alkylurea-substituted alkyl; N-arylurea-substituted alkyl; alkylcarbonylamino-substituted alkyl; aminocarbonyl-substituted alkyl; heterocyclyl; heterocyclyl-substituted alkyl; heterocyclyl-substituted amino; carboxyalkyl substituted aralkyl; oxocarbocyclyl-fused aryl; arylurea-substituted arylalkylcarbonylamino; heteroarylamido-substituted arylalkylcarbonylamino; and arylurea-substituted arylurea, and B is of Formula IIIa

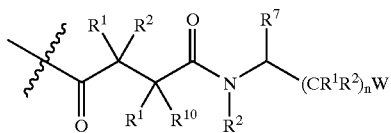

IIIa wherein n=0–5;

W is selected from the group consisting of $CO_2H$, $SO_3H$, $PO_4H_2$, tetrazole, and hydrogen;

each of $R^1$ and $R^2$, independently, is selected from the group consisting of hydrogen; alkyl; alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide;

$R^7$ is selected from the group consisting of hydrogen, aryl; aralkyl, alkenyl; and alkyl optionally substituted with heterocycle, thioalkoxy, carboxy, alkoxycarbonyl, alkoxy, or halogen; and $R^{10}$ is selected from the group consisting of $R^2$, $NHSO_2R^{11}$, $NH_2$, $OR^2$, and $NHZR^{12}$, where $R^{11}$ is selected from the group consisting of alkenyl; alkynyl; cycloalkyl; cycloalkenyl; aryl; aralkyl; heterocycle; and alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide; $R^{12}$ is selected from the group consisting of hydrogen; cycloalkenyl; aryl; aralkyl; heterocycle; and alkyl optionally substituted with cycloalkyl, heterocycle, alkoxyl, hydroxyl, halogen, aralkoxy, thioalkoxy, carboxy, alkoxycarbonyl, carboxamide, or aralkoxy; and Z is CO or $(CR^1R^2)_n$;

provided that $R^2$ and $R^7$ or $R^2$ and $R^{10}$ may be taken together to form —$(CH_2)_m$—, where m=1–4; further provided that the cell adhesion inhibitor does not impart GP $II_bIII_a$ activity.

25. The cell adhesion inhibitor according to claim 24, wherein A is selected from the group consisting of alkylamino; alkenylamino; alkynylamino; aryl-substituted alkylamino; aryl-substituted alkenylamino; aryl-substituted alkynylamino; arylamino; N-alkylurea-substituted alkyl; N-arylurea-substituted alkyl; alkylcarbonylamino-substituted alkyl; heterocyclyl; heterocyclyl-substituted amino; arylurea-substituted arylalkylcarbonylamino; heteroarylamido-substituted arylalkylcarbonylamino; arylurea-substituted arylurea and aliphatic acyl optionally substituted with N-alkyl- or N-arylamido.

26. The cell adhesion inhibitor according to claim 24, wherein A is (N-Ar'-urea)-para-substituted arylamino or is (N-Ar'-urea)-para-substituted aralkylamino.

27. The cell adhesion inhibitor according to claim 24, wherein each of $R^1$ and $R^2$ is independently hydrogen, or alkyl optionally substituted with cycloalkyl, cycloalkenyl, heterocycle, alkenyl, alkynyl, alkoxyl, hydroxyl, halogen, aralkoxy, thioalkoxy, carboxy, alkoxycarbonyl, or carboxamide and W is $CO_2H$.

* * * * *